(12) United States Patent
Purcell et al.

(10) Patent No.: US 10,070,631 B2
(45) Date of Patent: Sep. 11, 2018

(54) RODENTS HAVING A HUMANIZED TMPRSS GENE

(71) Applicant: REGENERON PHARMACEUTICALS, INC., Tarrytown, NY (US)

(72) Inventors: Lisa Purcell, Garnerville, NY (US); Alexander O. Mujica, Elmsford, NY (US); Yajun Tang, White Plains, NY (US)

(73) Assignee: REGENERON PHARMACEUTICALS, INC., Tarrytown, NY (US)

(*) Notice: Subject to any disclaimer, the term of this patent is extended or adjusted under 35 U.S.C. 154(b) by 0 days.

(21) Appl. No.: 15/624,774

(22) Filed: Jun. 16, 2017

(65) Prior Publication Data

US 2017/0290308 A1     Oct. 12, 2017

Related U.S. Application Data

(63) Continuation of application No. 15/442,857, filed on Feb. 27, 2017.

(60) Provisional application No. 62/301,023, filed on Feb. 29, 2016.

(51) Int. Cl.

| *A01K 67/027* | (2006.01) |
|---|---|
| *C07K 14/47* | (2006.01) |
| *C12N 15/63* | (2006.01) |
| *C12N 15/86* | (2006.01) |
| *C12N 15/09* | (2006.01) |
| *A61K 48/00* | (2006.01) |

(52) U.S. Cl.
CPC .......... *A01K 67/0275* (2013.01); *C07K 14/47* (2013.01); *C12N 15/63* (2013.01); *C12N 15/86* (2013.01); *A61K 48/00* (2013.01); *C12N 15/09* (2013.01); *C12N 2710/10332* (2013.01)

(58) Field of Classification Search
CPC ............ A61K 67/0278; A61K 2207/15; A61K 2217/072; A61K 2227/105; A61K 2267/0337; C12N 5/0606; C12N 9/6424
See application file for complete search history.

(56) References Cited

U.S. PATENT DOCUMENTS

| 6,586,251 B2 | 7/2003 | Economides et al. |
|---|---|---|
| 7,294,754 B2 | 11/2007 | Poueymirou et al. |
| 7,576,259 B2 | 8/2009 | Poueymirou et al. |
| 7,659,442 B2 | 2/2010 | Poueymirou et al. |
| 2004/0132156 A1* | 7/2004 | Parry ..................... C07K 16/30 435/226 |
| 2005/0003416 A1* | 1/2005 | Wu ..................... C12N 9/6424 435/6.16 |
| 2005/0022256 A1 | 1/2005 | Laferla |
| 2005/0026255 A1* | 2/2005 | Morser ..................... C12Q 1/37 435/69.1 |
| 2006/0101531 A1* | 5/2006 | Vasioukhin ......... A01K 67/0275 800/10 |
| 2008/0078000 A1 | 3/2008 | Poueymirou et al. |
| 2013/0273070 A1* | 10/2013 | Purcell Ngambo ......................... A61K 39/3955 424/158.1 |
| 2014/0235933 A1 | 8/2014 | Lee et al. |
| 2014/0310828 A1 | 10/2014 | Lee et al. |
| 2015/0106961 A1 | 4/2015 | Rojas et al. |
| 2015/0143558 A1 | 5/2015 | McWhirter et al. |
| 2015/0143559 A1 | 5/2015 | McWhirter et al. |
| 2017/0245482 A1* | 8/2017 | Purcell ............... A01K 67/0278 |

FOREIGN PATENT DOCUMENTS

| WO | 2011/044050 A2 | 4/2011 |
|---|---|---|
| WO | 2012/112544 A2 | 8/2012 |
| WO | 2013/063556 A1 | 5/2013 |
| WO | 2013/158516 A1 | 10/2013 |
| WO | 2013/192030 A1 | 12/2013 |
| WO | 2014/039782 A2 | 3/2014 |
| WO | 2015/042557 A1 | 3/2015 |
| WO | 2015/196051 A1 | 12/2015 |
| WO | 2016/089692 A1 | 6/2016 |
| WO | 2016/094481 A1 | 6/2016 |
| WO | 2015/171861 A1 | 11/2016 |

OTHER PUBLICATIONS

Sun, http://www.dtic.mil/docs/citations/ADA525092; 2009.*
NCBI NG_047085.1, 2017.*
Bottcher-Friebertshauser et al, J. Virol. 84(11):5605-5614, 2010.*
Kuhn, Studies on the host response to influenza A virus infections in mouse knock-out mutants, University of Veterinary Medicine, Hannover, 2015.*
Macchiarini et al, J. Exp. Med. 202(10):1307-1311, 2005.*
Bodewes et al, Expert Reviews Vaccines 9(1): 59-72, 2010.*
NCBI NG_011858.2, 2014.*
ENSG00000153802, https://www.ensembl.org/Homo_sapiens/Gene/Summary?g=ENSG00000153802; downloaded Dec. 7, 2017.*
GenBank CH471057.1, 2015 (relevant portion only).*
NCBI CCDS report for TMPRSS11D, https://www.ncbi.nlm.nih.gov/CCDS/CcdsBrowse.cgi?REQUEST=CCDS&DATA=CCDS3518; downloaded Dec. 7, 2017.*
NCBI NP_004253, 2015.*
Bertram S. et al., "Novel Insights into Proteolytic Cleavage of Influenza Virus Hemagglutinin", Rev. Med. Virol. 20:298-310 (2010).

(Continued)

*Primary Examiner* — Kevin Kai Hill
(74) *Attorney, Agent, or Firm* — Scully, Scott, Murphy & Presser, P.C.; Brian A. Cocca

(57) ABSTRACT

Genetically modified rodents such as mice and rats, and methods and compositions for making and using the same, are provided. The rodents comprise a humanization of at least one endogenous rodent Tmprss gene, such as an endogenous rodent Tmprss2, Tmprss4, or Tmprss11d gene.

22 Claims, 16 Drawing Sheets

Specification includes a Sequence Listing.

(56) References Cited

OTHER PUBLICATIONS

Böttcher-Friebertshäuser E. et al., "Cleavage of Influenza Virus Hemagglutinin by Airway Proteases TMPRSS2 and HAT Differs in Subcellular Localization and Susceptibility to Protease Inhibitors", Journal of Virology 84(11):5605-5614 (Jun. 2010).
Devoy A. et al., "Genomically Humanized Mice: Technologies and Promises", Nature Reviews Genetics 13(1):14-20 (Jan. 2012).
Kühn N., "Studies on the Host Response to Influenza A Virus Infections in Mouse Knock-Out Mutants", Thesis—University of Veterinary Medicine Hannover pp. 1-74 (2015).
MacDonald L.E. et al., "Precise and in Situ Genetic Humanization of 6 Mb of Mouse Immunoglobulin Genes", PNAS 111(14):5147-5152 (Apr. 8, 2014).
Murphy A.J. et al., "Mice With Megabase Humanization of Their Immunoglobulin Genes Generate Antibodies as Efficiently as Normal Mice", PNAS 111(14):5153-5158 (Apr. 8, 2014).
Radigan K.A. et al., "Modeling Human Influenza Infection in the Laboratory", Infection and Drug Resistance 8:311-320 (2015).
Rajagowthamee R. et al., "Animal Models for Influenza Virus Pathogenesis, Transmission, and Immunology", Journal of Immunological Methods 410:60-79 (2014).
Sun Y., "Characterization of the TMPRSS2 Protease as a Modulator of Prostate Cancer Metastasis", Defense Technical Information Center, pp. 1-12 (Mar. 2009).
International Search Report and Written Opinion dated Jun. 19, 2017 received in International Application No. PCT/US2017/019574.
Anderson P., "Post-Transcriptional Control of Cytokine Production", Nature Immunology 9(4):353-359 (Apr. 2008).
Bahgat M.M. et al., "Inhibition of Lung Serine Proteases in Mice: A Potentially New Approach to Control Influenza Infection", Virology Journal 8:27 (15 pagers) (2011).
Bertram S. et al., "TMPRSS2 and TMPRSS4 Facilitate Trypsin-Independent Spread of Influenza Virus in Caco-2 Cells", Journal of Virology 84(19):10016-10025 (Oct. 2010).
Böttcher-Friebertshäuser E. et al., "Inhibition of Influenza Virus Infection in Human Airway Cell Cultures by an Antisense Peptide-Conjugated Morpholino Oligomer Targeting the Hemagglutinin-Activating Protease TMPRSS2", Journal of Virology 85(4):1554-1562 (Feb. 2011).
Böttcher E. et al., "MDCK Cells that Express Proteases TMPRSS2 and HAT Provide a Cell System to Propagate Influenza Viruses in the Absence of Trypsin and to Study Cleavage of HA and its Inhibition", Vaccine 27:6324-6329 (2009).
Böttcher E. et al., "Proteolytic Activation of Influenza Viruses by Serine Proteases TMPRSS2 and HAT from Human Airway Epithelium", Journal of Virology 80(19):9896-9898 (Oct. 2006).
Bugge T.H. et al., "Type II Transmembrane Serine Proteases", The Journal of Biological Chemistry 284(35):23177-23181 and Supplementary Tables (Aug. 28, 2009).
Guipponi M. et al., "The Transmembrane Serine Protease (TMPRSS3) Mutated in Deafness DFNB8/10 Activates the Epithelial Sodium Channel (ENaC) In Vitro", Human Molecular Genetics 11(23):2829-2836 (2002).
Hooper J.D. et al., "Type II Transmembrance Serine Proteases", The Journal of Biological Chemistry 276 (2):857-860 (Jan. 12, 2001).
Rongvaux A. et al., "Human Thrombopoietin Knockin Mice Efficiently Support Human Hematopoiesis In Vivo", PNAS 108(6):2378-2383 (Feb. 8, 2011).
Szabo R. et al., "Type II Transmembrane Serine Proteases in Development and Disease", The International Journal of Biochemistry & Cell Biology 40:1297-1316 (2008).
Tong C. et al., "Generating Gene Knockout Rats by Homologous Recombination in Embryonic Stem Cells", Nature Protocols 6(6):827-844 (Jun. 2011).
Tong C. et al., "Production of p53 Gene Knockout Rats by Homologous Recombination in Embryonic Stem Cells", Nature 467:211-215 (Sep. 2010).
Valenzuela D.M. et al., "High-Throughput Engineering of the Mouse Genome Coupled With High-Resolution Expression Analysis", Nature Biotechnology 21(6):652-659 (Jun. 2003).
Vuagniaux G. et al., "Synergistic Activation of ENaC by Three Membrane-Bound Channel-Activating Serine Proteases (mCAP1, mCAP2, and mCAP3) and Serum- and Glucocorticoid-Regulated Kinase (Sgk1) in Xenopus Oocytes", J. Gen. Physiol. 120:191-201 (Aug. 2002).
Willinger T. et al., "Human IL-3/GM-CSF Knock-in Mice Support Human Alveolar Macrophage Development and Human Immune Responses in the Lung", PNAS 108(6):2390-2395 (Feb. 8, 2011).
Willinger T. et al., Improving Human Hemato-Lymphoid-System Mice by Cytokine Knock-in Gene Replacement, Trends in Immunology 32(7):321-327 (Jul. 2011).
GenBank NCBI Reference Sequence No. NM_005656.3 (5 pages) (Apr. 30, 2017).
GenBank NCBI Reference Sequence No. NM_015775.2 (5 pages) (Apr. 25, 2017).
GenBank NCBI Reference Sequence No. NM_145403.2 (4 pages) (Sep. 4, 2016).
GenBank NCBI Reference Sequence No. NM_001173551.1 (5 pages) (Apr. 17, 2017).
GenBank NCBI Reference Sequence No. NM_004262.2 (4 pages) (Sep. 9, 2016).
GenBank NCBI Reference Sequence No. NM_145561.2 (3 pages) (Feb. 15, 2015).

* cited by examiner

Tmprss2 protein alignment

```
                        10        20        30        40        50        60
hTMPRSS2           MALNSGSPPAIGPYYENHGYQPENPYPAQPTVVPTVYEVHPAQYYPSPVPQYAPRVLTQA
mTmpriss2          MALNSGSPPGIGPCYENHGYQSEHICPPRPPVAPNGYNLYPAQYYPSPVPQYAPRITTQA
7010 mutant pro    MALNSGSPPGIGPCYENHGYQSEHICPFRPPVAPNGYNLYPAQYYPSPVPQYAPRITTQA
                   ********* ** **********  *  * ** * *************** *****

70        80        90       100       110       120
hTMPRSS2           SNPVVCTQPKSPSGTVCTSKTKKALCITLTLGTFLVGAALAAGLLWKFMGSKCSNSGIEQ
mTmpriss2          STSVIHTHPKS-SGALCTSKSKKSLCLALALGTVLTGAAVAAVLLWRFWDSNCSTSEMEQ
7010 mutant pro    STSVIHTHPKS-SGALCTSKSKKSLCLALALGTVLTGAAVAAVLLWKFMGSKCSNSGIEQ
                   * *   * **  **  ****  *  * * ***.**** ***.***:*   .*   :*

130       140       150       160       170       180
hTMPRSS2           DSSGTCINPSNWCDGVSHCPGGEDENRCVRLYGPNFILQVYSSQRKSWHPVCQDDWNENY
mTmpriss2          GSSGTCISSSIWCDGVAHCPNGEDENRCVRLYGQSFILQVYSSQRKAWYPVCQDDWSESY
7010 mutant pro    DSSGTCINPSNWCDGVSHCPGGEDENRCVRLYGPNFILQVYSSQRKSWHPVCQDDWNENY
                    ****** . ****** ***.*********** .************* * *******. *

190       200       210       220       230       240
hTMPRSS2           GRAACRDMGYKNNFYSSQGIVDDSGSTSFMKLNTSAGNVDIYKKLYHSDACSSKAVVSLR
mTmpriss2          GRAACKDMGYKNNFYSSQGIPDQSGATSFMKLNVSSGNVDLYKKLYHSDCSSRMVVSLR
7010 mutant pro    GRAACRDMGYKNNFYSSQGIVDDSGSTSFMKLNTSAGNVDIYKKLYHSDACSSKAVVSLR
                   *****.************** *.**.*******.*:****:******** **: ****

250       260       270       280       290       300
hTMPRSS2           CHACGVNLNSSRQSRIVGGESALPGAWPWQVSLHVQNVHVCGGSIITPEWIVTAAHCVEK
mTmpriss2          CIECGVRS-VKRQSRIVGGLNASPGDWPWQVSLHVQGVHVCGGSIITPEWIVTAAHCVEE
7010 mutant pro    CHACGVNLNSSRQSRIVGGESALPGAWPWQVSLHVQNVHVCGGSIITPEWIVTAAHCVEK
                   * ***  .  :********  :.**.**********.**********************
```

Figure 1D

Tmprss2 protein alignment

```
                    310        320        330        340        350        360
hTMPRSS2         PLNNPWHWTAFAGILRQSFMFYGAGYQVEKVISHPNYDSKTKNNDIALMKLQKPLTFNDL
mTmprss2         PLSSPRYWTAFAGILRQSLMFYGSRHQVEKVISHPNYDSKTKNNDIALMKLQTPLAFNDL
7010 mutant pro  PLNNPWHWTAFAGILRQSFMFYGAGYQVEKVISHPNYDSKTKNNDIALMKLQKPLTFNDL
                 ***:**:*********:****: ****:********************** ** ****

370        380        390        400        410        420
hTMPRSS2         VKPVCLPNPGMMLQPEQLCWISGWGATEEKGKTSEVLNAAKVLLIETQRCNSRYVYDNLI
mTmprss2         VKPVCLPNPGMMLDLDQECWISGWGATYEKGKTSDVLNAAMVPLIEPSKCNSKYIYNNLI
7010 mutant pro  VKPVCLPNPGMMLQPEQLCWISGWGATEEKGKTSEVLNAAKVLLIETQRCNSRYVYDNLI
                 *************: : :*********  ******:****:* ***  :***:*:*:***

430        440        450        460        470        480
hTMPRSS2         TPAMICAGFLQGNVDSCQGDSGGPLVTSKNNIWWLIGDTSWGSGCAKAYRPGVYGNVMVF
mTmprss2         TPAMICAGFLQGSVDSCQGDSGGPLVTLKNGIWWLIGDTSWGSGCAKALRPGVYGNVTVF
7010 mutant pro  TPAMICAGFLQGNVDSCQGDSGGPLVTSKNNIWWLIGDTSWGSGCAKAYRPGVYGNVMVF
                 ************.************** **.**************** ********:**

490
hTMPRSS2         TDWIYRQMRADG
mTmprss2         TDWIYQQMRANS
7010 mutant pro  TDWIYRQMRADG
                 *****:****:.
``` solid line: TM
solid box: LDLRa
dotted box: SRCR domain
dotted line: peptidase S1

Figure 1D (Continued)

Tmprss4 protein alignment

```
                     10         20         30         40         50         60
hTMPRSS4        MLQDPDSDQPLNSLDVKPLRKPRIPMETFRKVGIPIIIALLSLASIIVVLIKVILDKY
mTmprss4        MESDSGQPLNNRDIVPFRKPRRPQETFKKVGIPIIAVLLSLIIAVLIVALLIKVILDKY
7224 mutant pro MESDSGQPLNNRDIVPFRKPRRPQETFKKVGIPIIAVLLSLIIALVIVALLIKVILDKY
                 *  ** ****  ** ***** * *** ** **** **  * *  * **  ******

70         80         90        100        110        120
hTMPRSS4        VFLCGQPLHFIPRKQLCDGELDCPLGEDEEHCVKSFPEGPAVAVRLSKDRSTLQVLDSAI
mTmprss4        IFICGSPLTFIQRGQLCDGHLDCASGEDEEHCVKDFPEKPGVAVRLSKDRSTLQVLDAAI
7224 mutant pro VFLCGQPLHFIPRKQLCDGELDCPLGEDEEHCVKSFPEGPAVAVRLSKDRSTLQVLDSAI
                 * **.** **.*.***** ***. ********. *** ***************. *

130        140        150        160        170        180
hTMPRSS4        GNWFSACFDNFTEALAETACRQMGYSSKPTFRAVEIGPDQDLDVVEITENSQELRMRNSS
mTmprss4        GTWASVCFDNFTEALAKTACRQMGYDSQPAFRAVEIRPDQNLPVAQVTGNSQELQVQNGS
7224 mutant pro GNWFSACFDNFTEALAETACRQMGYSSKPTFRAVEIGPDQDLDVVEITENSQELRMRNSS
                * *.* ********** ******** *.* ******.***.*. * . ****.. *.*

190        200        210        220        230        240
hTMPRSS4        GPCLSGSLVSLHCLACGKSLKTPRVVGGEEASVDSWMPWQVSIQYDKQHVCGGSILDPHWV
mTmprss4        RSCLSGSIVSLRCLDCGKSLKTPHVVGGVEAPVDSWMPWQVSIQYNKQHVCGGSILDPHWI
7224 mutant pro GPCLSGSLVSLHCLACGKSLKTPRVVGGVEEASVDSWMPWQVSIQYDKQHVCGGSILDPHWV
                 .*****.***.** ******** ****.* ..*********.************

250        260        270        280        290        300
hTMPRSS4        LTAAHCFRKHTDVFNWKVRAGSDKLGSFPSLAVAKIIIEFNPMYPKDNDIALMKLQFPL
mTmprss4        LTAAHCFRKYLDVSSWKVRAGSNILGNSPLPVAKIFIAEPNPLYPKEKDIALVKLQMPL
7224 mutant pro LTAAHCFRKHTDVFNWKVRAGSDKLGSFPSLAVAKIIIEFNPMYPKDNDIALMKLQFPL
                ********.  ** .******.. *. * * ***.* * ** ***. ****.***.**
```

Figure 2D

Tmprss11d protein alignment

```
                       10         20         30         40         50         60
hTMPRSS11D    MYRPARVTSTSRFLNPYVVCFIVVAGVVILAVTIALLVYFLAFD KSYFYRSSFQLLNVE
mTmprss11d    MYRPRPMLSPSRFFTPFAVAFVVIITVGLLAMMAGLLIHFLAFD KAYFYHSSFQILNVE
7226 mutant pro MYRPRPMLSPSRFFTPFAVAFVVIITVGLLAMMAGLLIHFLAFD KSYFYRSSFQLLNVE
              ****  :: :** :.*:.**** ****..* **: **:****** *::**:**** ****

70         80         90        100        110        120
hTMPRSS11D    YNSQLNSPATQEYRTLSGRIESLITKTFKESNLRNQFIRAHVAKLRQDGSGVRADVVMK
mTmprss11d    YTEALNSPATHEYRTLSERIEAMITDEFRGSSLKSEFIRTHVVKLRKEGTGVADVVMK
7226 mutant pro YNSQLNSPATQEYRTLSGRIESLITKTFKESNLRNQFIRAHVAKLRQDGSGVRADVVMK
              *.  ******:****** ***::**.:*: *.*:.:***::*.***::*:**:****

130        140        150        160        170        180
hTMPRSS11D    QFTRNNNGASMKSRIESVLRQMLNNSGNLEINPSTEITSLTDQ AAANWLINECGAGPDLI
mTmprss11d    RSSKRNNKKVMKTRIQSVLRR-LSSSGNLEIAPSNEITSLTDQ DTENVLTQECGARPDLI
7226 mutant pro QFTRNNNGASMKSRIESVLRQMLNNSGNLEINPSTEITSLTDQ AAANWLINECGAGPDLI
              :::**:..**.:**:***: *..********.** *******  .: ** :**** ****

190        200        210        220        230        240
hTMPRSS11D    TLSEQRILGGTEAEEGSWPWQVSLRLNNAAHHCGGSLINNMWILTAAHCFRSNSNPRDWIA
mTmprss11d    TLSEERIIGGMQAEPGDWPWQVSLQLNNVVHHCGGALISNMWVLTAAHCFKSYPNPQYWTA
7226 mutant pro TLSEQRILGGTEAEEGSWPWQVSLRLNNAAHHCGGSLINNMWILTAAHCFRSNSNPRDWIA
              ****:**:**  ** *.*******:***..*****:** ***:******:* .**: *:*

250        260        270        280        290        300
hTMPRSS11D    TSGISTTFPKLRMRVRNILIHNNYKSATHENDIALVRLENSVTFTKDIHSVCLPAATQNI
mTmprss11d    TFGVSTMSPRLRVRVRAILAHDGYSSVTRDNDIAVVQLDRSVAFSRNIHRVCLPAATQNI
7226 mutant pro TSGISTTFPKLRMRVRNILIHNNYKSATHENDIALVRLENSVTFTKDIHSVCLPAATQNI
              * *:** . :**:*** **::: **:.*:****:*:*: **:*::::** *********
```

Figure 3D

Tmprss11d protein alignment

```
                        310        320        330        340        350        360
hTMPRSS11D       PPGSTAYVTGWGAQEYAGHTVPELRQGQVRIISNDVCNAPHSYNGAILSGMLCAGVPQGG
mTmprss11d       IPGSVAYVTGWGSLTYGGNAVTNLRQGEVRIISSEECNTPAGYSGSVLPGMLCAGMRSGA
7226 mutant pro  PPGSTAYVTGWGAQEYAGHTVPELRQGQVRIISNDVCNAPHSYNGAILSGMLCAGVPQGG
                  **.*:*******.: **.**.***:**:**.:*   *..*:*.****:****:.*.:

370        380        390        400        410
hTMPRSS11D       VDACQGDSGGPLVQEDSRRLWFIVGIVSWGDQCGLPDKPGVYTRVTAYLDWIRQQTGI
mTmprss11d       VDACQGDSGGPLVQEDSRRLWFVVGIVSWGYQCGLPNKPGVYTRVTAYRNWIRQQTGI
7226 mutant pro  VDACQGDSGGPLVQEDSRRLWFIVGIVSWGDQCGLPDKPGVYTRVTAYLDWIRQQTGI
                 **********************:*******.*****:***********  *******
``` solid line: TM
solid box: SEA domain
dotted line: peptidase S1

Figure 3D (Continued)

SEQUENCE LISTING

<160> NUMBER OF SEQ ID NOS: 72

<210> SEQ ID NO 1
<211> LENGTH: 3175
<212> TYPE: DNA
<213> ORGANISM: Mus musculus

<400> SEQUENCE: 1

```
gcctttcctg gccgttccct ccttctggcc gaggtgcctg cgtttagggg tgtcaccctg      60
gctcccggga cgccgcctcc ggagatttaa gcgagaactg gagtaggtcg tgtacttgga     120
gcggacgagg aagccaagag ctcggacaga ggcggagagg ggcgggaagc gcaacaggtc     180
acctggagga agccccatac tgacctcctc atgctgctga cacaggcagg atggcattga     240
actcagggtc acctccagga atcggacctt gctatgagaa ccacgggtat cagtctgagc     300
acatctgtcc tccgagacca ccagtggctc ccaatggcta caacttgtat ccagcccagt     360
actacccatc tccagtgcct cagtatgctc cgaggattac aacgcaagcc tcaacatctg     420
```

```
tcatccacac acatcccaag tcctcaggag cactgtgcac ctcaaagtct aagaaatcgc      480
tgtgtttagc cctcgccctg ggcactgtcc tcacgggagc tgctgtggct gctgtcttgc      540
tttggaggtt ctgggacagc aactgttcta cgtctgagat ggagtgtggg tcttcaggca      600
catgcatcag ctcttctctc tggtgtgacg gggtagcaca ttgtcccaac ggagaagatg      660
agaaccgttg tgttcgtctc tacggacaaa gcttcatcct ccaggtttac tcatctcaga      720
ggaaagcctg gtatcccgtg tgccaggatg attggagtga gagctacggg agagcagcat      780
gtaaagacat gggatacaag aacaattttt attctagcca agggatacca gaccagagcg      840
gggcaacagc cttatgaagc tgaatgtgag gctcaggcac cgttgacctc tataaaaaac      900
tctaccacag tgactcatgt tcatcccgca tggtggtttc tttgcgctgt atagaatgcg      960
gggttcgctc agtgaaacgc agagcagga ttgtgggtgg attgaatgcc tcaccaggag     1020
actggccctg gcaggtcagc ctgcacgtcc aaggcgtcca cgtctgcgga ggctccatca     1080 tcaccccga gtggattgtg acggccgccc actgtgtgga agaaccccctc agcagcccga     1140 ggtactggac ggcatttgcg ggaattctga gacagtctct catgttctat ggaagtagac     1200
accaggtaga aaaagtaatt tcccatccaa attacgactc taagaccaag aataacgaca     1260
ttgctctcat gaagctgcag acacctttgg cttttaatga tctagtgaag ccagtgtgtc     1320
tgccgaaccc aggcatgatg ctagacctag accaggaatg ctggatttcg ggtgggggg      1380 ccacctatga gaaagggaag acctcggacg tgttgaatgc tgccatggta cccttgatcg     1440
agccctccaa atgtaatagt aaatacatat acaacaacct aatcacacca gccatgatct     1500
gtgccggctt cctccagggg tctgtcgact cttgccaggg agacagtgga gggccgctgg     1560
ttactttgaa gaatgggatc tggtggctga ttggggacac gagctggggc tcgggctgtg     1620
ccaaggcact cagacctgga gtatacggga acgtgacggt atttacagat tggatctacc     1680
agcaaatgag ggcgaacagc taatccacgt ggctttgtcc cagacttcct ttgtcttcaa     1740
caaccttctg caagaaaacc aagggcctga atttaactt cctgtgcaca atgtaccttt     1800
tgagatgatt cgaagggcct ttcactttta ttaaacagtg acttgtttga ctgtgctccc     1860
tggtcctgtg agggcttcag tgccccaccc ctgggccact ctgcagctc ccaccagaat      1920 ggatgaccag attctgttgg gtttgggcac atagggccaa aggcagagga gggtggcact     1980
ctcatgttgg aacttctttt gggctcatgc tcaggccttt tttggatcac taaggactat     2040
gacctctgag taacctgatg acctgagaaa gagtaaggag gccaggcagg gccttgggcc     2100
caggaacagg taccttgaga gtgagagcta cccattgcct gtggcctaaa tctgctgtgc     2160
aggttgggct ggtcatactg tcatgatttc attaacagcc tgggtgaaca tggctgggag     2220
taaagggctt gctctcctgc atgttgacat gacggccctt tccaagggtg atggaggctt     2280
tcccaagcta agggcctagg cagatctctc agagcaagaa gctaatgccg gcatgtccct     2340
tgggtgagct ctacatggtg ttattcagtc tggttcttgg ctccccacta ctgtttctct     2400
cagcctctca gagcctgaaa cttacctctt agctttggct acaggcatgg cctagtacct     2460
gatggagcct gtatagctca gctaatcaaa tggaggctca ggtccatcag aatcagggac     2520
ttgtgatttc agtcaccttg cttctgggtt gtgtttcttc tcttactacc tcactgcacc     2580
tggacactag agtggatgaa tgtctggagt tcacctgcat ttggactgtg tgattgtgcc     2640
tcagacacta gacctcttcc agatggttag gttgttctgt agactggcaa tgagattaga     2700
agttcctagc ttcagataaa gatgaaagag aggagatcat tgtcttctgt cttcttctgg     2760
```

```
                                            -continued ccctgggttt ataccaggaa agccatgcca gaattaccaa atatgaagta tgaatgtctt    2820
acccacggtg aggctctgcc tccttctctc tgcctggttc ttcagaaggc agtgaatggg    2880
tcataactgg gactccatct tgctgggga aagtctccca cctagggaat ggttaccact     2940
ccatgtaaag aaaactccct catgcgtcct ctgggacctt cttagatgct gtaaggtacc    3000
tacatacaga ctaaatgtgc aagcaccttg aagtgtgaga acctgtcccc tccttagctc    3060
tccttgtctt tgctgttggt tggttatttc ctgctttgtg tctgttctga gctgtgagat    3120
tccactgtga aatatatgaa taaagtatat aattctttta aaaaaaaaaa aaaaa         3175

<210> SEQ ID NO 2
<211> LENGTH: 490
<212> TYPE: PRT
<213> ORGANISM: Mus musculus

<400> SEQUENCE: 2

Met Ala Leu Asn Ser Gly Ser Pro Gly Ile Gly Pro Cys Tyr Glu
1               5                   10                  15

Asn His Gly Tyr Gln Ser Glu His Ile Cys Pro Arg Pro Pro Val
                20                  25                  30

Ala Pro Asn Gly Tyr Asn Leu Tyr Pro Ala Gln Tyr Tyr Pro Ser Pro
            35                  40                      45

Val Pro Gln Tyr Ala Pro Arg Ile Thr Thr Gln Ala Ser Thr Ser Val
50                  55                      60

Ile His Thr His Pro Lys Ser Ser Gly Ala Leu Cys Thr Ser Lys Ser
65                  70                  75                  80

Lys Lys Ser Leu Cys Leu Ala Leu Ala Leu Gly Thr Val Leu Thr Gly
                85                  90                  95

Ala Ala Val Ala Ala Val Leu Leu Trp Arg Phe Trp Asp Ser Asn Cys
            100                 105                 110

Ser Thr Ser Glu Met Glu Cys Gly Ser Ser Gly Thr Cys Ile Ser Ser
        115                 120                 125

Ser Leu Trp Cys Asp Gly Val Ala His Cys Pro Asn Gly Glu Asp Glu
130                 135                 140

Asn Arg Cys Val Arg Leu Tyr Gly Gln Ser Phe Ile Leu Gln Val Tyr
145                 150                 155                 160

Ser Ser Gln Arg Lys Ala Trp Tyr Pro Val Cys Gln Asp Asp Trp Ser
                165                 170                 175

Glu Ser Tyr Gly Arg Ala Ala Cys Lys Asp Met Gly Tyr Lys Asn Asn
            180                 185                 190

Phe Tyr Ser Ser Gln Gly Ile Pro Asp Gln Ser Gly Ala Thr Ser Phe
        195                 200                 205

Met Lys Leu Asn Val Ser Ser Gly Asn Val Asp Leu Tyr Lys Lys Leu
210                 215                 220

Tyr His Ser Asp Ser Cys Ser Ser Arg Met Val Val Ser Leu Arg Cys
225                 230                 235                 240

Ile Glu Cys Gly Val Arg Ser Val Lys Arg Gln Ser Arg Ile Val Gly
                245                 250                 255

Gly Leu Asn Ala Ser Pro Gly Asp Trp Pro Trp Gln Val Ser Leu His
            260                 265                 270

Val Gln Gly Val His Val Cys Gly Gly Ser Ile Ile Thr Pro Glu Trp
        275                 280                 285

Ile Val Thr Ala Ala His Cys Val Glu Glu Pro Leu Ser Ser Pro Arg
290                 295                 300
```

```
Tyr Trp Thr Ala Phe Ala Gly Ile Leu Arg Gln Ser Leu Met Phe Tyr
305                 310                 315                 320

Gly Ser Arg His Gln Val Glu Lys Val Ile Ser His Pro Asn Tyr Asp
            325                 330                 335

Ser Lys Thr Lys Asn Asn Asp Ile Ala Leu Met Lys Leu Gln Thr Pro
            340                 345                 350

Leu Ala Phe Asn Asp Leu Val Lys Pro Val Cys Leu Pro Asn Pro Gly
            355                 360                 365

Met Met Leu Asp Leu Asp Gln Glu Cys Trp Ile Ser Gly Trp Gly Ala
            370                 375                 380

Thr Tyr Glu Lys Gly Lys Thr Ser Asp Val Leu Asn Ala Ala Met Val
385                 390                 395                 400

Pro Leu Ile Glu Pro Ser Lys Cys Asn Ser Lys Tyr Ile Tyr Asn Asn
                405                 410                 415

Leu Ile Thr Pro Ala Met Ile Cys Ala Gly Phe Leu Gln Gly Ser Val
            420                 425                 430

Asp Ser Cys Gln Gly Asp Ser Gly Gly Pro Leu Val Thr Leu Lys Asn
            435                 440                 445

Gly Ile Trp Trp Leu Ile Gly Asp Thr Ser Trp Gly Ser Gly Cys Ala
450                 455                 460

Lys Ala Leu Arg Pro Gly Val Tyr Gly Asn Val Thr Val Phe Thr Asp
465                 470                 475                 480

Trp Ile Tyr Gln Gln Met Arg Ala Asn Ser
                485                 490

<210> SEQ ID NO 3
<211> LENGTH: 3212
<212> TYPE: DNA
<213> ORGANISM: Homo sapiens

<400> SEQUENCE: 3
gagtaggcgc gagctaagca ggaggcggag gcggaggcgg agggcgaggg gcggggagcg      60
ccgcctggag cgcggcaggt catattgaac attccagata cctatcatta ctcgatgctg     120
ttgataacag caagatggct ttgaactcag ggtcaccacc agctattgga ccttactatg     180
aaaaccatgg ataccaaccg gaaaacccct atcccgcaca gcccactgtg gtccccactg     240
tctacgaggt gcatccggct cagtactacc gtcccccgt gccccagtac gccccgaggg      300
tcctgacgca ggcttccaac cccgtcgtct gcacgcagcc caaatcccca tccgggacag     360
tgtgcacctc aaagactaag aaagcactgt gcatcacctt gacctggggg accttcctcg     420
tgggagctgc gctggccgct ggcctactct ggaagttcat gggcagcaag tgctccaact     480
ctgggataga gtgcgactcc tcaggtacct gcatcaaccc ctctaactgg tgtgatggcg     540
tgtcacactg ccccggcggg gaggacgaga tcggtgtgt tcgcctctac ggaccaaact     600
tcatccttca ggtgtactca tctcagagga agtcctggca cctgtgtgc caagacgact      660 ggaacgagaa ctacgggcgg gcggcctgca gggacatggg ctataagaat aatttttact     720
ctagccaagg aatagtggat gacagcggat ccaccagctt tatgaaactg aacacaagtg     780
ccggcaatgt cgatatctat aaaaaactgt accacagtga tgcctgttct tcaaaagcag     840
tggtttcttt acgctgtata gcctgcgggg tcaacttgaa ctcaagccgc agagcagga      900 ttgtgggcgg cgagagcgcg ctcccggggg cctggccctg gcaggtcagc ctgcacgtcc     960
agaacgtcca cgtgtgcgga ggctccatca tcacccccga gtggatcgtg acagccgccc    1020
actgcgtgga aaaacctctt aacaatccat ggcattggac ggcatttgcg gggatttttga   1080
```

```
gacaatctttt catgttctat ggagccggat accaagtaga aaaagtgatt tctcatccaa    1140
attatgactc caagaccaag aacaatgaca ttgcgctgat gaagctgcag aagcctctga    1200
ctttcaacga cctagtgaaa ccagtgtgtc tgcccaaccc aggcatgatg ctgcagccag    1260
aacagctctg ctggatttcc gggtgggggg ccaccgagga gaaagggaag acctcagaag    1320
tgctgaacgc tgccaaggtg cttctcattg agacacagag atgcaacagc agatatgtct    1380
atgcaaccct gatcacacca gccatgatct gtgccggctt cctgcagggg aacgtcgatt    1440
cttgccaggg tgacagtgga gggcctctgg tcacttcgaa gaacaatatc tggtggctga    1500
taggggatac aagctggggt tctggctgtg ccaaagctta cagaccagga gtgtacggga    1560
atgtgatggt attcacggac tggatttatc gacaaatgag ggcagacggc taatccacat    1620
ggtcttcgtc cttgacgtcg ttttacaaga aaacaatggg gctggttttg cttcccgtg    1680 catgatttac tcttagagat gattcagagg tcacttcatt tttattaaac agtgaacttg    1740
tctggctttg gcactctctg ccattctgtg caggctgcag tggctcccct gcccagcctg    1800
ctctccctaa ccccttgtcc gcaaggggtg atggccggct ggttgtgggc actggcggtc    1860
aagtgtggag gagaggggtg gaggctgccc cattgagatc ttcctgctga gtcctttcca    1920
ggggccaatt ttggatgagc atggagctgt cacctctcag ctgctggatg acttgagatg    1980
aaaaaggaga gacatggaaa gggagacagc caggtgcac ctgcagcggc tgccctctgg    2040
ggccacttgg tagtgtcccc agcctacctc tccacaaggg gattttgctg atgggttctt    2100
agagccttag cagccctgga tggtggccag aaataaaggg accagccctt catgggtggt    2160
gacgtggtag tcacttgtaa ggggaacaga aacattttg ttcttatggg gtgagaatat    2220
agacagtgcc cttggtgcga gggaagcaat tgaaaaggaa cttgccctga gcactcctgg    2280
tgcaggtctc cacctgcaca ttgggtgggg ctcctgggag ggagactcag ccttcctcct    2340
catcctccct gaccctgctc ctagcaccct ggagagtgca catgcccctt ggtcctggca    2400
gggcgccaag tctggcacca tgttggcctc ttcaggcctg ctagtcactg gaaattgagg    2460
tccatggggg aaatcaagga tgctcagttt aaggtacact gtttccatgt tatgtttcta    2520
cacattgcta cctcagtgct cctggaaact tagcttttga tgtctccaag tagtccacct    2580
tcatttaact ctttgaaact gtatcatctt tgccaagtaa gagtggtggc ctatttcagc    2640
tgctttgaca aaatgactgg ctcctgactt aacgttctat aaatgaatgt gctgaagcaa    2700
agtgcccatg gtggcggcga agaagagaaa gatgtgtttt gttttggact ctctgtggtc    2760
ccttccaatg ctgtgggttt ccaaccaggg gaagggtccc ttttgcattg ccaagtgcca    2820
taaccatgag cactactcta ccatggttct gcctcctggc caagcaggct ggtttgcaag    2880
aatgaaatga atgattctac agctaggact taaccttgaa atggaaagtc atgcaatccc    2940
atttgcagga tctgtctgtg cacatgcctc tgtagagagc agcattccca gggaccttgg    3000
aaacagttgg cactgtaagg tgcttgctcc ccaagcacaa tcctaaaagg tgttgtaatg    3060
gtgaaaacgt cttccttctt tattgcccct tcttatttat gtgaacaact gtttgtctt    3120 ttttgtatct tttttaaact gtaaagttca attgtgaaaa tgaatatcat gcaaataaat    3180
tatgcaattt ttttttcaaa gtaaaaaaaa aa                                 3212
```

<210> SEQ ID NO 4
<211> LENGTH: 492
<212> TYPE: PRT
<213> ORGANISM: Homo sapiens -continued

<400> SEQUENCE: 4

```
Met Ala Leu Asn Ser Gly Ser Pro Pro Ala Ile Gly Pro Tyr Tyr Glu
1               5                   10                  15

Asn His Gly Tyr Gln Pro Glu Asn Pro Tyr Pro Ala Gln Pro Thr Val
            20                  25                  30

Val Pro Thr Val Tyr Glu Val His Pro Ala Gln Tyr Tyr Pro Ser Pro
        35                  40                  45

Val Pro Gln Tyr Ala Pro Arg Val Leu Thr Gln Ala Ser Asn Pro Val
    50                  55                  60

Val Cys Thr Gln Pro Lys Ser Pro Ser Gly Thr Val Cys Thr Ser Lys
65                  70                  75                  80

Thr Lys Lys Ala Leu Cys Ile Thr Leu Thr Leu Gly Thr Phe Leu Val
                85                  90                  95

Gly Ala Ala Leu Ala Ala Gly Leu Leu Trp Lys Phe Met Gly Ser Lys
            100                 105                 110

Cys Ser Asn Ser Gly Ile Glu Cys Asp Ser Ser Gly Thr Cys Ile Asn
        115                 120                 125

Pro Ser Asn Trp Cys Asp Gly Val Ser His Cys Pro Gly Gly Glu Asp
    130                 135                 140

Glu Asn Arg Cys Val Arg Leu Tyr Gly Pro Asn Phe Ile Leu Gln Val
145                 150                 155                 160

Tyr Ser Ser Gln Arg Lys Ser Trp His Pro Val Cys Gln Asp Asp Trp
                165                 170                 175

Asn Glu Asn Tyr Gly Arg Ala Ala Cys Arg Asp Met Gly Tyr Lys Asn
            180                 185                 190

Asn Phe Tyr Ser Ser Gln Gly Ile Val Asp Asp Ser Gly Ser Thr Ser
        195                 200                 205

Phe Met Lys Leu Asn Thr Ser Ala Gly Asn Val Asp Ile Tyr Lys Lys
    210                 215                 220

Leu Tyr His Ser Asp Ala Cys Ser Ser Lys Ala Val Val Ser Leu Arg
225                 230                 235                 240

Cys Ile Ala Cys Gly Val Asn Leu Asn Ser Ser Arg Gln Ser Arg Ile
                245                 250                 255

Val Gly Gly Glu Ser Ala Leu Pro Gly Ala Trp Pro Trp Gln Val Ser
            260                 265                 270

Leu His Val Gln Asn Val His Val Cys Gly Gly Ser Ile Ile Thr Pro
        275                 280                 285

Glu Trp Ile Val Thr Ala Ala His Cys Val Glu Lys Pro Leu Asn Asn
    290                 295                 300

Pro Trp His Trp Thr Ala Phe Ala Gly Ile Leu Arg Gln Ser Phe Met
305                 310                 315                 320

Phe Tyr Gly Ala Gly Tyr Gln Val Glu Lys Val Ile Ser His Pro Asn
                325                 330                 335

Tyr Asp Ser Lys Thr Lys Asn Asn Asp Ile Ala Leu Met Lys Leu Gln
            340                 345                 350

Lys Pro Leu Thr Phe Asn Asp Leu Val Lys Pro Val Cys Leu Pro Asn
        355                 360                 365

Pro Gly Met Met Leu Gln Pro Glu Gln Leu Cys Trp Ile Ser Gly Trp
    370                 375                 380

Gly Ala Thr Glu Glu Lys Gly Lys Thr Ser Glu Val Leu Asn Ala Ala
385                 390                 395                 400

Lys Val Leu Leu Ile Glu Thr Gln Arg Cys Asn Ser Arg Tyr Val Tyr
                405                 410                 415
```

Asp Asn Leu Ile Thr Pro Ala Met Ile Cys Ala Gly Phe Leu Gln Gly
                420                 425                 430

Asn Val Asp Ser Cys Gln Gly Asp Ser Gly Gly Pro Leu Val Thr Ser
            435                 440                 445

Lys Asn Asn Ile Trp Trp Leu Ile Gly Asp Thr Ser Trp Gly Ser Gly
        450                 455                 460

Cys Ala Lys Ala Tyr Arg Pro Gly Val Tyr Gly Asn Val Met Val Phe
465                 470                 475                 480

Thr Asp Trp Ile Tyr Arg Gln Met Arg Ala Asp Gly
                485                 490

<210> SEQ ID NO 5
<211> LENGTH: 27947
<212> TYPE: DNA
<213> ORGANISM: Artificial Sequence
<220> FEATURE:
<223> OTHER INFORMATION: Recombinant polynucleotide

<400> SEQUENCE: 5

```
gcagagtcta agaaatcgct gtgtttagcc ctcgccctgg gcactgtcct cacgggagct      60
gctgtggctg ctgtcttgct ttggaagttc agtaagtgca gggagcctcg atcccaccat     120
gtgctcctgc agtccccagt gctctgagcc agaccctgct ctctgggcta ttgagacctc     180
tggaggccct ccgtgaggtt cctctcttac ataacgaggc tgtctctctt cccttctctt     240
gtttagctat gagattgaca catcatgggg aaagcattta gaatgtaccc agtgctttgg     300
ggtgcttggt gccacccagc actgtgagca caggttcttc taccttgggg ccacacccag     360
ttacctgtat ctcactgcac agcagtggct gttggggacc aggcccaccc ctccatgtcc     420
cacctcctgc aactgcagcc tgagccttcc catcagcctg gggtggtgca gacccatgtg     480
ccattgtgga tccttcaagt tacctgtgtg gcagagagga cgtgtgagtg ccgtccaaac     540
ccaaacactg agagggtcct tcccattgcc cccacgaaag taaggtgccc cagtgctaat     600
tccacttata cttgctggtg gcaaggacac ttctcctcct tattaaagtg ggggattggc     660
tgggtgaggt ggctcacgcc tgttatccca gcactttaag aggccaaggc aggtggacca     720
cctgaggtca ggagtttgag accacaagcc tggccaacat gttgaaactc catctctact     780
aaaaatacaa aaattagtca ggcgtggtgg cgtgcacctg taatcccagc tacttaggag     840
gctgggcag gaggatcact tgaacccagg agttggaggt tgcagtgagc caagattgtg      900
cccctgcact ccagcctggg tgacagaatg agacttcatc tcaaaaacaa aacaaaacaa     960
aacacagtgg ggccaggagt tggaggctgc agcgagctac agtaatgcca cggtgttcct    1020
cactccatga ggctcattgc gtttctcagc ctgaagggca cctctcttct gttttctctg    1080
caagtgggca gcaagtgctc caactctggg atagagtgcg actcctcagg tacctgcatc    1140
aacccctcta actggtgtga tggcgtgtca cactgccccg gcggggagga cgagaatcgg    1200
tgtggtgagt cagccttgac cttgggaagg gactcctctg ctcaccttgg agacagcagc    1260
cgggtccagg ggcctttggg tgactgggcc tggcgtgcgt ccagtacgct gacacatgat    1320
gtcattgaat ccctgctcca ggctgagccc tgggctcag agaggttgtg tttccggccc     1380
aacctcaccc agcaggtggg agatgacagg gccaccgagg actgtgtcat ggaaccaca     1440
cgtgctctga actgccacag gaagtcagtt aagatgagca aactgtttat aaagttggag    1500
atgcaggcta ggaacggtgg ctcatgcctg taatcccagc actttgggag gccgaggcag    1560
atggatcacc tgaggtcagg agtttgagac cagcctgacc aatatggtga aaccttatct    1620
```

```
ccactaaaaa tacaaaaatt agccaagcgc ggtggcgggt gcctgtaatt ccagctattc    1680
aggaggctga ggcaggagaa tcacttgaac ctggaggcg gaggttgcag tgagctgaga    1740
tcacgccact gcattccagc ctgggagaca gagctggctc aaaaaataaa ttaattaatt    1800
aaaaacaaaa ttggagatgc actatgttat tttcaaaaca agctgccttt aaagatctat    1860
ctgttgtcac agggtgggct catctgtttc attttatttt ctgtggttta tctatttatt    1920
cattttaatg aactaggaag cattgctcct atttatggca taccacatga tgtttggata    1980
cgtgtatgcc tgtggcatgg ctaagtcaag ctagaacatg ggccttacct catatacgtg    2040
tcttattaag aacacataaa acctactctt gtagtgattt tcaaatatgc aacatatagt    2100
ttattaactg cagtcactat gatgtacaat agattgctcg aacttattcc tcctgtctaa    2160
ctaagatttt gtgaccctctg accaacatct ccccagtgtt gtcaccccccc gccccagcc    2220 tctgatagct gccttctac tctctgcttc tgtgagtttg atgtttatac attccacatg    2280
taagtggcct catgcagtgt ttctgtctct gtgtctggct tgttcactta gcgtaatgtc    2340
ctccagcttc atctatgttg ttggaaatga caggatttcc ttctttcttg tggctgaata    2400
gtattgcctt gtgcatatac accacatttt ctttatccct tcattcactg atggactctt    2460
aggttgatgt catgtcttgg ctgttgtgaa aaatgccgca gtgagcgtgg gcgtgcaggt    2520
ccctcttcaa cacacggatt tccttttctt tggatataaa cccagcagtg agattgctgg    2580
atcacatggc agttctgttt ctcaccttt gaggaaactc catactgttt tccataatgg    2640
ctgtagcaac ttccactccc accccacgg tgcaaagtct ccatttctct tctacaacct    2700
caccaactcc tgttattttc catctttctg atagtagcca tttgaagagg tatgagatga    2760
tacctcattg tggttttcat ttgcattttt atttgtattt ttcatgaatt tttgagggtg    2820
atttcaaggg tagttagtga ctcgaacagg gaaacgatcc tgagtatgag ggttgtgcta    2880
atcatccccc tcctgccagc tgcgtacgga atggggctct gcagatggca gggagctggc    2940
tcgtttctct ttaagagctg cctttactt ttcttcctct tcctttaaaa cttatttcct    3000
ggccggacgc agtggctcat gcctgtaatc ccagcacttt gggaggccga ggtgggcgga    3060
tcacgaggtc aggaattcca gaccagcctg gccaacatgg tgaaaccccg tctctactaa    3120
aaatacaaaa attagccaga cgtggtggtg cgggcctata gtcccagcta ctcgggaggc    3180
tgaggcagga gaatcacttg aacctgggag gaggggttg cagtgagccg agattgcgcc    3240
actgcactcc agcctgggcg acagagccag actccatctc aaaaaacaaa aaaaagttat    3300
ttcccaagca cagccatgta ttccaggctt gtggatcagc gttggtggtg gtgtgtgctc    3360
tcatatctta gttccagcta agcacactct gacatgttta cactagaacc atttgttttt    3420
tctagaaata gaaatttcag aattgtagag tcagaggact taccagaaat ctcttaggta    3480
gttctcctcc cctccctcaa gtgcagtcct aacctcctgg agttttctgt agaaaccaca    3540
agcctcagag ctgccgaga attctagcca aagatttttc catgccaaag taatccccccc    3600 tctcctaagg gccatccttg gtggggactg gtttcctgtt aagccctcgc tgtcagtcct    3660
ggctgtggaa tttcctggtg aggagcactg gcccgtggag ctcggccctc gtgccggcct    3720
tgagcaggcc caagtgttcc gtgttcttga taccttttcct ccagcacagt cttgcttccc    3780
agaaaaaggt ttgcacttga aaatgatgca tttgctgatt aaacatagtt cttttgcttt    3840
atttggtttc taaataaag tgggagtttt tgagattgag taacgtgagg ttaagatagc    3900
acgtggaatg gcttttctt ttctttctat tttttttttt ttttcctgg agacagggtt    3960
```

```
tcactctgtt gcccaggctg gagtgcagag gcatgaccat ggctcactgc aacttcgatg    4020
tcctggggtt aagcgatccc ccagcctcag ccccccaagt ggctgggact acaggtgctc    4080
gccaccacac ctggctaatt tttgtatttt ttgtagaaaa tgggtttcat caatgttgtc    4140
cagactggtc tcgaactcct gacctcaagc aattctcctg cctcagcctc ccagactgct    4200
gggattacag gcgtgaacta ccacgcctgg cctggaatgg cttttgatgt tctcctatgt    4260
gcacatgtgg gtgaataaac accaacaaag tccttatgtt acctgaagag ttgctctctt    4320
cttaatattt aagtcgtatt tatttaaata ctttaatagt tgtacactat taaagtatta    4380
ttaggtcaaa atcaaggaag tacaaaaggg tatgctgtga aaaatctctt cttccttgct    4440
ctgcttactt acctaccccg catccccccca tacaccccag acacacacac acacacacac    4500
acacacacac acacacgcat cactcccata catgcccacc tgtttaccag ccaatcacat    4560
ttcttggggc aactcatctg agttgcttct cttttccagag agttttttgca taaagaagca    4620 caggtatttc tgcgttacca tgaccctatt tcccagtggt tcctagccag ttgactctcc    4680
tgcactggat accatcctgg acagcattcc ttagggaaat gagcccctg ttttttccca    4740 ccatggcaca gttggtcctt tgcatggacg caccattatt gcccctgtct cttcttggtg    4800
gaccttaagg ttttctccat ccttttgctg taacacacac tgctccaagt gtgtgagcat    4860
atcagtagga aacgcttcca ggagtagaac tgctaggtca gagggcgtgt ggatctgtaa    4920
cctgacagac ctagaccggc ttcagtttgg ttttatccag tttccatatt gattattcat    4980
ataaaaggaa acagacaaac ataacgctgt gcatgtattc tctcttagac cagaacaggc    5040 ataggggtgca cttttaattt gtccatttcg tagagtagaa attgttttg ctgaaatgaa    5100 caccttagga tgctgaagaa tatgacccgt cccatggaaa acattcaaaa atgtgtgtag    5160
cgctttcttc ccaagggtgt gtgtgcgcat atttaacac taattcactt tctacttccg    5220
ttgctatcct ttctgtgagt cttttctcaga atctcagaaa agaaactaaa ttgttcactc    5280
tagttatcaa tgctgtactc tatacctgga atttgctaaa agggcagatt ttaagtattc    5340
tcaccacaga aaagagaaaa gaaaatggta attatgtgac gtggtggaca tgttaactag    5400
ctttattatg gtgagcattt cacagcggat atccagtcat cacgctgtac acattaaaca    5460
tgtacaattg ggttttttg agacaaggtc tccttctgtc acccagtctg gagtgcagtg    5520
gctcagtcat ggctcattgc agcctcgacc tcctgggctc aatccatcct tcccctcag    5580 cctcctgaaa agctggggcc acaggcatgt accatcatgc caggctaatg catatatatt    5640
tatatttttt ggtggagatg gggttggtct cgaactctgg gctcaagtga tcctcccgcc    5700
ttgcccttcc aaagtgctga gattacaggc atgaaccaca gcaccaggcc tacatgtaaa    5760 attttattt gtcaactata ctttgacaaa gctgagaaaa aaaatcctaa tatttaaaaa    5820
aaaaaaaaaa aggactagct tgagaccttt tccagctctc tggcttatca gctgccgtct    5880
cttccgggtg cagatagctg gaagggaaag aaaatcccta aaattaccca caagccaaga    5940
atgaagtgtc tcccttgag ccacagtggc agttttgttt taatcatag aagtgtattt    6000 tgagccgggt gtgctggctc acgcctgtaa tccccgcact ttgggaggcc gaggtggggg    6060
gcggaggggg tgggatcgc ctgaggtcag gagttcgaga ccagcctgac caacatggag    6120
aaaccccgtc tctactaaaa atacaaaatt agccggcgtg gtggtgcatg cctgtaatcc    6180
cagctactca tgaggctgag tcaggagaat ctcttgaacc caggaggtgg aggttgcggt    6240
gagctgagat catgccattg cactccagcc tgggaacaag aaaaaaaaag aagaagaaga    6300
agaagtgtat tcatttcagt tacttttaaa aaagtgaaca gactttatat tttagagcgg    6360
```

```
tttaggttt  acagaaaatg  aaacagacag  ggcagcgagc  tccttgtact  cctccccagc   6420
acacagttgc  cctgttatga  acatcccaca  tcagtgctgt  gcgttcatta  acaccgatga   6480
acctgatgca  tacattatga  tgaactgaag  tcctggactt  cacccttttct  cttgtacagt   6540 tctgtgggat  ttgacaaatg  cataatgctg  tacagccaca  atgatagtat  cgtccagagt   6600
agttctcctg  ccttaaaacc  tcttttgctg  cacctgtttc  tctctcccca  ctcacccccag  6660 ctatctgatc  ttcttagtgc  ctccgaagtt  ttggtctttt  caggatgttg  tagcgttgga   6720
atcatggagt  atgtagcctt  caccacatac  accttccttc  actttgttgg  cttcctttac   6780
ttagtaatat  gcattcaagt  ttcctccatg  cctttttcatg  gcttgatagc  tcatttcttt   6840
ttagcaccaa  ataatattcc  gttgtccaga  tgtagcacaa  tgtttatcca  ttcatgtaac   6900
ctgtgaccga  ctcacagata  ggatgtggaa  tcactcacca  cagaggcatt  agacaataat   6960
cagacccaag  tcatttcatg  ggggaacaag  cccacaggta  ccagactgtc  cagtgagtca   7020
gggccactcg  taggaagtaa  gaagagaggc  tagagcatag  ccaggtcctc  actttatact   7080
ttaagcccat  gtgtatttct  cccaaaccac  acagcattgt  ttccatgctt  tcagctttgc   7140
atgaataacg  tgatacttga  acgcatcatt  tatcacttgc  tctcttttccc  acagcgctgt   7200 tttcaagctt  cttcctgttc  atgatgctct  gcttaaccct  taagctgcat  gggattctgt   7260
tctgtgaata  cgcccacccc  atgtattatc  ctgcccagca  aaaagtcccc  aaaactctgg   7320
atggtggtta  cctctaggga  gggagagaag  agattgggaa  tagggagcga  cttcaacggt   7380
gtttgtaatg  ttttgtttct  ttaaataaaa  gagctgagat  catttcagca  gaatgttgat   7440
ttagagtctc  ctggacaatt  tgttgctcaa  agtgctctct  taaagagcac  tttaaaaaaa  7500 aaaaccttt   atcttattat  ttatttattt  atttattgag  acggagtttt  gctctgtcac   7560
ccaggctgga  gtggagtggt  gtgatctcag  ctcactgcaa  cctttacctc  ctgggttcaa   7620
gcaattcccc  tgcctcagcc  tcccaagtag  gtgggattac  agatgcgtgc  caccacactt   7680
ggctaatttt  tgcattttag  tagagatcgg  tttctccatg  ttggccaggc  tgatctcaaa   7740
cgcctgacct  caggtgatct  gcccgccttg  gcctcccaaa  gtgctggtat  tacaggcgtg   7800
agctaccatg  cctggcttat  cttatatatt  tttaaaaaca  gcttattgag  atctaattta   7860
tgtaccataa  aattcaagta  tataattcag  tgcttttata  tataaaacat  atatatgaaa   7920
tagcttattg  agatataatt  ttttatataa  aacagcttat  tgatatgtaa  tgtatgtacc   7980
ataaaattta  aatatataat  tcactggctt  ttatatattc  acgaatatgt  gcaactatca   8040
ccacagtcaa  ttttagcata  ttttcatcag  ctcataaaga  aacccaagc   ccttgaacta   8100 tcaccccata  tccctcctcc  cagcccgtcc  ctcctactca  taagcaacca  ctaatctact   8160
tagtgtctat  agatttccta  ctctaggcat  tccatgtgag  cggatcatg   caatacgtgg   8220 gctcacacaa  tataagtggc  attccatgtg  agtcggctca  tgcagtatgt  ccggctcctt   8280
tcactgagca  taaggtcttc  agcactcatc  caggttgcag  cctgtgtctg  aatttcattc   8340
cctcttctgg  ctgaatcgta  ttccattgtg  tatcttggac  atatcctatt  ctgctcaccc   8400
agccgttggt  gggcgtttgg  agtgttttcg  cctttcagct  gtttttaagag  ggttgcagtg   8460 aacatttgta  caagttttgg  acccaatgcc  tgttttcaat  tctcttgtgt  agagagcact   8520
ttttagcaga  aaaagaatag  atttgtggcc  tcccttgtg   tgcggtcagt  gccttgagaa   8580
gagtgaactg  tgctgccacc  tccggagccg  tggagagcgc  ggggcttggg  tagcagctag   8640
gacgatacaa  gttgggacaa  ggccaggtgc  aatggctcac  gcctgtaatt  ccaacacttt   8700
```

-continued

```
gggagaccga ggcaggggga tcacctgagg tcaggagttc aagaccagcc tggccaacat   8760
ggtgaaaccc catctctaat aaaacagaaa aattaactgg acggggtggt ggacgcctgt   8820
aatcccagct actcgggagg ctgaggcagg agaatcactt gaacctggga ggcggaggct   8880
gcagtgagtg gagatcagac cactgcactt cagcctaggt gacagagcga gactccgtct   8940 caaaaaaag aaaaaaaag aagaaactc atggataatc ctccctctcg tgcagttcgc   9000
ctctacggac caaacttcat ccttcaggtg tactcatctc agaggaagtc ctggcaccct   9060
gtgtgccaag acgactggaa cgagaactac gggcgggcgg cctgcaggga catgggctat   9120
aagtgagtat ggggcagcac ccgccgagtg acagtaacag acagcagaaa cacgagaaga   9180
ccctctctct gcctccctgt gaaagcaccg gcacatgagt gctggggaca attgtcacct   9240
tccaaaagct gagccctata accagcaggt ggaatttgtc ctgctagggc tgtgcccagc   9300
acacagacct tggctcactg ccaccttgcc ctgcctcctc cttggcctct atagactcct   9360
ggttgctcgg gagtgcccag tgctgtggtc atctggtcag aggggtaggc tgagggcgtt   9420
aggtgcctct ttttccaagg tgcctctcag ccagggtcca ttcacctccc tgggtagagg   9480
ttggaccaga acagctggcg aggagggttg ggctggggag agcagcagag acaaatcctg   9540
tgccagtttc acttcattcg ggagccatgg aagccttttg agctggggag agaatcaatc   9600
aatcagactg atacttaaaa aatgtcattc ctgctcgtag ctctgaggga aggtgggaag   9660
gcttaacagg gtgtgtgtcg cctgacagtg attcctaacg ggggtggggc ggtggttacc   9720
atttaccagc actgcctggg gagatgcggc agccctcagg catcggggga gagggtggta   9780
ggatgctact gccactttgt tttccatggg agggtcccca ggtgatttct atgcaacttt   9840
agggtattca atatgccagt tttcagaatg aattaccact cggtgagaaa gttggcatct   9900
tagctagtca ctgtgacatc cctaaacagc aggggtgaat tacacagcaa agccccccca   9960
tcacagtcca ggaacctggt ggaattgata actggggcca tgttaacatc tgtacctttt  10020
attagattaa atgtgtgtat gattatacaa tcctatgtcc ttctcatagt ttcttgatcc  10080
taacctggat aagaaacacg accaatgaag gaattttgtc tgacactta gggttattga  10140 atcgaaaaat cgttacaata ttctagcact tggttagaac gtgtgatttt ttttcctaaa  10200
tgctaaggtt tttccctctt attctgaatg tcgtatgagc ggtattatga catagtatag  10260
gatttgtgtt tgcttatgcc ttaaccatta tcacaaataa ggttttcttt tttaggaata  10320 attttactc tagccaagga atagtggatg acagcggatc caccagcttt atgaaactga  10380
acacaagtgc cggcaatgtc gatatctata aaaaactgta ccacaggtat gcagcaattt  10440
cttcttgaaa aattttggaa tgaaatcaac taggagacac catgggaat cgttgtcctg  10500 agtctgattt ctctgagctg caatactcgg tctggatggg ttttgcattg ggaggagatt  10560
agagtctgac caggcctggt tactctaagc agcccttggt ttattcatag gaagtggctg  10620
aggtttctct gctatttcat tttcagcctc taccgtctgc ccttgttggt agcggctcac  10680
acttgcaaca tcgacattca actctatttta gttttctttc ctcttcagac atttagaggt  10740 gtacctatt tgtcagggcg tggttctagg aatccaagat aatgtctcag tgtcccagcc  10800
agggtgaccg gctcattcca gtttgccagg gacttcactg gcttgagcaa gggaagtcct  10860
gctccattcc aggcagctgg gctggctggt cccgttagcc ccaaccccgg gacagcagtg  10920
ccagagggtg ctctgtgagg gatgggcagc attctggcgg cctgggaatg agttgtggtg  10980
tttccagggg gtagaagtgg gtacaagcca caggtcacat gatgagtggc tgacctggct  11040
gggagggcag aagaggggat ggacttaggc tcttcctttt gctttgcaca tatttaggat  11100
```

```
gtttgcagac ttgctatgat tgttgctgtt atgtgttttc tgatgtgaaa gatacacagt    11160
gtcctttgcc catgagctct ccttgcctcc caggtcccca gggcttatgc ctggtgtcta    11220
ggcatcacct ccctgcctgc caggtgccag gtgctgcatt tcggggagg atgaactaat     11280 cacccgcgc caccttcct ctgagtggga gcctggggca ggtttgcatt cctggaggcc      11340
gctggtggag gggtctgggg gcctgacttc cactgcagcc tgctgtcctg gggaatgtgg    11400
cagggcaagc ccagtgggga gggctgtgca cggccaggtg cacccatcaa aacagcaggg    11460
ctgcggtttg tccctgtgga gaagctaaac acagctgcct gggcactttg taaatgctga    11520
gtggttcttt gtctttctgg gttacacacg gaatcaggga gccaagtcca gccgggcagg   11580
gacgggggga ggggaggagg tgctgccgtc ccttggcaag agccttggga actcacaagg    11640
aggctggagg gcttggaaga aagaagagaa ggccattgtc tggtaggctc tattctatct    11700
cggtggtggt ggtgggggga ggcgcacttc tttcctctt tctgtgcagc agttgccctt     11760
tgatgcctga gttcttggct tgttttctgt cgggcttctg tgaataacca catgtgccct    11820
ggcgctgtga ccacacaggg ctatccctac cgaccttagg attcttagga aatgtcttct    11880
cttaaagggg acatgtcttc acttggccgt gtcagtgccc cagagccaga gtccacctgg    11940
aatgcacctg tagtcactga gaacccgggg ggtgtgcctt agtaagaagg tgtcaggaag    12000
gacctattat tgtagggcct gggctcctgc aaggtggttt gggggtggtt ggaggaagca    12060
gagatttgct ctggattgga tgctgtcagg aagcagggt aattctgtga ggctgcttta     12120 ttatttttt tctaggagga ggttggaatg aggctaggct aaagctgtga ttggtaaaga    12180
aacgtccgtc gctcaagtta gccaggacag gaggagacat cagatcgtga ttttgtggtt   12240
gtgagcacaa ggttcctgtt ctgtctgttc agacatcatt tcggaggagg ctccttgtgt   12300
cttgccccat ctcaggcatg gagggcctc gtccgatatt gacgctcagt gaaataattc    12360
aggttccgca gagcacacgg cccagctatc agggcgggcc agctctgcat gccaggggcc    12420
gcgtcttccc ttctcagcat agcctgggaa attcactgca ggacaaatg catcagttac     12480 ttcctcttca tccataaccct gggatgtttg actcccaaat gagtaactct tacgtttctt   12540
ctaatcctag ggaaactatt ggttatattg ctttcaacac tacaaattta aagcagttat    12600
aggagcccag aggtttccaa atggcttcct taaaaattag aagatgattt taaattccaa    12660
gaggaaaaac aaaactagca ttattgtata cttaccctca caaccgtcct aggagctggt    12720
acaattttaa gagaggttaa gtaacttgcc caaggtcaca ctgtggggat gtgagccgcg    12780
taccttggct cagtgtctgg tctttgccac tgtccctata tggatttact taccttattg    12840
gagttgtaac tagcagaccc ttctatgtct cagaagacag gagagggaac atcggaagaa    12900
atgactgatt tctaagcatg tgagaggcag gtgactccgc actatcgtga ccagaatttc    12960
ccctgttctt tttgcagtga tgcctgttct tcaaaagcag tggtttcttt acgctgtata    13020
ggtaagttca tctggagtcc ccctttgat acttctaact aggaaaagct ctctactttc      13080
agaacagtac tccctgtgtc tctggggcg tgggaggaa gaaggtgggg tcacgggttg      13140
gaatgtgccc agcggcgtct cgctctttcc aaggagctcc tggtttagat ttccatggcc    13200
tgtagacacc ttcagccttg ggtccaaggg acacccctg agatcaggca cgctcaagaa    13260
gctgacaaag ccctacactt tatgccaccc atgagctgga ggcccggcag gtctctttct    13320
ccagaaagca aaggggggtg gcgttagtga gccctggcag ccacctaacg tggacttgga    13380
gcatctgcgg ggctgtggtc cagcaccacc gtgtggccac caggtgctca tcagccagtg    13440
```

| | | | | | |
|---|---|---|---|---|---|
| ggacccggga | ggagggacaa | gaccagagaa | caacagtgct | cttgcctctt | ctctcctgaa 13500 |
| ttttggacgg | tggcttagac | ttgggtgtcc | ccatctctgt | gtttagagtg | cttacagttt 13560 |
| ccaaactgtt | tgcaaatgtg | gaagccaccg | tccctctcct | ctgggatggc | ccagtgctgt 13620 |
| cgtggggccg | tggtcctgag | ctcagctttt | catttgaaga | ggtggaagga | gctgacaccg 13680 |
| tcccatcccg | gcagggctgg | ctcaggtctt | ctttaggtcc | tgagtggggg | tccagcacag 13740 |
| ccccaagggt | gcgtggcacc | cgccctgccc | tctgcccatg | cactcatctc | ctggtggaga 13800 |
| agacactcac | acacaggaag | cagggaaggc | agcagacctc | actcacccct | caccccctca 13860 |
| ctcaccccct | actcaccccc | tcaacctctc | attcaccacc | caccccctcg | ccccctcact 13920 |
| caccccctca | ctccctcaac | cctcactcac | ctcctcactc | cctcaaccct | cactcacctc 13980 |
| ctcacctcct | cactctcccc | ctcatccctc | cctcacccca | ccccgtcacc | tcctcactca 14040 |
| cctcctcacc | ccctcactca | cccttcaccc | cctcactcac | cacctcacct | cctcactcac 14100 |
| cccctactca | acccctcatt | cacccctcac | cccctcactc | acccctgcac | cccctcactc 14160 |
| accccttcat | ccactcaccc | acctgctcac | ctcctcactc | aacccctcac | cccctcacta 14220 |
| atccctcact | ccctcacccc | ctcacgccct | cactcacacc | ttcacctcct | cactcacccc 14280 |
| ctcaccccct | caacccctta | cttaccccct | cactcatccc | ttcacccctc | actcaccccc 14340 |
| tctctcaccc | attcaccccc | tcactcatgc | cttcaccccc | tcactcacct | cctcactcac 14400 |
| accttcaccc | ctcagtcacc | ccctcactca | ccccttcacc | ccctcaatca | tgccttcact 14460 |
| ccctcactca | ccccttcacc | ctctgaatta | ctccctcatc | ccctcactca | ccccctcact 14520 |
| caccccttca | ccccctcacc | caccacctca | cccacccctc | acccaccccc | tcacctcctt 14580 |
| acccctcacc | cccctcactc | acccctcacc | ccctcactca | ccacctcacc | cacccctcac 14640 |
| ccaccccctc | actcactccc | tcatcccctc | actcaccccc | tcaccccctc | actcaccccc 14700 |
| tcacccaccc | ctcacccacc | ccctcacccc | ctcactcacc | ccttcacccc | ctcactcacc 14760 |
| ccctcactca | ccccttcacc | ccctcactca | ccacctcacc | cacccctcac | ccaccccctc 14820 |
| actcactccc | tcaccccctc | actcaccccc | tcaccccctc | actcaccccc | tcatctcctc 14880 |
| actcaccccc | tcacctcctc | actcacccgc | tcacctcctc | actcaccccc | tcgccccctc 14940 |
| actcacccct | caccccctca | cccctcact | cacccctcac | cccctcgccc | cctcactcac 15000 |
| cccctcgccc | cctcactcac | ccctcacccc | ctcaccccct | cactcatccc | ctcacctcct 15060 |
| cactcacсccс | ctcacctcct | cactcacccc | ctcacctcct | cactcacсccc | ctcacctcct 15120 |
| cacccacccc | ctcactcact | ccctcacccc | ctcaccccct | cactcacccc | ctcacctcct 15180 |
| cactcacсccс | ctcacctcct | cacccacccc | ctcactcact | ccctcacccc | ctcaccccct 15240 |
| cactcacccc | ctcacctcct | cactcacccc | ctcacctcct | cactcacсccс | ctcacctcct 15300 |
| cactcatgcc | ctcaccccct | cactcacсcct | ttcacctcct | tgctcatccc | ctcacttacc 15360 |
| ccctcacttc | gtcaatcacc | ccccaccctc | gtcaatcacc | ccctcacctt | ttcactcacc 15420 |
| ccctcactca | cccccttact | tcctcactta | cctcctcacc | cccactcac | ccctcacccc 15480 |
| cccactcacc | ccctcacccc | acactcaccc | cctcaccccc | cactcacccc | ctcacccctc 15540 |
| tcacctcctc | actcaccсccс | tcacctcctc | acttatcсccс | tcaccccctc | aattaccccc 15600 |
| tcaccccctc | aattactccc | tcatcctttc | aattacccac | tcaccccctc | acctcctcac 15660 |
| tcctcactca | ctccctcact | caccccttca | ccttctcact | cacctcctcg | tctcctcacc 15720 |
| ccctcactca | cttccagccc | tgcccctccc | atcttccttt | tctttgtgtg | agaatctggg 15780 |
| gtccctgagt | ggtgtcagtc | cctccaagac | tcaaggagtc | cccagggcct | tgttatccag 15840 |

```
aacaccccca cctgggtccc gggagacccc atgggatcac aggagtgttc agggaagtgg    15900
tgcttcctgg gtctgggtgg gctggagggg catcctccct tccccaagag gagaccccca    15960
ggagcccct aagtccatcc ccagcagtgg tgccctgcc ctgtccttgc agcctgggag     16020
acccttggga ggggcgggcg ctgggtggct gggcggcttc tgctggtctc accccactgg    16080
cctcctgttt gtcatcctca gcctgcgggg tcaacttgaa ctcaagccgc cagagcagga    16140
ttgtgggcgg cgagagcgcg ctcccggggg cctggccctg gcaggtcagc ctgcacgtcc    16200
agaacgtcca cgtgtgcgga ggctccatca tcaccccga gtggatcgtg cagccgccc     16260
actgcgtgga aaagtatgcc aggggcgcg cgggccgggt gggggctcag ggctggccta    16320
cagccaccct gtgaccttga gcaggtctca acccttgcag ccccggcatc cttgtgttta    16380
aatggggaga gtattgcacc tgcttcctag ggctgtgaga catcaagtgc gctcatgcca    16440
ggcagtgcat ggctgtatgc actgagtgtc ccctgcacgc agggcacagg gtgcaggtgg    16500
aacattctcc acgatgtcgc cgtgaccagc gttccttcca gccactgtcc tctgagctct    16560
gtcctgccct tgagcaaagc ccctgcccc tgaggtatcc tgtctccggg acgctagtcc     16620
caggagaggg cacactcaga caggcttcag gctgccctgc tggaaggtcc ctggggttaa    16680
gcgttcttgg ccacagcatt gctcatgcag agggttaggt aggggtgagg ctagccgtga    16740
cagtattagc atttatggac gctaccaccc cctcccttt tccttaaaca catagtgctt     16800
ttggtcacat gctgctttgg aggaggcctc acttggcgga tgtatttttc tgccttagag    16860
agaggctgaa ctgggtttga ctgttggccc agccctctct tgctgcgtgc ccttagacga    16920
ttcactcaac gtctctgatc catggcatgt acaactataa gatgggcatg cccttctcct    16980
ctcgggctgt tatgaaggtc aaggaagcaa gggctgttac ccaagggtgc tcccttctct    17040
cccctcttc acaccccag gtgctctggg ccctctagga actgggtttc tctcaagggc      17100
tgttacccaa gggtgctccc ttctctcccc ctcttcacac cactgggtgc tctgggccca    17160
ctaggagctg ggattctctt aagagggaaa ctcttggata aggaaatgg tttgattgat     17220
atcggacaag tctgttcatt agtatccatt tattaagcac ctaccatgtg ccaggaaatg    17280
ctttggcgta caaaggaaaa taagggccag tcctgctaga aatggcctg aaaccccagg     17340
gagggatgtc ggcccattgt gggtgctgca gattccttga aggtgatgca agagccagaa    17400
agaaggatga tgtggggggc tgaggcaggg agtcgggtt gggggagtgt ggggagaag      17460
gggagaccga gcacctcttc cactatctcc ctgtgtggtt tttggtgaac catcctgcct    17520
ctgggtgtct tgcctccagc ttctgacgtt ggaagttcat ccactgagag ctctgtgttt    17580
atggctctga gatactgagt ccttcttctc tcccagacct cttaacaatc catggcattg    17640
gacggcattt gcgggattt tgagacaatc tttcatgttc tatggagccg gataccaagt    17700
agaaaaagtg atttctcatc caaattatga ctccaagacc aagaacaatg acattgcgct    17760
gatgaagctg cagaagcctc tgactttcaa cggtacgtgt ggctcaggct tggcaagcag    17820
gttggcagaa tcttaaagag atgttgattg gaaatgacac ttgtgctatg ccaaatggaa    17880
gggaggcatt tgcgttgagc gagggtagcg tgcagcgggt ggccaatggg agaggctcac    17940
agaggctaag agcacctgcc gcattttggg ggaggcagca gccaccacat ctgttctgta    18000
ctgtactgag tggtggtgat tcaagccagg catggaaaag gctagaacag ggctttccca    18060
ctgcagcacc cttgacatct gggtggttct ctgttgtagg gctctcttgt gccttgtagg    18120
atgtttaaca gcgtccccag cctctaccca ctggaggcca gtagctacca agctgtgaca    18180
```

```
accagtgttg cctgctgaca ttgccaaaca tccgctttga ggcaaagtca cttccagttg   18240
agaactactg gcctaaaatg tgtaaagatc cttgattttt aaagatacat tctaaaacca   18300
agttgcttaa ttcaggacaa acatgctttc tcttagcctc ttattcggtc ccactctggt   18360
ccatccaagg gtctggaatg ttctagcccc atgtggatac agaagaagca aaacctcagc   18420
cctccctaca gcatgtctgt attcacattg ggaaatggtt cacatataga agagcgaatg   18480
cctgagcaat ggcgtggtgc ctctggggcg aaagctgact ccattgactc catcggcttt   18540
ttggctgttg cctcctgtgt gtctttcccg tcttgatcac ctggagatat gtaattttgg   18600
aagcagagct agcaaataat tcctcttata agcagagcta gcaaataatt ctacttataa   18660
gtagcataac gtcttgcctg ccagaaggag aggtctggca gggggagaaa gtgagaatgt   18720
gggacttgtt gggatgcagg gtcctctggg caggtggcc agggtgccag gcccagcagc    18780
ctgcatgtgg gaaggccagg tggagacata ggtgataccc gcctggctca ctgtgttttc   18840
tcttcttgaa acagacctag tgaaaccagt gtgtctgccc aacccaggca tgatgctgca   18900
gccagaacag ctctgctgga tttccgggtg ggggccacc gaggagaaag gtgaggctgc    18960
tcctgggcac acaggactgc agggcccaca gatggagcat tggttcgga agtgggaggt    19020 ccaggtttta atcccagttc tactactcaa tgactggatg actttggttg attccccag    19080 tccttgtgcc tcagtttctc catctgctaa gtgggagaaa tcctgcccag cctacctaat   19140
acactgtgtt cttatcgtga tcacacagag cagcatgtgg aatggctttt gaagtatctg   19200
ggccatacga gtttagaggt gcaggatctc ctgtgttgca ctcattgtga gtttagagct   19260
gccctggaga tcccaccaag gcctgcgtgg ctgagtgaca gggggcttgg tgaggacggg   19320
catcctggac ccatggtggc cacatctaag cctgtcctct gccctgataa ccacagagag   19380
aggctctctc cacccacttc cttttgcaatc tgcatttctc tctgacagtc tttcaaatga   19440
agggagcctg gctgcttcat ttttatggag ggttggaagt gcttagtggc aggcacaaag   19500
gttcatttta catattgttt atatccttct caaaagcgtc taggccatac agacaacaaa   19560
tcctttcaaa caaggggaaa agtacaaagg ttgggtgatt tctggggagc gtcagggaag   19620
gtagtggggg gcatcctggc tcctcatcag cagaaactta ctacagtaga gccacaggct   19680
gggcaaaaga cctcatggaa tccaagatga agggaatatc gacaaatatt tgtgcgcacc   19740
tgcacctagt acaggctggg tgctactcag gtgctgggaa tgcagaagtg aacagagtaa   19800
gacaaatgtc tctgctgtca ggagctttac ctctcttctg gatgtcggtg gtggggacgg   19860
ggcaggtgtg gtcagacaga tgggagacaa acaactgagc gaggtacttc caaacatctg   19920
agggtgggga tcacaaggtc ccggctattt tgaaggggtg gtcaggaaag gcttctcgga   19980
agaggtggca tttgagctga gactcaaatg gcaaaaatgt gtacacatca aaaaggctag   20040
tgcatgtatc ttcaggtgtg gtcaaggggc caaggaggtg ggctgggcc agattgcata    20100 ggtccttgtg gattatggtg aagacaccag cttctcatct gcttgaggtg gggagatcgt   20160
gagccgggga gtgccatgat ctggcagctg cgtggggagt ggggatgaat ggatggagac   20220
gaggatgatg gtgacaagtc cattgctgtg gttccttgag acaggaagcc agctcatagc   20280
agagtgcggg cgtggatgtg aagagatgag ggtacactag gctagagcc accagactta    20340 ctgatgggtt gcatgtctgt gggagagaga gtgagaagtc agggacgatg gctttccact   20400
ctgtggctga gccccagggt tggcgggtgg tgccattttt caagccagga aatattggtt   20460
ggtgagaatt tggggtggga aaggtgtga cggaggggttc tggttttgca cactaagccc    20520
acggtgccca gaagatgccc gaggggaggc agcaaagcga gagtgggaaa tgcagaggtg   20580
```

```
gcaagtgcag gccgtgtctt gagaagctct aatgtgcagg ggagccgaga agcaggcggc   20640
ctagggaggg tcacgtgtgc tccagaagag tgtgtgcatg ccagagggga aacaggcgcc   20700
tgtgtgtcct gggtgggggtt cagtgaggag tgggaaattg gttcagcaga accaagccgt   20760
tgggtgaata agaggggggat tccatggcac tgatagagcc ctatagtttc agagctggga   20820
atttctttcc ctgaagctga actccagagc tgcattcagc acaggcaccg ccagttgtaa   20880
ggagaatcca ggtttcccag gagagggggtt ggtgctggga tgagctgacc ggggcagggc   20940
tggaaaatag ggctgtgacc atctgtgtag tgcgtgtgga ggtctcaggg agggaagtgt   21000
gctctccctg cgagagctgc aggcaacact gggagctcaa caagtctccc tgtccttagg   21060
gaagacctca gaagtgctga acgctgccaa ggtgcttctc attgagacac agagatgcaa   21120
cagcagatat gtctatgaca acctgatcac accagccatg atctgtgccg gcttcctgca   21180
ggggaacgtc gattcttgcc aggtaattca acatttttat tctacctttg gtccttacca   21240
gatcctactg aacccccccat gagagagagg gcattcttgg ggtcagcaga gcctcctcag   21300
tgacacggag ccagctcggg gcagtcatgg gaagtgacgg ccacaaacag tgcgaacgct   21360
tctggtggca gaaggaagta cagtcaacaa atcacacaca ccctctgaaa aaccggtatt   21420
tggtaaaagt gccagtggaa cagaaacaag tatttagact attttaaatt atgaacggca   21480
atttatttag taacttttag cttgaacaga ttaaaattca ggatgggggc tatctctttg   21540
ggggttacat ctctgttacc atcaccccctt gatggtggag attcgaagcc cacacagtca   21600
ctcgtaactc acactgcgac ccccgccccc caactcctct aggcctggtc agtggtgtgc   21660
ggcagattgt gacttgattt tctgctctct gtaccttgct gtgtcccaca gggtgacagt   21720
ggagggcctc tggtcacttc gaagaacaat atctggtggc tgataggggaa tacaagctgg   21780 ggttctggct gtgccaaagc ttacagacca ggagtgtacg ggaatgtgat ggtattcacg   21840
gactggattt atcgacaaat gagggtaact atcctgtcct ccttctgact gtgttctccg   21900
attcctcgag ccaaagccag acatctgtta ggcgtggttc tgctgctgga agctgactgg   21960
tgaccactgg tcagcatgaa gcaaactctg cttcctccag ccacagcccc atccccccag   22020
tgtccaccca ttgcccattg cctctcactg gcttcacttg catatttccc ctggtgtttg   22080
gatgaaaagc gctggggctc agcttgtgtg aaattccttg gtgctctgcc aaccacactt   22140
cgttctggct cagctgactc agctgttcca cccaggccac ctcacatcaa acttttttttt   22200 tttttttttg agatggagtc tcactgtgtc gcccaggctg gagtgcagtg gcacaatctc   22260
gactcactgc aaccttgcc tcctgggttc aagtgattct cctgcctcag cctcccaagt   22320
agctgggact acaggcatgc gccaccacgc ccagctactt tttgtatttt tagtagagat   22380
ggggtttctc catgttggcc aggctggtct cgaagccctg acctcaggtg attcacccac   22440
ctcagcctcc cacagtgctg ggattacaag tgtgaaccac ggtgcccggc ctcacatgaa   22500
acttttgatt tatagagagc agagggaaga gccggctgtg cccatccttt tctgggggcca   22560 tcgagtggct cctgggcagc ccccaaggtt aggaagggca ggagcagcca gggttctctg   22620
atgccccaga ctcaagcacg agggaaggtc tcagggggttc catgtgagcc tcatggatgt   22680
ctctgcttag cagagccctg gctttgggca ttgtccagat aggggggtgag aaccagatct   22740 tctcatctcc aggacctcag acgtatagtt ttctcagatt tctgtgcttt ctggggctgg   22800
gctactagtg gaagaaagca gtctattctg tcttctccca aatctcccag atgcccagtc   22860
tgttgaagga ggagcagaac caggggggcct ttcccgctga ggcccgacct gtgtctcctt   22920
```

```
caaatgacac gcgggactca gggccttccc atgaccatgg ggcccagggg gcgtcacctg  22980
gcccagggcc cagtgctaga aacagatgac cccaggagga ggaggcaggg caggagggaa  23040
gctggcaggg ctgggatggt cagccaggct gaggggcgga ctcgcaccag gatggagcta  23100
ggaaatgatc caggtgtgtt tggcggctgc aggtgggtcc gcatggctgt gcagggaggg  23160
aagggctgcg tggcaggaga gcagccgggg gaggcccaga ctctgctgaa gagatgcctg  23220
ttgtgccggc ctccacatcc gctgcccgct ccttccggag ctcctgcccc gccatgctca  23280
gcctgactct gaccaacacg ttggagagaa gaatgatccc tttgtgctat taagcttgct  23340
tatttggttt ctaagtgctt catgcgaacc tagaggaaaa aattattttc ccctttgtt   23400
tgtcttaaga aaataacaca ctttttttt tcctatttga acaggcagac ggctaatcca  23460
catggtcttc gtccttgacg tcgttttaca agaaaacaat ggggctggtt ttgcttcccc  23520
gtgcatgatt tactcttaga gatgattcag aggtcacttc atttttatta aacagtgaac  23580
ttgtctggct ttggcactct ctgccattct gtgcaggctg cagtggctcc cctgcccagc  23640
ctgctctccc taaccccttg tccgcaaggg gtgatggccg gctggttgtg ggcactggcg  23700
gtcaagtgtg gaggagaggg gtggaggctg ccccattgag atcttcctgc tgagtccttt  23760
ccaggggcca attttggatg agcatggagc tgtcacctct cagctgctgg atgacttgag  23820
atgaaaaagg agacacatgg aaagggagag agccaggtgg cacctgcagc ggctgccctc  23880
tggggccact tggtagtgtc cccagcctac ctctccacaa ggggattttg ctgatgggtt  23940
cttagagcct tagcagccct ggatggtggc cagaaataaa gggaccagcc cttcatgggt  24000
ggtgacgtgg tagtcacttg taaggggaac agaaacattt ttgttcttat ggggtgagaa  24060
tatagacagt gcccttggtg cgagggaagc aattgaaaag gaacttgccc tgagcactcc  24120
tggtgcaggt ctccacctgc acattgggtg gggctcctgg gagggagact cagccttcct  24180
cctcatcctc cctgaccctg ctcctagcac cctggagagt gcacatgccc cttggtcctg  24240
gcagggcgcc aagtctggca ccatgttggc ctcttcaggc ctgctagtca ctggaaattg  24300
aggtccatgg gggaaatcaa ggatgctcag tttaaggtac actgtttcca tgttatgttt  24360
ctacacattg ctacctcagt gctcctggaa acttagcttt tgatgtctcc aagtagtcca  24420
ccttcattta actctttgaa actgtatcat cttttgccaag taagagtggt ggcctatttc  24480
agctgctttg acaaaatgac tggctcctga cttaacgttc tataaatgaa tgtgctgaag  24540
caaagtgccc atggtggcgg cgaagaagag aaagatgtgt tttgttttgg actctctgtg  24600
gtcccttcca atgctgtggg tttcaaacca ggggaagggt cccttttgca ttgccaagtg  24660
ccataaccat gagcactact ctaccatggt tctgcctcct ggccaagcag gctggtttgc  24720
aagaatgaaa tgaatgattc tacagctagg acttaacctt gaaatggaaa gtcatgcaat  24780
cccatttgca ggatctgtct gtgcacatgc ctctgtagag agcagcattc ccagggacct  24840
tggaaacagt tggcactgta aggtgcttgc tccccaagac acatcctaaa aggtgttgta  24900
atggtgaaaa cgtcttcctt ctttattgcc ccttcttatt tatgtgaaca actgtttgtc  24960
ttttttttgta tcttttttaa actgtaaagt tcaattgtga aaatgaatat catgcaaata  25020
aattatgcaa ttttttttttc aaagtaacta ctgcatcttt gaagttctgc ctggtgagta  25080
ggaccagcct ccatttcctt ataaggggt gatgttgagg ctgctggtca gaggaccaaa   25140
ggtgaggcaa ggccagactt ggtgctcctg tggttctcga gataacttcg tataatgtat  25200
gctatacgaa gttatatgca tggcctccgc gccgggtttt ggcgcctccc gcgggcgccc  25260
ccctcctcac ggcgagcgct gccacgtcag acgaagggcg cagcgagcgt cctgatcctt  25320
```

```
ccgcccggac gctcaggaca gcggcccgct gctcataaga ctcggcctta gaaccccagt    25380
atcagcagaa ggacatttta ggacgggact tgggtgactc tagggcactg gttttctttc    25440
cagagagcgg aacaggcgag gaaaagtagt cccttctcgg cgattctgcg gagggatctc    25500
cgtggggcgg tgaacgccga tgattatata aggacgcgcc gggtgtggca cagctagttc    25560
cgtcgcagcc gggatttggg tcgcggttct tgtttgtgga tcgctgtgat cgtcacttgg    25620
tgagtagcgg gctgctgggc tggccggggc tttcgtggcc gccgggccgc tcggtgggac    25680
ggaagcgtgt ggagagaccg ccaagggctg tagtctgggt ccgcgagcaa ggttgccctg    25740
aactgggggt tgggggagc gcagcaaaat ggcggctgtt cccgagtctt gaatggaaga    25800
cgcttgtgag gcgggctgtg aggtcgttga aacaaggtgg ggggcatggt gggcggcaag    25860
aacccaaggt cttgaggcct tcgctaatgc gggaaagctc ttattcgggt gagatgggct    25920
ggggcaccat ctggggaccc tgacgtgaag tttgtcactg actggagaac tcggtttgtc    25980
gtctgttgcg gggcggcag ttatggcggt gccgttgggc agtgcacccg tacctttggg    26040
agcgcgcgcc ctcgtcgtgt cgtgacgtca cccgttctgt tggcttataa tgcagggtgg    26100
ggccacctgc cggtaggtgt gcggtaggct tttctccgtc gcaggacgca gggttcgggc    26160
ctagggtagg ctctcctgaa tcgacaggcg ccggacctct ggtgagggga gggataagtg    26220
aggcgtcagt ttctttggtc ggttttatgt acctatcttc ttaagtagct gaagctccgg    26280
ttttgaacta tgcgctcggg gttggcgagt gtgttttgtg aagtttttta ggcacctttt    26340
gaaatgtaat catttgggtc aatatgtaat tttcagtgtt agactagtaa attgtccgct    26400
aaattctggc cgttttttggc tttttgtta gacgtgttga caattaatca tcggcatagt    26460
atatcggcat agtataatac gacaaggtga ggaactaaac catgggatcg gccattgaac    26520
aagatggatt gcacgcaggt tctccggccg cttgggtgga gaggctattc ggctatgact    26580
gggcacaaca gacaatcggc tgctctgatg ccgccgtgtt ccggctgtca gcgcaggggc    26640
gcccggttct ttttgtcaag accgacctgt ccggtgccct gaatgaactg caggacgagg    26700
cagcgcggct atcgtggctg gccacgacgg gcgttccttg cgcagctgtg ctcgacgttg    26760
tcactgaagc gggaagggac tggctgctat tgggcgaagt gccggggcag gatctcctgt    26820
catctcacct tgctcctgcc gagaaagtat ccatcatggc tgatgcaatg cggcggctgc    26880
atacgcttga tccggctacc tgcccattcg accaccaagc gaaacatcgc atcgagcgag    26940
cacgtactcg gatggaagcc ggtcttgtcg atcaggatga tctggacgaa gagcatcagg    27000
ggctcgcgcc agccgaactg ttcgccaggc tcaaggcgcg catgcccgac ggcgatgatc    27060
tcgtcgtgac ccatggcgat gcctgcttgc cgaatatcat ggtggaaaat ggccgctttt    27120
ctggattcat cgactgtggc cggctgggtg tggcggaccg ctatcaggac atagcgttgg    27180
ctacccgtga tattgctgaa gagcttggcg gcgaatgggc tgaccgcttc ctcgtgcttt    27240
acggtatcgc cgctcccgat tcgcagcgca tcgccttcta tcgccttctt gacgagttct    27300
tctgagggga tccgctgtaa gtctgcagaa attgatgatc tattaaacaa taaagatgtc    27360
cactaaaatg gaagtttttc ctgtcatact ttgttaagaa gggtgagaac agagtaccta    27420
cattttgaat ggaaggattg gagctacggg ggtgggggtg gggtgggatt agataaatgc    27480
ctgctcttta ctgaaggctc tttactattg ctttatgata atgtttcata gttggatatc    27540
ataatttaaa caagcaaaac caaattaagg gccagctcat tcctcccact catgatctat    27600
agatctatag atctctcgtg ggatcattgt ttttctcttg attcccactt tgtggttcta    27660
```

| | |
|---|---|
| agtactgtgg tttccaaatg tgtcagtttc atagcctgaa gaacgagatc agcagcctct | 27720 |
| gttccacata cacttcattc tcagtattgt tttgccaagt tctaattcca tcagacctcg | 27780 |
| acctgcagcc cctagataac ttcgtataat gtatgctata cgaagttatg ctagtaacta | 27840 |
| taacggtcct aaggtagcga gctagctcca cgtggctttg tcccagactt cctttgtctt | 27900 |
| caacaacctt ctgcaagaaa accaagggcc tgaattttaa cttcctg | 27947 |

<210> SEQ ID NO 6
<211> LENGTH: 25333
<212> TYPE: DNA
<213> ORGANISM: Artificial Sequence
<220> FEATURE:
<223> OTHER INFORMATION: Recombinant polynucleotide

<400> SEQUENCE: 6

| | |
|---|---|
| gcagagtcta agaaatcgct gtgtttagcc ctcgccctgg gcactgtcct cacgggagct | 60 |
| gctgtggctg ctgtcttgct ttggaagttc agtaagtgca gggagcctcg atcccaccat | 120 |
| gtgctcctgc agtccccagt gctctgagcc agaccctgct ctctgggcta ttgagacctc | 180 |
| tggaggccct ccgtgaggtt cctctcttac ataacgaggc tgtctctctt cccttctctt | 240 |
| gtttagctat gagattgaca catcatgggg aaagcattta gaatgtaccc agtgctttgg | 300 |
| ggtgcttggt gccacccagc actgtgagca caggttcttc taccttgggg ccacacccag | 360 |
| ttacctgtat ctcactgcac agcagtggct gttggggacc aggcccaccc ctccatgtcc | 420 |
| cacctcctgc aactgcagcc tgagccttcc catcagcctg gggtggtgca gacccatgtg | 480 |
| ccattgtgga tccttcaagt tacctgtgtg gcagagagga cgtgtgagtg ccgtccaaac | 540 |
| ccaaacactg agagggtcct tcccattgcc cccacggaag taaggtgccc cagtgctaat | 600 |
| tccacttata cttgctggtg gcaaggacac ttctcctcct tattaaagtg ggggattggc | 660 |
| tgggtgaggt ggctcacgcc tgttatccca gcactttaag aggccaaggc aggtggacca | 720 |
| cctgaggtca ggagtttgag accacaagcc tggccaacat gttgaaactc catctctact | 780 |
| aaaaatacaa aaattagtca gccgtggtgg cgtgcacctg taatcccagc tacttaggag | 840 |
| gctgggcag gaggatcact tgaacccagg agttggaggt tgcagtgagc caagattgtg | 900 |
| cccctgcact ccagcctggg tgacagaatg agacttcatc tcaaaaacaa aacaaaacaa | 960 |
| aacacagtgg ggccaggagt tggaggctgc agcgagctac agtaatgcca cggtgttcct | 1020 |
| cactccatga ggctcattgc gtttctcagc ctgaagggca cctctcttct gttttctctg | 1080 |
| caagtgggca gcaagtgctc caactctggg atagagtgcg actcctcagg tacctgcatc | 1140 |
| aacccctcta actggtgtga tggcgtgtca cactgccccg gcggggagga cgagaatcgg | 1200 |
| tgtggtgagt cagccttgac cttgggaagg gactcctctg ctcaccttgg agacagcagc | 1260 |
| cgggtccagg ggcctttggg tgactgggcc tggcgtgcgt ccagtacgct gacacatgat | 1320 |
| gtcattgaat ccctgctcca ggctgagccc tggggctcag agaggttgtg tttccggccc | 1380 |
| aacctcaccc agcaggtggg agatgacagg gccaccgagg actgtgtcat ggaaccaca | 1440 |
| cgtgctctga actgccacag gaagtcagtt aagatgagca aactgtttat aaagttggag | 1500 |
| atgcaggcta ggaacggtgg ctcatgcctg taatcccagc actttgggag gccgaggcag | 1560 |
| atggatcacc tgaggtcagg agtttgagac cagcctgacc aatatggtga aaccttatct | 1620 |
| ccactaaaaa tacaaaaatt agccaagcgc ggtggcgggt gcctgtaatt ccagctattc | 1680 |
| aggaggctga ggcaggagaa tcacttgaac ctggagggcg gaggttgcag tgagctgaga | 1740 |
| tcacgccact gcattccagc ctgggagaca gagctggctc aaaaaaataaa ttaattaatt | 1800 |

```
aaaaacaaaa ttggagatgc actatgttat tttcaaaaca agctgccttt aaagatctat    1860
ctgttgtcac agggtgggct catctgtttc attttatttt ctgtggttta tctatttatt    1920
cattttaatg aactaggaag cattgctcct atttatggca taccacatga tgtttggata    1980
cgtgtatgcc tgtggcatgg ctaagtcaag ctagaacatg gccttacct catatacgtg     2040 tcttattaag aacacataaa acctactctt gtagtgattt tcaaatatgc aacatatagt    2100
ttattaactg cagtcactat gatgtacaat agattgctcg aacttattcc tcctgtctaa    2160
ctaagatttt gtgacctctg accaacatct ccccagtgtt gtcaccccc gccccagcc      2220 tctgatagct gccttctac tctctgcttc tgtgagtttg atgtttatac attccacatg     2280
taagtggcct catgcagtgt ttctgtctct gtgtctggct tgttcactta gcgtaatgtc    2340
ctccagcttc atctatgttg ttggaaatga caggatttcc ttctttcttg tggctgaata    2400
gtattgcctt gtgcatatac accacatttt ctttatccct tcattcactg atggactctt    2460
aggttgatgt catgtcttgg ctgttgtgaa aaatgccgca gtgagcgtgg gcgtgcaggt    2520
ccctcttcaa cacacggatt tcctttcctt tggatataaa cccagcagtg agattgctgg    2580
atcacatggc agttctgttt ctcaccttt gaggaaactc catactgttt tccataatgg     2640
ctgtagcaac ttccactccc accccacgg tgcaaagtct ccatttctct tctacaacct     2700
caccaactcc tgttatttc catctttctg atagtagcca tttgaagagg tatgagatga    2760
tacctcattg tggttttcat ttgcattttt atttgtattt tcatgaatt tttgagggtg     2820 atttcaaggg tagttagtga ctcgaacagg gaaacgatcc tgagtatgag ggttgtgcta    2880
atcatccccc tcctgccagc tgcgtacgga atggggctct gcagatggca gggagctggc    2940
tcgtttctct ttaagagctg ccttttactt ttcttcctct tccttttaaaa cttatttcct    3000 ggccggacgc agtggctcat gcctgtaatc ccagcacttt gggaggccga ggtgggcgga    3060
tcacgaggtc aggaattcca gaccagcctg ccaacatgg tgaaacccg tctctactaa      3120 aaatacaaaa attagccaga cgtggtggtg cgggcctata gtcccagcta ctcgggaggc    3180
tgaggcagga gaatcacttg aacctgggag gaggggttg cagtgagccg agattgcgcc     3240
actgcactcc agcctgggcg acagagccag actccatctc aaaaaacaaa aaaagttat     3300 ttcccaagca cagccatgta ttccaggctt gtggatcagc gttggtggtg gtgtgtgctc    3360
tcatatctta gttccagcta agcacactct gacatgttta cactagaacc atttgttttt    3420
tctagaaata gaaatttcag aattgtagag tcagaggact taccagaaat ctcttaggta    3480
gttctcctcc cctccctcaa gtgcagtcct aacctcctgg agttttctgt agaaaccaca    3540
agcctcagag ctggccgaga attctagcca aagattttc catgccaaag taatccccc      3600 tctcctaagg gccatccttg gtggggactg gtttcctgtt aagccctcgc tgtcagtcct    3660
ggctgtggaa tttcctggtg aggagcactg gcccgtggag ctcggccctc gtgccggcct    3720
tgagcaggcc caagtgttcc gtgttcttga tacctttcct ccagcacagt cttgcttccc    3780
agaaaaaggt ttgcacttga aaatgatgca tttgctgatt aaacatagtt cttttgcttt    3840
atttggtttc taaaataaag tgggagtttt tgagattgag taacgtgagg ttaagatagc    3900
acgtggaatg gcttttttctt ttctttctat tttttttttt ttttccctgg agacagggt    3960 tcactctgtt gcccaggctg gagtgcagag gcatgaccat ggctcactgc aacttcgatg    4020 tcctgggggtt aagcgatccc ccagcctcag cccccaagt ggctgggact acaggtgctc     4080
gccaccacac ctggctaatt tttgtatttt ttgtagaaaa tggggtttcat caatgttgtc    4140
```

```
cagactggtc tcgaactcct gacctcaagc aattctcctg cctcagcctc ccagactgct    4200
gggattacag gcgtgaacta ccacgcctgg cctggaatgg cttttgatgt tctcctatgt    4260
gcacatgtgg gtgaataaac accaacaaag tccttatgtt acctgaagag ttgctctctt    4320
cttaatattt aagtcgtatt tatttaaata ctttaatagt tgtacactat taaagtatta    4380
ttaggtcaaa atcaaggaag tacaaaaggg tatgctgtga aaaatctctt cttccttgct    4440
ctgcttactt acctaccccg catccccccca tacaccccag acacacacac acacacacac    4500
acacacacac acacacgcat cactcccata catgcccacc tgtttaccag ccaatcacat    4560 ttcttgggc aactcatctg agttgcttct cttccagag agttttttgca taaagaagca    4620 caggtatttc tgcgttacca tgaccctatt tcccagtggt tcctagccag ttgactctcc    4680
tgcactggat accatcctgg acagcattcc ttagggaaat gagcccctg ttttttccca    4740 ccatggcaca gttggtcctt tgcatggacg caccattatt gcccctgtct cttcttggtg    4800
gaccttaagg ttttctccat cctttttgctg taacacacac tgctccaagt gtgtgagcat    4860
atcagtagga aacgcttcca ggagtagaac tgctaggtca gagggcgtgt ggatctgtaa    4920
cctgacagac ctagaccggc ttcagtttgg ttttatccag tttccatatt gattattcat    4980 ataaaggaa acagacaaac ataacgctgt gcatgtattc tctcttagac cagaacaggc    5040
atagggtgca ctttttaattt gtccatttcg tagagtagaa attgttttttg ctgaaatgaa    5100 caccttagga tgctgaagaa tatgacccgt cccatgaaaa acattcaaaa atgtgtgtag    5160
cgctttcttc ccaagggtgt gtgtgcgcat attttaacac taattcactt tctacttccg    5220
ttgctatcct ttctgtgagt cttttctcaga atctcagaaa agaaactaaa ttgttcactc    5280
tagttatcaa tgctgtactc tatacctgga atttgctaaa agggcagatt ttaagtattc    5340
tcaccacaga aaagagaaaa gaaaatggta attatgtgac gtggtggaca tgttaactag    5400
ctttattatg gtgagcattt cacagcggat atccagtcat cacgctgtac acattaaaca    5460
tgtacaattg ggtttttttg agacaaggtc tccttctgtc acccagtctg gagtgcagtg    5520
gctcagtcat ggctcattgc agcctcgacc tcctgggctc aatccatcct tcccccctcag    5580 cctcctgaaa agctggggcc acaggcatgt accatcatgc caggctaatg catatatatt    5640 tatattttttt ggtggagatg gggttggtct cgaactctgg gctcaagtga tcctcccgcc    5700
ttgcccttcc aaagtgctga gattacaggc atgaaccaca gcaccaggcc tacatgtaaa    5760 attttttattt gtcaactata ctttgacaaa gctgagaaaa aaatcctaa tatttaaaaa    5820 aaaaaaaaaa aggactagct tgagaccttt tccagctctc tggcttatca gctgccgtct    5880
cttccgggtg cagatagctg gaagggaaag aaaatcccta aaattaccca caagccaaga    5940
atgaagtgtc tccctttgag ccacagtggc agttttgttt ttaatcatag aagtgtatt    6000 tgagccgggt gtgctggctc acgcctgtaa tcccgcact ttgggaggcc gaggtggggg    6060
gcggaggggg tggggatcgc ctgaggtcag gagttcgaga ccagcctgac caacatggag    6120
aaaccccgtc tctactaaaa atacaaaatt agccggcgtg gtggtgcatg cctgtaatcc    6180
cagctactca tgaggctgag tcaggagaat ctcttgaacc caggaggtgg aggttgcggt    6240
gagctgagat catgccattg cactccagcc tgggaacaag aaaaaaaaag aagaagaaga    6300
agaagtgtat tcatttcagt tacttttaaa aaagtgaaca gactttatat tttagagcgg    6360
ttttaggttt acagaaaatg aaacagacag ggcagcgagc tccttgtact cctccccagc    6420
acacagttgc cctgttatga acatcccaca tcagtgctgt gcgttcatta acaccgatga    6480
acctgatgca tacattatga tgaactgaag tcctggactt cacccttcct cttgtacagt    6540
```

```
tctgtgggat tgacaaatg cataatgctg tacagccaca atgatagtat cgtccagagt    6600
agttctcctg ccttaaaacc tcttttgctg cacctgtttc tctctcccca ctcaccccag    6660
ctatctgatc ttcttagtgc ctccgaagtt ttggtctttt caggatgttg tagcgttgga    6720
atcatggagt atgtagcctt caccacatac accttcctte actttgttgg cttcctttac    6780
ttagtaatat gcattcaagt ttcctccatg ccttttcatg gcttgatagc tcatttcttt    6840
ttagcaccaa ataatattcc gttgtccaga tgtagcacaa tgtttatcca ttcatgtaac    6900
ctgtgaccga ctcacagata ggatgtggaa tcactcacca cagaggcatt agacaataat    6960
cagacccaag tcatttcatg ggggaacaag cccacaggta ccagactgtc cagtgagtca    7020
gggccactcg taggaagtaa aagagaggc tagagcatag ccaggtcctc actttatact    7080
ttaagcccat gtgtatttct cccaaaccac acagcattgt ttccatgctt tcagctttgc    7140
atgaataacg tgatacttga acgcatcatt tatcacttgc tctctttccc acagcgctgt    7200
tttcaagctt cttcctgttc atgatgctct gcttaaccct taagctgcat gggattctgt    7260
tctgtgaata cgcccacccc atgtattatc ctgcccagca aaagtcccc aaaactctgg    7320 atggtggtta cctctaggga gggagagaag agattgggaa tagggagcga cttcaacggt    7380
gtttgtaatg ttttgtttct ttaaataaaa gagctgagat catttcagca gaatgttgat    7440
ttagagtctc ctggacaatt tgttgctcaa agtgctctct taaagagcac tttaaaaaaa    7500
aaaacctttt atcttattat ttatttattt atttattgag acggagtttt gctctgtcac    7560
ccaggctgga gtgagtggt gtgatctcag ctcactgcaa cctttacctc ctgggttcaa    7620
gcaattcccc tgcctcagcc tcccaagtag gtgggattac agatgcgtgc caccacactt    7680
ggctaatttt tgcattttag tagagatcgg tttctccatg ttggccaggc tgatctcaaa    7740
cgcctgacct caggtgatct gcccgccttg gcctcccaaa gtgctggtat tacaggcgtg    7800
agctaccatg cctggcttat cttatatatt tttaaaaaca gcttattgag atctaattta    7860
tgtaccataa aattcaagta tataattcag tgctttttata tataaaacat atatatgaaa    7920
tagcttattg agatataatt ttttatataa aacagcttat tgatatgtaa tgtatgtacc    7980
ataaaattta aatatataat tcactggctt ttatatattc acgaatatgt gcaactatca    8040
ccacagtcaa ttttagcata ttttcatcag ctcataaaga aacccccaagc ccttgaacta    8100 tcaccccata tccctcctcc cagcccgtcc ctcctactca taagcaacca ctaatctact    8160
tagtgtctat agatttccta ctctaggcat tccatgtgag cgggatcatg caatacgtgg    8220
gctcacacaa tataagtggc attccatgtg agtcggctca tgcagtatgt ccggctcctt    8280
tcactgagca taaggtcttc agcactcatc caggttgcag cctgtgtctg aatttcattc    8340
cctcttctgg ctgaatcgta ttccattgtg tatcttggac atatcctatt ctgctcaccc    8400
agccgttggt gggcgtttgg agtgtttcg cctttcagct gttttaagag ggttgcagtg    8460
aacatttgta caagttttgg acccaatgcc tgttttcaat tctcttgtgt agagagcact    8520
ttttagcaga aaagaatag atttgtggcc tcccttttgtg tgcggtcagt gccttgagaa    8580
gagtgaactg tgctgccacc tccggagccg tggagagcgc ggggcttggg tagcagctag    8640
gacgatacaa gttgggacaa ggccaggtgc aatggctcac gcctgtaatt ccaacacttt    8700
gggagaccga ggcagggga tcacctgagg tcaggagttc aagaccagcc tggccaacat    8760
ggtgaaaccc catctctaat aaaacagaaa aattaactgg acggggtggt ggacgcctgt    8820
aatcccagct actcgggagg ctgaggcagg agaatcactt gaacctggga ggcggaggct    8880
```

```
gcagtgagtg gagatcagac cactgcactt cagcctaggt gacagagcga gactccgtct   8940
caaaaaaaag aaaaaaaaag aaagaaactc atggataatc ctccctctcg tgcagttcgc   9000
ctctacggac caaacttcat ccttcaggtg tactcatctc agaggaagtc ctggcaccct   9060
gtgtgccaag acgactggaa cgagaactac gggcgggcgg cctgcaggga catgggctat   9120
aagtgagtat ggggcagcac ccgccgagtg acagtaacag acagcagaaa cacgagaaga   9180
ccctctctct gcctcccgt gaaagcaccg gcacatgagt gctggggaca attgtcacct   9240
tccaaaagct gagccctata accagcaggt ggaatttgtc ctgctagggc tgtgcccagc   9300
acacagacct tggctcactg ccaccttgcc ctgcctcctc cttggcctct atagactcct   9360
ggttgctcgg gagtgcccag tgctgtggtc atctggtcag aggggtaggc tgagggcgtt   9420
aggtgcctct ttttccaagg tgcctctcag ccagggtcca ttcacctccc tgggtagagg   9480
ttggaccaga acagctggcg aggagggttg ggctggggag agcagcagag acaaatcctg   9540
tgccagtttc acttcattcg ggagccatgg aagccttttg agctggggag agaatcaatc   9600
aatcagactg atacttaaaa aatgtcattc ctgctcgtag ctctgaggga aggtgggaag   9660
gcttaacagg gtgtgtgtcg cctgacagtg attcctaacg ggggtggggc ggtggttacc   9720
atttaccagc actgcctggg gagatgcggc agccctcagg catcggggga gagggtggta   9780
ggatgctact gccactttgt tttccatggg agggtcccca ggtgatttct atgcaacttt   9840
agggtattca atatgccagt tttcagaatg aattaccact cggtgagaaa gttggcatct   9900
tagctagtca ctgtgacatc cctaaacagc aggggtgaat tacacagcaa agccccccca   9960
tcacagtcca ggaacctggt ggaattgata actggggcca tgttaacatc tgtacctttt  10020
attagattaa atgtgtgtat gattatacaa tcctatgtcc ttctcatagt ttcttgatcc  10080
taacctggat aagaaacacg accaatgaag gaattttgtc tgacacttta gggttattga  10140
atcgaaaaat cgttacaata ttctagcact tggttagaac gtgtgatttt ttttcctaaa  10200
tgctaaggtt ttttccctctt attctgaatg tcgtatgagc ggtattatga catagtatag  10260
gatttgtgtt tgcttatgcc ttaaccatta tcacaaataa ggttttcttt tttaggaata  10320
atttttactc tagccaagga atagtggatg acagcggatc caccagcttt atgaaactga  10380
acacaagtgc cggcaatgtc gatatctata aaaaactgta ccacaggtat gcagcaattt  10440
cttcttgaaa aattttggaa tgaaatcaac taggagacac catggggaat cgttgtcctg  10500
agtctgattt ctctgagctg caatactcgg tctggatggg ttttgcattg ggaggagatt  10560
agagtctgac caggcctggt tactctaagc agccctggt ttattcatag gaagtggctg   10620
aggtttctct gctatttcat tttcagcctc taccgtctgc ccttgttggt agcggctcac  10680
acttgcaaca tcgacattca actctattta gttttctttc ctcttcagac atttagaggt  10740
gtacctattt tgtcagggcg tggttctagg aatccaagat aatgtctcag tgtcccagcc  10800
agggtgaccg gctcattcca gtttgccagg gacttcactg gcttgagcaa gggaagtcct  10860
gctccattcc aggcagctgg gctggctggt cccgttagcc caaccccgg acagcagtg   10920 ccagagggtg ctctgtgagg gatgggcagc attctggcgg cctgggaatg agttgtggtg  10980
tttccagggg gtagaagtgg gtacaagcca caggtcacat gatgagtggc tgacctggct  11040
gggagggcag aagaggggat ggacttaggc tcttcctttt gctttgcaca tatttaggat  11100
gtttgcagac ttgctatgat tgttgctgtt atgtgttttc tgatgtgaaa gatacacagt  11160
gtcctttgcc catgagctct ccttgcctcc caggtcccca gggcttatgc ctggtgtcta  11220
ggcatcacct ccctgcctgc caggtgccag gtgctgcatt tcggggagg atgaactaat   11280
```

```
caccccgcgc cacctttcct ctgagtggga gcctggggca ggtttgcatt cctggaggcc   11340
gctggtggag gggtctgggg gcctgacttc cactgcagcc tgctgtcctg gggaatgtgg   11400
cagggcaagc ccagtgggga gggctgtgca cggccaggtg cacccatcaa aacagcaggg   11460
ctgcggtttg tccctgtgga gaagctaaac acagctgcct gggcactttg taaatgctga   11520
gtggttcttt gtctttctgg gttacacacg gaatcaggga gccaagtcca gccgggcagg   11580
gacgggggga gggaggagg tgctgccgtc ccttggcaag agccttggga actcacaagg   11640
aggctggagg gcttggaaga aagaagagaa ggccattgtc tggtaggctc tattctatct   11700
cggtggtggt ggtgggggga ggcgcacttc ttttcctctt tctgtgcagc agttgccctt   11760
tgatgcctga gttcttggct tgttttctgt cgggcttctg tgaataacca catgtgccct   11820
ggcgctgtga ccacacaggg ctatccctac cgaccttagg attcttagga aatgtcttct   11880
cttaaagggg acatgtcttc acttggccgt gtcagtgccc cagagccaga gtccacctgg   11940
aatgcacctg tagtcactga gaacccgggg ggtgtgcctt agtaagaagg tgtcaggaag   12000
gacctattat tgtagggcct gggctcctgc aaggtggttt ggggtggtt ggaggaagca   12060 gagatttgct ctggattgga tgctgtcagg aagcagggg aattctgtga ggctgcttta   12120
ttattttttt tctaggagga ggttggaatg aggctaggct aaagctgtga ttggtaaaga   12180
aacgtccgtc gctcaagtta gccaggacag gaggagacat cagatcgtga ttttgtggtt   12240
gtgagcacaa ggttcctgtt ctgtctgttc agacatcatt tcggaggagg ctccttgtgt   12300
cttgccccat ctcaggcatg gagggcccta gtccgatatt gacgctcagt gaaataattc   12360
aggttccgca gagcacacgg cccagctatc agggcgggcc agctctgcat gccagggggcc   12420 gcgtcttccc ttctcagcat agcctgggaa attcactgca ggacaaaatg catcagttac   12480
ttcctcttca tccataacct gggatgtttg actcccaaat gagtaactct tacgtttctt   12540
ctaatcctag ggaaactatt ggttatattg cttttcaacac tacaaattta aagcagttat   12600
aggagcccag aggtttccaa atggcttcct taaaaattag aagatgattt taaattccaa   12660
gaggaaaaac aaaactagca ttattgtata cttaccctca caaccgtcct aggagctggt   12720
acaattttaa gagaggttaa gtaacttgcc caaggtcaca ctgtggggat gtgagccgcg   12780
taccttggct cagtgtctgg tctttgccac tgtccctata tggatttact taccttattg   12840
gagttgtaac tagcagaccc ttctatgtct cagaagacag gagagggaac atcggaagaa   12900
atgactgatt tctaagcatg tgagaggcag gtgactccgc actatcgtga ccagaatttc   12960
ccctgttctt tttgcagtga tgcctgttct tcaaaagcag tggtttcttt acgctgtata   13020
ggtaagttca tctggagtcc ccctttttgat acttctaact aggaaaagct ctctactttc   13080
agaacagtac tccctgtgtc tctggggcg tgggagggaa gaaggtgggg tcacgggttg   13140
gaatgtgccc agcggcgtct cgctcttttcc aaggagctcc tggtttagat tccatggcc   13200 tgtagacacc ttcagccttg ggtccaaggg acacccctg agatcaggca cgctcaagaa   13260
gctgacaaag ccctacactt tatgccaccc atgagctgga ggcccggcag gtctctttct   13320
ccagaaagca aaggggggtg gcgttagtga gccctggcag ccacctaacg tggacttgga   13380
gcatctgcgg ggctgtggtc cagcaccacc gtgtggccac caggtgctca tcagccagtg   13440
ggacccggga ggagggacaa gaccagagaa caacagtgct cttgcctctt ctctcctgaa   13500
ttttggacgg tggcttagac ttgggtgtcc ccatctctgt gtttagagtg cttacagtttt   13560 ccaaactgtt tgcaaatgtg gaagccaccg tccctctcct ctgggatggc ccagtgctgt   13620
```

```
cgtggggccg tggtcctgag ctcagctttt catttgaaga ggtggaagga gctgacaccg   13680
tcccatcccg gcagggctgg ctcaggtctt ctttaggtcc tgagtggggg tccagcacag   13740
ccccaagggt gcgtggcacc cgccctgccc tctgcccatg cactcatctc ctggtggaga   13800
agacactcac acacaggaag cagggaaggc agcagacctc actcacccct cacccccctca  13860 ctcacccccct actcaccccc tcaacctctc attcaccacc caccccctcg cccctcact   13920 cacccccctca ctccctcaac cctcactcac ctcctcactc cctcaaccct cactcacctc   13980
ctcacctcct cactctcccc ctcatccctc cctcacccca cccgtcacc tcctcactca    14040 cctcctcacc ccctcactca cccttcaccc cctcactcac cacctcacct cctcactcac   14100 ccctactca accctcatt caccccctcac ccctcactc accctgcac ccctcactc      14160 acccttcat ccactcaccc acctgctcac ctcctcactc aaccctcac ccctcacta      14220 atccctcact ccctcacccc ctcacgccct cactcacacc ttacctcct cactcacccc    14280 ctcacccct caaccccttta cttacccct cactcatccc ttcacccct actcacccc     14340 tctctcaccc attcaccccc tcactcatgc cttcacccc tcactcacct cctcactcac    14400
accttcaccc ctcagtcacc ccctcactca cccccttcacc ccctcaatca tgccttcact  14460
ccctcactca cccccttcacc ctctgaatta ctccctcatc ccctcactca cccccctcact 14520 caccccttca cccccctcacc caccacctca cccacccctc acccaccccc tcacctcctt  14580
acccctcacc ccctcactc accctcacc cctcactca ccacctcacc caccctcac      14640 ccacccctc actcactccc tcatccctc actcaccccc tcacccctc actcacccc      14700 tcacccaccc ctcacccacc ccctcacccc ctcactcacc ccttcacccc ctcactcacc   14760
ccctcactca cccttcacc cctcactca ccacctcacc caccctcac ccacccctc       14820 actcactccc tcacccctc actcacccc tcacccctc actcacccc tcatctcctc       14880 actcacccc tcacctcctc actcaccgc tcacctcctc actcacccc tcgccccctc     14940 actcacccct cacccctca ccccctcact caccctcac ccctcgccc cctcactcac      15000 ccctcgccc cctcactcac ccctcacccc ctcaccccct cactcatccc ctcacctcct   15060
cactcacccc ctcacctcct cactcaccccc ctcacctcct cactcacccc ctcacctcct 15120
cacccacccc ctcactcact ccctcacccc ctcacccct cactcacccc ctcacctcct   15180
cactcacccc ctcacctcct cacccacccc ctcactcact ccctcacccc ctcaccccct  15240
cactcacccc ctcacctcct cactcacccc ctcacctcct cactcacccc ctcacctcct  15300
cactcatgcc ctcacccct cactcaccct ttcacctcct tgctcatccc ctcacttacc   15360
ccctcacttc gtcaatcacc ccccacctc gtcaatcacc ccctcaccctt ttcactcacc  15420 ccctcactca cccccttact tcctcactta cctcctcacc ccccactcac ccctcaccc   15480 cccactcacc ccctcacccc acactcaccc cctcaccccc cactcaccccc ctcaccctc   15540 tcacctcctc actcacccccc tcacctcctc acttatcccc tcaccccctc aattacccc    15600 tcacccccctc aattactccc tcatcctttc aattacccac tcacccccctc acctcctcac  15660 tcctcactca ctccctcact caccccttca ccttctcact cacctcctcg tctcctcacc    15720
ccctcactca cttccagccc tgcccctccc atcttccttt tctttgtgtg agaatctggg    15780
gtccctgagt ggtgtcagtc cctccaagac tcaaggagtc cccagggcct tgttatccag    15840
aacaccccca cctgggtccc gggagacccc atgggatcac aggagtgttc agggaagtgg    15900
tgcttcctgg gtctgggtgg gctggagggg catcctccct tccccaagag gagaccccca    15960 ggagcccct aagtccatcc ccagcagtgg tgccctgcc ctgtccttgc agcctgggag      16020
```

```
acccttggga ggggcgggcg ctgggtggct gggcggcttc tgctggtctc accccactgg   16080
cctcctgttt gtcatcctca gcctgcgggg tcaacttgaa ctcaagccgc cagagcagga   16140
ttgtgggcgg cgagagcgcg ctcccggggg cctggccctg gcaggtcagc ctgcacgtcc   16200
agaacgtcca cgtgtgcgga ggctccatca tcaccccga gtggatcgtg acagccgccc   16260
actgcgtgga aaagtatgcc aggggcggcg cgggccgggt gggggctcag ggctggccta   16320
cagccaccct gtgaccttga gcaggtctca acccttgcag ccccggcatc cttgtgttta   16380
aatggggaga gtattgcacc tgcttcctag gctgtgaga catcaagtgc gctcatgcca   16440
ggcagtgcat ggctgtatgc actgagtgtc cctgcacgc agggcacagg gtgcaggtgg   16500
aacattctcc acgatgtcgc cgtgaccagc gttccttcca gccactgtcc tctgagctct   16560
gtcctgccct tgagcaaagc ccctgccccc tgaggtatcc tgtctccggg acgctagtcc   16620
caggagaggg cacactcaga caggcttcag gctgccctgc tggaaggtcc ctggggttaa   16680
gcgttcttgg ccacagcatt gctcatgcag agggttaggt aggggtgagg ctagccgtga   16740
cagtattagc atttatggac gctaccaccc cctccccttt tccttaaaca catagtgctt   16800
ttggtcacat gctgctttgg aggaggcctc acttggcgga tgtatttttc tgccttagag   16860
agaggctgaa ctgggtttga ctgttggccc agccctctct tgctgcgtgc ccttagacga   16920
ttcactcaac gtctctgatc catggcatgt acaactataa gatgggcatg cccttctcct   16980
ctcgggctgt tatgaaggtc aaggaagcaa gggctgttac ccaagggtgc tcccttctct   17040 cccctcttc acaccccag gtgctctggg ccctctagga actgggtttc tctcaagggc    17100
tgttacccaa gggtgctccc ttctctcccc ctcttcacac cactgggtgc tctgggccca   17160
ctaggagctg ggattctctt aagagggaaa ctcttggata aggaaatgg tttgattgat     17220 atcggacaag tctgttcatt agtatccatt tattaagcac ctaccatgtg ccaggaaatg   17280
ctttggcgta caaaggaaaa taagggccag tcctgctaga aatggccttg aaaccccagg   17340
gagggatgtc ggcccattgt gggtgctgca gattccttga aggtgatgca agagccagaa   17400
agaaggatga tgtgggggc tgaggcaggg agtcggggtt gggggagtgt ggggagaag     17460 gggagaccga gcacctcttc cactatctcc ctgtgtggtt tttggtgaac catcctgcct   17520
ctgggtgtct tgcctccagc ttctgacgtt ggaagttcat ccactgagag ctctgtgttt   17580
atggctctga gatactgagt ccttcttctc tcccagacct cttaacaatc catggcattg   17640
gacggcattt gcggggattt tgagacaatc tttcatgttc tatggagccg gataccaagt   17700
agaaaaagtg atttctcatc caaattatga ctccaagacc aagaacaatg acattgcgct   17760
gatgaagctg cagaagcctc tgactttcaa cggtacgtgt ggctcaggct tggcaagcag   17820
gttggcagaa tcttaaagag atgttgattg gaaatgacac ttgtgctatg ccaaatggaa   17880
gggaggcatt tgcgttgagc gagggtagcg tgcagcgggt ggccaatggg agaggctcac   17940
agaggctaag agcacctgcc gcattttggg ggaggcagca gccaccacat ctgttctgta   18000
ctgtactgag tggtggtgat tcaagccagg catggaaaag gctagaacag ggctttccca   18060
ctgcagcacc cttgacatct gggtggttct ctgttgtagg gctctcttgt gccttgtagg   18120
atgtttaaca gcgtccccag cctctaccca ctggaggcca gtagctacca agctgtgaca   18180
accagtgttg cctgctgaca ttgccaaaca tccgctttga ggcaaagtca cttccagttg   18240
agaactactg gcctaaaatg tgtaaagatc cttgatttt aaagatacat tctaaaacca    18300
agttgcttaa ttcaggacaa acatgctttc tcttagcctc ttattcggtc ccactctggt   18360
```

```
ccatccaagg gtctggaatg ttctagcccc atgtggatac agaagaagca aaacctcagc    18420
cctccctaca gcatgtctgt attcacattg ggaaatggtt cacatataga agagcgaatg    18480
cctgagcaat ggcgtggtgc ctctggggcg aaagctgact ccattgactc catcggcttt    18540
ttggctgttg cctcctgtgt gtctttcccg tcttgatcac ctggagatat gtaattttgg    18600
aagcagagct agcaaataat tcctcttata agcagagcta gcaaataatt ctacttataa    18660
gtagcataac gtcttgcctg ccagaaggag aggtctggca gggggagaaa gtgagaatgt    18720
gggacttgtt gggatgcagg gtcctctggg cagggtggcc agggtgccag gcccagcagc    18780
ctgcatgtgg gaaggccagg tggagacata ggtgataccc gcctggctca ctgtgttttc    18840
tcttcttgaa acagacctag tgaaaccagt gtgtctgccc aacccaggca tgatgctgca    18900
gccagaacag ctctgctgga tttccgggtg gggggccacc gaggagaaag gtgaggctgc    18960
tcctgggcac acaggactgc agggcccaca gatggagcat tgggttcgga agtgggaggt    19020
ccaggtttta atcccagttc tactactcaa tgactggatg actttggttg attccccag    19080 tccttgtgcc tcagtttctc catctgctaa gtgggagaaa tcctgcccag cctacctaat    19140
acactgtgtt cttatcgtga tcacacagag cagcatgtgg aatggctttt gaagtatctg    19200
ggccatacga gtttagaggt gcaggatctc ctgtgttgca ctcattgtga gtttagagct    19260
gccctggaga tcccaccaag gcctgcgtgg ctgagtgaca ggggggcttgg tgaggacggg    19320 catcctggac ccatggtggc cacatctaag cctgtcctct gccctgataa ccacagagag    19380
aggctctctc cacccacttc ctttgcaatc tgcatttctc tctgacagtc tttcaaatga    19440
agggagcctg gctgcttcat ttttatggag ggttggaagt gcttagtggc aggcacaaag    19500 gttcattta catattgttt atatccttct caaaagcgtc taggccatac agacaacaaa    19560
tcctttcaaa caagggaaa agtacaaagg ttgggtgatt tctggggagc gtcagggaag    19620 gtagtgggggg gcatcctggc tcctcatcag cagaaactta ctacagtaga gccacaggct    19680
gggcaaaaga cctcatggaa tccaagatga agggaatatc gacaaatatt tgtgcgcacc    19740
tgcacctagt acaggctggg tgctactcag gtgctgggaa tgcagaagtg aacagagtaa    19800
gacaaatgtc tctgctgtca ggagctttac ctctcttctg gatgtcggtg gtggggacgg    19860
ggcaggtgtg gtcagacaga tgggagacaa acaactgagc gaggtacttc caaacatctg    19920
agggtgggga tcacaaggtc ccggctattt tgaaggggtg gtcaggaaag gcttctcgga    19980
agaggtggca tttgagctga gactcaaatg gcaaaaatgt gtacacatca aaaaggctag    20040
tgcatgtatc ttcaggtgtg gtcaaggggc caaggaggtg ggctgggggcc agattgcata    20100 ggtccttgtg gattatggtg aagacaccag cttctcatct gcttgaggtg gggagatcgt    20160
gagccgggga gtgccatgat ctggcagctg cgtggggagt ggggatgaat ggatggagac    20220
gaggatgatg gtgacaagtc cattgctgtg gttccttgag acaggaagcc agctcatagc    20280
agagtgcggg cgtggatgtg aagagatgag ggtacactag gctagagcc accagactta    20340 ctgatgggtt gcatgtctgt gggagagaga gtgagaagtc agggacgatg gctttccact    20400
ctgtggctga gccccaggg tggcgggtgg tgccattttt caagccagga aatattggtt    20460
ggtgagaatt tggggtggga aaggtgtga cggagggttc tggttttgca cactaagccc    20520
acggtgccca gaagatgccc gaggggaggc agcaaagcga gagtgggaaa tgcagaggtg    20580
gcaagtgcag gccgtgtctt gagaagctct aatgtgcagg ggagccgaga agcaggcggc    20640
ctagggaggg tcacgtgtgc tccagaagag tgtgtgcatg ccagggggga aacaggcgcc    20700
tgtgtgtcct gggtgggggtt cagtgaggag tgggaaattg gttcagcaga accaagccgt    20760
```

```
tgggtgaata agaggggat tccatggcac tgatagagcc ctatagtttc agagctggga    20820
atttctttcc ctgaagctga actccagagc tgcattcagc acaggcaccg ccagttgtaa    20880
ggagaatcca ggtttcccag gagagggggtt ggtgctggga tgagctgacc ggggcagggc    20940
tggaaaatag ggctgtgacc atctgtgtag tgcgtgtgga ggtctcaggg agggaagtgt    21000
gctctccctg cgagagctgc aggcaacact gggagctcaa caagtctccc tgtccttagg    21060
gaagacctca gaagtgctga acgctgccaa ggtgcttctc attgagacac agagatgcaa    21120
cagcagatat gtctatgaca acctgatcac accagccatg atctgtgccg gcttcctgca    21180
ggggaacgtc gattcttgcc aggtaattca acattttat tctacctttg gtccttacca    21240
gatcctactg aaccccccat gagagagagg gcattcttgg ggtcagcaga gcctcctcag    21300
tgacacggag ccagctcggg gcagtcatgg gaagtgacgg ccacaaacag tgcgaacgct    21360
tctggtggca gaaggaagta cagtcaacaa atcacacaca ccctctgaaa aaccggtatt    21420
tggtaaaagt gccagtggaa cagaaacaag tatttagact attttaaatt atgaacggca    21480
atttatttag taacttttag cttgaacaga ttaaaattca ggatgggggc tatctctttg    21540
ggggttacat ctctgttacc atcaccccctt gatggtggag attcgaagcc cacacagtca    21600
ctcgtaactc acactgcgac ccccgccccc caactcctct aggcctggtc agtggtgtgc    21660
ggcagattgt gacttgattt tctgctctct gtaccttgct gtgtcccaca gggtgacagt    21720
ggagggcctc tggtcacttc gaagaacaat atctggtggc tgatagggga tacaagctgg    21780
ggttctggct gtgccaaagc ttacagacca ggagtgtacg ggaatgtgat ggtattcacg    21840
gactggattt atcgacaaat gagggtaact atcctgtcct ccttctgact gtgttctccg    21900
attcctcgag ccaaagccag acatctgtta ggcgtggttc tgctgctgga agctgactgg    21960
tgaccactgg tcagcatgaa gcaaactctg cttcctccag ccacagcccc atcccccag    22020
tgtccaccca ttgcccattg cctctcactg gcttcacttg catatttccc ctggtgtttg    22080
gatgaaaagc gctgggggctc agcttgtgtg aaattccttg gtgctctgcc aaccacactt    22140
cgttctggct cagctgactc agctgttcca cccaggccac ctcacatcaa actttttttt    22200
ttttttttg agatggagtc tcactgtgtc gcccaggctg gagtgcagtg gcacaatctc    22260
gactcactgc aacctttgcc tcctgggttc aagtgattct cctgcctcag cctcccaagt    22320
agctgggact acaggcatgc gccaccacgc ccagctactt tttgtatttt tagtagagat    22380
ggggtttctc catgttggcc aggctggtct cgaagccctg acctcaggtg attcacccac    22440
ctcagcctcc cacagtgctg ggattacaag tgtgaaccac ggtgcccggc ctcacatgaa    22500
acttttgatt tatagagagc agagggaaga gccggctgtg cccatccttt tctggggcca    22560
tcgagtggct cctgggcagc ccccaaggtt aggaagggca ggagcagcca gggttctctg    22620
atgccccaga ctcaagcacg agggaaggtc tcaggggttc catgtgagcc tcatggatgt    22680
ctctgcttag cagagccctg gctttgggca ttgtccagat aggggtgag aaccagatct    22740
tctcatctcc aggacctcag acgtatagtt ttctcagatt tctgtgcttt ctggggctgg    22800
gctactagtg gaagaaagca gtctattctg tcttctccca aatctcccag atgcccagtc    22860
tgttgaagga ggagcagaac caggggggcct ttcccgctga ggcccgacct gtgtctcctt    22920
caaatgacac gcgggactca gggccttccc atgaccatgg ggcccagggg gcgtcacctg    22980
gcccagggcc cagtgctaga aacagatgac cccaggagga ggaggcaggg caggagggaa    23040
gctggcaggg ctgggatggt cagccaggct gaggggcgga ctcgcaccag gatggagcta    23100
```

```
ggaaatgatc caggtgtgtt tggcggctgc aggtgggtcc gcatggctgt gcagggaggg    23160
aagggctgcg tggcaggaga gcagccgggg gaggcccaga ctctgctgaa gagatgcctg    23220
ttgtgccggc ctccacatcc gctgcccgct ccttccggag ctcctgcccc gccatgctca    23280
gcctgactct gaccaacacg ttggagagaa gaatgatccc tttgtgctat taagcttgct    23340
tatttggttt ctaagtgctt catgcgaacc tagaggaaaa aattattttc cacctttgtt    23400
tgtcttaaga aaataacaca cttttttttt tcctatttga acaggcagac ggctaatcca    23460
catggtcttc gtccttgacg tcgttttaca agaaaacaat ggggctggtt ttgcttcccc    23520
gtgcatgatt tactcttaga gatgattcag aggtcacttc atttttatta aacagtgaac    23580
ttgtctggct ttggcactct ctgccattct gtgcaggctg cagtggctcc cctgcccagc    23640
ctgctctccc taaccccttg tccgcaaggg gtgatggccg gctggttgtg ggcactggcg    23700
gtcaagtgtg gaggagaggg gtggaggctg ccccattgag atcttcctgc tgagtccttt    23760
ccaggggcca attttggatg agcatgggag ctgtcacctct cagctgctgg atgacttgag    23820
atgaaaaagg agagacatgg aaaggagac agccaggtgg cacctgcagc ggctgccctc    23880
tggggccact tggtagtgtc cccagcctac ctctccacaa ggggattttg ctgatgggtt    23940
cttagagcct tagcagccct ggatggtggc cagaaataaa gggaccagcc cttcatgggt    24000
ggtgacgtgg tagtcacttg taaggggaac agaaacattt tgttcttat ggggtgagaa    24060 tatagacagt gcccttggtg cgaggaagc aattgaaaag gaacttgccc tgagcactcc    24120
tggtgcaggt ctccacctgc acattgggtg gggctcctgg gagggagact cagccttcct    24180
cctcatcctc cctgacctg ctcctagcac cctggagagt gcacatgccc cttggtcctg    24240
gcagggcgcc aagtctggca ccatgttggc ctcttcaggc ctgctagtca ctggaaattg    24300
aggtccatgg gggaaatcaa ggatgctcag tttaaggtac actgttttcca tgttatgttt    24360 ctacacattg ctacctcagt gctcctggaa acttagcttt tgatgtctcc aagtagtcca    24420
ccttcattta actctttgaa actgtatcat cttttgccaag taagagtggt ggcctatttc    24480
agctgctttg acaaaatgac tggctcctga cttaacgttc tataaatgaa tgtgctgaag    24540
caaagtgccc atggtggcgg cgaagaagag aaagatgtgt tttgttttgg actctctgtg    24600
gtcccttcca atgctgtggg tttccaacca ggggaagggt ccctttttgca ttgccaagtg    24660 ccataaccat gagcactact ctaccatggt tctgcctcct ggccaagcag gctggtttgc    24720
aagaatgaaa tgaatgattc tacagctagg acttaacctt gaaatggaaa gtcatgcaat    24780
cccatttgca ggatctgtct gtgcacatgc ctctgtagag agcagcattc ccagggacct    24840
tggaaacagt tggcactgta aggtgcttgc tccccaagac acatcctaaa aggtgttgta    24900
atggtgaaaa cgtcttcctt ctttattgcc ccttcttatt tatgtgaaca actgtttgtc    24960 ttttttttgta tctttttttaa actgtaaagt tcaattgtga aaatgaatat catgcaaata    25020
aattatgcaa tttttttttc aaagtaacta ctgcatcttt gaagttctgc ctggtgagta    25080
ggaccagcct ccatttcctt ataagggggt gatgttgagg ctgctggtca gaggaccaaa    25140
ggtgaggcaa ggccagactt ggtgctcctg tggttctcga gataacttcg tataatgtat    25200
gctatacgaa gttatgctag taactataac ggtcctaagg tagcgagcta gctccacgtg    25260
gctttgtccc agacttcctt tgtcttcaac aaccttctgc aagaaaacca agggcctgaa    25320
ttttaacttc ctg                                                      25333

<210> SEQ ID NO 7
<211> LENGTH: 491
```

<212> TYPE: PRT
<213> ORGANISM: Artificial Sequence
<220> FEATURE:
<223> OTHER INFORMATION: Recombinant protein

<400> SEQUENCE: 7

```
Met Ala Leu Asn Ser Gly Ser Pro Pro Gly Ile Gly Pro Cys Tyr Glu
1               5                   10                  15

Asn His Gly Tyr Gln Ser Glu His Ile Cys Pro Pro Arg Pro Pro Val
            20                  25                  30

Ala Pro Asn Gly Tyr Asn Leu Tyr Pro Ala Gln Tyr Tyr Pro Ser Pro
        35                  40                  45

Val Pro Gln Tyr Ala Pro Arg Ile Thr Thr Gln Ala Ser Thr Ser Val
    50                  55                  60

Ile His Thr His Pro Lys Ser Ser Gly Ala Leu Cys Thr Ser Lys Ser
65                  70                  75                  80

Lys Lys Ser Leu Cys Leu Ala Leu Ala Leu Gly Thr Val Leu Thr Gly
                85                  90                  95

Ala Ala Val Ala Ala Val Leu Leu Trp Lys Phe Met Gly Ser Lys Cys
            100                 105                 110

Ser Asn Ser Gly Ile Glu Cys Asp Ser Ser Gly Thr Cys Ile Asn Pro
        115                 120                 125

Ser Asn Trp Cys Asp Gly Val Ser His Cys Pro Gly Gly Glu Asp Glu
130                 135                 140

Asn Arg Cys Val Arg Leu Tyr Gly Pro Asn Phe Ile Leu Gln Val Tyr
145                 150                 155                 160

Ser Ser Gln Arg Lys Ser Trp His Pro Val Cys Gln Asp Asp Trp Asn
                165                 170                 175

Glu Asn Tyr Gly Arg Ala Ala Cys Arg Asp Met Gly Tyr Lys Asn Asn
            180                 185                 190

Phe Tyr Ser Ser Gln Gly Ile Val Asp Asp Ser Gly Ser Thr Ser Phe
        195                 200                 205

Met Lys Leu Asn Thr Ser Ala Gly Asn Val Asp Ile Tyr Lys Lys Leu
    210                 215                 220

Tyr His Ser Asp Ala Cys Ser Ser Lys Ala Val Val Ser Leu Arg Cys
225                 230                 235                 240

Ile Ala Cys Gly Val Asn Leu Asn Ser Ser Arg Gln Ser Arg Ile Val
                245                 250                 255

Gly Gly Glu Ser Ala Leu Pro Gly Ala Trp Pro Trp Gln Val Ser Leu
            260                 265                 270

His Val Gln Asn Val His Val Cys Gly Gly Ser Ile Ile Thr Pro Glu
        275                 280                 285

Trp Ile Val Thr Ala Ala His Cys Val Glu Lys Pro Leu Asn Asn Pro
    290                 295                 300

Trp His Trp Thr Ala Phe Ala Gly Ile Leu Arg Gln Ser Phe Met Phe
305                 310                 315                 320

Tyr Gly Ala Gly Tyr Gln Val Glu Lys Val Ile Ser His Pro Asn Tyr
                325                 330                 335

Asp Ser Lys Thr Lys Asn Asn Asp Ile Ala Leu Met Lys Leu Gln Lys
            340                 345                 350

Pro Leu Thr Phe Asn Asp Leu Val Lys Pro Val Cys Leu Pro Asn Pro
        355                 360                 365

Gly Met Met Leu Gln Pro Glu Gln Leu Cys Trp Ile Ser Gly Trp Gly
    370                 375                 380
```

```
Ala Thr Glu Glu Lys Gly Lys Thr Ser Glu Val Leu Asn Ala Ala Lys
385                 390                 395                 400

Val Leu Leu Ile Glu Thr Gln Arg Cys Asn Ser Arg Tyr Val Tyr Asp
            405                 410                 415

Asn Leu Ile Thr Pro Ala Met Ile Cys Ala Gly Phe Leu Gln Gly Asn
                420                 425                 430

Val Asp Ser Cys Gln Gly Asp Ser Gly Gly Pro Leu Val Thr Ser Lys
            435                 440                 445

Asn Asn Ile Trp Trp Leu Ile Gly Asp Thr Ser Trp Gly Ser Gly Cys
                450                 455                 460

Ala Lys Ala Tyr Arg Pro Gly Val Tyr Gly Asn Val Met Val Phe Thr
465                 470                 475                 480

Asp Trp Ile Tyr Arg Gln Met Arg Ala Asp Gly
                485                 490

<210> SEQ ID NO 8
<211> LENGTH: 2267
<212> TYPE: DNA
<213> ORGANISM: Mus musculus

<400> SEQUENCE: 8
ccggttgtgt tataggactt gaccagcccc aatagtcctc aagtcactcc tagatacagt      60
ggcaggtggt agctggcttg cggaaggaag aggaagaaga gaatgtgggc catcaaggag     120
caaggccagc cttgcacttg gccccctct gctcagtgct gaccagggct ttctgagccg      180
cttcctaatg aggctcattt gaagaccccc ccccaccccc ctcctgctgt cttgggtggc     240
agagctagct ccaggctgta agaaaattag gaggattacc aaagcagtat ggagtcagac     300
agtggccaac ccctcaacaa ccgtgatatt gttccctttc gcaaacccg aaggccccag     360 gagaccttca aaaggtggg gatccccatc attgcagtgc tgctgagcct gatagccctc     420
gtgattgtgg cccttctcat caaggtgatt ctggataaat actacttcat ctgcggcagt     480
cccctgacct tcattcagag gggccagttg tgtgacggcc accttgactg cgcctcaggg     540
gaggatgagg aacactgtgt caaggacttc cctgaaaagc ccggagtggc agtccggctc     600
tccaaggaca gatccaccct gcaggtgctg gatgcagcca gggacctg gcctcagtc       660 tgtttcgaca acttcacaga agcactggcc aagacagcct gcagacagat gggctatgac     720
agccagcccg ctttcagagc agtggagatc cgtccagatc agaacctccc tgttgctcaa     780
gtcacaggaa acagccagga acttcaggtg cagaatggaa gcagatcctg cctctcaggc     840
tccctggttt ccttgcgctg ccttgactgt ggaaagagcc tgaagactcc tcgtgtggtg     900
ggtggggtgg aggcccctgt ggattcttgg ccgtggcagg tcagcatcca gtacaacaag     960
cagcatgtct gtggtgggag catcctggat ccccactgga tcctcacagc agcccactgc    1020
ttcaggaagt atcttgatgt gtcaagctgg aaggtcaggg caggctcaaa catactgggt    1080
aactctccat ccttgcctgt ggccaagatc ttcatcgctg aacccaatcc tctgtacccc    1140
aaagagaagg acattgccct tgttaagctg cagatgccac tcacattctc aggctcagtc    1200
aggcccatct gcctgccctt ctctgatgag gtgcttgtcc cagccacacc agtctgggtc    1260
attggatggg gctttacaga agaaaacgga ggaaagatgt ctgacatgct actgcaggca    1320
tcagtccagg tcattgacag cacacggtgc aatgcagagg atgcctacga aggggaagtg    1380
accgctgaga tgctgtgtgc aggtaccccca cagggtggca aggacacctg ccagggtgac    1440
agtggtgggc ctttgatgta ccattctgac aagtggcagg tagtaggcat cgtgagctgg    1500
```

```
ggccatggat gcggcggccc aagtactcct ggagtgtata ccaaggtcac tgcctatctc   1560
aactggatct acaatgttcg gaagtctgag atgtaacgct gccgtccccc acatccagaa   1620
gctgcttccc ttcagaccta cctacggcat gacccctcaa agtcagatat gggacaagag   1680
cctccttgaa caaactctgg tatccctgca gcaagcaagg atacattgca gaggtgcccg   1740
gagtggagtc agatgggcta gctcagccac ccctgcatct cccaaaccct gggagacatg   1800
tggcccatgg gagtaaatcc aggacattga ctcaactctc agaagtgtta ttcagtcaag   1860
gaggctctcc cttccactga aggaaggaaa gtcagctctc tcctgaaagg ccagatcact   1920
ggctgagtag atgagacaag ggtatgaaag gcctttgcca tcttctttgc ccagtcctga   1980
aagcactgac gtaagagacc agtcagttct aatgtaaggt gtatatttta gtgtcagggt   2040
attgcaattg tcacctctgt ggtcaatatc attaaacagg tatgagaatt cgctggcata   2100
gacttcctgg tctgcttaat aagaatccaa ctaaggatgt cacatgacag tttcccagaa   2160
aatgtgaaca gtgtccatc tgacacacgg caccaatgac aaaccaaaga agttattctg    2220
cctgagtctc agttgctgaa ctaataaatt agctgcggtt tcttgca                 2267
```

<210> SEQ ID NO 9
<211> LENGTH: 435
<212> TYPE: PRT
<213> ORGANISM: Mus musculus

<400> SEQUENCE: 9

```
Met Glu Ser Asp Ser Gly Gln Pro Leu Asn Asn Arg Asp Ile Val Pro
1               5                   10                  15

Phe Arg Lys Pro Arg Arg Pro Gln Glu Thr Phe Lys Lys Val Gly Ile
            20                  25                  30

Pro Ile Ile Ala Val Leu Leu Ser Leu Ile Ala Leu Val Ile Val Ala
        35                  40                  45

Leu Leu Ile Lys Val Ile Leu Asp Lys Tyr Tyr Phe Ile Cys Gly Ser
    50                  55                  60

Pro Leu Thr Phe Ile Gln Arg Gly Gln Leu Cys Asp Gly His Leu Asp
65                  70                  75                  80

Cys Ala Ser Gly Glu Asp Glu Glu His Cys Val Lys Asp Phe Pro Glu
                85                  90                  95

Lys Pro Gly Val Ala Val Arg Leu Ser Lys Asp Arg Ser Thr Leu Gln
            100                 105                 110

Val Leu Asp Ala Ala Thr Gly Thr Trp Ala Ser Val Cys Phe Asp Asn
        115                 120                 125

Phe Thr Glu Ala Leu Ala Lys Thr Ala Cys Arg Gln Met Gly Tyr Asp
    130                 135                 140

Ser Gln Pro Ala Phe Arg Ala Val Glu Ile Arg Pro Asp Gln Asn Leu
145                 150                 155                 160

Pro Val Ala Gln Val Thr Gly Asn Ser Gln Glu Leu Gln Val Gln Asn
                165                 170                 175

Gly Ser Arg Ser Cys Leu Ser Gly Ser Leu Val Ser Leu Arg Cys Leu
            180                 185                 190

Asp Cys Gly Lys Ser Leu Lys Thr Pro Arg Val Gly Gly Val Glu
        195                 200                 205

Ala Pro Val Asp Ser Trp Pro Trp Gln Val Ser Ile Gln Tyr Asn Lys
    210                 215                 220

Gln His Val Cys Gly Gly Ser Ile Leu Asp Pro His Trp Ile Leu Thr
225                 230                 235                 240
```

```
Ala Ala His Cys Phe Arg Lys Tyr Leu Asp Val Ser Ser Trp Lys Val
            245                 250                 255

Arg Ala Gly Ser Asn Ile Leu Gly Asn Ser Pro Ser Leu Pro Val Ala
        260                 265                 270

Lys Ile Phe Ile Ala Glu Pro Asn Pro Leu Tyr Pro Lys Glu Lys Asp
    275                 280                 285

Ile Ala Leu Val Lys Leu Gln Met Pro Leu Thr Phe Ser Gly Ser Val
    290                 295                 300

Arg Pro Ile Cys Leu Pro Phe Ser Asp Glu Val Leu Val Pro Ala Thr
305                 310                 315                 320

Pro Val Trp Val Ile Gly Trp Gly Phe Thr Glu Glu Asn Gly Gly Lys
            325                 330                 335

Met Ser Asp Met Leu Leu Gln Ala Ser Val Gln Val Ile Asp Ser Thr
            340                 345                 350

Arg Cys Asn Ala Glu Asp Ala Tyr Glu Gly Glu Val Thr Ala Glu Met
        355                 360                 365

Leu Cys Ala Gly Thr Pro Gln Gly Gly Lys Asp Thr Cys Gln Gly Asp
    370                 375                 380

Ser Gly Gly Pro Leu Met Tyr His Ser Asp Lys Trp Gln Val Val Gly
385                 390                 395                 400

Ile Val Ser Trp Gly His Gly Cys Gly Gly Pro Ser Thr Pro Gly Val
            405                 410                 415

Tyr Thr Lys Val Thr Ala Tyr Leu Asn Trp Ile Tyr Asn Val Arg Lys
            420                 425                 430

Ser Glu Met
        435

<210> SEQ ID NO 10
<211> LENGTH: 3543
<212> TYPE: DNA
<213> ORGANISM: Homo sapiens

<400> SEQUENCE: 10
atcattccag tttggcaact tcacttgtag ggctgtttta atcaagctgc ccaaagtccc      60
ccaatcactc ctggaataca cagagagagg cagcagcttg tcagcggac aaggatgctg     120 ggcgtgaggg accaaggcct gccctgcact cgggcctcct ccagccagtg ctgaccaggg    180
acttctgacc tgctggccag ccaggacctg tgtggggagg ccctcctgct gccttggggt    240
gacaatctca gctccaggct acagggagac cgggaggatc acagagccag catggatcct    300
gacagtgatc aacctctgaa cagcctcgat gtcaaacccc tgcgcaaacc ccgtatcccc    360
atggagacct tcagaaaggt ggggatcccc atcatcatag cactactgag cctggcgagt    420
atcatcattg tggttgtcct catcaaggtg attctggata aatactactt cctctgcggg    480
cagcctctcc acttcatccc gaggaagcag ctgtgtgacg agagctgga ctgtcccttg     540 ggggaggacg aggagcactg tgtcaagagc ttccccgaag gcctgcagt ggcagtccgc     600 ctctccaagg accgatccac actgcaggtg ctggactcgg ccacagggaa ctggttctct    660
gcctgtttcg acaacttcac agaagctctc gctgagacag cctgtaggca gatgggctac    720
agcagcaaac ccactttcag agctgtggag attggcccag accaggatct ggatgttgtt    780
gaaatcacag aaaacagcca ggagcttcgc atgcggaact caagtgggcc ctgtctctca    840
ggctccctgg tctccctgca ctgtcttgcc tgtgggaaga gcctgaagac ccccgtgtg    900 gtgggtgggg aggaggcctc tgtggattct tggccttggc aggtcagcat ccagtacgac    960
```

```
aaacagcacg tctgtggagg gagcatcctg accccccact gggtcctcac ggcagcccac    1020
tgcttcagga acataccga tgtgttcaac tggaaggtgc gggcaggctc agacaaactg    1080
ggcagcttcc catccctggc tgtggccaag atcatcatca ttgaattcaa ccccatgtac    1140
cccaaagaca atgacatcgc cctcatgaag ctgcagttcc cactcacttt ctcaggcaca    1200
gtcaggccca tctgtctgcc cttctttgat gaggagctca ctccagccac cccactctgg    1260
atcattggat ggggctttac gaagcagaat ggagggaaga tgtctgacat actgctgcag    1320
gcgtcagtcc aggtcattga cagcacacgg tgcaatgcag acgatgcgta ccaggggaa     1380
gtcaccgaga agatgatgtg tgcaggcatc cggaagggg gtgtggacac ctgccagggt     1440
gacagtggtg ggcccctgat gtaccaatct gaccagtggc atgtggtggg catcgttagt    1500
tggggctatg gctgcggggg cccgagcacc ccaggagtat acaccaaggt ctcagcctat    1560
ctcaactgga tctacaatgt ctggaaggct gagctgtaat gctgctgccc ctttgcagtg    1620
ctgggagccg cttccttcct gccctgccca cctggggatc ccccaaagtc agacacagag    1680
caagagtccc cttgggtaca cccctctgcc cacagcctca gcatttcttg gagcagcaaa    1740
gggcctcaat tcctataaga accctcgca gcccagaggc gcccagagga agtcagcagc     1800
cctagctcgg ccacacttgg tgctcccagc atcccaggga gagacacagc ccactgaaca    1860
aggtctcagg ggtattgcta agccaagaag gaactttccc acactactga atggaagcag    1920
gctgtcttgt aaaagcccag atcactgtgg gctggagagg agaaggaaag ggtctgcgcc    1980
agccctgtcc gtcttcaccc atccccaagc ctactagagc aagaaaccag ttgtaatata    2040
aaatgcactg ccctactgtt ggtatgacta ccgttaccta ctgttgtcat tgttattaca    2100
gctatggcca ctattattaa agagctgtgt aacatctctg catagggcta gctggaatgc    2160
ttgataagaa ctgagctggg atgattgaac tttcattctt tggcttgggg agaaaagaag    2220
tcctggggaa gcaattgagt ctcaaagtag aggcagggga aaaagagtt agggagacca     2280
gatctgctga gtggcagcaa gagtgagctg cagattacag aaaccagggt gagcaagttt    2340
gagtcccaca cagggccttc tccctttgcc tctttccctc cctccctgcc tgtgataatc    2400
agccaggagc cagggataac ctatgacttg ggaaagagat gagttaggca gtcaaggggtg   2460
acattcaatc agggatccac aagtggctgg aaagaaatgc tggtcctgtg tcctaacttt    2520
ttccgcctgg agagccctca gtgtggcttc ttacatttaa aaaacaaaaa ggatcagctg    2580
ccaggtgtga ggcagtcccc aagctgagtt gtgaggatgt aagcatgaat aagtccctgc    2640
actcaaaatg gtcaaagaat taaaccccat ggctttttt ggcatctgta tgaaagcttg     2700
ggttttctga ggactgtctt gctatagtta agtcagatcc tagtgaaat atacttgttc     2760
atactgtact aggttcttag gaaacaacag aattcctcaa atgccaaaaa caagaaaat     2820
agaaacccag aaaacaaaac aaaataaaac aaaaccatca gaactgtgag tggaaactaa    2880
ggtgatgatc tgggagcaat acactaaaat cttgggtcga gacctatatg aaggctggca    2940
gtggagctaa acctggacac actgaagaca agggagctga accagggctc ctacatgaag    3000
cagggataac tgatggcagt aaatgtggtc tcaaattgca gatggtctgg aggaaaattt    3060
cccaaattta gagcctcagg attcccaaag atcctccaaa tatgagctca caatcaaaga    3120
tcagagacgt tgaaaaataa aaaacacctt aagtgggcag cataaaaaac agctaattta    3180
gaaccccaaa ggcttcagat gtcagaatat tagagactta tgataataag caatatttgc    3240
agagtatttg tatgtgccag acactattgt aagtgcttca tcatgtactg attcatttaa    3300
tactcacaga aatctgtgag atgggtatta ttcttatcct cactctatgg attaaaaaaa    3360
```

-continued

```
ctaaggcaca aagtggttaa gctccttgcc tgagattata gactgtaagt tgaacgtgag    3420
cacttggaat acagagttca tgctgtaaac taccacacta tagggcctcc aatatgataa    3480
tttataaaat atttgaataa aaaatgaata ctagttccac attttaaaaa aaaaaaaaaa    3540
aaa                                                                  3543
```

<210> SEQ ID NO 11
<211> LENGTH: 437
<212> TYPE: PRT
<213> ORGANISM: Homo sapiens

<400> SEQUENCE: 11

```
Met Leu Gln Asp Pro Asp Ser Asp Gln Pro Leu Asn Ser Leu Asp Val
1               5                   10                  15

Lys Pro Leu Arg Lys Pro Arg Ile Pro Met Glu Thr Phe Arg Lys Val
            20                  25                  30

Gly Ile Pro Ile Ile Ile Ala Leu Leu Ser Leu Ala Ser Ile Ile Ile
        35                  40                  45

Val Val Val Leu Ile Lys Val Ile Leu Asp Lys Tyr Tyr Phe Leu Cys
    50                  55                  60

Gly Gln Pro Leu His Phe Ile Pro Arg Lys Gln Leu Cys Asp Gly Glu
65                  70                  75                  80

Leu Asp Cys Pro Leu Gly Glu Asp Glu His Cys Val Lys Ser Phe
                85                  90                  95

Pro Glu Gly Pro Ala Val Ala Val Arg Leu Ser Lys Asp Arg Ser Thr
            100                 105                 110

Leu Gln Val Leu Asp Ser Ala Thr Gly Asn Trp Phe Ser Ala Cys Phe
        115                 120                 125

Asp Asn Phe Thr Glu Ala Leu Ala Glu Thr Ala Cys Arg Gln Met Gly
    130                 135                 140

Tyr Ser Ser Lys Pro Thr Phe Arg Ala Val Glu Ile Gly Pro Asp Gln
145                 150                 155                 160

Asp Leu Asp Val Val Glu Ile Thr Glu Asn Ser Gln Glu Leu Arg Met
                165                 170                 175

Arg Asn Ser Ser Gly Pro Cys Leu Ser Gly Ser Leu Val Ser Leu His
            180                 185                 190

Cys Leu Ala Cys Gly Lys Ser Leu Lys Thr Pro Arg Val Val Gly Gly
        195                 200                 205

Glu Glu Ala Ser Val Asp Ser Trp Pro Trp Gln Val Ser Ile Gln Tyr
    210                 215                 220

Asp Lys Gln His Val Cys Gly Gly Ser Ile Leu Asp Pro His Trp Val
225                 230                 235                 240

Leu Thr Ala Ala His Cys Phe Arg Lys His Thr Asp Val Phe Asn Trp
                245                 250                 255

Lys Val Arg Ala Gly Ser Asp Lys Leu Gly Ser Phe Pro Ser Leu Ala
            260                 265                 270

Val Ala Lys Ile Ile Ile Ile Glu Phe Asn Pro Met Tyr Pro Lys Asp
        275                 280                 285

Asn Asp Ile Ala Leu Met Lys Leu Gln Phe Pro Leu Thr Phe Ser Gly
    290                 295                 300

Thr Val Arg Pro Ile Cys Leu Pro Phe Asp Glu Glu Leu Thr Pro
305                 310                 315                 320

Ala Thr Pro Leu Trp Ile Ile Gly Trp Gly Phe Thr Lys Gln Asn Gly
                325                 330                 335
```

```
Gly Lys Met Ser Asp Ile Leu Leu Gln Ala Ser Val Gln Val Ile Asp
            340                 345                 350

Ser Thr Arg Cys Asn Ala Asp Ala Tyr Gln Gly Glu Val Thr Glu
            355                 360                 365

Lys Met Met Cys Ala Gly Ile Pro Glu Gly Gly Val Asp Thr Cys Gln
    370                 375                 380

Gly Asp Ser Gly Gly Pro Leu Met Tyr Gln Ser Asp Gln Trp His Val
385                 390                 395                 400

Val Gly Ile Val Ser Trp Gly Tyr Gly Cys Gly Gly Pro Ser Thr Pro
                405                 410                 415

Gly Val Tyr Thr Lys Val Ser Ala Tyr Leu Asn Trp Ile Tyr Asn Val
                420                 425                 430

Trp Lys Ala Glu Leu
            435

<210> SEQ ID NO 12
<211> LENGTH: 20078
<212> TYPE: DNA
<213> ORGANISM: Artificial Sequence
<220> FEATURE:
<223> OTHER INFORMATION: Recombinant polynucleotide

<400> SEQUENCE: 12
ccacccgcac acactacagt cgagataact tcgtataatg tatgctatac gaagttatat      60
gcatggcctc cgcgccgggt tttggcgcct cccgcgggcg cccccctcct cacggcgagc     120
gctgccacgt cagacgaagg gcgcagcgag cgtcctgatc cttccgcccg gacgctcagg     180
acagcggccc gctgctcata agactcggcc ttagaacccc agtatcagca aaggacatt     240 ttaggacggg acttgggtga ctctagggca ctggttttct ttccagagag cggaacaggc     300
gaggaaaagt agtcccttct cggcgattct gcggagggat ctccgtgggg cggtgaacgc     360
cgatgattat ataaggacgc gccgggtgtg gcacagctag ttccgtcgca gccgggattt     420
gggtcgcggt tcttgtttgt ggatcgctgt gatcgtcact tggtgagtag cgggctgctg     480
ggctggccgg ggctttcgtg gccgccggcc cgctcggtgg gacggaagcg tgtggagaga     540
ccgccaaggg ctgtagtctg ggtccgcgag caaggttgcc ctgaactggg ggttgggggg     600
agcgcagcaa aatggcggct gttcccgagt cttgaatgga agacgcttgt gaggcgggct     660
gtgaggtcgt tgaaacaagg tgggggggcat ggtgggcggc aagaacccaa ggtcttgagg     720
ccttcgctaa tgcgggaaag ctcttattcg ggtgagatgg gctggggcac catctgggga     780
ccctgacgtg aagtttgtca ctgactggag aactcggttt gtcgtctgtt gcggggggcgg     840 cagttatggc ggtgccgttg gcagtgcac ccgtaccttt gggagcgcgc gccctcgtcg     900
tgtcgtgacg tcacccgttc tgttggctta taatgcaggg tggggccacc tgccggtagg     960
tgtgcggtag gcttttctcc gtcgcaggac gcagggttcg ggcctagggt aggctctcct    1020
gaatcgacag gcgccggacc tctggtgagg ggagggataa gtgaggcgtc agtttctttg    1080
gtcggtttta tgtacctatc ttcttaagta gctgaagctc cggttttgaa ctatgcgctc    1140
ggggttggcg agtgtgtttt tgaagttttt ttaggcaccct tttgaaatgt aatcatttgg    1200
gtcaatatgt aattttcagt gttagactag taaattgtcc gctaaattct ggccgttttt    1260
ggcttttttg ttagacgtgt tgacaattaa tcatcggcat agtatatcgg catagtataa    1320
tacgacaagg tgaggaacta aaccatggga tcggccattg aacaagatgg attgcacgca    1380
ggttctccgg ccgcttgggt ggagaggcta ttcggctatg actgggcaca acagacaatc    1440
```

```
ggctgctctg atgccgccgt gttccggctg tcagcgcagg ggcgcccggt tcttttttgtc   1500 aagaccgacc tgtccggtgc cctgaatgaa ctgcaggacg aggcagcgcg gctatcgtgg   1560
ctggccacga cgggcgttcc ttgcgcagct gtgctcgacg ttgtcactga agcgggaagg   1620
gactggctgc tattgggcga agtgccgggg caggatctcc tgtcatctca ccttgctcct   1680
gccgagaaag tatccatcat ggctgatgca atgcggcggc tgcatacgct tgatccggct   1740
acctgcccat tcgaccacca agcgaaacat cgcatcgagc gagcacgtac tcggatggaa   1800
gccggtcttg tcgatcagga tgatctggac gaagagcatc aggggctcgc gccagccgaa   1860
ctgttcgcca ggctcaaggc gcgcatgccc gacggcgatg atctcgtcgt gacccatggc   1920
gatgcctgct tgccgaatat catggtggaa aatggccgct tttctggatt catcgactgt   1980
ggccggctgg gtgtggcgga ccgctatcag gacatagcgt tggctacccg tgatattgct   2040
gaagagcttg gcggcgaatg ggctgaccgc ttcctcgtgc tttacggtat cgccgctccc   2100
gattcgcagc gcatcgcctt ctatcgcctt cttgacgagt tcttctgagg ggatccgctg   2160
taagtctgca gaaattgatg atctattaaa caataaagat gtccactaaa atggaagttt   2220
ttcctgtcat actttgttaa gaagggtgag aacagagtac ctacattttg aatggaagga   2280
ttggagctac gggggtgggg gtggggtggg attagataaa tgcctgctct ttactgaagg   2340
ctctttacta ttgctttatg ataatgtttc atagttggat atcataattt aaacaagcaa   2400
aaccaaatta agggccagct cattcctccc actcatgatc tatagatcta tagatctctc   2460
gtgggatcat tgttttttctc ttgattccca ctttgtggtt ctaagtactg tggtttccaa   2520
atgtgtcagt ttcatagcct gaagaacgag atcagcagcc tctgttccac atacacttca   2580
ttctcagtat tgttttgcca agttctaatt ccatcagacc tcgacctgca gcccctagcc   2640
cgggcgccag tagcagcacc cacgtccacc ttctgtctag taatgtccaa cacctccctc   2700
agtccaaaca ctgctctgca tccatgtggc tcccatttat acctgaagca cttgatgggg   2760
cctcaatgtt ttactagagc ccacccccct gcaactctga caccctctgg atttgtctgt   2820
cagtgcctca ctggggcgtt ggataatttc ttaaaaggtc aagttccctc agcagcattc   2880
tctgagcagt ctgaagatgt gtgcttttca cagttcaaat ccatgtggct gtttcaccca   2940
cctgcctggc cttgggttat ctatcaggac ctagcctaga agcaggtgtg tggcacttaa   3000
cacctaagct gagtgactaa ctgaacactc aagtggatgc catctttgtc acttcttgac   3060
tgtgacacaa gcaactcctg atgccaaagc cctgcccacc cctctcatgc ccatatttgg   3120
acatggtaca ggtcctcact ggccatggtc tgtgaggtcc tggtcctctt tgacttcata   3180
attcctaggg ccactagta tctataagag aagagggtg ctggctccca ggccacagcc   3240
cacaaaattc cacctgctca caggttggct ggctcgaccc agtggtgtc ccctgctctg   3300 agccagctcc cggccaagcc agcaccatgg gtaccccaa gaagaagagg aaggtgcgta   3360
ccgatttaaa ttccaattta ctgaccgtac accaaaattt gcctgcatta ccggtcgatg   3420
caacgagtga tgaggttcgc aagaacctga tggacatgtt cagggatcgc caggcgtttt   3480
ctgagcatac ctggaaaatg cttctgtccg tttgccggtc gtgggcggca tggtgcaagt   3540
tgaataaccg gaaatggttt cccgcagaac ctgaagatgt tcgcgattat cttctatatc   3600
ttcaggcgcg cggtctggca gtaaaaacta tccagcaaca tttgggccag ctaaacatgc   3660
ttcatcgtcg gtccgggctg ccacgaccaa gtgcagcaa tgctgtttca ctggttatgc   3720
ggcggatccg aaaagaaaac gttgatgccg gtgaacgtgc aaaacaggct ctagcgttcg   3780
```

```
aacgcactga tttcgaccag gttcgttcac tcatggaaaa tagtgatcgc tgccaggata    3840
tacgtaatct ggcatttctg gggattgctt ataacaccct gttacgtata gccgaaattg    3900
ccaggatcag ggttaaagat atctcacgta ctgacggtgg gagaatgtta atccatattg    3960
gcagaacgaa aacgctggtt agcaccgcag gtgtagagaa ggcacttagc ctggggggtaa    4020 ctaaactggt cgagcgatgg atttccgtct ctggtgtagc tgatgatccg aataactacc    4080
tgttttgccg ggtcagaaaa aatggtgttg ccgcgccatc tgccaccagc cagctatcaa    4140
ctcgcgccct ggaagggatt tttgaagcaa ctcatcgatt gatttacggc gctaaggtaa    4200
atataaaatt tttaagtgta taatgtgtta aactactgat tctaattgtt tgtgtatttt    4260
aggatgactc tggtcagaga tacctggcct ggtctggaca cagtgcccgt gtcggagccg    4320
cgcgagatat ggcccgcgct ggagtttcaa taccggagat catgcaagct ggtggctgga    4380
ccaatgtaaa tattgtcatg aactatatcc gtaacctgga tagtgaaaca ggggcaatgg    4440
tgcgcctgct ggaagatggc gattgatcta gataagtaat gatcataatc agccatatca    4500
catctgtaga ggttttactt gctttaaaaa acctcccaca cctcccccgt aacctgaaac    4560
ataaaatgaa tgcaattgtt gttgttaaac ctgccctagt tgcggccaat tccagctgag    4620
cgtgcctccg caccattacc agttggtctg gtgtcaaaaa taataataac cgggcagggg    4680
ggatctaagc tctagataag taatgatcat aatcagccat atcacatctg tagaggtttt    4740
acttgcttta aaaaacctcc cacacctccc cctgaacctg aaacataaaa tgaatgcaat    4800
tgttgttgtt aacttgttta ttgcagctta taatggttac aaataaagca atagcatcac    4860
aaatttcaca aataaagcat ttttttcact gcattctagt tgtggtttgt ccaaactcat    4920
caatgtatct tatcatgtct ggaataactt cgtataatgt atgctatacg aagttatgct    4980
agtaactata acggtcctaa ggtagcgagc tagccaagtc tgtgtgctac caagtagcaa    5040
aactgagcct ggaactcaca catgcgtgtc tgagagccca gcactatcgc caggaaaacc    5100
cagcgtctcc ctgctcaagc ctgaccctca gccctctctg cctctccctg cacttgcctt    5160
ccagtcaagg tgattctgga taaatactac ttcctctgcg ggcagcctct ccacttcatc    5220
ccgaggaagc agctgtgtga cggagagctg gactgtccct tggggaggga cgaggagcac    5280
tgtgtcaaga gcttccccga agggcctgca gtggcaggtg agtgcagggt ctgaggcaca    5340
agagaagtgg gccagcagg aggtctgctc aggcccccac ggcccactgc atagtatctg    5400
ccccctactt gtcacttttc atccttgttg tataaggttc tttgtttgtt tgtttgttgt    5460
tgttttgagg cagagtgctc tgtggcccaa gatggagtgc agtgtcttgg tctcggctca    5520
ctgcaacctc tgcctcccag tttcaagtga ttcttctgcc tcagcctcat gagtagctgg    5580
gattacaggt gccagccacc acgcctggct aattttttata tttttagtag agacggggtt    5640
ttgccacatt ggtcaggctg atcttgaact cctgacctca ggtgatctgc ccgcctcagc    5700
ctcccaaagt gctgggatta caggcgtgag ccaccgtgcc cagctgtgta agtttcttga    5760
gagcaggacc ctgtcttgtc tacctttaaa tcctagtact taacacacag caaacagtaa    5820
ctatttgatg accaaatgtg agccagaaag gacaggaaat tgtaactgag gctgccccat    5880
gcgtgctgcg cctggtggat ttcaggcaga gggctagact gggtgacctt ggggcattcc    5940
tcctttctat gaaatttgtt atttcaagga gactagaaaa gagacttctc agccacttcg    6000
ccagctattg gtccttctat tcattagtgt ttgctgagac atgctatgtg acaggactga    6060
gccaggtcct ttcaatggat aggagatgtt ttgagcataa aatccacgtt ctctcttggg    6120
ctgggctctt ctaccttctt cccccctggtg cttgggctct gaagaaaaaa agataggtag    6180
```

```
gagatgagtg atggggcttc tgagggcagg gctgagtgac tttctgtgta tttgctcttt    6240
ctttatcaga agtcaaatgc ccacaggcac ctgtcatcct actgccagta ggacttctca    6300
ctcaaccttc ccctctgacc ttacttggag aaggacttag gtccctctct cagacatttc    6360
cccaggctgg gcaagttgtg tggaccatgg atgggtatgt ggtccataca atttaaacaa    6420
gctgtatatg gtcgctgggt agagtgacca cataattgat catcaaaact gatacctgta    6480
agagcaaaag ggggcactat taaccattgg gtcaggcaa caggtcaaaa tggagaccta     6540
ccctgggact tctggtcaca ctagctactg tcaaaatggg gcccaaatag acaaagccaa    6600
atggaagaaa ttcccttgac attgaaagtg ttggggctct gtggcacccc cagttctagg    6660
ttgggggagc ttgggctggt ctcatgatga gttctgaggg ggatgggcca gttgggcccc    6720
ccgttccatc taactcaggt tcctttcctc ccagtccgcc tctccaagga ccgatccaca    6780
ctgcaggtgc tggactcggc cacagggaac tggttctctg cctgtttcga caacttcaca    6840
gaagctctcg ctgagacagc ctgtaggcag atgggctaca gcaggtaacc aacctgggcc    6900
tctctccttt ttccctcctt cctccttcct cctcttcctc ctttccttcc tcccttcttc    6960
tctctttcct aaaaattacg ggcattggag ccaggcagaa tggcttttga atcccagcat    7020
ttcacttata agcaacatga agttaaattt cctaagcctc aggttcctca ggagttaatt    7080
gggggaacta atgccaacct cataggatag ttttgcaatg ccagtgagag aatgtgtgct    7140
gccctccaac acacacacac acacttctag cgtctatgca gtcctctcct ttcctttact    7200
cctcaacctt cactcctttg tgctggcttt gcaagaaact gttcctgccc agtaatacaa    7260
aagctaagtt aacttattca aagtttcgtt agttaagatt tagcttaagt gagcctagtt    7320
tcagtggggc cccatcttca gcaatcccag ctctctctgc aaatttcaaa agcagttcca    7380
aatctggagt ggatgaaaag gtgtaagatg atagtaagag taatttgcat tctatatatt    7440
tatattcact tgattttggc agaaaaccaa aaagatagtt attatatctt atatatagat    7500
atatattata tctatttcat aaataggctc aaacaaagta agtaacttgc tagggtacta    7560
gctgggaggt agagggctag aatttgagcc caagacccct aattcttgcg cattaggagt    7620
tcccacattg tttctgtttc tagactgagt aattctttat tctcatgtag gacatcatct    7680
ctaagggaag gggctaatga gatggttgat cactcagaga gtttagctgg agaggatgga    7740
aaagaaccca tacattcagt tgcagattga gatagcctat ctctggcagg cctcagattt    7800
cttcaggatt ctaacagact ggacccagag actaggccaa acaaacaaac aaacaaaaac    7860
tctactaggc agacatcacc aaccaatcac agaactctct cccatggatc cctaatacag    7920
cctcaaagtc cttttcagta aatgctccag gcagccatta caaatcaatc agaattattt    7980
gcctttctct tctctgctca acgggcttct gctgctctct actttccata gggggcaact    8040
tccattaccc tctagaaagc acacccccacc accttcattt caaggagagt gaggaactca    8100
tgcccagcac ctgctattct cccctcttcc tgcagccacg gagcccagcc tcgctgcagc    8160
cagccctgcc tccccactgt agtccagtca actgctgcat cagccgttcc tggcacagca    8220
ggctgagcct tgattatgaa acctgggtgt ctccaggggt tcttaagatg ataggctcct    8280
ggaatttctg tccttttgga gctcagtaag gcaccaaacc acctgagtct tgtgcttcac    8340
aaaatcaaag ttcatcagaa tcattcattg ggatggaatt ggtgaacaga agttaacttt    8400
cctgggaatg tccatttcca ccatattccg tccttctagg tctcagactt ctctactttc    8460
tttcctctct ctagatcgga ggcccttctt gtcctagaac cataggcatt tcaagatgtg    8520
```

```
ggagaccota gggatcatct agtccacgca tctttttttt tttttttga cagagtctca    8580
ctctgtcacc caggctggag tgcaatggca ccatctctgc ttactgcaac ctccacctcc    8640
caggttcaag tgattctttc gcctcagcct cccaagtagc tgggattaca ggcacgcacc    8700
atcatgccca gctaattttt atattttgt agagaccgag tttcaccatg ttggccaggc     8760
tggtcttgaa ctcctgacct caggtgatcc acccacctcg gcctcccaaa gtgctgggat    8820
tacaggcgtg agccactgca cccagccccg tgcatctttt tatagagggg gaaactgagg    8880
cttggagaga cccagaaaaa gaatatgacc tgcccaaggc cacacatcaa actagtgcca    8940
gagccaggga cagaacctag atcatgagga ctcttaaaat gcactctagt cctcccaggt    9000
ctgagacttg ggtccttcca ggaagtgcca gcattcctgc ctgagaatgt gccaatccac    9060
cagtattgcc aatgactcag ccctccatgg agagcttcta ctaacattac tagcatagtt    9120
agggatggaa ggaaaagatt tagaagaggc agattcagta aaggaacaat cagagagatg    9180
gaattaatca aggaaggctt cctggaggag gaaaaacttc aacccaaggt ttgaaagtag    9240
caagcatgga ttagcaggga gaaagaggga gagtggtcca gttgagagaa acgtttgtct    9300
ggattcatat gaagacagat ctagtcctgt tctattaaat atctctaagg gggccaaaaa    9360
catacccccg ctatcaaagt cagaccagat gctttgtttg gagaacgaaa tatccacatt    9420
ccaactccct cccaggtgag aagggagcta acctgagccc ctatgcctct ttgtttccct    9480
gctgtgaacc agaagacatt gctgggtat ttgaaatagg acagagctg ggaatatgga      9540
aaggagaccc ctaacatttc tccagggctc tgggttctgg atttggattc cccacccaag    9600
aaaagcaagtt acatcagcaa tgcactgagg gttgagtcct gggatgccaa gggtcggttc   9660
tttattgtat agcaaagcag gccccatctt cactgactaa gaccatctcc actccctggc    9720
cactccccac caagcattct ctgccactct ttctcctgaa agtgggggcc aactctacca    9780
tcttgttcta accccctgcc ccagctcaca actctctctc cctcttgatg tgagcagcaa    9840
acccactttc agagctgtgg agattggccc agaccaggat ctggatgttg ttgaaatcac    9900
agaaaacagc caggagcttc gcatgcggaa ctcaagtggg taagtgaggg gacaccttct    9960
ggcctacaga aggcccccac atggacgctg ctcttcaggt tgcaaccagc tcacctggaa   10020
ccccaagcag ccaggggaat gtaagcagac atcaggaaga actcctagcc agatggatca   10080
ttcaatgcca agagctatag actcacattt tggagaggtt ttctgtgttg acttgttttt   10140
aatacaatgg acagctggac aaagtgtgtt gtcctactca gagccagagg gatggataat   10200
gtgacctttc catcaatctg gatagtaaat agttttgtct actgctgtag gttttctaat   10260
aaattgccca ataggcaaga ttccaaagtc actttgtcct tccctaccac ttacccagcc   10320
agagctcccc accttcttga tgctccaggg aagaggctcc atggcccttg tgggtggcct   10380
gttcctgagc ctcgccaccc tgtgttagag cagagcatcc agatgaaatc tgtcacactg   10440
tggcaaagtg gctcagagag gaggctggct tcctagcatt cagggacgtt gctgagggcc   10500
gcttattcac cgaaaataaa tcttgaaaag gacagggctg gtagcagaat gatcctttac   10560
ctaaaattct atcaaaatcc cattcttcca tttggaaagc ccacagtgtc acagactctg   10620
ttccgggctc tgtcctcttc cctcttgggt cccaggagcc caggctgggc tttgaagcag   10680
gcagggccca gcacacagta ggtactcagc agtgggggtg ttgaatccaa tcaaacggaa   10740
gtgtcaatgc aggaaatgca atggatgtca atgcagtctc caaatgttcc ccactgtgca   10800
gcttccacat tcccgaggta ttgggagggg acttgaatta acagcttcgg gaggcctgag   10860
tccctgcctc ccagctgagg aagaagctta aatcacaggg cgctgtgtct gtcttccagg   10920
```

-continued

```
ccctgtctct caggctccct ggtctccctg cactgtcttg gtgagtaccc ccaatctctg   10980
agggtttggg gcctgggcca gcaatgagca gggaggaaga ccttcatctt cactcctaaa   11040
tttctgggac tccaagtttc attctgcctt ggtctacagc ccttgggctt gtcggtcaat   11100
gccccctcga gttgttggtg gccttgggca ggtcacattc tttttctggg tctttccaag   11160
ccccagtttc ccccttctac catctgtgca tggctccatg acctaagtgg agacctggga   11220
gagagtgtta ggaagaccga aaagggcagg acggggcctc cactgcctcc catccctggt   11280
ccgggcccac atagccttct tgtcacaat cagctcaggt atccaagatc agattaccca   11340
cattcattat ttgagcaact attcattgaa cagttagaat atgtctcact ctgtcagttg   11400
ctggctagaa gtagaaagta ccagatgagt gaaataattg gccactatcc ttggtagctg   11460
atgactaagt aagagagaga tgcaagacaa catgtggaaa atgccaaact gagtagcagt   11520
cacagttgac atgctgcaga gagagctggc cggggtcag aagacctggg caccagtcct   11580
gttcatttcc agtgtggcct cgagtcattc acctgacctc cctgaagttc attttcccaa   11640
gaagttgttt agtccaactg cccatcaagg atctttaggg accttctag ctctaacaga   11700 ggagatcaga aaagaaaaca agcaatgtgg ctcagctcat cctacaagct tcatagagaa   11760
ctgagactgg cctggaagca tagccagaaa ttagaacgcc taagggaaga aggtcacaac   11820
gctgcctctg caatttagga gtgtatatgc tttcctgcag gatgttgaga gtttcattca   11880
ttatcgtatg ccccctaccc cggccccaca atacctagtg cgtgggatct gacacgtggt   11940
ggctggtcaa tgaatgaatg aatgaatggt cacaccatct gaggttctgc actgagtagc   12000
cctgaaggct tgaagcagca taagtgacag gtcctcccct gaggggcctc tgttttacca   12060
ataagccaag acctaagctc aacaacactg aaagggtggc caatacccag acagcctgt   12120 gggaattcca gagaaaggga gattcccagg gactgggggc ccaggctaaa cactgaaaaa   12180
tgcatctgta ggctcaagga ggaaaagccc atgtctgtct gtcttgccca ccactctctc   12240
ccagcaccca gcactgcccc aggacagaga gcacttgaca caagttggtt agattaatga   12300
atgatttaga gttcagtggt ccccaacctt tttggcacaa gagactggtt gcatggaaga   12360
caatttttcc gcaaaccaag agggggatag agagcattag attctctctt tttttttttt   12420
ttgagaccaa gtctggctct tgtcactcag cctggagtaa agtgttgcga tctcggctca   12480
ctgcaacctc cgcctcctgg attcaagcga ttctcctgcc tcagcccct aaatagctgg   12540 gattacaggc acccgtcacc agcccagctg ggactatagg catgtgccac catgcccggc   12600
taatttttgt attttagta gagacggcgt ttcaccatgt tggccaggct agtctcgaac   12660
tcctgacctc aggtgatctg cccgcctgag cctcccaaag tgctgggatt acaggcatga   12720
gctgcctcac ccagcctaaa gtctcataag gaacgtacag catagatccc tcacatgtgc   12780
agttcacaat aaggttgtgc tcctacaaga atctaacgcc acctctgatc tgacaggagg   12840
tgaagctcag gtggtcatgc tcgcttgtcc ctgccactca cttcctaatg tacagccagg   12900
ttcctaacag gccacgaacc agtgggaagg gcatctttt ggatcaaaaa cagaattact   12960
ttttagagaa ctacaagcag atcaatttgg ctagacagag actttatatg aaacagcagg   13020
aggctgctag gaggagtgga aactctactt tgccctcaag ggagatcccg aagggctttg   13080
caggagcggg caaggtggca tgaagaaagc agtgtttgaa atcaggtggt atttgaaaag   13140
cccagccctt cccttagaa tggcccttct accatctgtg catggctcca caaccgtggt   13200
ggtggctgcc agaagaattg gaaaggcaga gcatgggtgg agaggggga cctgagggct   13260
```

-continued

```
ttacaggagt tccggggtg gtgagggtgt gaaagccagg tcagtcagta ggaagacagg     13320
atgtcagatt gagagactcc cctggccggg gaaacagact tggagaaggg ggagttttgg     13380
atgagacagt ccacttccga gtcacaaaat agcttgtggg tgtctgttta ctgttactca     13440
gtgggagtgg ctggggacac gccacctggg cagggctttc gtaattctgc atcacttgtg     13500
aaggtcacag attcccagca caacggacac acccatgttc atagtctgaa ctcctaaaca     13560
catcttaaac caaataaaa aaaaagaaa gaaagaaaga aaaggagag ggaggtttga       13620
ggaaagccta tggtctggga cactcaatac ctcccatgaa tatctcatat tgggctggtc     13680
ctctctccac tctggcccca gccataaggg ccctgcttag agcagatttt gggtgctgag     13740
tggaggcagc ctcatcccca acagcctgac ttcctgcctc ctccctgcct ctgcctgtgt     13800
ccagcctgtg ggaagagcct gaagaccccc cgtgtggtgg gtgtggagga ggcctctgtg     13860
gattcttggc cttggcaggt cagcatccag tacgacaaac agcacgtctg tggagggagc     13920
atcctggacc cccactgggt cctcacggca gcccactgct tcaggtaaga ccccagctgt     13980
aaggaggtct ctggggacca aggccagtca ggaccagaga gcttggggt cctgtctcct      14040
ggcaccgtcc ttctcttcac tctcccacta gagacgtttt ccaggttgtg gtggcccaa      14100
tgagacaatg ccatgatgc cctttgttag gcttttgggt gtctgagcag agggtgctgg      14160
tcaccaagca tggcctcttc ctggtgggac accagcagat acccagagtc ctcaccccac     14220
ccccatatcg ttcaagctac aaaagctctt cccacctgcc tcaacttcca agaactcact     14280
ctcttttttgc ttgtttccag gaagttgttc cagggtctag agtcatagcc acgtcctcat    14340
tatgtctgga aactttaaaa aaattaaaga gcataggttc ctttcagtcc acagagaagc     14400
ctggccttac ctcagggaag ggctactccc agacccctt cacttttttt ttttttttt       14460
ttttttttt ttttgagaca gagtcttgct ctgttgctta ggctggagcg cagcagcatg       14520
atcttggctc actgcaacct ccgcctcctg agttcaagca attctcctgc ctcagcttcc     14580
caagtagctg ggactatagg catgggccac catgcccggc taattttgt atttttggta      14640
gagacagggt ttcaccatgt tggccaggct gatctctaac tcctgacctc aagtgatctg     14700
cccacctcag cctcccaaac tgctgggatt acaggcatga gccagggcat ccggcttta      14760
tttattcatt cattcaatat ctaatgagca cctaccaggt accaaacacc agatgatgcg     14820
cccaagttca ttagaccccca ccgctgtctt caaggcactc atgatctagg ccagcgtttt    14880
ttaaccactt tttttttttt tttttttgag attctggtga gagctataaa ttctttcctg     14940
gaaaaacatc tctgcacact aagctgtgcc tggcattggg aaaaagaaag cacgtaatgt     15000
aactgacagc atgagtaaca cagtgagaaa ggttggagga gagagcgcca ggacctcaga    15060
actcaggcat tagaggagcc ccttcccag ccctccttga ggtttcgttg ggcaggtttc      15120
actgaggaaa aagggtcaaa tccctttttc gaatttgact tcttgtaagt gccagaagac     15180
tgccccttct ccaccatccc tgcctcacca tcatctttcc tcccaaggca gtgacatcca    15240
gcaccccgat ccctagggcc ctgggaccc agcctttggc aaagtctcct caggcttgga      15300
tcaggcctga acccagctgt ctctacccccc aggaaacata ccgatgtgtt caactggaag    15360
gtgcgggcag gctcagacaa actgggcagc ttcccatccc tggctgtggc caagatcatc    15420
atcattgaat tcaaccccat gtaccccaaa gacaatgaca tcgccctcat gaagctgcag    15480
ttcccactca ctttctcagg tgagaagcag ggcccaaggc cactcaagcc tcttacatca    15540
gttttcacgc ccactctgct attagctcac tgaccgccct tggcacataa tgtctcctct    15600
caagtcctca gcttgcccat ttgtctctaa tacgtcagcc taacatcact gatgccatga    15660
```

```
ggcctcctca agctgtcagc taacacctcc actccattcc ctgccagaga ttcttccaag    15720
gcctgtcttc cctatgtgga gcccctcgag tgagaactgg agtttcatcc aatcttggag    15780 tttaggaga ccttttaaaa agattatcga gctaattccc caccactgac caacacgcaa    15840
gagcctgctc agtatccctg ccaaggagtc attgtgcccc tgtttgctct cctccagggg    15900
cagggaaccc attacctgtg aggcagccca cagagtcttt gaacagctct gttggatgcc    15960
ttgtgcttat actgaaatgt atttagatca ggattcccaa ctgtggggtc cacaagacac    16020 tggcccttg gagaagagag gattccattg tcaaataagt ttggggaaca ttttcatact    16080
acagctccct tcttggaaca cattagttta ttaaaggtag gagaagtttt taaaataatc    16140
tgttttattg cgtttaacct acatttttta aatttatttg accacagaat cctttttca    16200 tgctacttct attagcatcc catagaacaa gtgttctaga gaccctggtg tgacccctt     16260 cagagagctt aactgccagg ctctcctgag ccctggtgtg tgtttcaaga tttgtgcctg    16320
ggaattgttt taatcaggta tggcaaggtg acagatacag acacagctat ctttgaaaga    16380
agagtttatt atttataatt cctgagagaa agggacatac cccacccccc aacacaggga    16440
cacccgggga agcagctggg tccaccagga ggcaggagtg aggggaaggc atggcccaga    16500
gccacctgtg gcttccatgg gcaggtctgg ccaaggtagg gtaggcaaga ttgagcatgc    16560
tcaggattgg atagtgtgga caattctcta ggctatagat gtcagcctct ggttgtctag    16620
tatctgtccc tggggtgatt tagggcaggg aaaatattgg cttggtgtct gagagtcaga    16680
taaaggaagt ggttggggat atgggctttg ggttggctgg tttgcctatt aaaggcgtgc    16740
ccaaagccaa gttgtttact atctgcagga attagctaac ccagtctctc ccagaccagc    16800
aagatcccca taatcataaa gcatcataat ttacagaaaa ttaacactta tgatgaataa    16860
aagatctcct tcttcctctg tgctcctggc aggcacagtc aggcccatct gtctgccctt    16920
ctttgatgag gagctcactc cagccacccc actctggatc attggatggg ctttacgaa     16980 gcagaatgga ggtaagtcct gggtgcagga ccacagggca ggagatgccc ttgtatgagg    17040
gagcagcttc cagaagtaat gggaaggagg accaccttc agagaaaccc atcctggagg     17100
accaagcacc aaggcgccag gcagaaagca aagtggtttg gcaatccagg gctgggggat    17160
agaaggcaag gatgggaatg tgagtgtttt taccctccca gggaagatgt ctgacatact    17220
gctgcaggcg tcagtccagg tcattgacag cacacggtgc aatgcagacg atgcgtacca    17280
gggggaagtc accgagaaga tgatgtgtgc aggcatcccg gaaggggtg tggacacctg     17340 ccaggtgggg cctccaagaa tcatggggag ttctaagaat aggggtttagg tcctagagag    17400 atgagaaaac ccagaggctg catgccctac aggaagcctt gcatatcatg ggcactcaat    17460
gtgtgatgat gggaggaaga gagggaggga aggaaaggat agtcagataa aagtgtacca    17520
atagatgagt gggtggatgg atggatgcag acaagcagag agatttcaaa tgtctctttc    17580
acattcgaag atgatgttac tggcctggca tggtggctca cgcttgtaat cccagcactt    17640
tgggaggctg aggcgggcag gtgatttgag gtcaggaatt caagaccagc ctggccaaca    17700
tggtgaaatc ccatctctac taaaaagaat acaaaaatta gctgggcgtg gtggcacgtg    17760
cctgtaatcc cagctacttg ggaggctgag gcaggagaat tgcttgaacc caggaggcag    17820
aggttgcagt aagctgagat tgcgccactg cactccagcc tgggtgaccc agcaagactc    17880
catctgaaaa caacaacaac aacaaagatg acattactca tccaccccac ccacccttct    17940
cactagctac agaatgatta gcccccttgag gtcaggaatc ccaggtctat tttctctgtg    18000
```

```
actctccccca agctgctgaa ctacactagg aaagaattac cgcctgcaga atgctggaag    18060
cacatctgtg tgtgccctca ccccggcctc attggccatc aggactgctt agcaatccct    18120
gtagaccttc ttcctccccc atacttccag aggatcttct gaactatttt cttttttat    18180 ttttctttt atgttttta acagagacag ggtcactatg ttgcccagtc tggtctcaaa    18240
ctcctgggtt caagggattc tcccacctca gctttccaaa atgctgggat tacaggcatg    18300
agccatcgtg cttggcctga accatttca ttaaaacccc taccctactc tcacctccat    18360
ttccagtcat taaattcctt catttaagag gcatctctta gtcatcgcat gtgtgccatg    18420
aacatggtag tctttggaga cccctcaggg agctcacagt ggttggggga aaggggggca    18480
ttaaacagac atttaagcta tagttttggg ttcagaggga ggaagcccca ggggctaaaa    18540
cagctgataa ggactcccag ataagtgcac ttttcactat ctggcatttt cttgttttgt    18600
tatttgcttg ttcactgtct ctcacccat ttgatcctaa gctttctgag ggcagggatc    18660 tttgttttt ttcatcagtt ggatcccaat tgcttagaac actacctggc acaaaatagg    18720
cactctataa gtgattacac aaattttgga acgactaggt taaacaatga taaccaggct    18780 tttttttt ttttgagac tgagtctcac tctgttgccc aggctagagt gaagtggttt    18840
gatctcggct cactgcagcc tccgcctctg ggttcgaatg attctccacc tcagcctcct    18900
gagtagctgg gattacaggt gcctgccact atgcccagct aattttgta tttgtagtag    18960 agacgggttt caccatgttg gccaggctgg tcttgaactc ctgacctcaa gtgattcacc    19020
cgcctcagcc tcccaaggtg ctgggattac aggtgtgagc caccgctcct ggccaacaac    19080
caggcttttt taagacatca ctcagagcct ttaatttgct aatgtgagtt gtgaatctct    19140
gagagaaggc taacggcatg cttgcaactt acttgtccac agacaagcct ttctgcccca    19200
gaagagaaga ccattctagg gtgctaatga gcaaagaggg tgagggtgga atatcggaga    19260
gcagcaggga gtgcagggga acagatggc cagttcaggg agcagagaag gagaagcccc    19320
cccacctcac ctgccctccc cagcagtctc tgttctggtc tctcacaggg tgacagtggt    19380
gggcccctga tgtaccaatc tgaccagtgg catgtggtgg gcatcgttag ttgggctat    19440 ggctgcgggg gcccgagcac cccaggagta tacaccaagg tctcagccta tctcaactgg    19500
atctacaatg tctggaaggt aaggtacctt tgccctaccc actgtgcctt ccctccagtc    19560
ctctacctgg ggggtgccaa tccatcctca ggtttgattt aaatggttct gacaactctt    19620
tacatcccaa ataacttcc ctccaagcaa gggacagcct gagattgcac tattaaggct    19680
gaaattcctt aggtcagaga tttctgataa atgcaaatac cttagggaat agaacacacc    19740 aagccttct ttctcttttc tgacagaatg agactatcag atccttcta gagagaagat    19800 tctgataagg aagagagtgg aaaggctcat gagacctcct ggccctctgc agggtaggga    19860
gagaagcaaa gtgttcaga aaaggaagac tcacgttaca catgtcacca ctttgtccag    19920
tttcagataa tctgactttc tcttcatcgg tctctcttat tctaggctga gctgtaacgc    19980
tgccgtcccc cacatccaga agctgcttcc cttcagacct acctacggca tgacccctca    20040
aagtcagata tgggacaaga gcctccttga acaaactc                           20078
```

<210> SEQ ID NO 13
<211> LENGTH: 15159
<212> TYPE: DNA
<213> ORGANISM: Artificial Sequence
<220> FEATURE:
<223> OTHER INFORMATION: Recombinant polynucleotide

<400> SEQUENCE: 13

```
ccacccgcac acactacagt cgagataact tcgtataatg tatgctatac gaagttatgc    60
tagtaactat aacggtccta aggtagcgag ctagccaagt ctgtgtgcta ccaagtagca   120
aaactgagcc tggaactcac acatgcgtgt ctgagagccc agcactatcg ccaggaaaac   180
ccagcgtctc cctgctcaag cctgaccctc agccctctct gcctctccct gcacttgcct   240
tccagtcaag gtgattctgg ataaatacta cttcctctgc gggcagcctc tccacttcat   300
cccgaggaag cagctgtgtg acggagagct ggactgtccc ttgggggagg acgaggagca   360
ctgtgtcaag agcttccccg aagggcctgc agtggcaggt gagtgcaggg tctgaggcac   420
aagagaagtg ggcccagcag gaggtctgct caggccccca cggcccactg catagtatct   480 gcccctact tgtcactttt catccttgtt gtataaggtt ctttgtttgt ttgtttgttg   540
ttgttttgag gcagagtgct ctgtggccca agatggagtg cagtgtcttg gtctcggctc   600
actgcaacct ctgcctccca gtttcaagtg attcttctgc ctcagcctca tgagtagctg   660
ggattacagg tgccagccac cacgcctggc taatttttat attttagta gagacggggt   720 tttgccacat tggtcaggct gatcttgaac tcctgacctc aggtgatctg cccgcctcag   780
cctcccaaag tgctgggatt acaggcgtga gccaccgtgc ccagctgtgt aagtttcttg   840
agagcaggac cctgtcttgt ctacctttaa atcctagtac ttaacacaca gcaaacagta   900
actatttgat gaccaaatgt gagccagaaa ggacaggaaa ttgtaactga gctgccccca   960
tgcgtgctgc gcctggtgga tttcaggcag agggctagac tgggtgacct tggggcattc  1020
ctcctttcta tgaaatttgt tatttcaagg agactagaaa agagacttct cagccacttc  1080
gccagctatt ggtccttcta ttcattagtg tttgctgaga catgctatgt gacaggactg  1140
agccaggtcc tttcaatgga taggagatgt tttgagcata aaatccacgt tctctcttgg  1200
gctgggctct tctaccttct tcccctggt gcttgggctc tgaagaaaaa aagataggta  1260
ggagatgagt gatggggctt ctgagggcag ggctgagtga cttctgtgt atttgctctt  1320 tctttatcag aagtcaaatg cccacaggca cctgtcatcc tactgccagt aggacttctc  1380
actcaacctt cccctctgac cttacttgga gaaggactta ggtccctctc tcagacattt  1440
ccccaggctg ggcaagttgt gtggaccatg gatgggtatg tggtccatac aatttaaaca  1500
agctgtatat ggtcgctggg tagagtgacc acataattga tcatcaaaac tgatacctgt  1560
aagagcaaaa gggggcacta ttaaccattg ggtcagggca acaggtcaaa atggagacct  1620
accctgggac ttctggtcac actagctact gtcaaaatgg ggcccaaata gacaaagcca  1680 aatgaagaa attcccttga cattgaaagt gttgggctc tgtggcaccc ccagttctag  1740
gttgggggag cttgggctgg tctcatgatg agttctgagg gggatgggcc agttgggccc  1800
cccgttccat ctaactcagg ttcctttcct cccagtccgc ctctccaagg accgatccac  1860
actgcaggtg ctggactcgg ccacagggaa ctggttctct gcctgtttcg acaacttcac  1920
agaagctctc gctgagacag cctgtaggca gatgggctac agcaggtaac caacctgggc  1980
ctctctcctt tttccctcct tcctccttcc tcctcttcct cctttccttc ctcccttctt  2040
ctctctttcc taaaaattac gggcattgga gccaggcaga atggcttttg aatcccagca  2100
tttcacttat aagcaacatg aagttaaatt tcctaagcct caggttcctc aggagttaat  2160
tgggggaact aatgccaacc tcataggata gttttgcaat gccagtgaga gaatgtgtgc  2220
tgccctccaa cacacacaca cacacttcta gcgtctatgc agtcctctcc tttccttac  2280 tcctcaacct tcactccttt gtgctggctt tgcaagaaac tgttcctgcc cagtaataca  2340
```

```
aaagctaagt taacttattc aaagtttcgt tagttaagat ttagcttaag tgagcctagt    2400
ttcagtgggg ccccatcttc agcaatccca gctctctctg caaatttcaa aagcagttcc    2460
aaatctggag tggatgaaaa ggtgtaagat gatagtaaga gtaatttgca ttctatatat    2520
ttatattcac ttgattttgg cagaaaacca aaaagatagt tattatatct tatataraga    2580
tatatattat atctatttca taaataggct caaacaaagt aagtaacttg ctagggtact    2640
agctgggagg tagagggcta gaatttgagc ccaagacccc taattcttgc gcattaggag    2700
ttcccacatt gtttctgttt ctagactgag taattcttta ttctcatgta ggacatcatc    2760
tctaagggaa ggggctaatg agatggttga tcactcagag agtttagctg gagaggatgg    2820
aaaagaaccc atacattcag ttgcagattg agatagccta tctctggcag gcctcagatt    2880
tcttcaggat tctaacagac tggacccaga gactaggcca aacaaacaaa caaacaaaaa    2940
ctctactagg cagacatcac caaccaatca cagaactctc tcccatggat ccctaataca    3000
gcctcaaagt ccttttcagt aaatgctcca ggcagccatt acaaatcaat cagaattatt    3060
tgcctttctc ttctctgctc aacgggcttc tgctgctctc tactttccat aggggcaac    3120 ttccattacc ctctagaaag cacaccccac caccttcatt tcaaggagag tgaggaactc    3180
atgcccagca cctgctattc tcccctcttc ctgcagccac ggagcccagc ctcgctgcag    3240
ccagccctgc ctccccactg tagtccagtc aactgctgca tcagccgttc ctggcacagc    3300
aggctgagcc ttgattatga aacctgggtg tctccagggg ttcttaagat gataggctcc    3360
tggaatttct gtccttttgg agctcagtaa ggcaccaaac cacctgagtc ttgtgcttca    3420
caaaatcaaa gttcatcaga atcattcatt gggatggaat tggtgaacag aagttaactt    3480
tcctgggaat gtccatttcc accatattcc gtccttctag gtctcagact tctctacttt    3540
ctttcctctc tctagatcgg aggcccttct tgtcctagaa ccataggcat ttcaagatgt    3600
gggagaccct agggatcatc tagtccacgc atcttttttt tttttttttg acagagtctc    3660
actctgtcac ccaggctgga gtgcaatggc accatctctg cttactgcaa cctccacctc    3720
ccaggttcaa gtgattcttt cgcctcagcc tcccaagtag ctgggattac aggcacgcac    3780
catcatgccc agctaatttt tatattttg tagagaccga gtttcaccat gttggccagg    3840
ctggtcttga actcctgacc tcaggtgatc cacccacctc ggcctcccaa agtgctggga    3900
ttacaggcgt gagccactgc acccagcccc gtgcatcttt ttatagaggg ggaaactgag    3960
gcttggagag acccagaaaa agaatatgac ctgcccaagg ccacacatca aactagtgcc    4020
agagccaggg acagaaccta gatcatgagg actcttaaaa tgcactctag tcctcccagg    4080
tctgagactt gggtccttcc aggaagtgcc agcattcctg cctgagaatg tgccaatcca    4140
ccagtattgc caatgactca gccctccatg gagagcttct actaacatta ctagcatagt    4200
tagggatgga aggaaaagat ttagaagagg cagattcagt aaaggaacaa tcagagagat    4260
ggaattaatc aaggaaggct tcctggagga ggaaaaactt caacccaagg tttgaaagta    4320
gcaagcatgg attagcaggg agaaagaggg agagtggtcc agttgagaga aacgtttgtc    4380
tggattcata tgaagacaga tctagtcctg ttctattaaa tatctctaag ggggccaaaa    4440
acataccccc gctatcaaag tcagaccaga tgctttgttt ggagaacgaa atatccacat    4500
tccaactccc tcccaggtga gaagggagct aacctgagcc cctatgcctc tttgtttccc    4560
tgctgtgaac cagaagacat tgctgggata tttgaaatag gacagagct gggaatatgg    4620 aaaggagacc cctaacattt ctccagggct ctggttctg gatttggatt ccccacccaa    4680
gaaagcaagt tacatcagca atgcactgag ggttgagtcc tgggatgcca agggtcggtt    4740
```

```
ctttattgta tagcaaagca ggccccatct tcactgacta agaccatctc cactccctgg    4800
ccactcccca ccaagcattc tctgccactc tttctcctga aagtgggggc caactctacc    4860
atcttgttct aaccccctgc cccagctcac aactctctct ccctcttgat gtgagcagca    4920
aacccacttt cagagctgtg gagattggcc cagaccagga tctggatgtt gttgaaatca    4980
cagaaaacag ccaggagctt cgcatgcgga actcaagtgg gtaagtgagg ggacaccttc    5040
tggcctacag aaggccccca catggacgct gctcttcagg ttgcaaccag ctcacctgga    5100
accccaagca gccaggggaa tgtaagcaga catcaggaag aactcctagc cagatggatc    5160
attcaatgcc aagagctata gactcacatt ttggagaggt tttctgtgtt gacttgtttt    5220
taatacaatg gacagctgga caaagtgtgt tgtcctactc agagccagag ggatggataa    5280
tgtgaccttt ccatcaatct ggatagtaaa tagtttttgc tactgctgta ggttttctaa    5340
taaattgccc aataggcaag attccaaagt cactttgtcc ttccctacca cttacccagc    5400
cagagctccc caccttcttg atgctccagg gaagaggctc catggccctt gtgggtggcc    5460
tgttcctgag cctcgccacc ctgtgttaga gcagagcatc cagatgaaat ctgtcacact    5520
gtggcaaagt ggctcagaga ggaggctggc ttcctagcat tcaggacgt tgctgagggc    5580 cgcttattca ccgaaaataa atcttgaaaa ggacagggct ggtagcagaa tgatccttta    5640
cctaaaattc tatcaaaatc ccattcttcc atttggaaag cccacagtgt cacagactct    5700
gttccgggct ctgtcctctt ccctcttggg tcccaggagc ccaggctggg ctttgaagca    5760
ggcagggccc agcacacagt aggtactcag cagtgggggt gttgaatcca atcaaacgga    5820
agtgtcaatg caggaaatgc aatggatgtc aatgcagtct ccaaatgttc cccactgtgc    5880
agcttccaca ttcccgaggt attgggaggg gacttgaatt aacagcttcg ggaggcctga    5940
gtccctgcct cccagctgag aagaagcttt aaatcacagg gcgctgtgtc tgtcttccag    6000
gccctgtctc tcaggctccc tggtctccct gcactgtctt ggtgagtacc cccaatctct    6060
gagggtttgg ggcctgggcc agcaatgagc agggaggaag accttcatct tcactcctaa    6120
atttctggga ctccaagttt cattctgcct tggtctacag cccttgggct tgtcggtcaa    6180 tgcccctcg agttgttggt ggccttgggc aggtcacatt cttttctgg gtctttccaa     6240 gcccagttt ccccttcta ccatctgtgc atggctccat gacctaagtg gagacctggg     6300
agagagtgtt aggaagaccg aaaagggcag gacggggcct ccactgcctc ccatccctgg    6360
tccgggccca catagccttc tttgtcacaa tcagctcagg tatccaagat cagattaccc    6420
acattcatta tttgagcaac tattcattga acagttagaa tatgtctcac tctgtcagtt    6480
gctggctaga agtagaaagt accagatgag tgaaataatt ggccactatc cttggtagct    6540
gatgactaag taagagagag atgcaagaca acatgtggaa aatgccaaac tgagtagcag    6600
tcacagttga catgctgcag agagagctgg ccgggggtca aagacctgg gcaccagtcc     6660 tgttcatttc cagtgtggcc tcgagtcatt cacctgacct ccctgaagtt cattttccca    6720
agaagttgtt tagtccaact gcccatcaag gatctttagg gacccttcta gctctaacag    6780
aggagatcag aaaagaaaac aagcaatgtg gctcagctca tcctacaagc ttcatagaga    6840
actgagactg gcctggaagc atagccagaa attagaacgc ctaagggaag aaggtcacaa    6900
cgctgcctct gcaatttagg agtgtatatg ctttcctgca ggatgttgag agtttcattc    6960
attatcgtat gccccctacc ccggcccac aatacctagt gcgtgggatc tgacacgtgg     7020
tggctggtca atgaatgaat gaatgaatgg tcacaccatc tgaggttctg cactgagtag    7080
```

```
ccctgaaggc ttgaagcagc ataagtgaca ggtcctccct tgaggggcct ctgttttacc       7140
aataagccaa gacctaagct caacaacact gaaagggtgg ccaataccca ggacagcctg       7200
tgggaattcc agagaaaggg agattcccag ggactggggg cccaggctaa acactgaaaa       7260
atgcatctgt aggctcaagg aggaaaagcc catgtctgtc tgtcttgccc accactctct       7320
cccagcaccc agcactgccc caggacagag agcacttgac acaagttggt tagattaatg       7380
aatgatttag agttcagtgg tccccaacct ttttggcaca agagactggt tgcatggaag       7440
acaattttc cgcaaaccaa gagggggata gagagcatta gattctctct ttttttttt        7500
tttgagacca gtctggctc ttgtcactca gcctggagta aagtgttgcg atctcggctc       7560
actgcaacct ccgcctcctg gattcaagcg attctcctgc ctcagccccc taaatagctg       7620
ggattacagg cacccgtcac cagcccagct gggactatag gcatgtgcca ccatgcccgg       7680
ctaattttg tatttttagt agagacggcg tttcaccatg ttggccaggc tagtctcgaa        7740
ctcctgacct caggtgatct gcccgcctga gcctcccaaa gtgctgggat tacaggcatg       7800
agctgcctca cccagcctaa agtctcataa ggaacgtaca gcatagatcc ctcacatgtg       7860
cagttcacaa taaggttgtg ctcctacaag aatctaacgc cacctctgat ctgacaggag       7920
gtgaagctca ggtggtcatg ctcgcttgtc cctgccactc acttcctaat gtacagccag       7980
gttcctaaca ggccacgaac cagtgggaag ggcatctttt tggatcaaaa acagaattac       8040
tttttagaga actacaagca gatcaatttg gctagacaga gactttatat gaaacagcag       8100
gaggctgcta ggaggagtgg aaactctact ttgccctcaa gggagatccc gaagggcttt       8160
gcaggagcgg gcaaggtggc atgaagaaag cagtgtttga aatcaggtgg tatttgaaaa       8220
gcccagccct tccccttaga atggcccttc taccatctgt gcatggctcc acaaccgtgg       8280
tggtggctgc cagaagaatt ggaaaggcag agcatgggtg gagaggggg acctgagggc        8340
tttacaggag ttccgggggt ggtgagggtg tgaaagccag gtcagtcagt aggaagacag       8400
gatgtcagat tgagagactc ccctggccgg ggaaacagac ttggagaagg gggagttttg       8460
gatgagacag tccacttccg agtcacaaaa tagcttgtgg gtgtctgttt actgttactc       8520
agtgggagtg gctggggaca cgccacctgg gcagggcttt cgtaattctg catcacttgt       8580
gaaggtcaca gattcccagc acaacggaca cacccatgtt catagtctga actcctaaac       8640
acatcttaaa ccaaaataaa aaaaaagaa agaaagaaag aaaaaggaga gggaggtttg       8700
aggaaagcct atggtctggg acactcaata cctcccatga atatctcata ttgggctggt       8760
cctctctcca ctctggcccc agccataagg gccctgctta gagcagattt tgggtgctga       8820
gtggaggcag cctcatcccc aacagcctga cttcctgcct cctccctgcc tctgcctgtg       8880
tccagcctgt gggaagagcc tgaagacccc ccgtgtggtg ggtgtggagg aggcctctgt       8940
ggattcttgg ccttggcagg tcagcatcca gtacgacaaa cagcacgtct gtggagggag       9000
catcctggac ccccactggg tcctcacggc agcccactgc ttcaggtaag acccagctg        9060
taaggaggtc tctgggacc aaggccagtc agggaccaga gagcttgggg tcctgtctcc        9120
tggcaccgtc cttctcttca ctctcccact agagacgttt ccaggttgt ggtggcccca        9180
atgagacaat ggccatgatg ccctttgtta ggcttttggg tgtctgagca gagggtgctg       9240
gtcaccaagc atggcctctt cctggtggga caccagcaga tacccagagt cctcacccca       9300
cccccatatc gttcaagcta caaaagctct tcccaccctgc ctcaacttcc aagaactcac       9360
tctctttttg cttgtttcca ggaagttgtt ccagggtcta gagtcatagc cacgtcctca       9420
ttatgtctgg aaacttaa aaaattaaag agcataggtt cctttcagtc cacagagaag        9480
```

-continued

```
cctggcctta cctcagggaa gggctactcc cagaccccct tcactttttt tttttttttt   9540
tttttttttt tttttgagac agagtcttgc tctgttgctt aggctggagc gcagcagcat   9600
gatcttggct cactgcaacc tccgcctcct gagttcaagc aattctcctg cctcagcttc   9660
ccaagtagct gggactatag gcatgggcca ccatgcccgg ctaattttg tattttggt     9720
agagacaggg tttcaccatg ttggccaggc tgatctctaa ctcctgacct caagtgatct   9780
gcccacctca gcctcccaaa ctgctgggat tacaggcatg agccagggca tccggctttt   9840
atttattcat tcattcaata tctaatgagc acctaccagg taccaaacac cagatgatgc   9900
gcccaagttc attagacccc accgctgtct tcaaggcact catgatctag gccagcgttt   9960
tttaaccact tttttttttt tttttttga gattctggtg agagctataa attctttcct  10020
ggaaaaacat ctctgcacac taagctgtgc ctggcattgg gaaaaagaaa gcacgtaatg  10080
taactgacag catgagtaac acagtgagaa aggttggagg agagagcgcc aggacctcag  10140
aactcaggca ttagaggagc cccttcccca gccctccttg aggtttcgtt gggcaggttt  10200
cactgaggaa aaagggtcaa atcccttttt cgaatttgac ttcttgtaag tgccagaaga  10260
ctgccccttc tccaccatcc ctgcctcacc atcatctttc ctcccaaggc agtgacatcc  10320
agcaccccga tccctagggc cctggggacc cagcctttgg caaagtctcc tcaggcttgg  10380
atcaggcctg aacccagctg tctctacccc caggaaacat accgatgtgt tcaactggaa  10440
ggtgcgggca ggctcagaca aactgggcag cttcccatcc ctggctgtgg ccaagatcat  10500
catcattgaa ttcaaccca tgtaccccaa agacaatgac atcgccctca tgaagctgca   10560
gttcccactc actttctcag gtgagaagca gggcccaagg ccactcaagc ctcttacatc  10620
agttttcacg cccactctgc tattagctca ctgaccgccc ttggcacata atgtctcctc  10680
tcaagtcctc agcttgccca tttgtctcta atacgtcagc ctaacatcac tgatgccatg  10740
aggcctcctc aagctgtcag ctaacacctc cactccattc cctgccagag attcttccaa  10800
ggcctgtctt ccctatgtgg agcccctcga gtgagaactg gagtttcatc caatcttgga  10860
gttttaggag acccttttaaa aagattatcg agctaattcc ccaccactga ccaacacgca  10920
agagcctgct cagtatccct gccaaggagt cattgtgccc ctgtttgctc tcctccaggg  10980
gcagggaacc cattacctgt gaggcagccc acagagtctt tgaacagctc tgttggatgc  11040
cttgtgctta tactgaaatg tatttagatc aggattccca actgtggggt ccacaagaca  11100
ctggcccctt ggagaagaga ggattccatt gtcaaataag tttggggaac attttcatac  11160
tacagctccc ttcttggaac acattagttt attaaaggta ggagaagttt ttaaaataat  11220
ctgtttatt gcgtttaacc tacattttt aaatttattt gaccacagaa tccttttttc     11280
atgctacttc tattagcatc ccatagaaca agtgttctag agaccctggt gtgacccctt  11340
tcagagagct taactgccag gctctcctga gccctggtgt gtgtttcaag atttgtgcct  11400
gggaattgtt ttaatcaggt atggcaaggt gacagataca gacacagcta tctttgaaag  11460
aagagtttat tatttataat tcctgagaga aagggacata ccccaccccc caacacaggg  11520
acacccgggg aagcagctgg gtccaccagg aggcaggagt gagggaagg catgcccag    11580
agccacctgt ggcttccatg ggcaggtctg gccaaggtag ggtaggcaag attgagcatg  11640
ctcaggattg gatagtgtgg acaattctct aggctataga tgtcagcctc tggttgtcta  11700
gtatctgtcc ctggggtgat ttagggcagg gaaaatattg gcttggtgtc tgagagtcag  11760
ataaaggaag tggttgggga tatgggcttt gggttggctg gtttgcctat taaaggcgtg  11820
```

```
cccaaagcca agttgtttac tatctgcagg aattagctaa cccagtctct cccagaccag    11880
caagatcccc ataatcataa agcatcataa tttacagaaa attaacactt atgatgaata    11940
aaagatctcc ttcttcctct gtgctcctgg caggcacagt caggcccatc tgtctgccct    12000
tctttgatga ggagctcact ccagccaccc cactctggat cattggatgg ggctttacga    12060
agcagaatgg aggtaagtcc tgggtgcagg accacagggc aggagatgcc cttgtatgag    12120
ggagcagctt ccagaagtaa tgggaaggag gaccaccctt cagagaaacc catcctggag    12180
gaccaagcac caaggcgcca ggcagaaagc aaagtggttt ggcaatccag ggctggggga    12240
tagaaggcaa ggatgggaat gtgagtgttt ttaccctccc agggaagatg tctgacatac    12300
tgctgcaggc gtcagtccag gtcattgaca gcacacggtg caatgcagac gatgcgtacc    12360 aggggaagt caccgagaag atgatgtgtg caggcatccc ggaaggggt gtggacacct    12420 gccaggtggg gcctccaaga atcatgggga gttctaagaa tagggtttag gtcctagaga    12480
gatgagaaaa cccagaggct gcatgcccta caggaagcct tgcatatcat gggcactcaa    12540
tgtgtgatga tgggaggaag agaggagggg aaggaaagga tagtcagata aaagtgtacc    12600
aatagatgag tgggtggatg gatggatgca gacaagcaga gagatttcaa atgtctcttt    12660
cacattcgaa gatgatgtta ctggcctggc atggtggctc acgcttgtaa tcccagcact    12720
ttgggaggct gaggcgggca ggtgatttga ggtcaggaat tcaagaccag cctggccaac    12780
atggtgaaat cccatctcta ctaaaaagaa tacaaaaatt agctgggcgt ggtggcacgt    12840
gcctgtaatc ccagctactt gggaggctga ggcaggagaa ttgcttgaac ccaggaggca    12900
gaggttgcag taagctgaga ttgcgccact gcactccagc ctgggtgacc cagcaagact    12960
ccatctgaaa acaacaacaa caacaaagat gacattactc atccaccccca cccacccttc    13020 tcactagcta cagaatgatt agcccccttga ggtcaggaat cccaggtcta ttttctctgt    13080
gactctcccc aagctgctga actacactag gaaagaatta ccgcctgcag aatgctggaa    13140
gcacatctgt gtgtgccctc accccggcct cattggccat caggactgct tagcaatccc    13200
tgtagacctt cttcctcccc catacttcca gaggatcttc tgaactattt tctttttta    13260 tttttttctt tatgtttttt aacagagaca gggtcactat gttgcccagt ctggtctcaa    13320
actcctgggt tcaagggatt ctcccacctc agctttccaa aatgctggga ttacaggcat    13380
gagccatcgt gcttggcctg aaccatttc attaaaaccc ctaccctact ctcacctcca    13440
tttccagtca ttaaattcct tcatttaaga ggcatctctt agtcatcgca tgtgtgccat    13500
gaacatggta gtctttggag acccctcagg gagctcacag tggttggggg aaaggggggc    13560
attaaacaga catttaagct atagttttgg gttcagaggg aggaagcccc aggggctaaa    13620
acagctgata aggactccca gataagtgca cttttcacta tctggcattt tcttgttttg    13680
ttatttgctt gttcactgtc tctcaccccca tttgatccta agctttctga gggcagggat    13740
ctttgttttt tttcatcagt tggatcccaa ttgcttagaa cactacctgg cacaaaatag    13800
gcactctata agtgattaca caaattttgg aacgactagg ttaaacaatg ataaccaggc    13860
tttttttttt tttttgaga ctgagtctca ctctgttgcc caggctagag tgaagtggtt    13920
tgatctcggc tcactgcagc ctccgcctct gggttcgaat gattctccac ctcagcctcc    13980
tgagtagctg ggattacagg tgcctgccac tatgcccagc taattttgt atttgtagta    14040 gagacgggtt tcaccatgtt ggccaggctg gtcttgaact cctgacctca agtgattcac    14100
ccgcctcagc ctcccaaggt gctgggatta caggtgtgag ccaccgctcc tggccaacaa    14160
ccaggctttt ttaagacatc actcagagcc tttaatttgc taatgtgagt tgtgaatctc    14220
```

```
tgagagaagg ctaacggcat gcttgcaact tacttgtcca cagacaagcc tttctgcccc   14280
agaagagaag accattctag ggtgctaatg agcaaagagg gtgagggtgg aatatcggag   14340
agcagcaggg agtgcagggg aacagatagg ccagttcagg gagcagagaa ggagaagccc   14400
ccccacctca cctgccctcc ccagcagtct ctgttctggt ctctcacagg gtgacagtgg   14460
tgggcccctg atgtaccaat ctgaccagtg gcatgtggtg ggcatcgtta gttggggcta   14520
tggctgcggg ggcccgagca ccccaggagt atacaccaag gtctcagcct atctcaactg   14580
gatctacaat gtctggaagg taaggtacct ttgccctacc cactgtgcct tccctccagt   14640
cctctacctg gggggtgcca atccatcctc aggtttgatt taaatggttc tgacaactct   14700
ttacatccca ataactttc cctccaagca agggacagcc tgagattgca ctattaaggc   14760
tgaaattcct taggtcagag atttctgata aatgcaaata ccttagggaa tagaacacac   14820
caagcctttc tttctctttt ctgacagaat gagactatca gatcctttct agagagaaga   14880
ttctgataag gaagagagtg gaaaggctca tgagacctcc tggccctctg cagggtaggg   14940
agagaagcaa agtgtttcag aaaaggaaga ctcacgttac acatgtcacc actttgtcca   15000
gtttcagata atctgacttt ctcttcatcg gtctctctta ttctaggctg agctgtaacg   15060
ctgccgtccc ccacatccag aagctgcttc ccttcagacc tacctacggc atgacccctc   15120
aaagtcagat atgggacaag agcctccttg aacaaactc                          15159

<210> SEQ ID NO 14
<211> LENGTH: 435
<212> TYPE: PRT
<213> ORGANISM: Artificial Sequence
<220> FEATURE:
<223> OTHER INFORMATION: Recombinant protein

<400> SEQUENCE: 14

Met Glu Ser Asp Ser Gly Gln Pro Leu Asn Asn Arg Asp Ile Val Pro
1               5                   10                  15

Phe Arg Lys Pro Arg Arg Pro Gln Glu Thr Phe Lys Lys Val Gly Ile
                20                  25                  30

Pro Ile Ile Ala Val Leu Leu Ser Leu Ile Ala Leu Val Ile Val Ala
            35                  40                  45

Leu Leu Ile Lys Val Ile Leu Asp Lys Tyr Tyr Phe Leu Cys Gly Gln
        50                  55                  60

Pro Leu His Phe Ile Pro Arg Lys Gln Leu Cys Asp Gly Glu Leu Asp
65                  70                  75                  80

Cys Pro Leu Gly Glu Asp Glu His Cys Val Lys Ser Phe Pro Glu
                85                  90                  95

Gly Pro Ala Val Ala Val Arg Leu Ser Lys Asp Arg Ser Thr Leu Gln
            100                 105                 110

Val Leu Asp Ser Ala Thr Gly Asn Trp Phe Ser Ala Cys Phe Asp Asn
        115                 120                 125

Phe Thr Glu Ala Leu Ala Glu Thr Ala Cys Arg Gln Met Gly Tyr Ser
    130                 135                 140

Ser Lys Pro Thr Phe Arg Ala Val Glu Ile Gly Pro Asp Gln Asp Leu
145                 150                 155                 160

Asp Val Val Glu Ile Thr Glu Asn Ser Gln Glu Leu Arg Met Arg Asn
                165                 170                 175

Ser Ser Gly Pro Cys Leu Ser Gly Ser Leu Val Ser Leu His Cys Leu
            180                 185                 190
```

```
Ala Cys Gly Lys Ser Leu Lys Thr Pro Arg Val Val Gly Val Glu Glu
            195                 200                 205

Ala Ser Val Asp Ser Trp Pro Trp Gln Val Ser Ile Gln Tyr Asp Lys
    210                 215                 220

Gln His Val Cys Gly Gly Ser Ile Leu Asp Pro His Trp Val Leu Thr
225                 230                 235                 240

Ala Ala His Cys Phe Arg Lys His Thr Asp Val Phe Asn Trp Lys Val
                245                 250                 255

Arg Ala Gly Ser Asp Lys Leu Gly Ser Phe Pro Ser Leu Ala Val Ala
            260                 265                 270

Lys Ile Ile Ile Glu Phe Asn Pro Met Tyr Pro Lys Asp Asn Asp
    275                 280                 285

Ile Ala Leu Met Lys Leu Gln Phe Pro Leu Thr Phe Ser Gly Thr Val
290                 295                 300

Arg Pro Ile Cys Leu Pro Phe Phe Asp Glu Glu Leu Thr Pro Ala Thr
305                 310                 315                 320

Pro Leu Trp Ile Ile Gly Trp Gly Phe Thr Lys Gln Asn Gly Gly Lys
                325                 330                 335

Met Ser Asp Ile Leu Leu Gln Ala Ser Val Gln Val Ile Asp Ser Thr
            340                 345                 350

Arg Cys Asn Ala Asp Asp Ala Tyr Gln Gly Glu Val Thr Glu Lys Met
        355                 360                 365

Met Cys Ala Gly Ile Pro Glu Gly Gly Val Asp Thr Cys Gln Gly Asp
    370                 375                 380

Ser Gly Gly Pro Leu Met Tyr Gln Ser Asp Gln Trp His Val Val Gly
385                 390                 395                 400

Ile Val Ser Trp Gly Tyr Gly Cys Gly Gly Pro Ser Thr Pro Gly Val
                405                 410                 415

Tyr Thr Lys Val Ser Ala Tyr Leu Asn Trp Ile Tyr Asn Val Trp Lys
            420                 425                 430

Ala Glu Leu
        435

<210> SEQ ID NO 15
<211> LENGTH: 2046
<212> TYPE: DNA
<213> ORGANISM: Mus musculus

<400> SEQUENCE: 15
cagaaacaag gacctcttca ttattcaaga gtaaaatgta taggccaaga ccaatgctat    60
caccgtcaag attcttcact cccttttgcag tagctttcgt tgtcataata acggtagggc  120
tcctggccat gatggcaggt ctacttattc actttttagc ttttgacaag aaagcttact   180
tttatcatag cagctttcaa atcctaaacg ttgaatacac tgaggcttta aactcaccag   240
ctacacacga atacagaacc ttgagtgaaa gaattgaggc tatgattact gatgaatttc   300
gaggatcaag tctaaaaagt gagtttatca ggacacatgt tgtcaaacta agaaaagaag   360
ggactggtgt ggttgcggat gttgtcatga aatttcgatc tagtaaacgt aacaacagaa   420
aggtaatgaa aaccagaatt caatctgtgc tacgaagact cagcagctct ggaaacttgg   480
aaatagcccc ttcgaatgag ataacatcac tcactgacca ggatacagaa atgttttga    540 ctcaagaatg tggagcacgt ccagacctta taacactgtc agaagagaga atcattggag   600
gcatgcaagc tgagcccggt gactggccct ggcaagtcag tctacagctc aataatgtcc   660
accactgtgg aggtgccctg atcagtaaca tgtgggtcct gacagcagct cattgcttca   720
```

```
aaagctatcc taatcctcaa tattggacag ccacctttgg ggtttctaca atgagccta     780 ggctgagagt gagagtaagg gctattttag cccacgacgg gtacagctcc gtaactcgtg    840
acaatgacat cgcagttgta caacttgaca gatctgtcgc cttttccaga aatatccata    900
gggtatgtct cccagcagca acccaaaata tcatccctgg ttctgtcgca tatgttacag    960 gatgggatc tctcacatat ggaggcaacg cagtcacaaa tctacggcaa ggagaggtca   1020
gaataataag ttcagaggaa tgcaatacgc cagctggtta cagtggaagt gtcttgccag   1080
gaatgctgtg tgctggaatg cgttcagggg ccgtggatgc atgccagggt gattcaggtg   1140
gcccgctagt acaagaagac tcaaggcggc tttggtttgt tgtgggcatt gtgagctggg   1200
gatatcagtg tggcctccca aataagccag gcgtgtatac tcgagtgaca gcctaccgca   1260
actggatcag acagcagacg ggaatctagt gcaaccgagg aaaaaacgtg ccatgaggtc   1320
tctgtatcca gtgtgactg actcggatgc catggcttca catttcaact gcaaaggaga   1380
ctggaaatgc cccttctgaa cgtcccatta cataaatatg gtttaactgt ttagtatttc   1440
tttgtcggta cagattttta ctttcttgag gaaaaaaaaa acatgaacat ggctaagtaa   1500
gaattatgtt aggctagtaa caggaagaca tttattacat gggtggtcag gtgtagtagt   1560
gagaagtcag gtaagttaag tcaataattt acagaaaata atgtcaggta gtcctaacgt   1620
taaatatgtg aggccacaga acaaatagtg ttagaactga agccatccca agtatttaac   1680
atttgttttc aagtgaaact aagaaacaga cttacatata gttttaatgg tgaattttca   1740
ttttaaatat tttatctaca tagaaaagac atatctcctt catgaagaag ctgaggtgat   1800
gaatcaacac agcctcttca gctatgtttg caaccacaag atttgtggga agaaatccc    1860 tactaccaac ttcctactgt tggcattatt ttttagagta acacgacgca caatagcaaa   1920
atttaagtaa caaattaaaa gttaatgatg aagaagaagt aaagagtttg tttgcaaaga   1980
caaaaattaa acagattaat atcaataaat ctggagacag aagggtctca gattcatatt   2040
ctctct                                                              2046
```

<210> SEQ ID NO 16
<211> LENGTH: 417
<212> TYPE: PRT
<213> ORGANISM: Mus musculus

<400> SEQUENCE: 16

```
Met Tyr Arg Pro Arg Pro Met Leu Ser Pro Ser Arg Phe Phe Thr Pro
1               5                   10                  15

Phe Ala Val Ala Phe Val Val Ile Ile Thr Val Gly Leu Leu Ala Met
            20                  25                  30

Met Ala Gly Leu Leu Ile His Phe Leu Ala Phe Asp Lys Lys Ala Tyr
        35                  40                  45

Phe Tyr His Ser Ser Phe Gln Ile Leu Asn Val Glu Tyr Thr Glu Ala
    50                  55                  60

Leu Asn Ser Pro Ala Thr His Glu Tyr Arg Thr Leu Ser Glu Arg Ile
65                  70                  75                  80

Glu Ala Met Ile Thr Asp Glu Phe Arg Gly Ser Ser Leu Lys Ser Glu
                85                  90                  95

Phe Ile Arg Thr His Val Val Lys Leu Arg Lys Glu Gly Thr Gly Val
            100                 105                 110

Val Ala Asp Val Val Met Lys Phe Arg Ser Ser Lys Arg Asn Asn Arg
        115                 120                 125
```

```
Lys Val Met Lys Thr Arg Ile Gln Ser Val Leu Arg Arg Leu Ser Ser
    130                 135                 140

Ser Gly Asn Leu Glu Ile Ala Pro Ser Asn Glu Ile Thr Ser Leu Thr
145                 150                 155                 160

Asp Gln Asp Thr Glu Asn Val Leu Thr Gln Glu Cys Gly Ala Arg Pro
                165                 170                 175

Asp Leu Ile Thr Leu Ser Glu Glu Arg Ile Ile Gly Gly Met Gln Ala
            180                 185                 190

Glu Pro Gly Asp Trp Pro Trp Gln Val Ser Leu Gln Leu Asn Asn Val
        195                 200                 205

His His Cys Gly Gly Ala Leu Ile Ser Asn Met Trp Val Leu Thr Ala
    210                 215                 220

Ala His Cys Phe Lys Ser Tyr Pro Asn Pro Gln Tyr Trp Thr Ala Thr
225                 230                 235                 240

Phe Gly Val Ser Thr Met Ser Pro Arg Leu Arg Val Arg Val Arg Ala
                245                 250                 255

Ile Leu Ala His Asp Gly Tyr Ser Ser Val Thr Arg Asp Asn Asp Ile
            260                 265                 270

Ala Val Val Gln Leu Asp Arg Ser Val Ala Phe Ser Arg Asn Ile His
        275                 280                 285

Arg Val Cys Leu Pro Ala Ala Thr Gln Asn Ile Ile Pro Gly Ser Val
    290                 295                 300

Ala Tyr Val Thr Gly Trp Gly Ser Leu Thr Tyr Gly Gly Asn Ala Val
305                 310                 315                 320

Thr Asn Leu Arg Gln Gly Glu Val Arg Ile Ile Ser Ser Glu Glu Cys
                325                 330                 335

Asn Thr Pro Ala Gly Tyr Ser Gly Ser Val Leu Pro Gly Met Leu Cys
            340                 345                 350

Ala Gly Met Arg Ser Gly Ala Val Asp Ala Cys Gln Gly Asp Ser Gly
        355                 360                 365

Gly Pro Leu Val Gln Glu Asp Ser Arg Arg Leu Trp Phe Val Val Gly
    370                 375                 380

Ile Val Ser Trp Gly Tyr Gln Cys Gly Leu Pro Asn Lys Pro Gly Val
385                 390                 395                 400

Tyr Thr Arg Val Thr Ala Tyr Arg Asn Trp Ile Arg Gln Gln Thr Gly
                405                 410                 415

Ile

<210> SEQ ID NO 17
<211> LENGTH: 2800
<212> TYPE: DNA
<213> ORGANISM: Homo sapiens

<400> SEQUENCE: 17
atttgagtgg gaatctcaaa gcagttgagt aggcagaaaa aagaacctct tcattaagga      60
ttaaaatgta taggccagca cgtgtaactt cgacttcaag atttctgaat ccatatgtag     120
tatgtttcat tgtcgtcgca ggggtagtga tcctggcagt caccatagct ctacttgttt     180 acttttagc ttttgatcaa aaatcttact tttataggag cagttttcaa ctcctaaatg      240
ttgaatataa tagtcagtta aattcaccag ctacacagga atacaggact ttgagtggaa     300
gaattgaatc tctgattact aaaacattca agaatcaaa tttaagaaat cagttcatca      360
gagctcatgt tgccaaactg aggcaagatg gtagtggtgt gagagcggat gttgtcatga     420
aatttcaatt cactagaaat aacaatggag catcaatgaa aagcagaatt gagtctgttt     480
```

```
tacgacaaat gctgaataac tctggaaacc tggaaataaa cccttcaact gagataacat    540
cacttactga ccaggctgca gcaaattggc ttattaatga atgtggggcc ggtccagacc    600
taataacatt gtctgagcag agaatccttg gaggcactga ggctgaggag gaagctggc     660 cgtggcaagt cagtctgcgg ctcaataatg cccaccactg tggaggcagc ctgatcaata    720
acatgtggat cctgacagca gctcactgct tcagaagcaa ctctaatcct cgtgactgga    780
ttgccacgtc tggtatttcc acaacatttc ctaaactaag aatgagagta agaaatattt    840
taattcataa caattataaa tctgcaactc atgaaaatga cattgcactt gtgagacttg    900
agaacagtgt cacctttacc aaagatatcc atagtgtgtg tctcccagct gctacccaga    960
atattccacc tggctctact gcttatgtaa caggatgggg cgctcaagaa tatgctggcc   1020
acacagttcc agagctaagg caaggacagg tcagaataat aagtaatgat gtatgtaatg   1080
caccacatag ttataatgga gccatcttgt ctggaatgct gtgtgctgga gtacctcaag   1140
gtggagtgga cgcatgtcag ggtgactctg gtggcccact agtacaagaa gactcacggc   1200
ggctttggtt tattgtgggg atagtaagct ggggagatca gtgtggcctg ccggataagc   1260
caggagtgta tactcgagtg acagcctacc ttgactggat taggcaacaa actgggatct   1320
agtgcaacaa gtgcatccct gttgcaaagt ctgtatgcag gtgtgcctgt cttaaattcc   1380
aaagctttac atttcaactg aaaaagaaac tagaaatgtc ctaatttaac atcttgttac   1440
ataaatatgg tttaacaaac actgtttaac ctttctttat tattaaaggt tttctatttt   1500
ctccagagaa ctatatgaat gttgcatagt actgtggctg tgtaacagaa gaaacacact   1560
aaactaatta caaagttaac aatttcatta cagttgtgct aaatgcccgt agtgagaaga   1620
acaggaacct tgagcatgta tagtagagga acctgcacag gtctgatggg tcagaggggt   1680
cttctctggg tttcactgag gatgagaagt aagcaaactg tggaaacatg caaggaaaa    1740 agtgatagaa taatattcaa gacaaaaaga acagtatgag gcaagagaaa taatatgtat   1800
ttaaaatttt tggttactca atatcttata cttagtatga gtcctaaaat taaaaatgtg   1860
aaactgttgt actatacgta taacctaacc ttaattattc tgtaagaaca tgcttccata   1920
ggaaatagtg gataattttc agctatttaa ggcaaaagct aaaatagttc actcctcaac   1980
tgagacccaa agaattatag atattttca tgatgaccca tgaaaaatat cactcatcta    2040
cataaaggag agactatatc tattttatag agaagctaag aaatatacct acacaaactt   2100
gtcaggtgct ttacaactac atagtacttt ttaacaacaa ataataatt ttaagaatga    2160 aaaatttaat catcgggaag aacgtcccac tacagacttc ctatcactgg cagttatatt   2220
tttgagcgta aaagggtcgt caaacgctaa atctaagtaa cgaattgaaa gtttaaagag   2280
ggggaagagt tggtttgcaa aggaaaagtt taaatagctt aatatcaata gaatgatcct   2340
gaagacagaa aaaactttgt cactcttcct ctctcatttt ctttctctct ctctcccctt   2400
ctcatacaca tgcctccccc accaaagaat aaatgtaaa ttaaatccac taaaatgtaa    2460
tggcatgaaa atctctgtag tctgaatcac taatattcct gagttttat gagctcctag    2520 tacagctaaa gtttgcctat gcatgatcat ctatgcgtca gagcttcctc cttctacaag   2580
ctaactccct gcatctgggc atcaggactg ctccatacat ttgctgaaaa cttcttgtat   2640
ttcctgatgt aaaattgtgc aaacacctac aataaagcca tctacttta gggaaggga    2700 gttgaaaatg caaccaactc ttggcgaact gtacaaacaa atctttgcta tactttattt   2760
caaataaatt cttttaaaa taaaaaaaaa aaaaaaaaa                           2800
```

<210> SEQ ID NO 18
<211> LENGTH: 418
<212> TYPE: PRT
<213> ORGANISM: Homo sapiens

<400> SEQUENCE: 18

Met Tyr Arg Pro Ala Arg Val Thr Ser Thr Ser Arg Phe Leu Asn Pro
1               5                   10                  15

Tyr Val Val Cys Phe Ile Val Val Ala Gly Val Val Ile Leu Ala Val
                20                  25                  30

Thr Ile Ala Leu Leu Val Tyr Phe Leu Ala Phe Asp Gln Lys Ser Tyr
            35                  40                  45

Phe Tyr Arg Ser Ser Phe Gln Leu Leu Asn Val Glu Tyr Asn Ser Gln
    50                  55                  60

Leu Asn Ser Pro Ala Thr Gln Glu Tyr Arg Thr Leu Ser Gly Arg Ile
65                  70                  75                  80

Glu Ser Leu Ile Thr Lys Thr Phe Lys Glu Ser Asn Leu Arg Asn Gln
                85                  90                  95

Phe Ile Arg Ala His Val Ala Lys Leu Arg Gln Asp Gly Ser Gly Val
            100                 105                 110

Arg Ala Asp Val Val Met Lys Phe Gln Phe Thr Arg Asn Asn Asn Gly
        115                 120                 125

Ala Ser Met Lys Ser Arg Ile Glu Ser Val Leu Arg Gln Met Leu Asn
130                 135                 140

Asn Ser Gly Asn Leu Glu Ile Asn Pro Ser Thr Glu Ile Thr Ser Leu
145                 150                 155                 160

Thr Asp Gln Ala Ala Ala Asn Trp Leu Ile Asn Glu Cys Gly Ala Gly
                165                 170                 175

Pro Asp Leu Ile Thr Leu Ser Glu Gln Arg Ile Leu Gly Gly Thr Glu
            180                 185                 190

Ala Glu Glu Gly Ser Trp Pro Trp Gln Val Ser Leu Arg Leu Asn Asn
        195                 200                 205

Ala His His Cys Gly Gly Ser Leu Ile Asn Asn Met Trp Ile Leu Thr
210                 215                 220

Ala Ala His Cys Phe Arg Ser Asn Ser Asn Pro Arg Asp Trp Ile Ala
225                 230                 235                 240

Thr Ser Gly Ile Ser Thr Thr Phe Pro Lys Leu Arg Met Arg Val Arg
                245                 250                 255

Asn Ile Leu Ile His Asn Asn Tyr Lys Ser Ala Thr His Glu Asn Asp
            260                 265                 270

Ile Ala Leu Val Arg Leu Glu Asn Ser Val Thr Phe Thr Lys Asp Ile
        275                 280                 285

His Ser Val Cys Leu Pro Ala Ala Thr Gln Asn Ile Pro Pro Gly Ser
290                 295                 300

Thr Ala Tyr Val Thr Gly Trp Gly Ala Gln Glu Tyr Ala Gly His Thr
305                 310                 315                 320

Val Pro Glu Leu Arg Gln Gly Gln Val Arg Ile Ile Ser Asn Asp Val
                325                 330                 335

Cys Asn Ala Pro His Ser Tyr Asn Gly Ala Ile Leu Ser Gly Met Leu
            340                 345                 350

Cys Ala Gly Val Pro Gln Gly Gly Val Asp Ala Cys Gln Gly Asp Ser
        355                 360                 365

Gly Gly Pro Leu Val Gln Glu Asp Ser Arg Arg Leu Trp Phe Ile Val
370                 375                 380

```
Gly Ile Val Ser Trp Gly Asp Gln Cys Gly Leu Pro Asp Lys Pro Gly
385                 390                 395                 400

Val Tyr Thr Arg Val Thr Ala Tyr Leu Asp Trp Ile Arg Gln Gln Thr
                405                 410                 415

Gly Ile

<210> SEQ ID NO 19
<211> LENGTH: 38992
<212> TYPE: DNA
<213> ORGANISM: Artificial Sequence
<220> FEATURE:
<223> OTHER INFORMATION: Recombinant polynucleotide

<400> SEQUENCE: 19
```

| | | | | | |
|---|---|---|---|---|---|
| gagggagggt | ggtgctttgc | taatggtgaa | ttactaactc | ctcaataaag | aatattattt | 60 |
| gaaataattt | ttgaaatttc | ataattactt | tgggttcttt | cttaatgata | aataaataat | 120 |
| agtatattac | aaacatacat | taatatttcc | tgaatgaata | caccacaaat | ctcccttaaa | 180 |
| atatagcaag | aataaaaatt | atactatttc | tgacaatttt | taatttctca | aataataata | 240 |
| ccactctgat | ttttaaacat | ctacaccact | ctggctttgc | caatcttttt | aaaaattgaa | 300 |
| aagataataa | ttttatcata | attacactga | agcatagaac | ttttctttc | aaggaaagca | 360 |
| aattttgaa | attctataat | ataacctccc | aatcctga | ataaattaaa | ggttcaacaa | 420 |
| cttagtaaag | taagactgac | cttcccttt | atttcttttt | cagatcaaaa | atcttacttt | 480 |
| tataggagca | gttttcaact | cctaaatgtt | gaatataata | gtcagttaaa | ttcaccagct | 540 |
| acacaggaat | acaggacttt | gagtggaaga | attgaatctc | tggtaagtta | atatttgtct | 600 |
| ttgctcttta | ttccattata | aaatgaatat | gataataaac | ctaatgtttt | gtaatatatt | 660 |
| ttcagttgct | aagtgctcta | catatttttcc | ttccttgaat | ggtgaaacat | gtgtttctct | 720 |
| ctgcttttat | ccagttagtt | tactcatata | ctggttctta | ttcacatctt | tgtcatgagt | 780 |
| aaaaagtgtt | agaaaggcca | cgagtaaata | tgcatttat | ttgtttatga | attcaaatac | 840 |
| taaaagttt | ttatttgttt | aattaagcat | tgacattgtc | tttttaaatt | cttttcattt | 900 |
| taccttcttc | cctcttcctt | atccaactaa | agacgcaaag | caggaggtgt | taaaaaacag | 960 |
| gtttaccata | tcagcagtaa | catagtttgg | acaacattac | actttggttc | aatgatagac | 1020 |
| atagaagttt | gaacagaaat | atgcaaagca | agtttgagct | ctaacttgaa | gagagcctct | 1080 |
| gggtgcctgc | caggaaacct | cacgagtgga | cccttaacat | tcatgtgtca | ccacaaacta | 1140 |
| ggggctgccc | tttagttttg | accagtctca | gtgtcactca | cttcccctta | ccttttcaaa | 1200 |
| aaaaagtcct | aagaatataa | agtaattcaa | tggttctaca | atttttagcat | gtaactgagt | 1260 |
| cacctggcag | ggttgctttg | gtgagctcaa | gataaaattt | tatcagcatt | tctacatttt | 1320 |
| ctggaatatt | ccttaatcca | ggcttttaat | cccttggtgc | ttttctgaac | cactgcaatg | 1380 |
| agcttctaac | tgttctcact | gtgtgcaggc | tcttttcctt | ctaatctaat | ttacacactt | 1440 |
| ctgaacacaa | atctctcaca | gcctgtttcc | ttcatgttac | ctccagctca | agactttttg | 1500 |
| cctacaaaat | aaaattcaaa | cttgttagct | aagcaccttc | tcatgtctat | gctttggctc | 1560 |
| atatttcagc | catcgtgtgc | cccacttatt | cttatagcca | acctgaaaag | ccatctttta | 1620 |
| taagaaacta | cctctgctct | ccatgattgg | atataattaa | tcctccttcc | acatcacctc | 1680 |
| gccacaaaat | tgtatctgtg | ttgatctcat | gccacatacc | tgtatgtatt | ttatattata | 1740 |
| aatatttgca | gacttgttta | atttgccatg | ttagactaag | ttccatgaag | acagctccat | 1800 |

-continued

```
atccattcca tttttatata tccacaacat ttggtcgggt tgatgcttaa taaatgttta    1860
ttgaaggaac aggagtctcc cacttctgac ataatgaact tatttccccc agtgttaacc    1920
ctacatctgg ttcctgtcca agagtctctt cccaaatcat tctgattcaa ctgttcattc    1980
tgatctcatt aaacatttaa atgatatatc taacttcgct tgctttattc tatgctcatc    2040
ctgcagtctc ctcataactt ggtttcaatg atgcttgctt ctagagaaaa aaatgtatta    2100
aataagctta tgattcagtc ctccagctgt gatggttctc actgaacatt agctcagtgg    2160
ttttcgaagt atggtctcta gcataaccta gaaacttgtt agaaatgcaa attcttgggc    2220
tcaccaagac atactaaatc aaaaattctg acattggggc ctagaaatct gtgttttaac    2280
aagcctgcca gtgcagcctg gtccctttc ttctcggagc cccactcaaa gctttcagtg    2340
ctcatctccc accaatgaca gggtcctcta tggaaaccgg caggacggtt tccaactcta    2400
actacgtttt agagtttgct tcctagggct atccaggcac caagtatcac aggttagttt    2460
cccaggaag cagactctga gacttgcatg cagggagtgt ctctggggtg ctctcaacca    2520
acaccttcag gaagagaagg aagcagcatt gggcagaggc atagtcaaac tacagtgctg    2580
ttggcacaga agactgaagg gagtcagagc caggggtag aggtgggccc ttagcatcca    2640
tccttcacca ttaggtgtga gttgccccac ctccttgatg gtgtaacctc agtcccaagg    2700
tgggtgggag tgcagcagag cagcccctac aagggccaaa ccagagatac accaggcgcc    2760
agaagtgctg ccagggaata gagaggaaag gatgggctta aggtaggatc cacagaactt    2820
ggcaatggat tagaagacag gatgagaagt gacaggttaa cactaacaca gaaatgtcta    2880
acttcggtag ataatggtgc cattggctag aagaggaaac cgaaatgaaa gcaggttgtt    2940
cagggagaca aaagttcact gtggacatct cagcagagtg attcagtggg gaaaggaatg    3000
gatgcccaga ccacctcaga ggaagatcta agctggagcc agcaataaag atacaagatg    3060
aacaatccct aacgaactgc tcctcagcca tgctccccag acacgctgct tcagatttat    3120
agtccgggtg aggctaggag gtgcgcctcc ctcagtggag gacagcaaag caccagtggc    3180
tccagggagt taaaatcttt tgataatttt tgttctagca tctgtctgca gagctgtctc    3240
tcagccattg cctgccttta cacaggagtg cagtccgaaa ttgggagatg agtgaaattt    3300
attatgccta gagatctgga tccccagttg tttgggagta tattttctga accacttgtt    3360
ggtttaagta atgcagattt attgatgcca cttctcttga atctgtgact ctggacccac    3420
catctaagtg aatgtgcaga gggaacggaa tggctgcaat agatctccat taaaaccagt    3480
gcatcctccc agacacatac agtagtaggg aggtgagtca atgtcaggac agcaccagct    3540
cccgcttcgg tacatttcca aagttctcag tctgtgtaca aaggtttgct ctggggcagc    3600
agaaatagcc ctgggcaggt agtcaaaggc ctggtttgat ttcctccact tccaggcaag    3660
tcactcgaag gctcacaggc ttttttcctca cctgccacat gggtccagtg agatctactg    3720
agctgtaaat aatgaaatga gtgtgtgtgc agtcatctat aagttgtaaa gtactagaaa    3780
atggtgaaac tttgggattt gggctattta aggctgaatg ctaaaaatgt caggcattgt    3840
ggagaaagga atttaaatat aagattgatt gactgggatt taaagacaaa tgaaggcaca    3900
cacgcaagtg cacacccaca ctgacactgc acagctcccg ttggaggcat atcctgacca    3960
tgcagacctg gggctctgcc tgtccaagtg cactcctta ctacataaac cctccttctc    4020
ttttggggct gtcacccca cagagctggc accgagccct tgctgctgcg cttccctggg    4080
gtgtcagctt ttgacagggt gtttcctccc tctgcaggag ccttaacatc ccttggactt    4140
ccttccccc acccaccccc agcagtttta tctcttccta actcgggacc ctttttttcc    4200
```

```
cacacaaagt ttattgtcag ttgctggttt catctgtttg agcggctgca acaaaatacc      4260
atagactggg tggcatatgc acgacaaaaa tttatttctc acaggagaag tcaaagatta      4320
atgcaccagc agatctggtg tctgaggggc caccttctgg tttgtagatg atgctttcta      4380
gttaaaacac ctatttaaca cactattaaa cactaagtgt gttaaatagt gcagttgatg      4440
tatttgtcat gtcaccttta tcatacacta aatccttctt tgtcttttt tctgtactct       4500 aatctctttc tgtaagtaat ctttgcttgc agcagtagga tatttagagt actgtggctt      4560
gacaatatat ttagtatttc aagatttcca tgaaattctt ctgatgtatg agttccctag      4620
ttaatcttac atatgtatcc ctttgtaaaa acactttgaa catttaaaat gatacatgaa      4680
tagtactcta atacaatgcc ataaaaatta taaatcattt gtatagactg gtaagtaaag      4740
attgtgagat taagaaacgc atcaaaggcc attgagctgg aaagtggtat aatgagaatt      4800
caaaccaggg tctcttgact caaaatctaa ggatcatacc atttctcatg ataatatgag      4860
tattattgtt atctctatcc catagacaaa gtgttaacac tgaatgagca gtgaaatagt      4920
ctcagaattt tttattttat ttagcaattc acttgtcatt tctggtcctc agtttattca      4980
cgagtaaaat aaaatagttg gactagataa tttctatagt acattcttac acaaaaaatc      5040
tatgattttg ttatttttaa tgtgatatac tcatggcact cattcacctc attttcccag      5100
cctgcctcac tggtcattac ttctctgtgt tctttacagg ctcccctcc tctacactgc       5160 cattaaatat tgaaacacct caaagcttta cttatgtcca cctctcctct gacactatca      5220
ttctgtctag atgatcccat acatacatgc ccattacttc aacctgtatt tatacgccaa      5280
tgattcacta tatttccagc ctagacattc ttttgtactc tagttaccag cttgatatcc      5340
ttacatggct gtttcaaaac aactcaaata tattatctct caaaatcaaa ctcatgatgt      5400
ccccacacca tcctagcttt ccaccaacaa tacctatccc tattaatagc aataccattt      5460
attcagttat ccaaatcaaa aacctagaat tcatccttaa aattctacta tcattccaaa      5520
tatcctatcc atcagcagcc actgtattct taatcccctg tatttccttc aaatccattc      5580
acctctctcc atatccattg ctgcatgact atccaagcca tcgcctctac cctagggtac      5640
caaaatagca acaaacctaa tctgttcatt tgcattattt tttctccaaa actgattatc      5700
tatatgtagc aagacagatt gttctcaaat tgcaaatccc actatattat cctcttgctt      5760
caaacacttc catggtttcc cattgtttat gataaaacca aatgcttcaa gttcgaagac      5820
cggcatgatt gggaatttcc tgtcacccta gcctacttgc tctccatggt acagttgcac      5880
tggctttctt tcattcctta agtacaacct gtttcctccc acctcaggac tgtgcatgtg      5940
ccattcattc tgctgaggag cctttttcct tccacttcaa tcagctaagt ctgattcttc      6000
ctgacaatct cagctcaata agcatttcct ctaagaaatg tctctaatat cattaattgg      6060
ctcaggtccc tctactgtat tgctgcactt ttcacagtta aattttact taattatgaa       6120 tgattatttg attaggtcta tttccatcca ttagacataa gcttcatgat ggccagatta      6180
ctgttttcta tccatcgttg tattccaata cctgacagaa ggagggcggg aggtggtggc      6240
acacaagaga tgctcaaaaa caattgttga ataagtaaat gaatgaggcc atttagaaat      6300
aacgaaagta cctgtttaca aagtacatgt atcaaaacta tgaatgcatt ctacttacat      6360
ggttttctcc aaataaaaca aaagacttca atcaggatta atacctggga taaactgagt      6420
cattaaatct ctcctttgcc atcaggagtg acattgaaac aaatgtctgc aaacaacaaa      6480
tacttttttc ccaaaatata ttgaatggca tttccataaa caaactagaa catgggagga      6540
```

```
gaaagaaagc aatattaatt taaaattaat cttatcacat aacttatacc atcagggatt    6600
tcgggtaaaa ttcctttcag gcacatccat ttaacaagaa ttgattgtta ctgaaagcct    6660
agaagagaat ttggcacata cttggtgttc aaatatttgt tgactgagtg aataaatgat    6720
gcaagtgtct aagaaacaca aaataaggac atgattacag tcacggtgga gttcacagtc    6780
atctccaaaa tgaggatatg catcccaggg aggaccaaca attcattgga gtgctgaaat    6840
aaaatactca aaggtcattt tacatgtatt ttttctctaa attacttttc ttaagacaca    6900
gaaaacaaaa aagaaacttt agctttgtta ctttctaaca aatagttaaa tcattaaaca    6960
ggattgacac tagcatcctt gtttggtctt atgccttagg ggaacatgaa atgtgtgaag    7020
acattctgag atctgaggga agggtagaca gtaatacagt gggactgacc aggcttcagc    7080
acacctttac ctcctctcag cagatttcag tgatgagcag tttacaacta gattgaaaga    7140
ttatattatc tagttctaaa agaaaactaa gcctcccaaa agcaacaagg gaactgagag    7200
gaatcctgca aaacaaaaac aaattttaaa acttgcactt tgtaataacc ctaatatgta    7260
atcacagtaa tgaacagtaa gataatgaca gaactgacat atttccttat ctattaaagc    7320
catattaaca ggtaaagcaa tgccagtcag tggtacactt cttagaagat atttaataca    7380
tactagacac atacacacac acaacatttt ccttcaaggt gtatgtatca gaaaatcact    7440
ttttaaggcc ggatgcagtg gctcaggcct gtaatcccag cactttggga ggccgacgtg    7500
ggcggatcat ctgaggtcag gagttcaaga ccagcctgcc caacatggcg aaaccccatc    7560
tctacaaaaa tacaaaaatt agccagggat gatggtggat gcttgtagtc ccagctactc    7620
aagaggcaga ggcaggagaa tcacttgaac ctggggaggca gaggttgcag tgagccaaga    7680
tcacccattg cactccagcc tgggcaacag agtgagactc tgtctcaaaa aaaaaaaaat    7740
cacttttttag ataaaattca tgctatagag agaagactac tgaaaatatgt ttagcaatgt    7800
gtccatcatt aggtgattga gtttcctttt gttttgtttt actgaaaatc atataaagta    7860
tgttatctgt aaaagttctc tgacatgcac acataaaaat ttgggagaaa agattaacta    7920
taatgtttaa tagattttgt acacatttct ttaaaaatat ataaaacaca caccttttca    7980
attggtttgc aagaataacc aattgacatc atggaaaatg gaaattcact tgctgaattt    8040
taacaaaaat ttgcatgatg agtgagactg acaacttagt gtcatgattt aatgaattat    8100
gccaatggta aacttcatgc acatggggcc aggtaattat gtggaaactt tttcaatgct    8160
taaagccaag tattgaaatt aaacttagaa tcagaccttt gaaccatttt atgacaatgt    8220
tcaaaaatta taaattctat ccacttatat tataatatta aaaatatcat tacaaaaaaa    8280
acctgtgttt atttttataac tcagcctttt taatttctaa tttcataaat atattataat    8340
ggatattgtt agtaatgtag tattattaca tgtatataat ttataagtaa atatacatgt    8400
tttggctact catgcataaa atgtttcacc cataggagca cataatcaga aatgtctgga    8460
gaccattata gtaatagata gatcatattg ccacatattt tatctcctcc ttgacaactg    8520
agctttccag atcttctggt gaaacgaaag agaaagttgt aacagaagag tgattaaaat    8580
gacaaaagca ttacttctat tacttctatt ctaataatat gagcaaagct ataactatca    8640
agtaataatg cactaaagaa ggtgattaat ctgatatatt cacaggcaac taataagacc    8700
tttctattgc agccatgaaa aatatgtgac aattatagat atcctgtgtg cagtgtttca    8760
acctttatgt gacctgttct actaacagat ttagtgatgt tcactttgtt agaatttttct    8820
tacacatgcc ataacttgct tcagtctttt gattatgaat attatggata ttaaggattc    8880
tagactattc tagatttaaa aaataatatt gtcacctcaa tcagaaggga aatattaaat    8940
```

```
agttctcatt ttttcaatgt ttactcagtt tttgtccaat gtaatgaaag tgtcagcagt    9000
acaggttaca aaataaaatg tgtattaaag taaactcatt tgaacaggtt aataattgta    9060
gagggaggga aaaggctaaa agattgaatg taaaacttat gaaaagtaga tacatcgtct    9120
ctatgatttg cagtagtcaa ctgcatacag atgaatcatt ttaatacacg ttaactactt    9180
tccttttaca gatggagaaa ctgagaggaa gaaagtttat atggttcatt aaactttgtg    9240
atgcaagcta aactaacctg tctctgtatt ttccatctac tgcccttatc actatctcat    9300
tagaatactc ttcaagcatc tccttactga ttttcttacc aagcatttgt taagttctaa    9360
tgagagttgg tagtaacatt ttcacccact ctgtgaaata tgaaatctta ttcataggcc    9420
tcttctttta ttcttgtatt tgcatatcaa ccaattaatc aacttgcttt ctttatgttg    9480
cttattatct tagtccttac taaattgcct cttaatgttg tccacataac agaaatgtta    9540
aggtggatac ttaacatttt agtccagtct agccggtgcc agtgcaatgc caaatcatga    9600
attaaaatat aattacaaga accacttatc aaattttaac aattccttca gctttgtgac    9660
agttttttct acttcgatta aagtcaagta aaattaaagt taaatatttt tattaaaata    9720
tctcctttaa cattccatat taataaacat attaaagctc atgcttctaa gtagattact    9780
agaagttact ttatcgaatt acagcaatgg ttaattctag atcatagaat ttagaatgac    9840
tttttgcctt cttctttttt ttcctttttt taaacagag tcttgctctg ttgtccaggc     9900
tggagtgtac tggcgcgatc ttgactcact gcgacctctg ccctgcaggt tcaagtgatt    9960
ctcctgcccc agcctcttaa gtagttggga ttacaggtgc ctgccaccac acctggctaa   10020
tttttttttt gtatttttag gagagacagg gtttcaccat gttggccaga ctggtctcga   10080
actcctgacc tcaagtgatc cacttgcctc agcctcccaa agtgctggga ttacaggtgt   10140
gagccactgt gcctggcctg acttttgct ttcttcttaa tacttactag tatttcttga    10200 attttaaaa aagaaacata aagtactttg ataaaaccaa cagtctcatt gttcttaaaa     10260
ttgttcaaag gttctctgga aaaaaaaag aaaattatca tttggttaag aatcatgttg     10320
gtctgacatc aatcatccta taggagtgaa tattgaaaaa gtaagatata ttgtggtata   10380
atcgagattg cataaatttt accattttg agaagaatct gctccaaatc ctggcttaat     10440
gtaatatcca gcatgctact taatttcctt gtcttcacct tttcatatcc acatccacct   10500
aggtgccacc tcacagtata agccagcata atccattctt ctcaatgaaa ccacaataca   10560
tctgaccctg catctcagga gaactgtatc agccacagca cttccagttg actatgaatc   10620
tgaatgttat gcctcaggag aaacatcctt gctgggactg agtagtgatt caaggagata   10680
gttatgattc agtcaagaaa ttaataatta gtgttatttt tattattgag acagagtctc   10740
gttctgtagc ccaggctgga gtacagtggc atgatctcgg ctcactgcaa cctctacctc   10800
cccggttcaa gtgattctcc tgcctcagcc tcccaaataa ctgggacagc aggcacttgc   10860
caccacgcct agctaatttt ttgtattttt agtagacg gagtttcacc gtgttagcca     10920
ggatggtctc gatctcctga cctcaaggtc cacctgcctc agcctcccaa agtgctggga   10980
ttacaggcgt gagccactgc gcccggccat aaattattaa ctgagccagg cacagtggta   11040
cacacttata gtcccagata ctcaggagac tgaggttgga gtatccttt ttatgttatt    11100 ttattttaa ttattatggg tacataatag gtgtacatac ccatggagta caagtcatgt    11160
tctgatacag acacataatg tttaataatc acatcagggt aattgggata tccatcacct   11220
caagcattta tctttctttg tgttaggaac attccacctc cactcttgga ataggcaccc   11280
```

```
tgttgtgcta ttaaatacga ggtcttattc atttcatcta actatatttt tctacccatt    11340
aaccatcacc tcttttcccc tcttccccac tacctttcct gtgaggctgc aggattctta    11400
agcacaacag ttagaggcca gcctggacaa catagtgaga ctcaatttct aaaaaataaa    11460
aaagaaatta ccaactaatg ctaaaaaaat agtctctgat gcttaggtat gaattagaaa    11520
tgaccaaaaa aaaaaaaaaa aaaagactg cccttgctt ccttctcccc ttctcttcaa     11580
gttttccatt gctactcatt ttagtctggt ttaatcaggt ttcatccatt aaaagcaatt    11640
gttgggatca cacattttga gttgtgtcag tggacttccc tcatgctggc atgattcctg    11700
ccccaagccc ttagtaaaag ccaccaagcc atataacata atctctcatt gagtaaaaca    11760
tctgatgtgt ttagaatgac ttctagcaaa aaaccagcct gtccagcatc atctctgtat    11820
aacagataaa ggaataggta ctgcatcaaa aggttataga acctgcccaa atcaatccca    11880
tgtgttttgc aatggaatta ggttgaacta aagtgaaaat tcagttttct actcctcatt    11940
aacatgtctc atgttgcaag gttgagagga aggagaagaa gaactgtatt tacagagaga    12000 ttcccctct ctttctttct acagattact aaaacattca aagaatcaaa tttaagaaat     12060
cagttcatca gagctcatgt tgccaaactg aggtgagtgg aactgtagaa aaaatattta    12120
agtatagata caatgtggca tacttgactt tttgtcacag aatgaatagt aaatgacatg    12180
ttcagataag ttgttgtaat attatgaaaa tagtatttta gtcagcttaa aaaccaatgc    12240 caaaaagcc aaacatatga tctatttagc tactaatgta aataaccata ttatatctat     12300
tcttattggg aagaggaaga aggggtggag agagagttgg ggtgaaggta cagtaacaag    12360
gccatcctat tgtaaaactc cagtggatat cattcacagt gcagcctatg taaacagtcc    12420
ctcctggagt tgtacaatgc tgtggtttgg gtgtatccat ccaagatcaa gacactatga    12480
ccaacatcaa aagtggcttt ttggttttat ctgcctgatg tgctataata aaagggtatt    12540
atggccaaat ccaaggcatg tctatcatga attaataata ggaggagtag cagcatgcat    12600
gctagttatt tgccattcct gccttagtta aatatgatgt gataaaacca gccttttccaa   12660 ctgaaatagt caccttact gactctcccg caaatgtctc aaatgaccac attgctctag     12720
tctttaaata atatgcaata gttctttggt agaagaggaa ttatactaat tctttctcaa    12780
atactagcat cacaagaaaa ttaattcttg ttctctggag agtcacctag taagtatctg    12840
gagcacagat gtctggtcag gtaagttttg atgaggagtt aaagggataa gaagagtcca    12900
tgagaagggt attttccaaa acacctttcg gtcaattcag tgcacattca cttagtactt    12960
tcttgtcagt atctgtatca gccactaatg ttcaaaagtg agtaagccct gaaaacctgt    13020
aggactacat gagccttctg cctttttctct ccttttgttc acttcccact tatcactcaa   13080
tcctctgcaa cctggcttca ataccaccat aaaatatcaa ctgctcttgc cgattcaaca    13140
atgacatcca gataacaaaa tccaaagaaa ccacatcagt cctattcttg gacctttcaa    13200
cagtatttgg tcctgttggc ctgtcactcc ttgaaatagg actatccctt ggtttgcatg    13260
gccttgtata cctgattttt cccctacct ccctagctat tccttcttag tttcctttac      13320
taggtcttac ttctttgtat attccttaaa tgttgctgaa catcaggctg tgctctaggc    13380
ctctcatctt ctcaggtcac actctctcct tccttggcc ttcactgcca cccatatgct     13440
gagtgctctc aaagttgtat ctctaggcca gtcctctttt gcctccaaac atgaatatat    13500
gcagccatct acttggtacc atcacatgga taattctcat gatctcttcc agtatgactg    13560 cttcttatt ttttctgggg ctcttttta gcattgcttt acatggaact ttatcatgtc      13620
tctcaacctc tattttatct tttatctatg tatgtagagt ctgtgtaatt tcttcatctc    13680
```

```
ttttagataa ctaatatctc ttcagctttg acttgtattc tgtgtaaccc atttattgcg   13740
ttttcaattt caatgagtat gttttcctat ctgcaagttc tatttgtttc ttttgagaat   13800
cttcctggtc ttttaaacac atttcttatt ttaattttg ggggtaccta gtagttgtat   13860 gtattttgg agtacatgag atgttttgat acaagcaaac aatgcataat aatcacattg   13920
tgtaaaatgg ggtatccatc ccctcaagca tttatccttt gtgttacaaa caatccaatt   13980
atattctttt agttattttt aaatgtacaa ttaaattatt attgaccata gtgactctgt   14040
tgtgctatca gatactaggt gatctttaa aaataatgtt ttctacttaa tctcattttt   14100
atgattccct cttttacgtc atttgtcatt tcaaatacag tcacttgtct gttgattcta   14160
ttatgtgaag tttttgagga taatcttttt gttactttga ttccaccttg gtatggtttg   14220
gctgtgcccc cactaaaatc tcatcttgaa ctctggttcc cataatccc acatgttgtg   14280 ggagggacct tgtgggaggt gattagatta tagggacgtt tccccccttt gctctgttct   14340
ttttcctgcc accatgtaag aaagatgtgt ttgcttcccc ttctgccatg attgtaaatt   14400
tcctgaggcc tccgcagcca tgcaggacct cttttctttg taaattaccc agtctccggc   14460
ggttctttat agctccgtga gaaaaaacta atacacacct catgatgtat tgtttaccac   14520
tgaaattgta tgcttaaatt taatctcact tgggaccctg tacaacctag acttaacata   14580
tctacctcca gagcagttac atctgtcaga cattctagag gaatcagcag cacatggact   14640
ttgttgttgt taatttgttg tcggggggagg ggggagggat agcattagga gatacaccta   14700
atgctaaatg acgagttaat gggtgcagca caccaacatg gcacatgtat acatatgtaa   14760
caaacctgca cgttgtgcac atatacccta aaacttaaag tataataata ataaaattaa   14820
aaaaaaaaag gttctgggag tattcaggta gtattaatga agattcagac atcgtgcagc   14880
caggcccatg cttatgaatt ttcaggtgat acttcttttt cttttttctt aatttaaagc   14940
tggatctcgg aaacagataa atttattttt ttatgacatg acgagcattt ttttcattct   15000
agttcatgct gttattgggt gtttagttct ttgagactcc tggcctttt ctaaaacctc   15060 aagttcaact tcctattttg cactggccca aggtcccatc tccagtctct atgtaaatgc   15120
taaacataag cctgtggaat attctagtct caccacatac tattcacatt cttctttgtt   15180
tttggtcttc caggattttc cttactttc tatgaaccca gtcttgcatt tgaaatggaa   15240
tttattatat attatctatc cttctatttt gtttatgca gaaagtgttt tctaaaatta   15300
tttaggcttc catattgcta gacatggaag ttgtaattat tgttcagtg cctgtttcta   15360 catctaaact gcaagaccca tatggcaact gtgaatctta gtcccagcta atttctgaag   15420
cttagaatag tgcctagcac aagaagttgt ttatctaaca tttttaaaaa taaatattaa   15480
attcatatct ggaatgaata ttaagttaga gctggtcatt gaggtgagag gaggaagcca   15540
agagagaata tgagagcctc aaagccaaat atctttaatg tacttttca gaaaagaaga   15600 cagccaatgt caggtggagg aactggttta tgaggtaact ttcctggaag aaaatagaaa   15660
ttactgaggt tttagataat ccaaatattt aatcaagtca ccaaggttta ttgtggggaa   15720 tcttattat taattaaaat gagtgatgaa atcttaatat acgacaaaag ttaaaatttg   15780 ctttgcagg cagatgaatg gtctaggtat caaaaaatta agttgagtct ctaactcaca   15840
caaatttaca accctatcac tttatgaatt tgtttaggag attattttta ataacactgg   15900
tgaagtctaa gaatagctaa aatttatagt acacttattg tgtgctattg actcttcttt   15960
gaagttttgc atatagtgat tcatctaatc ttcataaccc attttacatg tgaagaaact   16020
```

```
tagatataga aagattaaga aacttacata acttatccaa agttacacag taaaactctg    16080
gcattataac ttcaaaatca gctatcctac agtgagtaca gtgttctgtg cattgaaatc    16140
aaataagtga gatagcatcg tgatatagta ttacgtatgc aaacactgtt acagagatct    16200
gtctaaagtt aaattccaca aatgaattct ttaaaagggt ttaatcaaga agaatatata    16260
aacaggatgg tgaaaaattg tcatattatt tgttttttaa aatatcttta tgatttacag    16320
gcaagatggt agtggtgtga gagcggatgt tgtcatgaaa tttcaattca ctagaaataa    16380
caatggagca tcaatgaaaa gcagaattga gtctgtttta cgacaaatgc tgaataactc    16440
tggaaacctg gaaataaacc cttcaactga gataacatgt aagtataatt tttcataaac    16500
aattttattt caatatatcc ctcaagtttta ccaattcaaa ttcatatttt aattgagagg    16560 ctgactttc tttctttgaa actaaactgt gaaaacaatc cattaaaaag ctaaatatac    16620
catatagctc cctaacgtaa atcattctaa gacttaaaga atcatttggc atttatatag    16680
taaattttat ttgctaaaaa ttctcattaa ttatccctgc aacattcctt atgagtgatg    16740
ttactgtcag atgtcattag tggataggcc ataggagggg tacatagatg ctcaaggtca    16800
gagaactatt taattaatga tccacctcag aggcttcttc attttctttt gtaacattta    16860
tcacaattga aattacaaag ttatctgtgt aaattttgta ttgtttggct tcatcctaca    16920
ctgtaatcat cctaaaagaa agaaccagtc aaccttcttc atcctactac cctcctacca    16980
cccagtctcc atcatataac acatattcaa taaataattc ttgcatgact gaaagaaaag    17040
aaataatata tgcatagaat ttaaggacat tcctccaagt tggttacatt ctgctagttt    17100
aataagccat tatttcttct cgatgagctc aagattaaaa ggattttgat gattcccata    17160
ctagactggt aggtaccagt tacagatgta ctaactgtta aatattgaaa tgctttccta    17220
tttgttggta aacaattact gcatcaggcc cacaaagttg tcttccgaga tgtttcaaat    17280
ccactgcccc tgctgctaaa gagttatgct tagcaaagca aagcactcta agacactgct    17340
ccaactccat ggcctgattg catcttttat gactggccaa tgctcacgca ctgcagtttg    17400
ttaggtagtt gaatattacc tctgcttcca cacattaagg aatgctcccg aacgcacttc    17460
ccaagtgttt atttatttat cattatacta gacaatatgg tgatacgatg gtcacagaat    17520
agcggtttcc acctccagag cccataatct agttgaaggg aaagatattc caacacaaga    17580
gtgttgacaa tcaagataga atatgatcaa gggcccagtg tgaggccag gcaatgatca    17640 ctgcaggaat ctggggaaga aagagaccag cgtgcttggg atatctagca aaagtttcat    17700
gaaggagaat ggactttgac tttgaaatat gggtaggatt tacatatttt gagatgagaa    17760
aaagaaagtt cccagagaag gaaagcatga aaaggcaaac agtctgtact gaacgcgatg    17820
ctttgacaga ataatgaaga aagggacctg ctggaatgat tgatcagtgt tcatcattca    17880
caccatcatc atcaaaacac ttatttaatg agaacttact gttttttagg catggcttta    17940
atgccctata tgaatttttt tcttgattaa tccttacaac aaacatatcc catagatagt    18000
tttattgtcc cccttagaaa agataaattg cctaggctga cacagtcagt atatgaggca    18060
gtcaggattc aaactaagtc tgtttgttca aaaaattaag aatggccagc tttttaaaat    18120
tttctgtctc cagaagtatg atttggctcc actgaagttt gcaaaacaaa tgtgataccc    18180
aaaccttgtg aaacttttag tgggaaataa ctttgcataa gtcggtttga gagagcgtgg    18240
aaacctgtct tgaaaagttt taatttaact tgcaggaaat aaaaatgatg ggtttctcaa    18300
ttaaaaattt caatcaagga aggatatgag ctaacataac attttttttaa aaagatcagt    18360 ctggtaaggt agaggtgcat aaaactgaaaa ggagcaaaag tggtggaatt cagttagaaa    18420
```

```
attattgtaa ctgtactgat gtcaaatgat gaaaccatga actaaagtag taccaaaagg    18480
agtgaggagg atgaataat  tcaaaagata gaggacagat gtgcagaacc tggagattat    18540
aagatgtgaa aggaggagtt tgagaaaatt tcagattttg gaagtggtgt cattttacta    18600
aaaggatata ataagtagca aattttggat aaagttgggt cccactgagt ttgagatggc    18660
tgttggacat gcagagaaaa ctgtcttgta tgctgttctt aaattgaaat agacagacct    18720
ttaccctctg atactgacat attttccttt ccaggctcac cctccatttc cctaaacaca    18780
acacatgcac tagctctcct tactttattg ctccacaaac atcttacacc tccaagcatt    18840
tgtgcccact gtaccttcta tctggaatct cttttgtcct cttgtgtgcc tgaaaaattc    18900
ctttcagatc ttcaaaatac agtgcagatg ctatttcttc tagctcaaat attatctcct    18960
ccatataatt taattactct ctttttttctt ttctctactt tgcacttaca tttatttgaa    19020
tgattgcttg attaatttct acctgtaaat tatgtgaggg caggtcctct atattttgct    19080
cgcagttaaa tctgcagcac ttattataga gtggtatcat tagagtaata tacatatatt    19140
tgaggacatg ataaattaac ttcccctata gtatttatca cattgcatct caatgacttg    19200
cttatgtttc tgttttccca tataaattga gtaacttgaa aaagagata  tctattaagt    19260 atttaatgag aaattaaagt acaaacttta gtatgcataa caacaaattg ggaaaaggtt    19320
gtaaacaaag agatttgtag ggcccatgag ttagagatcg tttcagcagg tctgaaagga    19380
agcctaggaa tctgcatttt agaggaccac ctcccaaccc caacaagtaa ttctgcttct    19440
tgttgtctgg gtactgtact ttaagaaatt atggtgaaat gatatcagcc tttattgtat    19500
ttatcttatt ctcattttttt aatactagca cttactgacc aggctgcagc aaattggctt    19560
attaatggta agttttaata ttattttgta actgtaattt gccaaatcat aaagagtaaa    19620
agtgcaagtc ttttgtgtac ttttggccaa ggcagtatct atcaagttga tgtctttgtt    19680
cttagttcgc tcaggtggtg ttgaaacaag acagtgctga tcccaagtgt cccatggagt    19740
ggactttagg tttccccttt ccttttagaa aaaggaagaa gttgtagtgg aggactaccc    19800
actctgcact caaaattgcc ctcatgaaaa tttctttggc agctttgaga accttttact    19860
gccctggttc taaggtggca tttctgtaga cttacaaatt atgtttgatg acaccgttta    19920
tgtagcttct cctaaccacc agagtagctt gctttgttgt gaattcaggt taatcacaaa    19980 gtaataaaa  aaagaattgt cagaagtctt cccagctttg ggtctataac ctgaaggaaa    20040
agtcactact cttcaacatc atcctatgta ctctcaggct aggatagcag aaatgcaatc    20100
cctagaaaac agcaacttac ttctctgacc aaaaaaatgc agttaaaaat tagttcaatg    20160
tacctggtag ctggcctatc ttaggtactt cagtgatttt acaaagtgat ggtagtccta    20220
tgggtgtttt tcagcttcac tacgtattta attcatgctt attgttaatg aaactgtgat    20280
aagcaattta ctagggtatt tgtttgggag atgccacaaa ggaacacatg tatctcttaa    20340
tggaagcctg gtcctccttt atccaggaaa tttgctagga aaaaaagcc  tttaggtggt    20400 tgtgctatta aaccagggca ctacttaaaa gccagcccag caatagttgt gtgatttacc    20460
attaatttct tagtaataga ccacacaaaa gaagaaaatt atgggaatgc gagttgagag    20520
gaattgggtg atcagcctac cccagcccgt ttcagctctg gccagtagac tattcacgag    20580
ctctttgaaa acatttaaat aaaccttatt tagatactag aaaccctctg tcaccctcaa    20640
gaatattctg tggtatagcg actcctttat gagggcatgt ttggtaatac agcatcagtc    20700
ttggaggtgg actggattct acaaggtgaa ctgcagtcac taaggagtct tttggatgag    20760
```

```
accagttttc ctccaacttc aatgtgtgca tgaacctcac atcaaaatgt agctttagat   20820
ttgtcccatg atgtggttcc aagaatcagc acttctaata agtttccagg ggatgcccat   20880
gctgcaggcc cacaaaccac actgagcata gcaagactat tgagaaaaag gaaatttccc   20940
aggagtctgt ggcctgagct ggcacatcca ataatgacct atcttaacct caactcatga   21000
ggaattccag ggaactctga agctgctcaa aatttgaagc ctatatgcca actaaattca   21060
gaaatgttct ccaaaatgct atctataagc aacagtagtc acaaatgcat tgtagaaata   21120
tatcgatcat gcttttgga aaatccagca tgtcctgagg aagaatgtat aagacataaa    21180
agtcataaat tatggaaaga ctcttcagct tcttccaaat gtaaaggaat catgatcttc   21240
ccagcacatt aatgccctt ctcattagaa tgtggggccg gtccagacct aataacattg    21300
tctgagcaga gaatccttgg aggcactgag gctgaggagg gaagctggcc gtggcaagtc   21360
agtctgcggc tcaataatgc ccaccactgt ggaggcagcc tgatcaataa catgtggatc   21420
ctgacagcag ctcactgctt cagaaggtga ggccaccact acctacccat ctgggaacaa   21480
ttagaataga caggtcatga agactgcacc ctctaccca ggattgaatt gagccagaaa    21540
taattcaatg caaaaaaatc agtaagaatt ttcttcctat tcatgaaagg aaaaggattt   21600
ttccccttta gcatgctaat ttagtgctat ttctctgttt caggtaataa tatattagca   21660
cagtaaagaa caaagattta tatgtcagaa tgttttttaa atcctagcta taaaagctta   21720
agaaatttac taaatctcca taagctttat tttttttcca aattaaggga caacactgtt   21780
atctgtgact tagtgttact ggtagcattg agtacactaa tgtaaacata cgttaaatgt   21840
tagcgaaacg aattgctgtg gaagatttgc acattatatc atgggagctg atggctaacc   21900
tagagactgc cccatgccat taatttattc attcataaag attattgagt atctagtatg   21960
agcacagtgt tatatattgt agaagctact agtataaaca aagtattgcc tctgccttca   22020
aagagcttac actcgaatgt tggaatcaga atgcacaaaa ataatgatca attacaatga   22080
gtagcataaa taaaattaat gtaggcaact tacaagaatt cttaattgag gtgactaaac   22140
tattgccaac actagggtga tatgctacca gtggcgagta ggttgcataa acttaccta    22200 ttggtaaaaa gaaaagttca cattgctcat aaaagaagga ttttagattt cagcataact   22260
aaaatctgtt tcaaacctgc cttgttactg gggcatcgca gaccacaaca gttgttggga   22320
acttaactca aaaagttcac ccagaaaaat aatggagatt tgaactcgtg tgccctgac    22380 catatcaatt ttcttctcag actcttactc taaactggac ctccttatca cacacacaaa   22440
gccttccata ggcagatcaa tccagtctta tttctcaaag catgtacctt gagcttcaga   22500
taaacagcat tgttctcttc ccctggactc ttcctacatt tccctaccta tgagtatctg   22560
atcaatctgc ttatccttga aatgttaata tatttaccac atctctattt gaattttatg   22620 aaattttga taatttctaa gtagtttttt cagatttata ggcactactt catggtacag    22680
tgactgttac aaacgtattt gttaaattta gaaggaataa agatttaaaa gactagggta   22740
gttactgaac taaagtttta ggaaatccca aattatttca aattttttctt atggtaattt   22800 tatgacttaa tatttttata tgcagtgaac aaatttgaaa ctttaaaaga tactcccaga   22860
attatcagtt ttctgatgta gattggcaaa tttattacta tatcccaaat aacccaagag   22920
acaaaattca caaaaacatt tcaatttttca ttgccacttg aaaggccaaa aagcagaaat   22980
ggcacgcatt gatttcaatc gtactcttga gtgtgggaac caggaattaa aatacctgga   23040
cttatcaggc acttagcata accaagaacg gaatagaaac ctccctggat tctaagccct   23100
attcagtccc aatcaccaaa aaccaagtaa acgatatcac tataatgaaa gccacagtta   23160
```

```
taaatatcga caacgattac caaaggaatc catggaactt tgaattttgc cacccacat    23220
ccttctattc attaccatga ttgatccact aaagctaaca gactctgtga accttgtatt   23280
ggaccctcc ctaaagacct gattgtcact gagaaccatc agtgaggatt tgtttggggc    23340
atgaccagcc ttacatcaaa gtacatagaa gtgatgaggc cttatcaaag aggattattg   23400
aattatcacc tcttctatgt agctttccct gatactctct ttcctctcca ttgagttcca   23460
cagaaatttt tttatctgcc tttaacagtt gtcctcatga tttgtgatat ttgacttacc   23520
tcttgtcagt ttccttcact agtgtagagt tcctcaaaga aagagaccat aattacttat   23580
attttattc ctggagactc atactattcc ttatacaaag tagacactta acaatggctt     23640
gttgaactat aattaatgaa ataatagct accttcatga aagttcactt tgtgccaaac    23700
actatagttg acataataca tttgtctcat taatacttaa caattgtgtg agaaggtatc   23760
accaatcaca ttttatatgt aaataaaccc cagagctatt aattaacttg tcataaataa   23820
cactttcat atgtggcata gccaagattt aaatataaat gttactggtt ccaaaatgat    23880
gctctaattc acttgctgga aagaaggaaa ggaagaaaat aaacgagtgg aaggaagaga   23940
gggagggaag agagaaaagg aaggaaagaa aaaagagtct cttcagaacc ttcactgtaa   24000
agactccgag caaaagaagt tgaatataaa acaacatag gtttgtttgt tttctaatat    24060
tttttcttca aaattttaa ctcaggttca ctcttacaca aactactgtg tcttataaaa    24120
gtatttccgg tcatagaatt tttatttct gtattaactc cactatctaa tctccataaa    24180
actcctaaat tggtattatc ggtaacattt tgtttttact caacccttag gaacaatgtt   24240
aagttaatca gccctccaca tcacagatcc ttattttcat cagtctgtac aaggcatttc   24300
tctcattta attttttttc ctcctgtcat ccctggattt cactttcact gccctccttc    24360
cacccatatg cctcatacta atatattcga aatatacatg tcttaaaggt acatgcacgc   24420
acctacaaaa cctatagtgt ttttttgtat gtatatgtct ttaattaaa taagtagcat    24480
tgtgtaaaag tctaatattg tttcttactg ttttcactca attcttggaa ttttcatctg   24540
atgcactgct gcatagcacc ccatggtatg cagccaccat atttccttca tccaattagg   24600
ttgcatgacc taccttccca ttgccacaaa gagtacacac aaaatatttg tacttatctt   24660
tctgtaaacc ttcaggaatt tcagaagcac acatgcaggc tgctaaatat accagaatac   24720
tttccagcca cttaaatctt taccagtatt gcaaagagg ccccattcc ctccacatca     24780
acatttagta ttattctttt gtttaagttt tatcaatctt ttaaatgtac acaagatgct   24840
cattttata attttaattt ctcagattac tagtttgagt atcttttcat atatctaaga   24900
gctgttttga tctcccctac catgaactgc cactaatatt ctttgcctat tttacaatgg   24960
ttttttctgct tatttattac tggtttacag acttttaaaa tatattctac aaaaatttta  25020
gacattaaac attaccaata ttttcccatg gttcctcatc catctggtaa acttgtctat   25080
ggtatatcta attttgattt aatagaattc attctatttt tacctttag tttgtgtttt    25140
tgttgtttag ccaaaaagtc cccattccta ggtcataaag gtaatgtcct tttttttttt   25200
ttaacgctac tgttctctct ctgtctcccc ctatgtatat aggtgcacat atacttgtac   25260
acacatacat ataaccatat atgagggag ttcgataagt ttatggaaaa taaaattaaa    25320
agataaaata aaaaattata aactttattt ctcaacataa gctccttcaa gttcaagaca   25380
cttttgtaag caataatacc agccatatcg tccatcccta aagaactgag ggtcctgaga   25440
atttaactat gtcaatgcag tctttttac attactttt tacagtactt attgatgaaa    25500
```

```
aatgggtgcc ttttaaagat tgttttaaga ttagggaaca aaaataagtc agaggaagtc    25560
aaatcaggac tgaaaggtgg atgcctagtg atttattgct gaaactttca taaaactaac    25620
cttatttgat gagaggaatg agcatgagca tggttgtgat ggagaagaac tctggtggag    25680
ctttcctgga cacttttcct actaaagctt tggctaactt tcttactctc ataagaagaa    25740
gatgttattt ttcactgacc ctttagaagg tcaacaagca aaatgccttc agcatcccaa    25800
atgtctgttg tcatgacttt tgttcttgac tagtctggtt ttgctttgac tggaccactt    25860
ctacctcttt atagccattg ctttgatggt gctttgtctt caagattgta ttagtaaagc    25920
catatttcat cttctgttac aattcttcaa agaaatactt cagaatcttg atctgacatg    25980
tttaaaattt ctattggaag ctctgacctt gggtgcagct gatctgggcg aaacagtttt    26040
ggcatccatc aagtagaaag tttgctcaac tttagttttt cagtcagaat tgtataagct    26100
gaaccagttg agatgtctat ggtgttgtct attgtttctc acagttaatt gttggtcctc    26160
tttgagacat gaacaagatg aaattttttcc tagcaaactg atgtggatga tctgttgctg    26220
cgggcttcac cctcaacaac atctctttct ttcttgaaac aaattatcca ttagtaaact    26280
gatgattggg ggagatgctg tccccataaa cttttttgtaa ggcataaata atttcaccat    26340
tcttccagtt tcaccataaa tttgacgttt ttttgcttca attttagcag cattcatgtt    26400
gctttgataa gagctctttt caaattcatg tcttattcct cttagtgcct caaactagat    26460
cttgttcagt atgacaagtt agtatgagtt tatctgcatg caaaaatctt tgaaatccat    26520
gcatagtttg tttataatat acattttcaa tgaacttttg aagacccat acatacatat     26580 gtatatatat gcacacacac acacacacac acaccaaaat cttcaaccat tatcagactt    26640
agtgcagaaa aattattcat ccattaacaa gataagaatg ccccttatca tcactactat    26700
ttaaatggag ctcctggcta aaggaaaaga cagggattga aaaaaattag ttaaatctaa    26760
aatgtttatt atttcaggtt tcttagttgc ttaaatggga agggaggtat ggacaaaaga    26820
gaaatcaaag atatttgtgt tatgctactt atcattaaag tatcagaata acttcattgg    26880
aatagaaaaa caccaagatc accccacgat atgttttcta aaatcttctc catttcttta    26940
gacaagtgac catgtattcg gccagtgaag aattaaactc acttgccagc ttataatgca    27000
ggaaaatata gcaaagagat gtggatccaa tagtttctag atagtggtac aggatggcta    27060
agatgaattt atatatctga aatgttcaca aattccctac tcatatagca tgttttcata    27120
atgttttagc aactctaatc ctcgtgactg gattgccacg tctggtattt ccacaacatt    27180
tcctaaacta agaatgagag taagaaatat tttaattcat aacaattata aatctgcaac    27240
tcatgaaaat gacattgcac ttgtgagact tgagaacagt gtcacctttta ccaaagatat    27300 ccatagtgtg tgtctcccag ctgctaccca gaatattcca cctggctcta ctgcttatgt    27360
aacaggatgg ggcgctcaag aatatgctgg taagtgtctc ggaaaaaaaa attaacaata    27420
gaaatgtctt atatttgcta ttaggtaatt ttttaaatta ggaaacatct ggaataggtg    27480
tttctattct tctacagaca gaaccattct atattctgct cagcccaagc tctggctacc    27540
cctgagtctc cttagcaaag caaagcaatg ctccagaaac tatgggaatt ctcaaatata    27600
gtaataggaa aatgtaaaag aaagttatga agacacgagt tctttaataa tccagagatt    27660
ctataagatt caaatagctt ccctataaac aataaaaaag attttgtttg tttgtttgtt    27720
tgcttgtttt ttagagacaa agactttctc agactggagt gcagtggtgc aatcatggct    27780
tactgcagcc tcaaactctg gtcttaagaa atcctcttgc ttcagcctcc caagtagcta    27840
gaattataaa taagtgtgta ccaccatacc cagctttttt ttttttttttc tacagacagg    27900
```

```
ttcttgctct gttgcccagg ctggtctgga attcctgccc tcaagccatc ctcctgcctt   27960
gttggcctcc caaagcaatg ggaggattta gattagacat tgtatgaggg cttaataatc   28020
cttaaggtat taactgccct ttaaagtatt ctgggatatg gcaaaaactc gatgtgtata   28080
taaacattgg tcatatttgt ttattgaatg aataaaatgg aaactaaaat gaggacaatg   28140
cacaagagct actagaacca gtaagagtat cagcgaagga gtggaagggt agcattgaca   28200
atttccctgg gcttttaccc atgttgtaga ttgtctctcc aaggaataat acaaagcctt   28260
aatagtccta gaacacattc tattgtgttc ttatggccca agtaaattg gtgtagtaga    28320 taacatttgc accagtcatg aaaaactatt ggtgtcattc tgagagtaca tcaatataaa   28380
atagactagt tctttagcct tgaaactaga ctggtttctc ttttgctgct aggttaaagg   28440
ttattcaata tgtaatcttc caatccaaaa tctgtcagtg gataatttaa aagcttttag   28500
tcaattttaa gatatttgtt ttcttaaaat tttaagggc actgtgtcac aaagctaaag    28560 aaaaaaaga aaaaaaact gatctgtgaa agggttatc ctcatctact tggggaattt      28620
tggctgcgaa gaaactccaa agtaaatctt tagaagcctt cattgttaaa tatgaaataa   28680
tgtttggagt acatttattt cttctcaaat ttattatagg gtcaataatg tacacatctt   28740
gaagtccatt ttttcctgc ttttataaca aacaggccac acagttccag agctaaggca    28800
aggacaggtc agaataataa gtaatgatgt atgtaatgca ccacatagtt ataatggagc   28860
catcttgtct ggaatgctgt gtgctggagt acctcaaggt ggagtggacg catgtcaggt   28920
aagctcaaga caatctcatc catgtcatca tccaagaagt gtataagcac ttcctagtat   28980
gtgataatgt gatagacata agtgtaacag ttacaataca cagccctgtt cctctaaaat   29040
ttataatcta gattttagaa ataaattttt ttatgaatga agtttatcta tcatgaaagc   29100
attaactctg agaggccaaa ttacagagta gttaaccatc caaagctcaa gaatcagaaa   29160
gacctcgatt tgaattcctt aacctctatt accaagtctc taactaaaag ctggggataa   29220
tcataatagc acctaacttt tgggtacta agaaaagtta aatgaagact aaatatatca    29280
ggcacatggt aaacaacaaa gaaatctcat ctatttcact attattaatg tagaccatgg   29340
tcactcgtgt taataacttt aacctcaacc ttttaactgc tgtgaaggat taaataaaaa   29400
attaatcact atattataaa aattaattga tatataataa atgaatttta agagatacgt   29460
aataattcat ggactccttg aagatagaaa atttatacaa aatcctagta atttgagtca   29520
caaaagctcc tacaataatg aaacagtatg aatgaaaaag aaaagaaata actattatat   29580
ttggatctag cccataattt ttaaccaaat gcacaaaaac aaacaacaaa tatgaaattc   29640
tcactgtaaa gtgattaaaa tcaaatttga attctaaaat tttaaattaa attatctaaa   29700
cataattgat gcagttatat gttttaatag gttttgttca catatctgaa atccaactcc   29760
acacagtagc aggaacagct ggtgtcagaa attaaatatt cttttagtct ggagttttaa   29820
aaaatcaatc tgtttacttg agtaatttgt tgctgttttc atgggtgaat tgtatacaga   29880
aggataagaa ttattcttcg catcaaaagg tcactgactt tcatatttag tgctcatggt   29940
ctttaaaaag tggataaaaa gtagttctca catttcatgg aaagccccca atccatgagc   30000
acatttccca aaatgaaaca ttttttatcaa ctgcaagttg tgtgtaggtg gagatttgtt   30060
tttcaattgt caagatactg ttaattaccc agtcctttat ctccttttgg tggagatgtc   30120
tctgtgctag gaaacccttc ttgctctcct tcctgtttct cttttactac tggccctgaa   30180
acaacaaatt ctcaagtttc atgacagctt tccaaagaat ccatcaatca aataagcaac   30240
```

```
acaactcgac actgacaatt ccagacctac taagagcatt aattaagact taaaaataaa    30300
catgagtttt aaaagggtgt tattcattat tttcccattt ataacgtccc ttaccttctg    30360
tccttcagtg catacaaatt attatcttcc ttgaagccca gttcaagccg tacctcacca    30420
tgataccttc catgtatatt ccactctagg cctcactgat ttttaactga atactataa    30480 tgcatagttc acacttaaaa aaaaaaaaaa aacacagcac tttacataag agcttacagg    30540
atcctatttg ttttatccat tcttttgttc atttttacaa tcattaattc aaaggaatta    30600
tattaattac tttctatgca cccgacgttg tgttaacaca acaatactat ccctgcattc    30660
agcaagtcta tggtctacaa gagaggacac aaattcaaat gtctgtagtc aagcagtgaa    30720
gctggctaga tatggaaaaa ttacaagtcc ctcttgcttt aacatttgct tgcccacatt    30780
tggtcagaca tcatgcaaaa taatttctca ctatagaaaa aaaaacacta caaaacaat    30840 aatataaaga actgagaact ggttaactga agcatgcata tgtcatctaa aagaagcagg    30900
tgacgaccag cttcatgaag tacttgccat gcatattggc acttcacaca ctgacccttc    30960
tccccaccta gaccagtaat taaacaggta tggatgagct agctactaag agcagccaac    31020
tgaatagctg actaacttag aagcacactt ggtaataata gctgacttt attagtactg     31080 actatactat atgctaagct gtactcaaag tgctttgagt tttaaactga tacaaacatt    31140
atatgaggaa acagaggtac agagagctat tcaccagctt accaaaggtc acatagctgg    31200
taagtggagg acttaaaccc agactatcta gtttcagaac ccacagactt aatccatcgt    31260
gcagaacata agacatactc catctgtctc cccaactagg ttattatgtg cacaaatatt    31320
tattggttgg ttggttcatt attatgactg ggtggtaagt atgtcattag gagtgttttg    31380
cttatgacta tataaatttc ttcaccaaaa gaagactttc tgatgatata ctatgcatca    31440
gacaccacgc agggtgctaa ggttaggaag ataagtgaga cttctagaaa ctcattcatt    31500
caacaaatat ctcctaaggg ctagaagctt aggtttcagc agtgaacaga ataggtatgt    31560
tctctttcgt gttggacctt atagtatatc tgggaaaaca gacattgaat aaatatcaca    31620
aatgcaagtg agtgtttcag agacatgcag ctgctacatc aaaacaaaac agaacaaaac    31680
aaacaaacaa aaactgacca gtgggattaa gtgtaaatag gcacacaaat gcacaaatat    31740
gcttttataa aatagtgaag cagtgacaga gacacacaca agatataaag acacaatgaa    31800
gaacaattga gcccaaagct ggaaagggtg agagtgtgaa ggaaaaaggt tgatcagaga    31860
agttttcccg aaggagagaa agcctggatg attaggaggc aaccactcgg tgactgaggg    31920
aaatctgaaa aatgtatttg tcatcttctc agacttgctg aaggaatgac ttgggtactt    31980
tgaggatttc agtaattttt ccatgacttg gtataatatt tcaaaggaa ataggctgac     32040 tttatttgta taatgaatgt gactccttcc tcgactgcca tagaaataaa ctccttaata    32100
ttttgggttt gtctttgcac ttaagtaatc agtcattctg ttttttttaca gggtgactct    32160 ggtggcccac tagtacaaga agactcacgg cggctttggt ttattgtggg gatagtaagc    32220
tggggagatc agtgtggcct gccggataag ccaggagtgt atactcgagt gacagcctac    32280
cttgactgga ttaggcaaca aactgggatc tagtgcaaca agtgcatccc tgttgcaaag    32340
tctgtatgca ggtgtgcctg tcttaaattc caaagcttta catttcaact gaaaagaaa     32400 ctagaaatgt cctaatttaa catcttgtta cataaatatg gtttaacaaa cactgtttaa    32460
cctttcttta ttattaaagg ttttctattt tctccagaga actatatgaa tgttgcatag    32520
tactgtggct gtgtaacaga agaaacacac taaactaatt acaaagttaa caatttcatt    32580
acagttgtgc taaatgcccg tagtgagaag aacaggaacc ttgagcatgt atagtagagg    32640
```

```
aacctgcaca ggtctgatgg gtcagagggg tcttctctgg gtttcactga ggatgagaag   32700
taagcaaact gtggaaacat gcaaaggaaa aagtgatgaa ataatattca agacaaaaag   32760
aacagtatga ggcaagagaa ataatatgta tttaaaattt ttggttactc aatatcttat   32820
acttagtatg agtcctaaaa ttaaaaatgt gaaactgttg tactatacgt ataacctaac   32880
cttaattatt ctgtaagaac atgcttccat aggaaatagt ggataatttt cagctattta   32940
aggcaaaagc taaatagtt cactcctcaa ctgagaccca agaattata gatattttc     33000 atgatgaccc atgaaaaata tcactcatct acataaagga gagactatat ctattttata   33060
gagaagctaa gaaatatacc tacacaaact tgtcaggtgc tttacaacta catagtactt   33120
tttaacaaca aaataataat tttaagaatg aaaaatttaa tcatcgggaa gaacgtccca   33180
ctacagactt cctatcactg gcagttatat ttttgagcgt aaaagggtcg tcaaacgcta   33240
aatctaagta acgaattgaa agtttaaaga gggggaagag ttggtttgca aaggaaaagt   33300
ttaaatagct taatatcaat agaatgatcc tgaagacaga aaaaactttg tcactcttcc   33360
tctctcattt tcttttctctc tctctcccct tctcatacac atgcctcccc caccaaagaa   33420
tataatgtaa attaaatcca ctaaaatgta atggcatgaa atctctgta gtctgaatca    33480 ctaatattcc tgagttttta tgagctccta gtacagctaa agtttgccta tgcatgatca   33540
tctatgcgtc agagcttcct ccttctacaa gctaactccc tgcatctggg catcaggact   33600
gctccataca tttgctgaaa acttcttgta tttcctgatg taaaattgtg caaacaccta   33660
caataaagcc atctactttt agggaaaggg agttgaaaat gcaaccaact cttggcgaac   33720
tgtacaaaca aatctttgct atactttatt tcaaataaat tcttttaaa ataatttccc    33780 tgcctaatta tttatggaag ttatgacttt tgaaggacaa ttcaaaacca tttatttaat   33840
tggttctgca atgaaagaac tgccccatat actctactaa aggcttggca ctttctgctg   33900
ccttttaatc cagcgctata attgaggcaa gcgtccagct tgacacctcg agataacttc    33960
gtataatgta tgctatacga agttatatgc atggcctccg cgccgggttt tggcgcctcc   34020
cgcgggcgcc cccctcctca cggcgagcgc tgccacgtca gacgaagggc gcagcgagcg   34080
tcctgatcct tccgcccgga cgctcaggac agcggcccgc tgctcataag actcggcctt   34140
agaaccccag tatcagcaga aggacatttt aggacgggac ttgggtgact ctagggcact   34200
ggttttcttt ccagagagcg gaacaggcga ggaaaagtag tcccttctcg gcgattctgc   34260
ggagggatct ccgtggggcg gtgaacgccg atgattatat aaggacgcgc cgggtgtggc   34320
acagctagtt ccgtcgcagc cgggatttgg gtcgcggttc ttgtttgtgg atcgctgtga   34380
tcgtcacttg gtgagtagcg ggctgctggg ctggccgggg ctttcgtggc cgccgggccg   34440
ctcggtggga cggaagcgtg tggagagacc gccaagggct gtagtctggg tccgcgagca   34500
aggttgccct gaactggggg ttgggggag cgcagcaaaa tggcggctgt tcccgagtct     34560
tgaatggaag acgcttgtga ggcggctgt gaggtcgttg aaacaaggtg gggggcatgg     34620
tgggcggcaa gaacccaagg tcttgaggcc ttcgctaatg cgggaaagct cttattcggg   34680
tgagatgggc tggggcacca tctgggacc ctgacgtgaa gttgtcact gactggagaa      34740 ctcggtttgt cgtctgttgc ggggcggca gttatgcgg tgccgttggg cagtgcaccc      34800
gtacctttgg gagcgcgcgc cctcgtcgtg tcgtgacgtc acccgttctg ttggcttata   34860
atgcagggtg gggccacctg ccggtaggtg tgcggtaggc ttttctccgt cgcaggacgc   34920
agggttcggg cctagggtag gctctcctga atcgacaggc gccggacctc tggtgagggg   34980
```

```
agggataagt gaggcgtcag tttctttggt cggttttatg tacctatctt cttaagtagc    35040
tgaagctccg gttttgaact atgcgctcgg ggttggcgag tgtgttttgt gaagtttttt    35100
aggcaccttt tgaaatgtaa tcatttgggt caatatgtaa ttttcagtgt tagactagta    35160
aattgtccgc taaattctgg ccgttttggg cttttttgtt agacgtgttg acaattaatc    35220
atcggcatag tatatcggca tagtataata cgacaaggtg aggaactaaa ccatgggatc    35280
ggccattgaa caagatggat tgcacgcagg ttctccggcc gcttgggtgg agaggctatt    35340
cggctatgac tgggcacaac agacaatcgg ctgctctgat gccgccgtgt tccggctgtc    35400
agcgcagggg cgcccggttc ttttgtcaa gaccgacctg tccggtgccc tgaatgaact    35460
gcaggacgag gcagcgcggc tatcgtggct ggccacgacg ggcgttcctt gcgcagctgt    35520
gctcgacgtt gtcactgaag cgggaaggga ctggctgcta ttgggcgaag tgccggggca    35580
ggatctcctg tcatctcacc ttgctcctgc cgagaaagta tccatcatgg ctgatgcaat    35640
gcggcggctg catacgcttg atccggctac ctgcccattc gaccaccaag cgaaacatcg    35700
catcgagcga gcacgtactc ggatggaagc cggtcttgtc gatcaggatg atctggacga    35760
agagcatcag gggctcgcgc cagccgaact gttcgccagg ctcaaggcgc gcatgcccga    35820
cggcgatgat ctcgtcgtga cccatggcga tgcctgcttg ccgaatatca tggtggaaaa    35880
tggccgcttt tctggattca tcgactgtgg ccggctgggt gtggcggacc gctatcagga    35940
catagcgttg gctacccgtg atattgctga agagcttggc ggcgaatggg ctgaccgctt    36000
cctcgtgctt tacggtatcg ccgctcccga ttcgcagcgc atcgccttct atcgccttct    36060
tgacgagttc ttctgagggg atccgctgta agtctgcaga attgatgat ctattaaaca    36120
ataaagatgt ccactaaaat ggaagttttt cctgtcatac tttgttaaga agggtgagaa    36180
cagagtacct acattttgaa tggaaggatt ggagctacgg gggtgggggt ggggtgggat    36240
tagataaatg cctgctcttt actgaaggct ctttactatt gctttatgat aatgtttcat    36300
agttggatat cataatttaa acaagcaaaa ccaaattaag gccagctca ttcctcccac    36360
tcatgatcta tagatctata gatctctcgt gggatcattg ttttctctt gattcccact    36420
ttgtggttct aagtactgtg gtttccaaat gtgtcagttt catagcctga gaacgagat    36480
cagcagcctc tgttccacat acacttcatt ctcagtattg ttttgccaag ttctaattcc    36540
atcagacctc gacctgcagc ccctagcccg ggcgccagta gcagcaccca cgtccacctt    36600
ctgtctagta atgtccaaca cctccctcag tccaaacact gctctgcatc catgtggctc    36660
ccatttatac ctgaagcact tgatggggcc tcaatgtttt actagagccc accccctgc    36720
aactctgaga ccctctggat ttgtctgtca gtgcctcact ggggcgttgg ataatttctt    36780
aaaaggtcaa gttccctcag cagcattctc tgagcagtct gaagatgtgt gcttttcaca    36840
gttcaaatcc atgtggctgt ttcacccacc tgcctggcct tgggttatct atcaggacct    36900
agcctagaag caggtgtgtg gcacttaaca cctaagctga gtgactaact gaacactcaa    36960
gtggatgcca tctttgtcac ttcttgactg tgacacaagc aactcctgat gccaaagccc    37020
tgccacccc tctcatgccc atatttggac atggtacagg tcctcactgg ccatggtctg    37080
tgaggtcctg gtcctctttg acttcataat tcctaggggc cactagtatc tataagagga    37140
agagggtgct ggctcccagg ccacagccca caaaattcca cctgctcaca ggttggctgg    37200
ctcgacccag gtggtgtccc ctgctctgag ccagctcccg ccaagccag caccatgggt    37260
accccaaga agaagaggaa ggtgcgtacc gatttaaatt ccaatttact gaccgtacac    37320
caaaatttgc ctgcattacc ggtcgatgca acgagtgatg aggttcgcaa gaacctgatg    37380
```

```
gacatgttca gggatcgcca ggcgttttct gagcatacct ggaaaatgct tctgtccgtt    37440
tgccggtcgt gggcggcatg gtgcaagttg ataaccgga aatggtttcc cgcagaacct    37500
gaagatgttc gcgattatct tctatatctt caggcgcgcg gtctggcagt aaaaactatc    37560
cagcaacatt tgggccagct aaacatgctt catcgtcggt ccgggctgcc acgaccaagt    37620
gacagcaatg ctgtttcact ggttatgcgg cggatccgaa agaaaacgt tgatgccggt     37680 gaacgtgcaa aacaggctct agcgttcgaa cgcactgatt tcgaccaggt tcgttcactc    37740
atggaaaata gtgatcgctg ccaggatata cgtaatctgg catttctggg gattgcttat    37800
aacaccctgt tacgtatagc cgaaattgcc aggatcaggg ttaaagatat ctcacgtact    37860
gacggtggga gaatgttaat ccatattggc agaacgaaaa cgctggttag caccgcaggt    37920
gtagagaagg cacttagcct gggggtaact aaactggtcg agcgatggat ttccgtctct    37980
ggtgtagctg atgatccgaa taactacctg ttttgccggg tcagaaaaaa tggtgttgcc    38040
gcgccatctg ccaccagcca gctatcaact cgcgccctgg aagggatttt tgaagcaact    38100
catcgattga tttacggcgc taaggtaaat ataaaatttt taagtgtata atgtgttaaa    38160
ctactgattc taattgtttg tgtattttag gatgactctg gtcagagata cctggcctgg    38220
tctggacaca gtgcccgtgt cggagccgcg cgagatatgg cccgcgctgg agtttcaata    38280
ccggagatca tgcaagctgg tggctggacc aatgtaaata ttgtcatgaa ctatatccgt    38340
aacctggata gtgaaacagg ggcaatggtg cgcctgctgg aagatggcga ttgatctaga    38400
taagtaatga tcataatcag ccatatcaca tctgtagagg ttttacttgc tttaaaaaac    38460
ctcccacacc tccccctgaa cctgaaacat aaaatgaatg caattgttgt tgttaaacct    38520
gccctagttg cggccaattc cagctgagcg tgcctccgca ccattaccag ttggtctggt    38580
gtcaaaaata ataataaccg ggcagggggg atctaagctc tagataagta atgatcataa    38640
tcagccatat cacatctgta gaggttttac ttgctttaaa aaacctccca cacctccccc    38700
tgaacctgaa acataaaatg aatgcaattg ttgttgttaa cttgtttatt gcagcttata    38760
atggttacaa ataaagcaat agcatcacaa atttcacaaa taaagcattt ttttcactgc    38820
attctagttg tggtttgtcc aaactcatca atgtatctta tcatgtctgg ataacttcg    38880 tataatgtat gctatacgaa gttatgctag taactataac ggtcctaagg tagcgagcta    38940
gctgcaaccg aggaaaaaac gtgccatgag gtctctgtat ccaagtgtga ct            38992
```

<210> SEQ ID NO 20
<211> LENGTH: 34073
<212> TYPE: DNA
<213> ORGANISM: Artificial Sequence
<220> FEATURE:
<223> OTHER INFORMATION: Recombinant polynucleotide

<400> SEQUENCE: 20

```
gagggagggt ggtgctttgc taatggtgaa ttactaactc ctcaataaag aatattattt       60
gaaataattt ttgaaatttc ataattactt tgggttcttt cttaatgata ataaataat       120 agtatattac aaacatacat taatatttcc tgaatgaata caccacaaat ctcccttaaa      180
atatagcaag aataaaaatt atactatttc tgacaatttt taatttctca ataataata      240 ccactctgat ttttaaacat ctacaccact ctggctttgc caatcttttt aaaaattgaa      300
aagataataa tttatcata attacactga agcatagaac ttttctttc aaggaaagca       360 aattttgaa attctataat ataacctccc ataatcctga ataaattaaa ggttcaacaa      420
```

```
cttagtaaag taagactgac cttccctttt atttcttttt cagatcaaaa atcttacttt    480
tataggagca gttttcaact cctaaatgtt gaatataata gtcagttaaa ttcaccagct    540
acacaggaat acaggacttt gagtggaaga attgaatctc tggtaagtta atatttgtct    600
ttgctcttta ttccattata aaatgaatat gataataaac ctaatgtttt gtaatatatt    660
ttcagttgct aagtgctcta catattttcc ttccttgaat ggtgaaacat gtgtttctct    720
ctgcttttat ccagttagtt tactcatata ctggttctta ttcacatctt tgtcatgagt    780
aaaaagtgtt agaaaggcca cgagtaaata tgcattttat ttgtttatga attcaaatac    840 taaaagttttt ttatttgttt aattaagcat tgacattgtc ttttttaaatt cttttcattt    900 taccttcttc cctcttcctt atccaactaa agacgcaaag caggaggtgt taaaaaacag    960
gtttaccata tcagcagtaa catagtttgg acaacattac actttggttc aatgatagac    1020
atagaagttt gaacagaaat atgcaaagca agtttgagct ctaacttgaa gagagcctct    1080
gggtgcctgc caggaaacct cacgagtgga cccttaacat tcatgtgtca ccacaaacta    1140
ggggctgccc tttagttttg accagtctca gtgtcactca cttacccctta ccttttcaaa    1200 aaaaagtcct aagaatataa agtaattcaa tggttctaca attttagcat gtaactgagt    1260
cacctggcag ggttgctttg gtgagctcaa gataaaattt tatcagcatt tctacatttt    1320
ctggaatatt ccttaatcca ggcttttaat cccttggtgc ttttctgaac cactgcaatg    1380
agcttctaac tgttctcact gtgtgcaggc tcttttcctt ctaatctaat ttacacactt    1440
ctgaacacaa atctctcaca gcctgtttcc ttcatgttac ctccagctca agacttttttg    1500 cctacaaaat aaaattcaaa cttgttagct aagcaccttc tcatgtctat gctttggctc    1560
atatttcagc catcgtgtgc cccacttatt cttatagcca acctgaaaag ccatctttta    1620
taagaaacta cctctgctct ccatgattgg atataattaa tcctccttcc acatcacctc    1680
gccacaaaat tgtatctgtg ttgatctcat gccacatacc tgtatgtatt ttatattata    1740
aatatttgca gacttgttta atttgccatg ttagactaag ttccatgaag acagctccat    1800
atccattcca ttttttatata tccacaacat ttggtcgggt tgatgcttaa taaatgttta    1860
ttgaaggaac aggagtctcc cacttctgac ataatgaact tatttccccc agtgttaacc    1920
ctacatctgg ttcctgtcca agagtctctt cccaaatcat tctgattcaa ctgttcattc    1980
tgatctcatt aaacatttaa atgatatatc taacttcgct tgctttattc tatgctcatc    2040
ctgcagtctc ctcataactt ggtttcaatg atgcttgctt ctagagaaaa aaatgtatta    2100
aataagctta tgattcagtc ctccagctgt gatggttctc actgaacatt agctcagtgg    2160
ttttcgaagt atggtctcta gcataaccta gaaacttgtt agaaatgcaa attcttgggc    2220
tcaccaagac atactaaatc aaaaattctg acattgggc ctagaaatct gtgttttaac    2280
aagcctgcca gtgcagcctg gtcccttttc ttctcggagc cccactcaaa gctttcagtg    2340
ctcatctccc accaatgaca gggtcctcta tggaaaccgg caggacggtt tccaactcta    2400
actacgtttt agagtttgct tcctagggct atccaggcac caagtatcac aggttagttt    2460
cccagggaag cagactctga gacttgcatg cagggagtgt ctctggggtg ctctcaacca    2520
acaccttcag gaagagaagg aagcagcatt gggcagaggc atagtcaaac tacagtgctg    2580
ttggcacaga agactgaagg gagtcagagc cagggggtag aggtgggccc ttagcatcca    2640
tccttcacca ttaggtgtga gttgccccac ctccttgatg gtgtaacctc agtcccaagg    2700
tgggtgggag tgcagcagag cagccccctac aagggccaaa ccagagatac accaggcgcc    2760
agaagtgctg ccagggaata gagaggaaag gatgggctta aggtaggatc cacagaactt    2820
```

-continued

| | |
|---|---|
| ggcaatggat tagaagacag gatgagaagt gacaggttaa cactaacaca gaaatgtcta | 2880 |
| acttcggtag ataatggtgc cattggctag aagaggaaac cgaaatgaaa gcaggttgtt | 2940 |
| cagggagaca aaagttcact gtggacatct cagcagagtg attcagtggg gaaaggaatg | 3000 |
| gatgcccaga ccacctcaga ggaagatcta agctggagcc agcaataaag atacaagatg | 3060 |
| aacaatccct aacgaactgc tcctcagcca tgctccccag acacgctgct tcagatttat | 3120 |
| agtccgggtg aggctaggag gtgcgcctcc ctcagtggag gacagcaaag caccagtggc | 3180 |
| tccagggagt taaaatcttt tgataatttt tgttctagca tctgtctgca gagctgtctc | 3240 |
| tcagccattg cctgccttta cacaggagtg cagtccgaaa ttgggagatg agtgaaattt | 3300 |
| attatgccta gagatctgga tccccagttg tttgggagta tattttctga accacttgtt | 3360 |
| ggtttaagta atgcagattt attgatgcca cttctcttga atctgtgact ctggacccac | 3420 |
| catctaagtg aatgtgcaga gggaacggaa tggctgcaat agatctccat taaaaccagt | 3480 |
| gcatcctccc agacacatac agtagtaggg aggtgagtca atgtcaggac agcaccagct | 3540 |
| cccgcttcgg tacatttcca aagttctcag tctgtgtaca aaggtttgct ctggggcagc | 3600 |
| agaaatagcc ctgggcaggt agtcaaaggc ctggtttgat ttcctccact tccaggcaag | 3660 |
| tcactcgaag gctcacaggc ttttttcctca cctgccacat gggtccagtg agatctactg | 3720 |
| agctgtaaat aatgaaatga gtgtgtgtgc agtcatctat aagttgtaaa gtactagaaa | 3780 |
| atggtgaaac tttgggattt gggctattta aggctgaatg ctaaaaatgt caggcattgt | 3840 |
| ggagaaagga atttaaatat aagattgatt gactgggatt taaagacaaa tgaaggcaca | 3900 |
| cacgcaagtg cacacccaca ctgacactgc acagctcccg ttggaggcat atcctgacca | 3960 |
| tgcagacctg gggctctgcc tgtccaagtg cactccttta ctacataaac cctccttctc | 4020 |
| ttttggggct gtcaccccac cagagctggc accgagcccct tgctgctgcg cttccctggg | 4080 |
| gtgtcagctt ttgacagggt gtttcctccc tctgcaggag ccttaacatc ccttggactt | 4140 |
| ccttcccccc acccaccccc agcagttttta tctcttccta actcgggacc cttttttttcc | 4200 |
| cacacaaagt ttattgtcag ttgctggttt catctgtttg agcggctgca acaaaatacc | 4260 |
| atagactggg tggcatatgc acgacaaaaa tttattctc acaggagaag tcaaagatta | 4320 |
| atgcaccagc agatctggtg tctgagggggc caccttctgg tttgtagatg atgctttcta | 4380 |
| gttaaaacac ctatttaaca cactattaaa cactaagtgt gttaaatagt gcagttgatg | 4440 |
| tatttgtcat gtcacccttta tcatacacta aatccttctt tgtctttttt tctgtactct | 4500 |
| aatctctttc tgtaagtaat ctttgcttgc agcagtagga tatttagagt actgtggctt | 4560 |
| gacaatatat ttagtatttc aagatttcca tgaaattctt ctgatgtatg agttccctag | 4620 |
| ttaatcttac atatgtatcc ctttgtaaaa acactttgaa catttaaaat gatacatgaa | 4680 |
| tagtactcta atacaatgcc ataaaaatta taaatcattt gtatagactg gtaagtaaag | 4740 |
| attgtgagat taagaaacgc atcaaaggcc attgagctgg aaagtggtat aatgagaatt | 4800 |
| caaaccaggg tctcttgact caaaatctaa ggatcatacc atttctcatg ataatatgag | 4860 |
| tattattgtt atctctatcc catagacaaa gtgttaacac tgaatgagca gtgaaatagt | 4920 |
| ctcagaattt tttatttat ttagcaattc acttgtcatt tctggtcctc agtttattca | 4980 |
| cgagtaaaat aaaatagttg gactagataa tttctatagt acattcttac acaaaaaatc | 5040 |
| tatgattttg ttatttttaa tgtgatatac tcatggcact cattcacctc attttcccag | 5100 |
| cctgcctcac tggtcattac ttctctgtgt tctttacagg ctcccccctcc tctacactgc | 5160 |

```
cattaaatat tgaaacacct caaagcttta cttatgtcca cctctcctct gacactatca    5220
ttctgtctag atgatcccat acatacatgc ccattacttc aacctgtatt tatacgccaa    5280
tgattcacta tatttccagc ctagacattc ttttgtactc tagttaccag cttgatatcc    5340
ttacatggct gtttcaaaac aactcaaata tattatctct caaaatcaaa ctcatgatgt    5400
ccccacacca tcctagcttt ccaccaacaa tacctatccc tattaatagc aataccattt    5460
attcagttat ccaaatcaaa aacctagaat tcatccttaa aattctacta tcattccaaa    5520
tatcctatcc atcagcagcc actgtattct taatccnctg tatttccttc aaatccattc    5580
acctctctcc atatccattg ctgcatgact atccaagcca tcgcctctac cctagggtac    5640
caaaatagca acaaacctaa tctgttcatt tgcattattt tttctccaaa actgattatc    5700
tatatgtagc aagacagatt gttctcaaat tgcaaatccc actatattat cctcttgctt    5760
caaacacttc catggtttcc cattgtttat gataaaacca aatgcttcaa gttcgaagac    5820
cggcatgatt gggaatttcc tgtcacccta gcctacttgc tctccatggt acagttgcac    5880
tggctttctt tcattcctta agtacaacct gtttcctccc acctcaggac tgtgcatgtg    5940
ccattcattc tgctgaggag cctttttcct tccacttcaa tcagctaagt ctgattcttc    6000
ctgacaatct cagctcaata agcatttcct ctaagaaatg tctctaatat cattaattgg    6060
ctcaggtccc tctactgtat tgctgcactt ttcacagtta taattttact taattatgaa    6120
tgattatttg attaggtcta tttccatcca ttagacataa gcttcatgat ggccagatta    6180
ctgttttcta tccatcgttg tattccaata cctgacagaa ggagggcggg aggtggtggc    6240
acacaagaga tgctcaaaaa caattgttga ataagtaaat gaatgaggcc atttagaaat    6300
aacgaaagta cctgtttaca aagtacatgt atcaaaacta tgaatgcatt ctacttacat    6360
ggttttctcc aaataaaaca aaagacttca atcaggatta atacctggga taaactgagt    6420
cattaaatct ctcctttgcc atcaggagtg acattgaaac aaatgtctgc aaacaacaaa    6480 tactttttc ccaaaatata ttgaatggca tttccataaa caaactagaa catgggagga    6540
gaaagaaagc aatattaatt taaaattaat cttatcacat aacttatacc atcagggatt    6600
tcgggtaaaa ttcctttcag gcacatccat ttaacaagaa ttgattgtta ctgaaagcct    6660
agaagagaat ttggcacata cttggtgttc aaatatttgt tgactgagtg aataaatgat    6720
gcaagtgtct aagaaacaca aaataaggac atgattacag tcacggtgga gttcacagtc    6780
atctccaaaa tgaggatatg catcccaggg aggaccaaca attcattgga gtgctgaaat    6840
aaaatactca aaggtcattt tacatgtatt ttttctctaa attacttttc ttaagacaca    6900
gaaaacaaaa aaagaaactt agctttgtta cttttctaaca aatagttaaa tcattaaaca    6960
ggattgacac tagcatcctt gtttggtctt atgccttagg ggaacatgaa atgtgtgaag    7020
acattctgag atctgaggga agggtagaca gtaatacagt gggactgacc aggcttcagc    7080
acacctttac ctcctctcag cagatttcag tgatgagcag tttacaacta gattgaaaga    7140
ttatattatc tagttctaaa agaaaactaa gcctcccaaa agcaacaagg gaactgagag    7200
gaatcctgca aaacaaaaac aaattttaaa acttgcactt tgtaataacc ctaatatgta    7260
atcacagtaa tgaacagtaa gataatgaca gaactgacat atttccttat ctattaaagc    7320
catattaaca ggtaaagcaa tgccagtcag tggtacactt cttagaagat atttaataca    7380
tactagacac atacacacac acaacatttt ccttcaaggt gtatgtatca gaaaatcact    7440
ttttaaggcc ggatgcagtg gctcaggcct gtaatcccag cactttggga ggccgacgtg    7500
ggcggatcat ctgaggtcag gagttcaaga ccagcctgcc caacatggcg aaaccccatc    7560
```

-continued

```
tctacaaaaa tacaaaaatt agccagggat gatggtggat gcttgtagtc ccagctactc    7620
aagaggcaga ggcaggagaa tcacttgaac ctgggaggca gaggttgcag tgagccaaga    7680
tcacccattg cactccagcc tgggcaacag agtgagactc tgtctcaaaa aaaaaaaat    7740 cactttttag ataaaattca tgctatagag agaagactac gaaaatatgt ttagcaatgt    7800
gtccatcatt aggtgattga gtttcctttt gttttgtttt actgaaaatc atataaagta    7860
tgttatctgt aaaagttctc tgacatgcac acataaaaat ttgggagaaa agattaacta    7920
taatgtttaa tagattttgt acacatttct ttaaaaatat ataaaacaca cacctttca     7980 attggtttgc aagaataacc aattgacatc atggaaaatg gaaattcact tgctgaattt    8040
taacaaaaat ttgcatgatg agtgagactg acaacttagt gtcatgattt aatgaattat    8100
gccaatggta aacttcatgc acatggggcc aggtaattat gtggaaactt tttcaatgct    8160
taaagccaag tattgaaatt aaacttagaa tcagaccttt gaaccatttt atgacaatgt    8220
tcaaaaatta taaattctat ccacttatat tataatatta aaaatatcat tacaaaaaaa    8280
acctgtgttt attttataac tcagccttt taatttctaa tttcataaat atattataat    8340
ggatattgtt agtaatgtag tattattaca tgtatataat ttataagtaa atatacatgt    8400
tttggctact catgcataaa atgtttcacc cataggagca cataatcaga aatgtctgga    8460
gaccattata gtaatagata gatcatattg ccacatattt tatctcctcc ttgacaactg    8520
agctttccag atcttctggt gaaacgaaag agaaagttgt aacagaagag tgattaaaat    8580
gacaaaagca ttacttctat tacttctatt ctaataatat gagcaaagct ataactatca    8640
agtaataatg cactaaagaa ggtgattaat ctgatatatt cacaggcaac taataagacc    8700
tttctattgc agccatgaaa aatatgtgac aattatagat atcctgtgtg cagtgtttca    8760
acctttatgt gacctgttct actaacagat ttagtgatgt tcactttgtt agaattttct    8820
tacacatgcc ataacttgct tcagtctttt gattatgaat attatggata ttaaggattc    8880
tagactattc tagatttaaa aataatatt gtcacctcaa tcagaaggga aatattaaat    8940
agttctcatt ttttcaatgt ttactcagtt tttgtccaat gtaatgaaag tgtcagcagt    9000
acaggttaca aaataaaatg tgtattaaag taaactcatt tgaacaggtt aataattgta    9060
gagggaggga aaaggctaaa agattgaatg taaaacttat gaaaagtaga tacatcgtct    9120
ctatgatttg cagtagtcaa ctgcatacag atgaatcatt ttaatacacg ttaactactt    9180 tcctttaca gatggagaaa ctgagaggaa gaaagtttat atggttcatt aaactttgtg    9240
atgcaagcta aactaacctg tctctgtatt ttccatctac tgcccttatc actatctcat    9300
tagaatactc ttcaagcatc tccttactga ttttcttacc aagcatttgt taagttctaa    9360
tgagagttgg tagtaacatt ttcacccact ctgtgaaata tgaaatctta ttcataggcc    9420 tcttcttta ttcttgtatt tgcatatcaa ccaattaatc aacttgcttt ctttatgttg    9480
cttattatct tagtccttac taaattgcct cttaatgttg tccacataac agaaatgtta    9540
aggtggatac ttaacatttt agtccagtct agccggtgcc agtgcaatgc caaatcatga    9600
attaaaatat aattacaaga accacttatc aaattttaac aattccttca gctttgtgac    9660
agttttttct acttcgatta aagtcaagta aaattaaagt taaatatttt tattaaaata    9720 tctccttta a cattccatat taataaacat attaaagctc atgcttctaa gtagattact    9780
agaagttact ttatcgaatt acagcaatgg ttaattctag atcatagaat ttagaatgac    9840
tttttgcctt cttctttttt ttcctttttt ttaaacagag tcttgctctg ttgtccaggc    9900
```

```
tggagtgtac tggcgcgatc ttgactcact gcgacctctg ccctgcaggt tcaagtgatt    9960
ctcctgcccc agcctcttaa gtagttggga ttacaggtgc ctgccaccac acctggctaa   10020
tttttttttt gtatttttag gagagacagg gtttcaccat gttggccaga ctggtctcga   10080
actcctgacc tcaagtgatc cacttgcctc agcctcccaa agtgctggga ttacaggtgt   10140
gagccactgt gcctggcctg acttttgct ttcttcttaa tacttactag tatttcttga    10200 attttaaaa agaaacata aagtactttg ataaaaccaa cagtctcatt gttcttaaaa     10260
ttgttcaaag gttctctgga aaaaaaaag aaaattatca tttggttaag aatcatgttg    10320
gtctgacatc aatcatccta taggagtgaa tattgaaaaa gtaagatata ttgtggtata   10380
atcgagattg cataaatttt accattttg agaagaatct gctccaaatc ctggcttaat    10440
gtaatatcca gcatgctact taattttctt gtcttcacct tttcatatcc acatccacct   10500
aggtgccacc tcacagtata agccagcata atccattctt ctcaatgaaa ccacaataca   10560
tctgaccctg catctcagga gaactgtatc agccacagca cttccagttg actatgaatc   10620
tgaatgttat gcctcaggag aaacatcctt gctgggactg agtagtgatt caaggagata   10680
gttatgattc agtcaagaaa ttaataatta gtgttatttt tattattgag acagagtctc   10740
gttctgtagc ccaggctgga gtacagtggc atgatctcgg ctcactgcaa cctctacctc   10800
cccggttcaa gtgattctcc tgcctcagcc tcccaaataa ctgggacagc aggcacttgc   10860
caccacgcct agctaatttt ttgtattttt agtagagacg gagtttcacc gtgttagcca   10920
ggatggtctc gatctcctga cctcaaggtc cacctgcctc agcctcccaa agtgctggga   10980
ttacaggcgt gagccactgc gcccggccat aaattattaa ctgagccagg cacagtggta   11040
cacacttata gtcccagata ctcaggagac tgaggttgga gtatccttt tatgttatt     11100 ttatttttaa ttattatggg tacataatag gtgtacatac ccatggagta caagtcatgt   11160
tctgatacag acacataatg tttaataatc acatcagggt aattgggata tccatcacct   11220
caagcattta tctttctttg tgttaggaac attccacctc cactcttgga ataggcaccc   11280
tgttgtgcta ttaaatacga ggtcttattc atttcatcta actatatttt tctacccatt   11340
aaccatcacc tcttttcccc tcttcccac tacctttcct gtgaggctgc aggattctta    11400
agcacaacag ttagaggcca gcctggacaa catagtgaga ctcaatttct aaaaaataaa   11460
aaagaaatta ccaactaatg ctaaaaaaat agtctctgat gcttaggtat gaattagaaa   11520
tgaccaaaaa aaaaaaaaa aaaagactg ccctttgctt ccttctcccc ttctcttcaa     11580
gttttccatt gctactcatt ttagtctggt ttaatcaggt ttcatccatt aaaagcaatt   11640
gttgggatca cacattttga gttgtgtcag tggacttccc tcatgctggc atgattcctg   11700
ccccaagccc ttagtaaaag ccaccaagcc atataacata atctctcatt gagtaaaaca   11760
tctgatgtgt ttagaatgac ttctagcaaa aaaccagcct gtccagcatc atctctgtat   11820
aacagataaa ggaataggta ctgcatcaaa aggttataga acctgcccaa atcaatccca   11880
tgtgttttgc aatggaatta ggttgaacta aagtgaaaat tcagtttct actcctcatt    11940 aacatgtctc atgttgcaag gttgagagga aggagaagaa gaactgtatt tacagagaga   12000
ttccccctct ctttctttct acagattact aaaacattca aagaatcaaa tttaagaaat   12060
cagttcatca gagctcatgt tgccaaactg aggtgagtgg aactgtagaa aaaatattta   12120
agtatagata caatgtggca tacttgactt tttgtcacag aatgaatagt aaatgacatg   12180
ttcagataag ttgttgtaat attatgaaaa tagtatttta gtcagcttaa aaaccaatgc   12240
caaaaaagcc aaacatatga tctatttagc tactaatgta aataaccata ttatatctat   12300
```

```
tcttattggg aagaggaaga agggggtggag agagagttgg ggtgaaggta cagtaacaag    12360
gccatcctat tgtaaaactc cagtggatat cattcacagt gcagcctatg taaacagtcc    12420 ctccctggagt tgtacaatgc tgtggtttgg gtgtatccat ccaagatcaa gacactatga   12480
ccaacatcaa aagtggcttt ttggttttat ctgcctgatg tgctataata aaagggtatt    12540
atggccaaat ccaaggcatg tctatcatga attaataata ggaggagtag cagcatgcat    12600
gctagttatt tgccattcct gccttagtta aatatgatgt gataaaacca gcctttccaa    12660
ctgaaatagt caccttact gactctcccg caaatgtctc aaatgaccac attgctctag     12720
tctttaaata atatgcaata gttctttggt agaagaggaa ttatactaat tctttctcaa    12780
atactagcat cacaagaaaa ttaattcttg ttctctggag agtcacctag taagtatctg    12840
gagcacagat gtctggtcag gtaagttttg atgaggagtt aaagggataa aagagtcca    12900 tgagaagggt attttccaaa acacctttcg gtcaattcag tgcacattca cttagtactt    12960
tcttgtcagt atctgtatca gccactaatg ttcaaaagtg agtaagccct gaaaacctgt    13020
aggactacat gagccttctg ccttttctct ccttttgttc acttcccact tatcactcaa    13080
tcctctgcaa cctggcttca ataccaccat aaaatatcaa ctgctcttgc cgattcaaca    13140
atgacatcca gataacaaaa tccaaagaaa ccacatcagt cctattcttg gaccttttcaa   13200 cagtatttgg tcctgttggc ctgtcactcc ttgaaatagg actatccctt ggttgcatg     13260 gccttgtata ccctgatttt ccccttacct ccctagctat tccttcttag tttcctttac    13320
taggtcttac ttcttttgtat attccttaaa tgttgctgaa catcaggctg tgctctaggc   13380
ctctcatctt ctcaggtcac actctctcct ttccttggcc ttcactgcca cccatatgct    13440
gagtgctctc aaagttgtat ctctaggcca gtcctctttt gcctccaaac atgaatatat    13500
gcagccatct acttggtacc atcacatgga taattctcat gatctcttcc agtatgactg    13560 cttcttttatt ttttctgggg ctcttttta gcattgcttt acatggaact ttatcatgtc    13620
tctcaacctc tattttatct tttatctatg tatgtagagt ctgtgtaatt tcttcatctc    13680
ttttagataa ctaatatctc ttcagctttg acttgtattc tgtgtaaccc atttattgcg    13740 ttttcaatt caatgagtat gttttcctat ctgcaagttc tatttgtttc ttttgagaat    13800
cttcctggtc ttttaaacac atttcttatt ttaattttg ggggtaccta gtagttgtat     13860
gtatttttgg agtacatgag atgttttgat acaagcaaac aatgcataat aatcacattg    13920
tgtaaaatgg ggtatccatc ccctcaagca tttatccttt gtgttacaaa caatccaatt    13980
atattctttt agttattttt aaatgtacaa ttaaattatt attgaccata gtgactctgt    14040
tgtgctatca gatactaggt gatcttttaa aaataatgtt ttctacttaa tctcattttt    14100
atgattccct cttttacgtc atttgtcatt tcaaatacag tcacttgtct gttgattcta    14160
ttatgtgaag ttttttgagga taatcttttt gttactttga ttccaccttg gtatggtttg   14220
gctgtgcccc cactaaaatc tcatcttgaa ctctggttcc cataatacc acatgttgtg     14280 ggagggacct tgtgggaggt gattagatta tagggacgtt tccccccttt gctctgttct    14340
ttttcctgcc accatgtaag aaagatgtgt ttgcttcccc ttctgccatg attgtaaatt    14400
tcctgaggcc tccgcagcca tgcaggacct cttttctttg taaattaccc agtctccggc    14460
ggttctttat agctccgtga gaaaaaacta atacacacct catgatgtat tgtttaccac    14520
tgaaattgta tgcttaaatt taatctcact tgggaccctg tacaacctag acttaacata    14580
tctacctcca gagcagttac atctgtcaga cattctagag gaatcagcag cacatggact    14640
```

```
ttgttgttgt taatttgttg tcgggggagg ggggagggat agcattagga gatacaccta   14700
atgctaaatg acgagttaat gggtgcagca caccaacatg gcacatgtat acatatgtaa   14760
caaacctgca cgttgtgcac atataccccta aaacttaaag tataataata ataaaattaa   14820
aaaaaaaaag gttctgggag tattcaggta gtattaatga agattcagac atcgtgcagc   14880
caggcccatg cttatgaatt ttcaggtgat acttcttttt cttttttctt aatttaaagc   14940
tggatctcgg aaacagataa atttatttt ttatgacatg acgagcattt ttttcattct   15000
agttcatgct gttattgggt gtttagttct ttgagactcc tggcctttt ctaaaacctc   15060 aagttcaact tcctattttg cactggccca aggtcccatc tccagtctct atgtaaatgc   15120
taaacataag cctgtggaat attctagtct caccacatac tattcacatt cttctttgtt   15180
tttggtcttc caggattttc cttactttc tatgaaccca gtcttgcatt tgaaatggaa   15240
tttattatat attatctatc ctttctattt gttttatgca gaaagtgttt tctaaaatta   15300
tttaggcttc catattgcta gacatggaag ttgtaattat ttgttcagtg cctgtttcta   15360
catctaaact gcaagaccca tatggcaact gtgaatctta gtcccagcta atttctgaag   15420
cttagaatag tgcctagcac aagaagttgt ttatctaaca ttttaaaaa taaatattaa   15480 attcatatct ggaatgaata ttaagttaga gctggtcatt gaggtgagag gaggaagcca   15540
agagagaata tgagagcctc aaagccaaat atctttaatg tacttttca gaaaagaaga   15600 cagccaatgt caggtggagg aactggttta tgaggtaact ttcctggaag aaaatagaaa   15660
ttactgaggt tttagataat ccaaatattt aatcaagtca ccaaggttta ttgtggggaa   15720
tctttattat taattaaaat gagtgatgaa atcttaatat acgacaaaag ttaaaatttg   15780
cttttgcagg cagatgaatg gtctaggtat caaaaaatta agttgagtct ctaactcaca   15840
caaatttaca accctatcac tttatgaatt tgtttaggag attattttta ataacactgg   15900
tgaagtctaa gaatagctaa aatttatagt acacttattg tgtgctattg actcttcttt   15960
gaagttttgc atatagtgat tcatctaatc ttcataaccc attttacatg tgaagaaact   16020
tagatataga aagattaaga aacttacata acttatccaa agttacacag taaaactctg   16080
gcattataac ttcaaaatca gctatcctac agtgagtaca gtgttctgtg cattgaaatc   16140
aaataagtga gatagcatcg tgatatagta ttacgtatgc aaacactgtt acagagatct   16200
gtctaaagtt aaattccaca aatgaattct ttaaaagggt ttaatcaaga agaatatata   16260
aacaggatgg tgaaaaattg tcatattatt tgttttttaa aatatcttta tgatttacag   16320
gcaagatggc agtggtgtga gagcggatgt tgtcatgaaa tttcaattca ctagaaataa   16380
caatggagca tcaatgaaaa gcagaattga gtctgtttta cgacaaatgc tgaataactc   16440
tggaaacctg gaaataaacc cttcaactga gataacatgt aagtataatt tttcataaac   16500 aatttattt caatatatcc ctcaagttta ccaattcaaa ttcatatttt aattgagagg   16560 ctgactttc tttctttgaa actaaactgt gaaaacaatc cattaaaaag ctaaatatac   16620
catatagctc cctaacgtaa atcattctaa gacttaaaga atcatttggc atttatatag   16680 taaatttta ttgctaaaaa ttctcattaa ttatccctgc aacattcctt atgagtgatg   16740
ttactgtcag atgtcattag tggataggcc ataggagggg tacatagatg ctcaaggtca   16800
gagaactatt taattaatga tccacctcag aggcttcttc atttttcttt gtaacattta   16860
tcacaattga aattacaaag ttatctgtgt aaatttgta ttgtttggct tcatcctaca   16920
ctgtaatcat cctaaaagaa agaaccagtc aaccttcttc atcctactac cctcctacca   16980
cccagtctcc atcatataac acatattcaa taaataattc ttgcatgact gaaagaaaag   17040
```

```
aaataatata tgcatagaat ttaaggacat tcctccaagt tggttacatt ctgctagttt    17100
aataagccat tatttcttct cgatgagctc aagattaaaa ggattttgat gattcccata    17160
ctagactggt aggtaccagt tacagatgta ctaactgtta aatattgaaa tgctttccta    17220
tttgttggta aacaattact gcatcaggcc cacaaagttg tcttccgaga tgtttcaaat    17280
ccactgcccc tgctgctaaa gagttatgct tagcaaagca aagcactcta agacactgct    17340
ccaactccat ggcctgattg catctttat gactggccaa tgctcacgca ctgcagtttg     17400
ttaggtagtt gaatattacc tctgcttcca cacattaagg aatgctcccg aacgcacttc    17460
ccaagtgttt atttatttat cattatacta gacaatatgg tgatacgatg gtcacagaat    17520
agcggtttcc acctccagag cccataatct agttgaaggg aaagatattc aacacaaga    17580 gtgttgacaa tcaagataga atatgatcaa gggcccagtg tgaggcccag gcaatgatca    17640
ctgcaggaat ctggggaaga aagagaccag cgtgcttggg atatctagca aaagtttcat    17700
gaaggagaat ggactttgac tttgaaatat gggtaggatt tacatatttt gagatgagaa    17760
aaagaaagtt cccagagaag gaaagcatga aaaggcaaac agtctgtact gaacgcgatg    17820
ctttgacaga ataatgaaga aagggacctg ctggaatgat tgatcagtgt tcatcattca    17880
caccatcatc atcaaaacac ttatttaatg agaacttact gttttttagg catggcttta    17940
atgccctata tgaattttt tcttgattaa tccttacaac aaacatatcc catagatagt     18000
tttattgtcc cccttagaaa agataaattg cctaggctga cacagtcagt atatgaggca    18060
gtcaggattc aaactaagtc tgtttgttca aaaaattaag aatggccagc ttttaaat      18120 tttctgtctc cagaagtatg atttggctcc actgaagttt gcaaacaaa tgtgataccc     18180 aaaccttgtg aaacttttag tgggaaataa ctttgcataa gtcggtttga gagagcgtgg    18240
aaacctgtct tgaaaagttt taatttaact tgcaggaaat aaaaatgatg ggtttctcaa    18300
ttaaaaattt caatcaagga aggatatgag ctaacataac attttttaa aaagatcagt     18360 ctggtaaggt agaggtgcat aaactgaaaa ggagcaaaag tggtggaatt cagttagaaa    18420
attattgtaa ctgtactgat gtcaaatgat gaaaccatga actaaagtag taccaaaagg    18480
agtgaggagg atgaataat tcaaaagata gaggacagat gtgcagaacc tggagattat     18540
aagatgtgaa aggaggagtt tgagaaaatt tcagattttg gaagtggtgt catttactga   18600
aaaggatata ataagtagca aattttggat aaagttgggt cccactgagt ttgagatggc    18660
tgttggacat gcagagaaaa ctgtcttgta tgctgttctt aaattgaaat agacagacct    18720
ttaccctctg atactgacat attttccttt ccaggctcac cctccatttc cctaaacaca    18780
acacatgcac tagctctcct tactttattg ctccacaaac atcttacacc tccaagcatt    18840
tgtgcccact gtaccttcta tctggaatct cttttgtcct cttgtgtgcc tgaaaaattc    18900
ctttcagatc ttcaaaatac agtgcagatg ctatttcttc tagctcaaat attatctcct    18960
ccatataatt taattactct ctttttctt ttctctactt tgcacttaca tttatttgaa     19020
tgattgcttg attaatttct acctgtaaat tatgtgaggg caggtcctct atattttgct    19080
cgcagttaaa tctgcagcac ttattataga gtggtatcat tagagtaata tacatatatt    19140
tgaggacatg ataaattaac ttcccctata gtatttatca cattgcatct caatgacttg    19200
cttatgtttc tgttttccca tataaattga gtaacttgaa aaaagagata tctattaagt    19260
atttaatgag aaattaaagt acaaacttta gtatgcataa caacaaattg ggaaaaggtt    19320
gtaaacaaag agatttgtag ggcccatgag ttagagatcg tttcagcagg tctgaaagga    19380
```

```
agcctaggaa tctgcatttt agaggaccac ctcccaaccc caacaagtaa ttctgcttct    19440
tgttgtctgg gtactgtact ttaagaaatt atggtgaaat gatatcagcc tttattgtat    19500
ttatcttatt ctcatttttt aatactagca cttactgacc aggctgcagc aaattggctt    19560
attaatggta agttttaata ttattttgta actgtaattt gccaaatcat aaagagtaaa    19620
agtgcaagtc ttttgtgtac ttttggccaa ggcagtatct atcaagttga tgtctttgtt    19680
cttagttcgc tcaggtggtg ttgaaacaag acagtgctga tcccaagtgt cccatggagt    19740
ggactttagg tttcccctttt cctttttagaa aaaggaagaa gttgtagtgg aggactaccc    19800
actctgcact caaaattgcc ctcatgaaaa tttctttggc agctttgaga acctttttact  19860 gccctggttc taaggtggca tttctgtaga cttacaaatt atgtttgatg acaccgttta    19920
tgtagcttct cctaaccacc agagtagctt gctttgttgt gaattcaggt taatcacaaa    19980
gtataataaa aaagaattgt cagaagtctt cccagctttg ggtctataac ctgaaggaaa    20040
agtcactact cttcaacatc atcctatgta ctctcaggct aggatagcag aaatgcaatc    20100
cctagaaaac agcaacttac ttctctgacc aaaaaaatgc agttaaaaat tagttcaatg    20160
tacctggtag ctggcctatc ttaggtactt cagtgatttt acaaagtgat ggtagtccta    20220
tgggtgtttt tcagcttcac tacgtattta attcatgctt attgttaatg aaactgtgat    20280
aagcaattta ctagggtatt tgtttgggag atgccacaaa ggaacacatg tatctcttaa    20340
tggaagcctg gtcctccttt atccaggaaa tttgctagga aaaaaaagcc tttaggtggt    20400
tgtgctatta aaccagggca ctacttaaaa gccagcccag caatagttgt gtgatttacc    20460
attaatttct tagtaataga ccacacaaaa gaagaaaatt atgggaatgc gagttgagag    20520
gaattgggtg atcagcctac cccagcccgt ttcagctctg gccagtagac tattcacgag    20580
ctctttgaaa acatttaaat aaaccttatt tagatactag aaaccctctg tcaccctcaa    20640
gaatattctg tggtatagcg actcctttat gagggcatgt ttggtaatac agcatcagtc    20700
ttggaggtgg actggattct acaaggtgaa ctgcagtcac taaggagtct tttggatgag    20760
accagttttc ctccaacttc aatgtgtgca tgaacctcac atcaaaatgt agctttagat    20820
ttgtcccatg atgtggttcc aagaatcagc acttctaata agtttccagg ggatgcccat    20880
gctgcaggcc cacaaaccac actgagcata gcaagactat tgagaaaaag gaaatttccc    20940
aggagtctgt ggcctgagct ggcacatcca ataatgacct atcttaacct caactcatga    21000
ggaattccag ggaactctga agctgctcaa aatttgaagc ctatatgcca actaaattca    21060
gaaatgttct ccaaaatgct atctataagc aacagtagtc acaaatgcat tgtagaaata    21120
tatcgatcat gcttttggga aaatccagca tgtcctgagg aagaatgtat aagacataaa    21180
agtcataaat tatggaaaga ctcttcagct tcttccaaat gtaaaggaat catgatcttc    21240
ccagcacatt aatgcccttt ctcattagaa tgtggggccg gtccagacct aataacattg    21300
tctgagcaga gaatccttgg aggcactgag gctgaggagg gaagctggcc gtggcaagtc    21360
agtctgcggc tcaataatgc ccaccactgt ggaggcagcc tgatcaataa catgtggatc    21420
ctgacagcag ctcactgctt cagaaggtga ggccaccact acctacccat ctgggaacaa    21480
ttagaataga caggtcatga agactgcacc ctctacccta ggattgaatt gagccagaaa    21540
taattcaatg caaaaaaatc agtaagaatt ttcttcctat tcatgaaagg aaaaggattt    21600
ttccccttta gcatgctaat ttagtgctat ttctctgttt caggtaataa tatattagca    21660
cagtaaagaa caaagattta tatgtcagaa tgtttttaa atcctagcta taaaagctta    21720
agaaatttac taaatctcca taagctttat ttttttttcca aattaaggga caacactgtt    21780
```

```
atctgtgact tagtgttact ggtagcattg agtacactaa tgtaaacata cgttaaatgt    21840
tagcgaaacg aattgctgtg gaagatttgc acattatatc atgggagctg atggctaacc    21900
tagagactgc cccatgccat taatttattc attcataaag attattgagt atctagtatg    21960
agcacagtgt tatatattgt agaagctact agtataaaca aagtattgcc tctgccttca    22020
aagagcttac actcgaatgt tggaatcaga atgcacaaaa ataatgatca attacaatga    22080
gtagcataaa taaaattaat gtaggcaact tacaagaatt cttaattgag gtgactaaac    22140
tattgccaac actagggtga tatgctacca gtggcgagta ggttgcataa acttaccttta    22200 ttggtaaaaa gaaaagttca cattgctcat aaaagaagga ttttagattt cagcataact    22260
aaaatctgtt tcaaacctgc cttgttactg gggcatcgca gaccacaaca gttgttggga    22320
acttaactca aaaagttcac ccagaaaaat aatggagatt tgaactcgtg tgccctgac    22380 catatcaatt ttcttctcag actcttactc taaactggac ctccttatca cacacaaa    22440 gccttccata ggcagatcaa tccagtctta tttctcaaag catgtacctt gagcttcaga    22500
taaacagcat tgttctcttc ccctggactc ttcctacatt tccctaccta tgagtatctg    22560
atcaatctgc ttatccttga aatgttaata tatttaccac atctctattt gaattttatg    22620 aaattttga taatttctaa gtagtttttt cagatttata ggcactactt catggtacag    22680
tgactgttac aaacgtattt gttaaattta gaaggaataa agatttaaaa gactagggta    22740
gttactgaac taaagtttta ggaaatccca aattatttca aatttttctt atggtaattt    22800
tatgacttaa tatttttata tgcagtgaac aaatttgaaa cttaaaaga tactcccaga    22860 attatcagtt ttctgatgta gattggcaaa tttattacta tatcccaaat aacccaagag    22920
acaaaattca caaaaacatt tcaattttca ttgccacttg aaaggccaaa aagcagaaat    22980
ggcacgcatt gatttcaatc gtactcttga gtgtgggaac caggaattaa aatacctgga    23040
cttatcaggc acttagcata accaagaacg gaatagaaac ctccctggat tctaagccct    23100
attcagtccc aatcaccaaa aaccaagtaa acgatatcac tataatgaaa gccacagtta    23160
taaatatcga caacgattac caaaggaatc catggaactt tgaattttgc cacccccacat    23220 ccttctattc attaccatga ttgatccact aaagctaaca gactctgtga accttgtatt    23280
ggacccctcc ctaaagacct gattgtcact gagaaccatc agtgaggatt tgtttggggc    23340
atgaccagcc ttcatcaaa gtacatagaa gtgatgaggt cttatcaaag aggattattg    23400
aattatcacc tcttctatgt agctttccct gatactctct ttcctctcca ttgagttcca    23460
cagaaatttt tttatctgcc tttaacagtt gtcctcatga tttgtgatat ttgacttacc    23520
tcttgtcagt ttccttcact agtgtagagt tcctcaaaga aagagaccat aattacttat    23580 attttattc ctggagactc atactattcc ttatacaaag tagacactta acaatggctt    23640
gttgaactat aattaatgaa aataatagct accttcatga aagttcactt tgtgccaaac    23700
actatagttg acataataca tttgtctcat taatacttaa caattgtgtg agaaggtatc    23760
accaatcaca ttttatatgt aaataaaccc cagagctatt aattaacttg tcataaataa    23820
cacttttcat atgtggcata gccaagattt aaatataaat gttactggtt ccaaaatgat    23880
gctctaattc acttgctgga aagaaggaaa ggaagaaaat aaacgagtgg aaggaagaga    23940
gggagggaag agagaaaagg aaggaaagaa aaaagagtct cttcagaacc ttcactgtaa    24000
agactccgag caaagaagt tgaatataaa acaacatag gtttgtttgt tttctaatat    24060
tttttcttca aaatttttaa ctcaggttca ctcttacaca aactactgtg tcttataaaa    24120
```

```
gtatttccgg tcatagaatt tttattttct gtattaactc cactatctaa tctccataaa    24180
actcctaaat tggtattatc ggtaacattt tgttttact caaccctag gaacaatgtt      24240 aagttaatca gccctccaca tcacagatcc ttattttcat cagtctgtac aaggcatttc    24300
tctcatttta atttttttc ctcctgtcat ccctggattt cactttcact gccctccttc    24360
cacccatatg cctcatacta atatattcga aatatacatg tcttaaaggt acatgcacgc   24420
acctacaaaa cctatagtgt ttttttgtat gtatatgtct ttaatttaaa taagtagcat   24480
tgtgtaaaag tctaatattg tttcttactg ttttcactca attcttggaa ttttcatctg   24540
atgcactgct gcatagcacc ccatggtatg cagccaccat atttccttca tccaattagg   24600
ttgcatgacc taccttccca ttgccacaaa gagtacacac aaaatatttg tacttatctt   24660
tctgtaaacc ttcaggaatt tcagaagcac acatgcaggc tgctaaatat accagaatac   24720
tttccagcca cttaaatctt taccagtatt gcaaagagg ccccatttcc ctccacatca    24780
acatttagta ttattctttt gtttaagttt tatcaatctt ttaaatgtac acaagatgct   24840
catttttata atttaattt ctcagattac tagtttgagt atcttttcat atatctaaga    24900
gctgttttga tctcccctac catgaactgc cactaatatt ctttgcctat tttacaatgg   24960 ttttctgct tatttattac tggtttacag acttttaaaa tatattctac aaaaatttta    25020
gacattaaac attaccaata ttttcccatg gttcctcatc catctggtaa acttgtctat   25080
ggtatatcta attttgattt aatagaattc attctatttt tacctttag tttgtgtttt    25140 tgttgtttag ccaaaaagtc cccattccta ggtcataaag gtaatgtcct ttttttttt    25200 ttaacgctac tgttctctct ctgtctcccc ctatgtatat aggtgcacat atacttgtac   25260
acacatacat atacctatat atgaggggag ttcgataagt ttatggaaaa taaaattaaa   25320
agataaaata aaaaattata aactttattt ctcaacataa gctccttcaa gttcaagaca   25380
cttttgtaag caataatacc agccatatcg tccatcccta agaactgag ggtcctgaga    25440 atttaactat gtcaatgcag tcttttttac attactttt tacagtactt attgatgaaa    25500
aatgggtgcc ttttaaagat tgttttaaga ttagggaaca aaaataagtc agaggaagtc   25560
aaatcaggac tgaaaggtgg atgcctagtg atttattgct gaaacttca taaaactaac    25620 cttatttgat gagaggaatg agcatgagca tggttgtgat ggagaagaac tctggtggag   25680 cttcctgga cacttttct actaaagctt tggctaactt tcttactctc ataagaagaa     25740
gatgttattt ttcactgacc ctttagaagg tcaacaagca aaatgccttc agcatcccaa   25800
atgtctgttg tcatgacttt tgttcttgac tagtctggtt ttgctttgac tggaccactt   25860
ctacctcttt atagccattg ctttgatggt gctttgtctt caagattgta ttagtaaagc   25920
catatttcat cttctgttac aattcttcaa agaaatactt cagaatcttg atctgacatg   25980
tttaaaattt ctattggaag ctctgacctt gggtgcagct gatctgggcg aaacagtttt   26040
ggcatccatc aagtagaaag tttgctcaac tttagttttt cagtcagaat tgtataagct   26100
gaaccagttg agatgtctat ggtgttgtct attgttctc acagttaatt gttggtcctc    26160
tttgagacat gaacaagatg aaattttcc tagcaaactg atgtggatga tctgttgctg    26220
cgggcttcac cctcaacaac atctctttct ttccttgaaac aaattatcca ttagtaaact   26280
gatgattggg ggagatgctg tccccataaa cttttttgtaa ggcataaata atttcaccat   26340
tcttccagtt tcaccataaa tttgacgttt ttttgcttca attttagcag cattcatgtt   26400
gctttgataa gagctcttt caaattcatg tcttattcct cttagtgcct caaactagat    26460
cttgttcagt atgacaagtt agtatgagtt tatctgcatg caaaaatctt tgaaatccat   26520
```

```
gcatagtttg tttataatat acattttcaa tgaacttttg aagacccat acatacatat    26580 gtatatatat gcacacacac acacacacac acaccaaaat cttcaaccat tatcagactt    26640
agtgcagaaa aattattcat ccattaacaa gataagaatg ccccttatca tcactactat    26700
ttaaatggag ctcctggcta aaggaaaaga cagggattga aaaaaattag ttaaatctaa    26760
aatgtttatt atttcaggtt tcttagttgc ttaaatggga agggaggtat ggacaaaaga    26820
gaaatcaaag atatttgtgt tatgctactt atcattaaag tatcagaata acttcattgg    26880
aatagaaaaa caccaagatc accccacgat atgttttcta aaatcttctc catttcttta    26940
gacaagtgac catgtattcg gccagtgaag aattaaactc acttgccagc ttataatgca    27000
ggaaaatata gcaaagagat gtggatccaa tagtttctag atagtggtac aggatggcta    27060
agatgaattt atatatctga aatgttcaca aattccctac tcatatagca tgttttcata    27120
atgttttagc aactctaatc ctcgtgactg gattgccacg tctggtattt ccacaacatt    27180
tcctaaacta agaatgagag taagaaatat tttaattcat aacaattata aatctgcaac    27240
tcatgaaaat gacattgcac ttgtgagact tgagaacagt gtcacccttta ccaaagatat    27300 ccatagtgtg tgtctcccag ctgctaccca gaatattcca cctggctcta ctgcttatgt    27360
aacaggatgg ggcgctcaag aatatgctgg taagtgtctc ggaaaaaaaa attaacaata    27420
gaaatgtctt atatttgcta ttaggtaatt ttttaaatta ggaacatct ggaataggtg    27480 tttctattct tctacagaca gaaccattct atattctgct cagcccaagc tctggctacc    27540
cctgagtctc cttagcaaag caaagcaatg ctccagaaac tatgggaatt ctcaaatata    27600
gtaataggaa aatgtaaaag aaagttatga agacacgagt tctttaataa tccagagatt    27660
ctataagatt caaatagctt ccctataaac aataaaaag attttgtttg tttgtttgtt    27720
tgcttgtttt ttagagacaa agactttctc agactggagt gcagtggtgc aatcatggct    27780
tactgcagcc tcaaactctg gtcttaagaa atcctcttgc ttcagcctcc caagtagcta    27840
gaattataaa taagtgtgta ccaccatacc cagctttttt ttttttttc tacagacagg    27900 ttcttgctct gttgcccagg ctggtctgga attcctgccc tcaagccatc ctcctgcctt    27960
gttggcctcc caaagcaatg ggaggattta gattagacat tgtatgaggg cttaataatc    28020
cttaaggtat taactgccct ttaaagtatt ctgggatatg gcaaaaactc gatgtgtata    28080
taaacattgg tcatatttgt ttattgaatg aataaaatgg aaactaaaat gaggacaatg    28140
cacaagagct actagaacca gtaagagtat cagcgaagga gtggaagggt agcattgaca    28200
atttccctgg gcttttaccc atgttgtaga ttgtctctcc aaggaataat acaaagcctt    28260
aatagtccta gaacacattc tattgtgttc ttatggccca agtaaattg gtgtagtaga    28320 taacatttgc accagtcatg aaaaactatt ggtgtcattc tgagagtaca tcaatataaa    28380
atagactagt tctttagcct tgaaactaga ctggtttctc ttttgctgct aggttaaagg    28440
ttattcaata tgtaatcttc caatccaaaa tctgtcagtg gataatttaa aagcttttag    28500
tcaattttaa gatatttgtt ttcttaaaat tttaaggggc actgtgtcac aaagctaaag    28560
aaaaaaaaga aaaaaaaact gatctgtgaa aggggttatc ctcatctact tggggaattt    28620
tggctgcgaa gaaactccaa agtaaatctt tagaagcctt cattgttaaa tatgaaataa    28680
tgtttggagt acatttattt cttctcaaat ttattatagg gtcaataatg tacacatctt    28740
gaagtccatt ttttcctgc ttttataaca aacaggccac acagttccag agctaaggca    28800
aggacaggtc agaataataa gtaatgatgt atgtaatgca ccacatagtt ataatggagc    28860
```

```
catcttgtct ggaatgctgt gtgctggagt acctcaaggt ggagtggacg catgtcaggt    28920
aagctcaaga caatctcatc catgtcatca tccaagaagt gtataagcac ttcctagtat    28980
gtgataatgt gatagacata agtgtaacag ttacaataca cagccctgtt cctctaaaat    29040
ttataatcta gattttagaa ataaattttt ttatgaatga agtttatcta tcatgaaagc    29100
attaactctg agaggccaaa ttacagagta gttaaccatc caaagctcaa gaatcagaaa    29160
gacctcgatt tgaattcctt aacctctatt accaagtctc taactaaaag ctggggataa    29220
tcataatagc acctaacttt ttgggtacta agaaaagtta aatgaagact aaatatatca    29280
ggcacatggt aaacaacaaa gaaatctcat ctatttcact attattaatg tagaccatgg    29340
tcactcgtgt taataacttt aacctcaacc ttttaactgc tgtgaaggat taaataaaaa    29400
attaatcact atattataaa aattaattga tatataataa atgaattttta agagatacgt    29460 aataattcat ggactccttg aagatagaaa atttatacaa aatcctagta atttgagtca    29520
caaaagctcc tacaataatg aaacagtatg aatgaaaaag aaaagaaata actattatat    29580
ttggatctag cccataattt ttaaccaaat gcacaaaaac aaacaacaaa tatgaaattc    29640
tcactgtaaa gtgattaaaa tcaaatttga attctaaaat tttaaattaa attatctaaa    29700
cataattgat gcagttatat gttttaatag gttttgttca catatctgaa atccaactcc    29760
acacagtagc aggaacagct ggtgtcagaa attaaatatt cttttagtct ggagttttaa    29820
aaaatcaatc tgtttacttg agtaatttgt tgctgttttc atgggtgaat tgtatacaga    29880
aggataagaa ttattcttcg catcaaaagg tcactgactt tcatatttag tgctcatggt    29940
cttaaaaaag tggataaaaa gtagttctca catttcatgg aaagccccca atccatgagc    30000
acatttccca aaatgaaaca ttttttatcaa ctgcaagttg tgtgtaggtg gagatttgtt    30060
tttcaattgt caagatactg ttaattaccc agtcctttat ctccttttgg tggagatgtc    30120
tctgtgctag gaaacccttc ttgctctcct tcctgtttct cttttactac tggccctgaa    30180
acaacaaatt ctcaagtttc atgacagctt tccaaagaat ccatcaatca aataagcaac    30240
acaactcgac actgacaatt ccagacctac taagagcatt aattaagact taaaaataaa    30300
catgagtttt aaaagggtgt tattcattat tttcccatttt ataacgtccc ttaccttctg    30360
tccttcagtg catacaaatt attatcttcc ttgaagccca gttcaagccg tacctcacca    30420 tgatacctttc catgtatatt ccactctagg cctcactgat ttttaactga atactataa    30480 tgcatagttc acacttaaaa aaaaaaaaaa aacacagcac tttacataag agcttacagg    30540
atcctatttg ttttatccat tcttttgttc attttttacaa tcattaattc aaaggaatta    30600
tattaattac tttctatgca cccgacgttg tgttaacaca acaatactat ccctgcattc    30660
agcaagtcta tggtctacaa gagaggacac aaattcaaat gtctgtagtc aagcagtgaa    30720
gctggctaga tatggaaaaa ttacaagtcc ctcttgcttt aacatttgct tgcccacatt    30780
tggtcagaca tcatgcaaaa taatttctca ctatagaaaa aaaacacta caaaaacaat    30840 aatataaaga actgagaact ggttaactga agcatgcata tgtcatctaa aagaagcagg    30900
tgacgaccag cttcatgaag tacttgccat gcatattggc acttcacaca ctgacccttc    30960
tccccaccta gaccagtaat taaacaggta tggatgagct agctactaag agcagccaac    31020
tgaatagctg actaacttag aagcacactt ggtaataata gctgactttt attagtactg    31080
actatactat atgctaagct gtactcaaag tgctttgagt tttaaactga tacaaacatt    31140
atatgaggaa acagaggtac agagagctat tcaccagctt accaaggtc acatagctgg    31200 taagtggagg acttaaaccc agactatcta gtttcagaac ccacagactt aatccatcgt    31260
```

```
gcagaacata agacatactc catctgtctc cccaactagg ttattatgtg cacaaatatt   31320
tattggttgg ttggttcatt attatgactg ggtggtaagt atgtcattag gagtgttttg   31380
cttatgacta tataaatttc ttcaccaaaa gaagactttc tgatgatata ctatgcatca   31440
gacaccacgc agggtgctaa ggttaggaag ataagtgaga cttctagaaa ctcattcatt   31500
caacaaatat ctcctaaggg ctagaagctt aggtttcagc agtgaacaga ataggtatgt   31560
tctctttcgt gttggacctt atagtatatc tgggaaaaca gacattgaat aaatatcaca   31620
aatgcaagtg agtgtttcag agacatgcag ctgctacatc aaaacaaaac agaacaaaac   31680
aaacaaacaa aaactgacca gtgggattaa gtgtaaatag gcacacaaat gcacaaatat   31740
gcttttataa aatagtgaag cagtgacaga gacacacaca agatataaag acacaatgaa   31800
gaacaattga gcccaaagct ggaaagggtg agagtgtgaa ggaaaaaggt tgatcagaga   31860
agttttcccg aaggagagaa agcctggatg attaggaggc aaccactcgg tgactgaggg   31920
aaatctgaaa aatgtatttg tcatcttctc agacttgctg aaggaatgac ttgggtactt   31980
tgaggatttc agtaattttt ccatgacttg gtataatatt tcaaaaggaa ataggctgac   32040
tttatttgta taatgaatgt gactccttcc tcgactgcca tagaaataaa ctccttaata   32100
ttttgggttt gtctttgcac ttaagtaatc agtcattctg ttttttttaca gggtgactct   32160 ggtgcccac tagtacaaga agactcacgg cggctttggt ttattgtggg gatagtaagc   32220
tggggagatc agtgtggcct gccggataag ccaggagtgt atactcgagt gacagcctac   32280
cttgactgga ttaggcaaca aactgggatc tagtgcaaca agtgcatccc tgttgcaaag   32340
tctgtatgca ggtgtgcctg tcttaaattc caaagcttta catttcaact gaaaaagaaa   32400
ctagaaatgt cctaatttaa catcttgtta cataaatatg gtttaacaaa cactgtttaa   32460
cctttcttta ttattaaagg ttttctattt tctccagaga actatatgaa tgttgcatag   32520
tactgtggct gtgtaacaga agaaacacac taaactaatt acaaagttaa caatttcatt   32580
acagttgtgc taaatgcccg tagtgagaag aacaggaacc ttgagcatgt atagtagagg   32640
aacctgcaca ggtctgatgg gtcagagggg tcttctctgg gtttcactga ggatgagaag   32700
taagcaaact gtggaaacat gcaaaggaaa aagtgataga ataatattca agacaaaaag   32760
aacagtatga ggcaagagaa ataatatgta tttaaaattt ttggttactc aatatcttat   32820
acttagtatg agtcctaaaa ttaaaaatgt gaaactgttg tactatacgt ataacctaac   32880
cttaattatt ctgtaagaac atgcttccat aggaaatagt ggataatttt cagctattta   32940
aggcaaaagc taaatagtt cactcctcaa ctgagaccca aagaattata gatattttc   33000 atgatgaccc atgaaaaata tcactcatct acataaagga gagactatat ctattttata   33060
gagaagctaa gaaatatacc tacacaaact tgtcaggtgc tttacaacta catagtactt   33120
tttaacaaca aaataataat tttaagaatg aaaaatttaa tcatcgggaa gaacgtccca   33180
ctacagactt cctatcactg gcagttatat ttttgagcgt aaaagggtcg tcaaacgcta   33240
aatctaagta acgaattgaa agtttaaaga gggggaagag ttggtttgca aaggaaaagt   33300
ttaaatagct taatatcaat agaatgatcc tgaagacaga aaaaactttg tcactcttcc   33360
tctctcattt tctttctctc tctctcccct tctcatacac atgcctcccc caccaaagaa   33420
tataatgtaa attaaatcca ctaaaatgta atggcatgaa aatctctgta gtctgaatca   33480
ctaatattcc tgagttttta tgagctccta gtacagctaa agtttgccta tgcatgatca   33540
tctatgcgtc agagcttcct ccttctacaa gctaactccc tgcatctggg catcaggact   33600
```

```
gctccataca tttgctgaaa acttcttgta tttcctgatg taaaattgtg caaacaccta    33660
caataaagcc atctactttt agggaaaggg agttgaaaat gcaaccaact cttggcgaac    33720
tgtacaaaca aatctttgct atactttatt tcaataaaat tcttttaaa ataatttccc     33780 tgcctaatta tttatggaag ttatgacttt tgaaggacaa ttcaaaacca tttatttaat    33840
tggttctgca atgaaagaac tgccccatat actctactaa aggcttggca ctttctgctg    33900
ccttttaatc cagcgctata attgaggcaa gcgtccagct tgacacctcg agataacttc    33960
gtataatgta tgctatacga agttatgcta gtaactataa cggtcctaag gtagcgagct    34020
agctgcaacc gaggaaaaaa cgtgccatga ggtctctgta tccaagtgtg act           34073
```

```
<210> SEQ ID NO 21
<211> LENGTH: 418
<212> TYPE: PRT
<213> ORGANISM: Artificial Sequence
<220> FEATURE:
<223> OTHER INFORMATION: Recombinant protein

<400> SEQUENCE: 21

Met Tyr Arg Pro Arg Pro Met Leu Ser Pro Ser Arg Phe Phe Thr Pro
1               5                   10                  15

Phe Ala Val Ala Phe Val Val Ile Ile Thr Val Gly Leu Leu Ala Met
                20                  25                  30

Met Ala Gly Leu Leu Ile His Phe Leu Ala Phe Asp Gln Lys Ser Tyr
            35                  40                  45

Phe Tyr Arg Ser Ser Phe Gln Leu Leu Asn Val Glu Tyr Asn Ser Gln
        50                  55                  60

Leu Asn Ser Pro Ala Thr Gln Glu Tyr Arg Thr Leu Ser Gly Arg Ile
65                  70                  75                  80

Glu Ser Leu Ile Thr Lys Thr Phe Lys Glu Ser Asn Leu Arg Asn Gln
                85                  90                  95

Phe Ile Arg Ala His Val Ala Lys Leu Arg Gln Asp Gly Ser Gly Val
            100                 105                 110

Arg Ala Asp Val Val Met Lys Phe Gln Phe Thr Arg Asn Asn Asn Gly
        115                 120                 125

Ala Ser Met Lys Ser Arg Ile Glu Ser Val Leu Arg Gln Met Leu Asn
    130                 135                 140

Asn Ser Gly Asn Leu Glu Ile Asn Pro Ser Thr Glu Ile Thr Ser Leu
145                 150                 155                 160

Thr Asp Gln Ala Ala Ala Asn Trp Leu Ile Asn Glu Cys Gly Ala Gly
                165                 170                 175

Pro Asp Leu Ile Thr Leu Ser Glu Gln Arg Ile Leu Gly Gly Thr Glu
            180                 185                 190

Ala Glu Glu Gly Ser Trp Pro Trp Gln Val Ser Leu Arg Leu Asn Asn
        195                 200                 205

Ala His His Cys Gly Gly Ser Leu Ile Asn Asn Met Trp Ile Leu Thr
    210                 215                 220

Ala Ala His Cys Phe Arg Ser Asn Ser Asn Pro Arg Asp Trp Ile Ala
225                 230                 235                 240

Thr Ser Gly Ile Ser Thr Thr Phe Pro Lys Leu Arg Met Arg Val Arg
                245                 250                 255

Asn Ile Leu Ile His Asn Asn Tyr Lys Ser Ala Thr His Glu Asn Asp
            260                 265                 270

Ile Ala Leu Val Arg Leu Glu Asn Ser Val Thr Phe Thr Lys Asp Ile
        275                 280                 285
```

```
His Ser Val Cys Leu Pro Ala Ala Thr Gln Asn Ile Pro Pro Gly Ser
    290                 295                 300

Thr Ala Tyr Val Thr Gly Trp Gly Ala Gln Glu Tyr Ala Gly His Thr
305                 310                 315                 320

Val Pro Glu Leu Arg Gln Gly Gln Val Arg Ile Ile Ser Asn Asp Val
            325                 330                 335

Cys Asn Ala Pro His Ser Tyr Asn Gly Ala Ile Leu Ser Gly Met Leu
        340                 345                 350

Cys Ala Gly Val Pro Gln Gly Gly Val Asp Ala Cys Gln Gly Asp Ser
        355                 360                 365

Gly Gly Pro Leu Val Gln Glu Asp Ser Arg Arg Leu Trp Phe Ile Val
    370                 375                 380

Gly Ile Val Ser Trp Gly Asp Gln Cys Gly Leu Pro Asp Lys Pro Gly
385                 390                 395                 400

Val Tyr Thr Arg Val Thr Ala Tyr Leu Asp Trp Ile Arg Gln Gln Thr
            405                 410                 415

Gly Ile

<210> SEQ ID NO 22
<211> LENGTH: 257
<212> TYPE: DNA
<213> ORGANISM: Artificial Sequence
<220> FEATURE:
<223> OTHER INFORMATION: synthetic oligonucleotide

<400> SEQUENCE: 22
agcacccctc tcttccgcag agtctaagaa atcgctgtgt ttagccctcg ccctgggcac     60
tgtcctcacg ggagctgctg tggctgctgt cttgctttgg aagttcagta agtgcaggga    120
gcctcgatcc caccatgtgc tcctgcagtc cccagtgctc tgagccagac cctgctctct    180
gggctattga gacctctgga ggccctccgt gaggttcctc tcttacataa cgaggctgtc    240
tctcttccct tctcttg                                                   257

<210> SEQ ID NO 23
<211> LENGTH: 190
<212> TYPE: DNA
<213> ORGANISM: Artificial Sequence
<220> FEATURE:
<223> OTHER INFORMATION: synthetic oligonucleotide

<400> SEQUENCE: 23
ggtcagagga ccaaaggtga ggcaaggcca gacttggtgc tcctgtggtt ctcgagataa     60
cttcgtataa tgtatgctat acgaagttat atgcatggcc tccgcgccgg gttttggcgc    120
ctcccgcggg cgccccctc ctcacggcga gcgctgccac gtcagacgaa gggcgcagcg    180
agcgtcctga                                                           190

<210> SEQ ID NO 24
<211> LENGTH: 171
<212> TYPE: DNA
<213> ORGANISM: Artificial Sequence
<220> FEATURE:
<223> OTHER INFORMATION: synthetic oligonucleotide

<400> SEQUENCE: 24
attgttttgc caagttctaa ttccatcaga cctcgacctg cagccctag ataacttcgt      60 ataatgtatg ctatacgaag ttatgctagt aactataacg gtcctaaggt agcgagctag    120
```
ctccacgtgg ctttgtccca gacttccttt gtcttcaaca accttctgca a        171

<210> SEQ ID NO 25
<211> LENGTH: 177
<212> TYPE: DNA
<213> ORGANISM: Artificial Sequence
<220> FEATURE:
<223> OTHER INFORMATION: synthetic oligonucleotide

<400> SEQUENCE: 25
ggtcagagga ccaaaggtga ggcaaggcca gacttggtgc tcctgtggtt ctcgagataa        60
cttcgtataa tgtatgctat acgaagttat gctagtaact ataacggtcc taaggtagcg       120
agctagctcc acgtggcttt gtcccagact tcctttgtct caacaacct tctgcaa          177

<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
gccgtgactg tgaccttctc        20

<210> SEQ ID NO 27
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 27
tggaggagcc acctgatgcc tc        22

<210> SEQ ID NO 28
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 28
gccttgccct caatggaaac        20

<210> SEQ ID NO 29
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 29
ggttgcacag caaggaagaa g        21

<210> SEQ ID NO 30
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 30
ccaggagttc ctgtgagcct accc        24

```
<210> SEQ ID NO 31
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 31
tggaatggaa ggagctggag                                                 20

<210> SEQ ID NO 32
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 32
gtcccacctc ctgcaactg                                                  19

<210> SEQ ID NO 33
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 33
tgagccttcc catcagcctg gg                                              22

<210> SEQ ID NO 34
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 34
ccacaatggc acatgggtct g                                               21

<210> SEQ ID NO 35
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 35
ggtgcttgct ccccaaga                                                   18

<210> SEQ ID NO 36
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 36
cctaaaaggt gttgtaatgg                                                 20

<210> SEQ ID NO 37
<211> LENGTH: 24
<212> TYPE: DNA
<213> ORGANISM: Artificial Sequence
<220> FEATURE:
<223> OTHER INFORMATION: synthetic oligonucleotide
```

<400> SEQUENCE: 37
ggcaataaag aaggaagacg tttt                                              24

<210> SEQ ID NO 38
<211> LENGTH: 120
<212> TYPE: DNA
<213> ORGANISM: Artificial Sequence
<220> FEATURE:
<223> OTHER INFORMATION: synthetic oligonucleotide

<400> SEQUENCE: 38
ccagtcaggg acacacatgc tcacacgccc gcccacccgc acacactaca gtcgagataa      60
cttcgtataa tgtatgctat acgaagttat atgcatggcc tccgcgccgg gttttggcgc     120

<210> SEQ ID NO 39
<211> LENGTH: 198
<212> TYPE: DNA
<213> ORGANISM: Artificial Sequence
<220> FEATURE:
<223> OTHER INFORMATION: synthetic oligonucleotide

<400> SEQUENCE: 39
attctagttg tggtttgtcc aaactcatca atgtatctta tcatgtctgg aataacttcg      60
tataatgtat gctatacgaa gttatgctag taactataac ggtcctaagg tagcgagcta     120
gccaagtctg tgtgctacca agtagcaaaa ctgagcctgg aactcacaca tgcgtgtctg     180
agagcccagc actatcgc                                                    198

<210> SEQ ID NO 40
<211> LENGTH: 100
<212> TYPE: DNA
<213> ORGANISM: Artificial Sequence
<220> FEATURE:
<223> OTHER INFORMATION: synthetic oligonucleotide

<400> SEQUENCE: 40
taatctgact ttctcttcat cggtctctct tattctaggc tgagctgtaa cgctgccgtc      60
ccccacatcc agaagctgct tcccttcaga cctacctacg                           100

<210> SEQ ID NO 41
<211> LENGTH: 177
<212> TYPE: DNA
<213> ORGANISM: Artificial Sequence
<220> FEATURE:
<223> OTHER INFORMATION: synthetic oligonucleotide

<400> SEQUENCE: 41
ccagtcaggg acacacatgc tcacacgccc gcccacccgc acacactaca gtcgagataa      60
cttcgtataa tgtatgctat acgaagttat gctagtaact ataacggtcc taaggtagcg     120
agctagccaa gtctgtgtgc taccaagtag caaaactgag cctggaactc acacatg       177

<210> SEQ ID NO 42
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 42
gagcagggcc atgacacat                                                    19

```
<210> SEQ ID NO 43
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 43
accattagat cccagcactg gaca                                              24

<210> SEQ ID NO 44
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 44
aaacccttcc cgagagagaa                                                   20

<210> SEQ ID NO 45
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 45
gaggaacact gtgtcaagga ctt                                               23

<210> SEQ ID NO 46
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 46
cctgaaaagc ccggagtggc ag                                                22

<210> SEQ ID NO 47
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 47
gggcagagac cacatctga                                                    19

<210> SEQ ID NO 48
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 48
ggaagccctc tctcgatact tg                                                22

<210> SEQ ID NO 49
<211> LENGTH: 22
<212> TYPE: DNA
<213> ORGANISM: Artificial Sequence
<220> FEATURE:
<223> OTHER INFORMATION: synthetic oligonucleotide
```

<400> SEQUENCE: 49
ttctaccctg agggcatgca gc                                         22

<210> SEQ ID NO 50
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 50
tgggatgtag aaggttgtca ga                                         22

<210> SEQ ID NO 51
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 51
ctgagcctgg aactcacaca tg                                         22

<210> SEQ ID NO 52
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 52
tctgagagcc cagcactatc gcc                                        23

<210> SEQ ID NO 53
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 53
gctgagggtc aggcttgag                                             19

<210> SEQ ID NO 54
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 54
tctgcagggt agggagagaa g                                          21

<210> SEQ ID NO 55
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 55
tgtttcagaa aaggaagact cacgttaca                                  29

<210> SEQ ID NO 56
<211> LENGTH: 24

```
<212> TYPE: DNA
<213> ORGANISM: Artificial Sequence
<220> FEATURE:
<223> OTHER INFORMATION: synthetic oligonucleotide

<400> SEQUENCE: 56
gagaccgatg aagagaaagt caga                                           24

<210> SEQ ID NO 57
<211> LENGTH: 100
<212> TYPE: DNA
<213> ORGANISM: Artificial Sequence
<220> FEATURE:
<223> OTHER INFORMATION: synthetic oligonucleotide

<400> SEQUENCE: 57 gaccattta aggttttgct tggttgtttt ggagggaggg tggtgctttg ctaatggtga     60
attactaact cctcaataaa gaatattatt tgaaataatt                         100

<210> SEQ ID NO 58
<211> LENGTH: 190
<212> TYPE: DNA
<213> ORGANISM: Artificial Sequence
<220> FEATURE:
<223> OTHER INFORMATION: synthetic oligonucleotide

<400> SEQUENCE: 58 gctgccttt aatccagcgc tataattgag gcaagcgtcc agcttgacac ctcgagataa     60
cttcgtataa tgtatgctat acgaagttat atgcatggcc tccgcgccgg gttttggcgc   120
ctcccgcggg cgccccctc ctcacggcga gcgctgccac gtcagacgaa gggcgcagcg   180
agcgtcctga                                                          190

<210> SEQ ID NO 59
<211> LENGTH: 171
<212> TYPE: DNA
<213> ORGANISM: Artificial Sequence
<220> FEATURE:
<223> OTHER INFORMATION: synthetic oligonucleotide

<400> SEQUENCE: 59
attgttttgc caagttctaa ttccatcaga cctcgacctg cagcccctag ataacttcgt    60
ataatgtatg ctatacgaag ttatgctagt aactataacg gtcctaaggt agcgagctag  120
ctgcaaccga ggaaaaaacg tgccatgagg tctctgtatc caagtgtgac t            171

<210> SEQ ID NO 60
<211> LENGTH: 177
<212> TYPE: DNA
<213> ORGANISM: Artificial Sequence
<220> FEATURE:
<223> OTHER INFORMATION: synthetic oligonucleotide

<400> SEQUENCE: 60
ccagtcaggg acacacatgc tcacacgccc gcccacccgc acacactaca ctcgagataa    60
cttcgtataa tgtatgctat acgaagttat gctagtaact ataacggtcc taaggtagcg   120
agctagctgc aaccgaggaa aaaacgtgcc atgaggtctc tgtatccaag tgtgact      177

<210> SEQ ID NO 61
<211> LENGTH: 21
<212> TYPE: DNA
<213> ORGANISM: Artificial Sequence
<220> FEATURE:
```

```
<223> OTHER INFORMATION: synthetic oligonucleotide

<400> SEQUENCE: 61
tcctctccag acaagaaagc t                                              21

<210> SEQ ID NO 62
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 62
tcatagcagc tttcaaatcc taaacgttga                                     30

<210> SEQ ID NO 63
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 63
tcgtgtgtag ctggtgagtt                                                20

<210> SEQ ID NO 64
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 64
catgcgatca caggaggaga tc                                             22

<210> SEQ ID NO 65
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 65
aattgggccc gaagccagat gc                                             22

<210> SEQ ID NO 66
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 66
cggaaggctt ctgtgacttc                                                20

<210> SEQ ID NO 67
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 67
gtctcccact tctgacataa tgaac                                          25
```

```
<210> SEQ ID NO 68
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 68
cccagtgtta accctacatc tggttcc                                               27

<210> SEQ ID NO 69
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 69
tgggaagaga ctcttggaca                                                       20

<210> SEQ ID NO 70
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 70
atgagctcct agtacagcta aagtt                                                 25

<210> SEQ ID NO 71
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 71
atgcatgatc atctatgcgt cagagc                                                26

<210> SEQ ID NO 72
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 72
tgcccagatg cagggagtta g                                                     21
```

RODENTS HAVING A HUMANIZED TMPRSS GENE

CROSS REFERENCE TO RELATED APPLICATION

This application is a continuation of U.S. patent application Ser. No. 15/442,857, filed Feb. 27, 2017, which claims the benefit of priority from U.S. Provisional Application No. 62/301,023, filed Feb. 29, 2016, the entire contents of which are incorporated herein by reference.

INCORPORATION BY REFERENCE OF SEQUENCE LISTING

The Sequence Listing in the ASCII text file, named as 33093Z_10234US02_SequenceListing.txt of 275 KB, created on May 22, 2017, and submitted to the United States Patent and Trademark Office via EFS-Web, is incorporated herein by reference.

BACKGROUND

Type II transmembrane serine proteases are a family of proteases characterized by an N-terminal transmembrane domain (Bugge et al., *J. Biol. Chem.* 284 (35): 23177-23181, 2009; Hooper et al., *J. Biol. Chem.* 272(2): 857-860, 2001). All members of this family are expressed as single-chain zymogens and are proteolytically activated by cleavage within a highly conserved R/(IV)VGG motif. One member of the family, transmembrane protease, serine type 4 (TMPRSS4), has been shown to activate the epithelial sodium channel (ENaC) regulating the sodium and water flux across epithelia (Guipponi et al. 2002 *Hum. Mol. Genet.* 11:2829; Vuagniaux et al. 2002 *J. Gen. Physiol.* 120:191). The proteolytical activators of TMPRSS4 are unknown; however, data available to date suggests that the protein is autoactivated. When activated, the catalytic domain of TMPRSS4 remains bound to the N-terminus of the protein via a disulphide linkage. TMPRSS4, TMPRSS2 and TMPRSS11D (or Human Airway Trypsin-like protease; "HAT") have been shown in vitro to cleave influenza A hemagglutinin (HA), which is the first essential step in the viral life cycle. This cleavage is essential for activity of HA, as the protein is synthesized as a precursor protein (HA0) and requires cleavage into HA1 and HA2 for activity. RNAi knock-down of TMPRSS4 in Caco-2 cells resulted in reduced spread of the virus. In addition, TMPRSS4 was shown to be strongly upregulated in the lungs of mice infected with influenza (Böttcher et al. 2006 *J. Virol.* 80:9896; Böttcher et al. 2009 *Vaccine* 27: 6324; Böttcher-Friebershäusser et al. 2010 *J. Virol.* 84: 5604; Bertam et al. 2010 *J. Virol.* 84:10016; Bertam et al. 2010 *J. Virol.* 84:10016; Böttcher-Friebershäusser et al. 2011 *J. Virol.* 85: 1554; Bahgat et al. 2011 *Virol. J.* 8:27).

Development of an in vivo system, e.g., a rodent model of infection, is needed in order to identify and test compounds including antibodies that specifically target human type II transmembrane serine proteases for the treatment and prevention of viral infection and other diseases.

SUMMARY

The present invention encompasses the recognition that it is desirable to engineer rodent animals to provide in vivo systems for identifying and developing new therapeutics. For example, the present invention encompasses the recognition that rodents having a humanized Tmprss gene are desirable for use in identifying and developing therapeutics for the treatment and prevention of viral infections.

In one aspect, the invention provides a rodent whose genome contains a humanized Tmprss gene that includes a nucleotide sequence of an endogenous rodent Tmprss gene and a nucleotide sequence of a cognate human TMPRSS gene, wherein the humanized Tmprss gene is under control of a 5' regulatory sequence(s), such as the promoter and/or enhancer(s), of the endogenous rodent Tmprss gene.

In some embodiments, the humanized Tmprss gene in rodents disclosed herein encodes a humanized Tmprss protein that contains an ectodomain substantially identical (e.g., at least 85%, 90%, 95%, 98%, 99% or 100% identical in sequence) to the ectodomain of a human TMPRSS protein. In some embodiments, the humanized Tmprss protein contains a cytoplasmic and transmembrane portion that is substantially identical (e.g., at least 85%, 90%, 95%, 98%, 99% or 100% identical in sequence) to the cytoplasmic and transmembrane portion of an endogenous rodent Tmprss protein.

In some embodiments, a rodent disclosed herein contains a humanized Tmprss gene that includes a nucleotide sequence of an endogenous rodent Tmprss gene and a nucleotide sequence of a cognate human TMPRSS gene, wherein the nucleotide sequence of the cognate human TMPRSS gene encodes a polypeptide substantially identical (e.g., at least 85%, 90%, 95%, 98%, 99% or 100% identical in sequence) to the ectodomain of the human TMPRSS protein encoded by the cognate human TMPRSS gene. In some embodiments, a rodent disclosed herein contains a humanized Tmprss gene that includes a nucleotide sequence of an endogenous rodent Tmprss gene and a nucleotide sequence of a cognate human TMPRSS gene, wherein the nucleotide sequence of the endogenous rodent Tmprss gene encodes a polypeptide substantially identical (e.g., at least 85%, 90%, 95%, 98%, 99% or 100% identical in sequence) to the cytoplasmic and transmembrane portion of the endogenous rodent Tmprss protein encoded by the endogenous rodent Tmprss gene.

In some embodiments, a rodent disclosed herein contains a humanized Tmprss gene located at an endogenous rodent Tmprss locus that results from a replacement of a contiguous genomic sequence of an endogenous rodent Tmprss gene with a contiguous genomic sequence of a cognate human TMPRSS gene. In specific embodiments, the contiguous genomic sequence of a cognate human TMPRSS gene being inserted includes exon sequences encoding an ectodomain substantially identical with the ectodomain of the human TMPRSS protein encoded by human TMPRSS gene. In some embodiments, the contiguous genomic sequence of a cognate human TMPRSS gene also includes the 3' UTR of the cognate human TMPRSS gene.

In some embodiments, a rodent disclosed herein is heterozygous for a humanized Tmprss gene at an endogenous rodent Tmprss locus. In other embodiments, a rodent is homozygous for a humanized Tmprss gene at an endogenous rodent Tmprss locus.

In further embodiments, a rodent contains two or more humanized Tmprss genes at different endogenous rodent Tmprss loci with each endogenous rodent Tmprss locus being humanized with a respective cognate human TMPRSS gene; for example, two or more of humanized Tmprss2, humanized Tmprss4, and humanized Tmprss11d genes.

In some embodiments, a rodent disclosed herein contains a humanized Tmprss2 gene that includes a nucleotide sequence of an endogenous rodent Tmprss2 gene and a nucleotide sequence of a human TMPRSS2 gene, wherein the humanized Tmprss2 gene is under control of the promoter of the endogenous rodent Tmprss2 gene.

In some embodiments, the humanized Tmprss2 gene encodes a humanized Tmprss2 protein that contains an ectodomain substantially identical (e.g., at least 85%, 90%, 95%, 98%, 99% or 100% identical in sequence) with the ectodomain of the human TMPRSS2 protein encoded by the human TMPRSS2 gene used in humanization. The human TMPRSS2 protein contains, in some embodiments, an amino acid sequence at least 85% identical (e.g., at least 90%, 95%, 98%, 99% or 100% identical) with the amino acid sequence as set forth in SEQ ID NO: 4. In some embodiments, a humanized Tmprss2 protein contains an ectodomain substantially identical (e.g., at least 85%, 90%, 95%, 98%, 99% or 100% identical) with the amino acid sequence composed of residues W106 to G492 or the C-terminal 387 amino acids of a human TMPRSS2 protein as set forth in, e.g., SEQ ID NO: 4. In some embodiments, the humanized Tmprss2 gene encodes a humanized Tmprss2 protein that further contains a cytoplasmic and transmembrane portion that is substantially identical (e.g., at least 85%, 90%, 95%, 98%, 99% or 100% identical) with the cytoplasmic and transmembrane portion of the rodent Tmprss2 protein encoded by the endogenous rodent Tmprss2 gene being humanized. An exemplary endogenous rodent Tmprss2 protein is set forth in SEQ ID NO: 2.

In some embodiments, a rodent contains a humanized Tmprss2 gene that includes a nucleotide sequence of an endogenous rodent Tmprss2 gene and a nucleotide sequence of a human TMPRSS2 gene, wherein the nucleotide sequence of the human TMPRSS2 gene encodes an ectodomain substantially identical (e.g., at least 85%, 90%, 95%, 98%, 99% or 100% identical in sequence) with the ectodomain of the human TMPRSS2 protein encoded by the human TMPRSS2 gene. In specific embodiments, the nucleotide sequence of a human TMPRSS2 gene is a contiguous genomic sequence of a human TMPRSS2 gene containing coding exon 4 through the stop codon in coding exon 13 of the human TMPRSS2 gene. In particular embodiments, the contiguous genomic sequence of a human TMPRSS2 gene further contains the 3' UTR of the human TMPRSS2 gene. In some embodiments, the nucleotide sequence of an endogenous rodent Tmprss2 gene included in a humanized Tmprss2 gene encodes a cytoplasmic and transmembrane portion that is substantially identical (e.g., at least 85%, 90%, 95%, 98%, 99% or 100% identical) with the cytoplasmic and transmembrane portion of the endogenous rodent Tmprss2 protein encoded by the endogenous rodent Tmprss2 gene.

In particular embodiments, a humanized Tmprss2 gene contains coding exons 1-2 of an endogenous rodent Tmprss2 gene, and coding exon 4 through coding exon 13 of a human TMPRSS2 gene, wherein the humanized Tmprss2 gene encodes a humanized Tmprss2 protein that contains a cytoplasmic and transmembrane portion that is substantially identical with the cytoplasmic and transmembrane portion of the rodent Tmprss2 protein encoded by the endogenous rodent Tmprss2 gene, and an ectodomain that is substantially identical with the ectodomain of the human TMPRSS2 protein encoded by the human TMPRSS2 gene. The humanized Tmprss2 gene contains an exon 3 that in some embodiments is coding exon 3 of a human TMPRSS2 gene, and in other embodiments is coding exon 3 of an endogenous rodent Tmprss2 gene. In some embodiments, the humanized Tmprss2 gene contains an exon 3 that includes a 5' portion of coding exon 3 of an endogenous rodent Tmprss2 gene and a 3' portion of coding exon 3 of a human TMPRSS2 gene.

In some embodiments, a rodent disclosed herein contains a humanized Tmprss4 gene that includes a nucleotide sequence of an endogenous rodent Tmprss4 gene and a nucleotide sequence of a human TMPRSS4 gene, wherein the humanized Tmprss4 gene is under control of the promoter of the endogenous rodent Tmprss4 gene.

In some embodiments, the humanized Tmprss4 gene encodes a humanized Tmprss4 protein that contains an ectodomain substantially identical (e.g., at least 85%, 90%, 95%, 98%, 99% or 100% identical in sequence) with the ectodomain of the human TMPRSS4 protein encoded by the human TMPRSS4 gene used in humanization. The human TMPRSS4 protein contains, in some embodiments, an amino acid sequence at least 85% identical (e.g., at least 90%, 95%, 98%, 99% or 100% identical) with the amino acid sequence as set forth in SEQ ID NO: 11. In some embodiments, a humanized Tmprss4 protein contains an ectodomain substantially identical (e.g., at least 85%, 90%, 95%, 98%, 99% or 100% identical) with the amino acid sequence composed of residues K54 to L437 or the C-terminal 384 amino acids of a human TMPRSS4 protein as set forth in, e.g., SEQ ID NO: 11. In some embodiments, the humanized Tmprss4 gene encodes a humanized Tmprss4 protein that further contains a cytoplasmic and transmembrane portion that is substantially identical (e.g., at least 85%, 90%, 95%, 98%, 99% or 100% identical) with the cytoplasmic and transmembrane portion of the rodent Tmprss4 protein encoded by the endogenous rodent Tmprss4 gene being humanized. An exemplary endogenous rodent Tmprss4 protein is set forth in SEQ ID NO: 9.

In some embodiments, a rodent contains a humanized Tmprss4 gene that includes a nucleotide sequence of an endogenous rodent Tmprss4 gene and a nucleotide sequence of a human TMPRSS4 gene, wherein the nucleotide sequence of a human TMPRSS4 gene encodes an ectodomain substantially identical with the ectodomain of the human TMPRSS4 protein encoded by the human TMPRSS4 gene. In specific embodiments, the nucleotide sequence of a human TMPRSS4 gene is a contiguous genomic sequence containing coding exon 4 through the stop codon in coding exon 13 of a human TMPRSS4 gene. In some embodiments, the nucleotide sequence of an endogenous rodent Tmprss4 gene included in a humanized Tmprss4 gene encodes a cytoplasmic and transmembrane portion that is substantially identical with the cytoplasmic and transmembrane portion of the rodent Tmprss4 protein encoded by the endogenous rodent Tmprss4 gene.

In particular embodiments, a humanized Tmprss4 gene contains coding exon 1 through coding exon 3 of an endogenous rodent Tmprss4 gene, and coding exon 4 through the stop codon in coding exon 13 of a human TMPRSS4 gene.

In some embodiments, a rodent disclosed herein contains a humanized Tmprss11d gene that includes a nucleotide sequence of an endogenous rodent Tmprss11d gene and a nucleotide sequence of a human TMPRSS11D gene, wherein the humanized Tmprss11d gene is under control of the promoter of the endogenous rodent Tmprss11d gene.

In some embodiments, the humanized Tmprss11d gene encodes a humanized Tmprss11d protein that contains an ectodomain substantially identical (e.g., at least 85%, 90%, 95%, 98%, 99% or 100% identical in sequence) with the ectodomain of the human TMPRSS11D protein encoded by the human TMPRSS11D gene used in humanization. The human TMPRSS11D protein contains, in some embodiments, an amino acid sequence at least 85% identical (e.g., at least 90%, 95%, 98%, 99% or 100% identical) with the amino acid sequence as set forth in SEQ ID NO: 18. In some embodiments, a humanized Tmprss11d protein contains an ectodomain substantially identical (e.g., at least 85%, 90%, 95%, 98%, 99% or 100% identical) with the amino acid sequence composed of residues A42-I418 or the C-terminal 377 amino acids of a human TMPRSS11D protein as set forth in, e.g., SEQ ID NO: 18. In some embodiments, the humanized Tmprss11d gene encodes a humanized Tmprss11d protein that further contains a cytoplasmic and transmembrane portion that is substantially identical (e.g., at least 85%, 90%, 95%, 98%, 99% or 100% identical) with the cytoplasmic and transmembrane portion of the endogenous rodent Tmprss11d protein encoded by the endogenous rodent Tmprss11d gene being humanized. An exemplary endogenous rodent Tmprss11d protein is set forth in SEQ ID NO: 16.

In some embodiments, a rodent contains a humanized Tmprss11d gene that includes a nucleotide sequence of an endogenous rodent Tmprss11d gene and a nucleotide sequence of a human TMPRSS11D gene, wherein the nucleotide sequence of the human TMPRSS11D gene encodes an ectodomain substantially identical with the ectodomain of the human TMPRSS11D protein encoded by the human TMPRSS11D gene. In specific embodiments, the nucleotide sequence of a human TMPRSS11d gene is a contiguous genomic sequence containing coding exon 3 through the stop codon in coding exon 10 of a human TMPRSS11D gene. In particular embodiments, the contiguous genomic sequence of a human TMPRSS11D gene further contains the 3' UTR of the human TMPRSS11D gene. In some embodiments, the nucleotide sequence of an endogenous rodent Tmprss11d gene included in a humanized Tmprss11d gene encodes a cytoplasmic and transmembrane portion that is substantially identical with the cytoplasmic and transmembrane portion of the rodent Tmprss11d protein encoded by the endogenous rodent Tmprss11d gene.

In particular embodiments, a humanized Tmprss11d gene contains coding exons 1-2 of an endogenous rodent Tmprss11d gene, and coding exon 3 through coding exon 13 of a human TMPRSS11D gene.

In another aspect, the invention provides an isolated rodent cell or tissue whose genome contains a humanized Tmprss gene as described herein. In specific embodiments, the humanized Tmprss gene is selected from the group consisting of a humanized Tmprss2 gene, a humanized Tmprss4 gene, and a humanized Tmprss11d gene.

In still another aspect, the invention provides a rodent embryonic stem cell whose genome contains a humanized Tmprss gene as described herein. In specific embodiments, the humanized Tmprss gene is selected from the group consisting of a humanized Tmprss2 gene, a humanized Tmprss4 gene, and a humanized Tmprss11d gene.

In another aspect, a rodent embryo generated from the rodent embryonic stem cell disclosed herein is also provided.

In one aspect, the invention provides a nucleic acid vector suitable for use in humanizing an endogenous Tmprss gene in a rodent. In some embodiments, the nucleic acid vector includes a human Tmprss nucleic acid sequence (e.g., a human genomic DNA encoding the ectodomain of a human TMPRSS protein), flanked by a 5' homology arm and a 3' homology arm. The 5' and 3' homology arms are nucleic acid sequences that are placed at 5' and 3', respectively, to the human Tmprss nucleic acid sequence and are homologous to genomic DNA sequences at an endogenous Tmprss locus in a rodent that flank a rodent genomic DNA encoding the ectodomain of a cognate rodent Tmprss protein. Thus, the 5' and 3' homology arms are capable of mediating homologous recombination and replacement of the rodent genomic DNA encoding the ectodomain of the cognate rodent Tmprss protein with the human Tmprss nucleic acid sequence to form a humanized Tmprss gene as described herein.

In a further aspect, the invention is directed to a method of providing a rodent whose genome contains a humanized Tmprss gene. The method includes modifying the genome of a rodent to replace a genomic sequence of an endogenous rodent Tmprss gene with a genomic sequence of a cognate human TMPRSS gene to form a humanized Tmprss gene.

In some embodiments, the invention provides a method of making a rodent (such as a mouse or a rat) having a humanized Tmprss gene, the method including the steps of (a) inserting a genomic fragment into an endogenous rodent Tmprss locus in a rodent embryonic stem cell, wherein the genomic fragment contains a nucleotide sequence of a cognate human TMPRSS gene, thereby forming a humanized Tmprss gene (such as those described herein); (b) obtaining a rodent embryonic stem cell comprising the humanized Tmprss gene of (a); and (c) creating a rodent using the rodent embryonic stem cell of (b).

In some embodiments, the humanized Tmprss gene is selected from the group consisting of a humanized Tmprss2 gene, a humanized Tmprss4 gene, and a humanized Tmprss11d gene. In various embodiments, the humanized Tmprss gene encodes a humanized Tmprss protein that contains an ectodomain substantially identical (e.g., at least 90%, 95%, 98%, 99% or 100% identical in sequence) to the ectodomain of the human TMPRSS protein encoded by the human TMPRSS gene used for humanization. In specific embodiments, the humanized Tmprss protein contains the ectodomain of a human TMPRSS protein selected from the group consisting of a human TMPRSS2 protein, a human TMPRSS4 protein, and a human TMPRSS11D protein. In specific embodiments, the humanized Tmprss protein further contains a cytoplasmic and transmembrane portion that is substantially identical with the cytoplasmic and transmembrane portion of the rodent Tmprss protein encoded by the endogenous rodent Tmprss gene being humanized.

In another aspect, the invention provides a method of using a rodent disclosed herein to assess the therapeutic efficacy of a compound (e.g., candidate inhibitors that specifically target a human TMPRSS protein) in treating influenza virus infection. The method can include the steps of providing a rodent described herein, administering an influenza virus and a candidate compound to the rodent; and monitoring the presence and severity of influenza virus infection in the rodent to determine the therapeutic efficacy of the drug candidate.

In some embodiments, the influenza virus is administered to the rodent before the compound. In other embodiments, the influenza virus is administered to the rodent after the compound.

In some embodiments, the candidate compound is an antibody or antigen-binding fragment thereof specific for a human TMPRSS protein. In specific embodiments, the candidate compound is an antibody or antigen-binding fragment thereof specific for a human TMPRSS protein selected from the group consisting of a human TMPRSS2 protein, a human TMPRSS4 protein, and a human TMPRSS11D protein.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The Drawings included herein, which are composed of the following Figures, are for illustration purposes only and not for limitation.

FIGS. 1A-1D. Exemplary strategy for humanization of mouse Tmprss2.

FIG. 1A shows a diagram, not to scale, of the genomic organization of mouse Tmprss2 and human TMPRSS2 genes. Exons are represented by thin bars placed across the genomic sequences, with the first coding exon for both genes indicated by the start codon "ATG" above the exon, and the last coding exon indicated by the "Stop" codon above the exon. A mouse genomic fragment of about 25,291 bp to be deleted and a human genomic fragment of about 25,091 bp to be inserted are indicated. Locations of probes used in an assay described in Example 1 are indicated. TM: transmembrane domain; SRCR: scavenger receptor cysteine-rich like domain; LDLRa: low density lipoprotein receptor class A.

FIG. 1B illustrates, not to scale, an exemplary modified BAC vector for humanization of an endogenous mouse Tmprss2 gene, along with the junction sequences (SEQ ID NOS: 22, 23 and 24).

FIG. 1C illustrates, not to scale, a humanized Tmprss2 allele after the neomycin cassette has been deleted, along with the junction sequences (SEQ ID NOS: 22 and 25).

FIG. 1D sets forth a sequence alignment of a human TMPRSS2 protein (SEQ ID NO: 4), a mouse Tmprss2 protein (SEQ ID NO: 2), and a humanized Tmprss2 protein ("7010 mutant pro") (SEQ ID NO: 7).

FIG. 2A shows a diagram, not to scale, of the genomic organization of mouse Tmprss4 and human TMPRSS4 genes. Exons are represented by thin bars placed across the genomic sequences, with the first exon (also the first coding exon) for both genes indicated by the start codon "ATG" above the exon, and the last coding exon indicated by the "Stop" codon above the exon. The mouse genomic fragment of about 11,074 bp to be deleted and the human genomic fragment of about 14,963 bp to be inserted are indicated. Locations of probes used in an assay described in Example 2 are indicated. TM: transmembrane domain; SRCR: scavenger receptor cysteine-rich like domain; LDLRa: low density lipoprotein receptor class A.

FIG. 2B illustrates, not to scale, an exemplary modified BAC vector for humanization of an endogenous mouse Tmprss4 gene, along with the junction sequences (SEQ ID NOS: 38, 39 and 40).

FIG. 2C illustrates, not to scale, a humanized Tmprss4 allele after the neomycin cassette has been deleted, along with the junction sequences (SEQ ID NOS: 41 and 40).

FIG. 2D sets forth a sequence alignment of a human TMPRSS4 protein (SEQ ID NO: 11), a mouse Tmprss4 protein (SEQ ID NO: 9), and a humanized Tmprss4 protein ("7224 mutant pro") (SEQ ID NO: 14).

FIGS. 3A-3D. Exemplary strategy for humanization of mouse Tmprss11d.

FIG. 3A shows a diagram, not to scale, of the genomic organization of mouse Tmprss11d and human TMPRSS11D genes. Exons are represented by thin bars placed across the genomic sequences, with the first exon (also the first codon exon) for both genes indicated by the start codon "ATG" above the exon, and the last coding exon indicated by the "Stop" codon above the exon. A mouse genomic fragment of about 35,667 bp to be deleted and a human genomic fragment of about 33,927 bp to be inserted are indicated. Locations of probes used in an assay described in Example 3 are indicated. TM: transmembrane domain; SEA: domain found in sea urchin sperm protein, enterokinase and agrin.

FIG. 3B illustrates, not to scale, an exemplary modified BAC vector for humanization of an endogenous mouse Tmprss11d gene, along with the junction sequences (SEQ ID NOS: 57, 58 and 59).

FIG. 3C illustrates, not to scale, a humanized Tmprss11 allele after the neomycin cassette has been deleted, along with the junction sequences (SEQ ID NOS: 57 and 60).

FIG. 3D sets forth a sequence alignment of a human TMPRSS11D protein (SEQ ID NO: 18), a mouse Tmprss11d protein (SEQ ID NO: 16), and a humanized Tmprss11d protein ("7226 mutant pro") (SEQ ID NO: 21).

DETAILED DESCRIPTION OF CERTAIN EMBODIMENTS

Figure 1A:
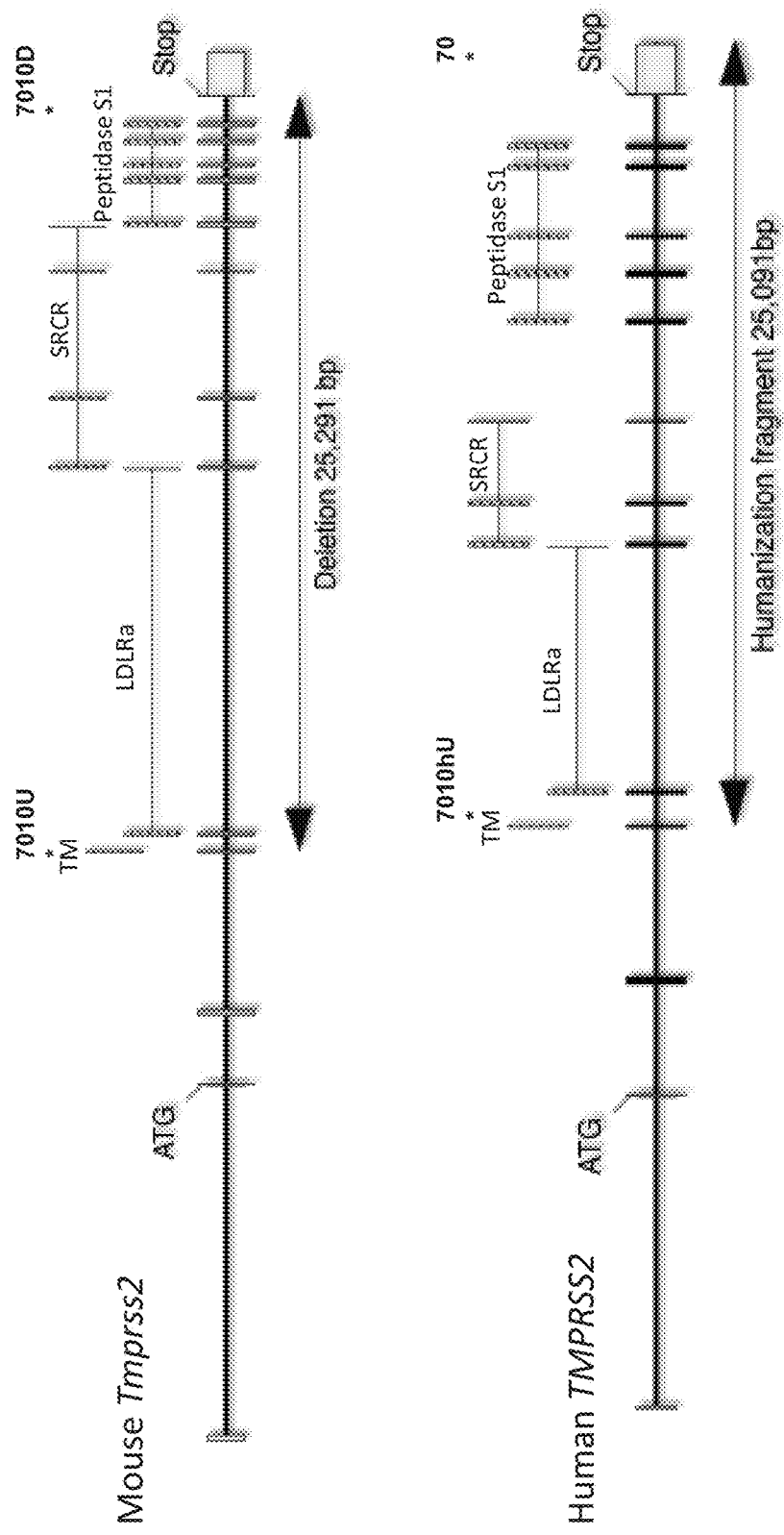

The present invention relates to genetically modified rodents (e.g., mice and rats) having a humanized gene encoding a type II transmembrane serine protease (or "Tmprss", for transmembrane protease/serine). The genetically modified rodents are suitable for use in screening for candidate compounds that specifically target a human TMPRSS molecule for the treatment and prevention of diseases such as influenza virus infection. Accordingly, the present invention provides genetically modified rodents having a humanized Tmprss gene, cells and tissues isolated from the genetically modified rodents, methods and compositions for making the genetically modified rodents, and use of the genetically modified rodents for screening and testing therapeutic compounds. The various embodiments of the present invention are further described below.

Type II Transmembrane Serine Proteases ("Tmprss")

Type II transmembrane serine proteases, also referred to herein as "Tmprss" for non-human molecules or "TMPRSS" for human molecules ("transmembrane protease/serine"), are a family of proteins characterized by an N-terminal transmembrane domain and a C-terminal extracellular serine protease domain. At least 18 members have been identified in the family, which are grouped into four subfamilies (Bugge et al. (2009), supra). All members share several common structural features that define the family, including (i) a short N-terminal cytoplasmic domain, (ii) a transmembrane domain, and (iii) an ectodomain that contains a protease domain and a stem region that links the transmembrane domain with the protease domain. The stem region contains a combination of modular structural domains of six different types: a SEA (sea urchin sperm protein/enteropeptidase/agrin) domain, a group A scavenger receptor domain, a LDLA (low-density lipoprotein receptor class A) domain, a CUB (Cls/Clr urchin embryonic growth factor, bone morphogenetic protein-1) domain, a MAM (meprin/A5 antigen/receptor protein phosphatase mu) domain, and a frizzled domain. See review by Bugge et al. (2009), supra. For example, TMPRSS2 and TMPRSS4, both of which belong to the hepsin/TMPRSS subfamily, have a group A scavenger receptor domain, preceded by a single LDLA domain in the stem region. TMPRSS11D, also known as "HAT" for human airway trypsin-like protease that belongs to the HAT/DESC subfamily, has a single SEA domain. See FIG. 1 of Bugge et al. (2009), supra.

Type II transmembrane serine proteases are produced initially as inactive proenzymes that require activation by cleavage following a basic amino acid residue in a consensus activation motif preceding the protease domain. Some of the activated proteases remain membrane bound as a result of a disulfide bond between the prodomain and the protease domain. The extracellular domains are considered to be critical for cellular localization, activation, inhibition, and/or substrate specificity of these proteases (Bugge et al. (2009), supra; Szabo et al., *Int. J. Biochem. Cell Biol.* 40: 1297-1316 (2008)).

Various biochemical and pathophysiological information has been documented for members of the type II transmembrane serine proteases. TMPRSS2, TMPRSS4 and TMPRSS11D have been shown in vitro to cleave influenza A hemagglutinin (HA), which is the first essential step in the viral life cycle. Genetically modified rodent animals having a humanized Tmprss gene disclosed herein provide useful in vivo systems that allow for a thorough understanding of the biological functions of the TMPRSS molecules, as well as for screening therapeutic compounds that specifically target human TMPRSS molecules.

Exemplary Tmprss sequences, including mouse, human and humanized Tmprss nucleic acid and protein sequences, are provided in this application and are summarized in the following table. Primer and probe sequences used in the assays described in the examples section, and insertion junction sequences of exemplary humanized Tmprss alleles, are also included in the table.

Summary Description of Sequences

| SEQ ID NO | Description | Features |
|---|---|---|
| 1. | *Mus musculus* Tmprss2, mRNA, NM_015775.2 | Length: 3175 bp<br>CDS: 231-1703<br>Exons: 1-177; 178-245 (second exon, and first coding exon); 246-465; 466-552; 553-672; 673-799; 800-910; 911-954; 955-1123; 1124-1299; 1300-1395; 1396-1538; 1539-1691; 1692-3161. |
| 2 | *Mus musculus* Tmprss2, protein | Length: 490 aa |
| 3 | *Homo sapiens* TMPRSS2, transcript variant 2, mRNA, NM_005656.3 | Length: 3212 bp<br>CDS: 135-1613<br>Exons: 1-78; 79-149 (second exon, and first coding exon); 150-372; 373-459; 460-579; 580-706; 707-817; 818-861; 862-1033; 1034-1209; 1210-1305; 1306-1448; 1449-1601; 1602-3204. |
| 4 | *Homo sapiens* TMPRSS2, transcript variant 2, protein | Length: 492 aa<br>Ectodomain: begins at W106. |
| 5 | Humanization Tmprss2 genomic fragment | Length: 27,947 bp<br>1-84: mouse sequence<br>85-25175: human sequence (total 25091 bp)<br>25176-27866: XhoI-LoxP-Cassette-loxP-ICeUI-NheI (total 2691 bp)<br>27867-27947: mouse sequence |
| 6 | Humanization Tmprss2 genomic fragment with cassette deleted | Length: 25,333bp<br>1-84: mouse sequence<br>85-25175: human sequence (total 25091 bp)<br>25176-25252: XhoI-loxP-ICeUI-NheI (77 bp)<br>25253-25333: mouse sequence |
| 7 | Humanized Tmprss2 protein | Length: 491 aa |
| 8 | *Mus musculus* Tmprss4, mRNA, NM_145403.2 | Length: 2267 bp<br>CDS: 289-1596<br>Exons: 1-291 (first exon and first coding exon); 292-325; 326-439; 440-592; 593-722; 723-824; 825-865; 866-1025; 1026-1192; 1193-1291; 1292-1434; 1435-1584; 1585-2267. |
| 9 | *Mus musculus* Tmprss4, protein | Length: 435 aa |
| 10 | *Homo sapiens* TMPRSS4, transcript variant 4, mRNA, NM_001173551.1 | Length: 3543 bp<br>CDS: 292-1599<br>Exons: 1-294 (first exon and first coding exon); 295-328; 329-442; 443-595; 596-725; 726-827; 828-868; 869-1028; 1029-1195; 1196-1294; 1295-1437; 1438-1587; 1588-3529. |
| 11 | *Homo sapiens* TMPRSS4, transcript variant 4, protein | Length: 437 aa<br>Ectodomain: begins at K54. |

| SEQ ID NO | Description | Features |
|---|---|---|
| 12 | Humanization Tmprss4 genomic fragment containing cassette | Length: 20,078 bp<br>1-18: mouse sequence<br>19-5014: SalI/XhoI-LoxP-hUbi-EM7-Neo-Pm-Cre-loxP-ICeuI-NheI (total 4996 bp)<br>5015-19977: HUMAN sequence (total 14963 bp)<br>19978-20078: mouse sequence |
| 13 | Humanization Tmprss4 genomic fragment with cassette deleted | Length: 15159 bp<br>1-18: mouse sequence<br>19-95: SalI/XhoI-LoxP-ICeuI-NheI (total 77 bp)<br>96-15058: HUMAN sequence (total 14963 bp)<br>15059-15159: mouse sequence |
| 14 | Humanized Tmprss4 Protein | Length: 435 aa |
| 15 | *Mus musculus* Tmprss11d, mRNA, NM_145561.2 | Length: 2046 hp<br>CDS: 36-1289<br>Exons: 1-43 (first exon and first coding exon), 44-165, 166-284; 285-352; 353-507; 508-546; 547-724; 725-984; 985-1127; 1128-2046. |
| 16 | *Mus musculus* Tmprss11d, protein | Length: 417 aa |
| 17 | *Homo sapiens* TMPRSS11D, mRNA, NM_004262.2 | Length: 2800 bp<br>CDS: 66-1322<br>Exons: 1-73 (first exon and first coding exon); 74-195; 196-314; 315-382; 383-540; 541-579; 580-757; 758-1017; 1018-1160; 1161-2783. |
| 18 | *Homo sapiens* TMPRSS11D, protein | Length: 418 aa<br>Ectodomain begins at A42. |
| 19 | Humanization Tmprss11d genomic fragment containing cassette | Length: 38,992<br>1-19: mouse sequence<br>20-33,946: HUMAN sequence (total 33,927 bp)<br>33,947-38,942: XhoI-LoxP-hUbi-EM7-Neo-Pm-Cre-loxP-ICeuI-NheI (total 4,996 bp)<br>38,943-38,992: mouse sequence |
| 20 | Humanization Tmprss11d genomic fragment with cassette deleted | Length: 34,073 bp<br>1-19: mouse sequence<br>20-33,946: HUMAN sequence total 33,927 bp)<br>33,947-34,023: XhoI-LoxP-ICeuI-NheI (77 bp)<br>34,024-34,073: mouse sequence |
| 21 | Humanized Tmprss11d Protein | 418 aa |
| 22 | 5' mouse/5' human junction sequence for Tmprss2 humanization | 5' mouse//5' human |
| 23 | 3' human/cassette junction sequence for Tmprss2 humanization | Human//XhoI//loxP Cassette |
| 24 | Cassette/3' mouse junction sequence for Tmprss2 humanization | Cassette (loxP)/ICEUI//NheI//mouse |
| 25 | 3' human/loxP/3' mouse junction for Tmprss2 humanization | 3' human//XhoI//(loxP)/ICEUI//NheI//3' mouse |
| 26-37 | Primers and probes for loss of allele and gain of allele assays for Tmprss2 humanization | Table 1 |
| 38 | 5' mouse/Cassette junction sequence for Tmprss4 humanization | 5' mouse//SalI-XhoI//(loxP) Cassette |
| 39 | Cassette/5' human junction sequence for Tmprss4 humanization | Cassette (loxP)/ICEUI//NheI//5' human |
| 40 | 3' human/3' mouse junction sequence for Tmprss4 humanization | 3' human/3' mouse |
| 41 | 5' mouse/loxP/5' human junction for Tmprss4 humanization | 5' mouse//SalI//XhoI//(loxP)/ICEUI//NheI//5' human |
| 42-56 | Primers and probes for loss of allele and gain of allele assays for Tmprss4 humanization | Table 2 |
| 57 | 5' mouse/5' human junction sequence for Tmprss11d humanization | 5' mouse//5' human |
| 58 | 3' human/cassette junction sequence for Tmprss11d humanization | 3' human//XhoI//(loxP) Cassette |

-continued

| SEQ ID NO | Description | Features |
|---|---|---|
| 59 | Cassette/3' mouse junction sequence for Tmprss11d humanization | Cassette (loxP)/ICEUI//NheI//3' mouse |
| 60 | 3' human/loxP/3' mouse junction for Tmprss11d humanization | 3' human//XhoI//(loxP)/ICEUI//NheI//3' mouse |
| 61-72 | Primers and probes for loss of allele and gain of allele assays for Tmprss11d humanization | Table 3 |

Humanized Tmprss Rodent Animals

In one aspect, the present invention provides rodent animals that contain in the germline a humanized Tmprss gene encoding a humanized Tmprss protein.

The term "humanized", when used in the context of nucleic acids or proteins, refers to nucleic acids or proteins whose structures (i.e., nucleotide or amino acid sequences) include portions that correspond substantially or identically with structures of a particular gene or protein found in nature in a rodent animal, and also include portions that differ from that found in the relevant rodent gene or protein and instead correspond more closely or identically with structures found in a corresponding human gene or protein. A rodent containing a humanized gene or expressing a humanized protein is a "humanized" rodent.

In some embodiments, a rodent of the present invention is selected from a mouse, a rat, and a hamster. In some embodiments, a rodent of the present invention is selected from the superfamily Muroidea. In some embodiments, a genetically modified rodent of the present invention is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In some certain embodiments, a genetically modified rodent of the present invention is selected from a true mouse or rat (family Muridae), a gerbil, a spiny mouse, and a crested rat. In some certain embodiments, a genetically modified mouse of the present invention is from a member of the family Muridae.

In some embodiments, the rodent disclosed herein contains a humanized Tmprss gene in the genome that includes a nucleotide sequence of an endogenous rodent Tmprss gene and a nucleotide sequence of a human TMPRSS gene, wherein the nucleotide sequence of the endogenous rodent Tmprss gene and the nucleotide sequence of the human TMPRSS gene are operably linked to each other such that the humanized Tmprss gene encodes a Tmprss protein and is under control of a 5' regulatory element(s), such as the promoter and/or enhancer(s), of the endogenous rodent Tmprss gene.

The present invention is particularly directed to like-for-like humanization; in other words, a nucleotide sequence of an endogenous rodent Tmprss gene is operably linked to a nucleotide sequence of a cognate human TMPRSS gene to form a humanized gene. For example, in some embodiments, a nucleotide sequence of an endogenous rodent Tmprss2 gene is operably linked to a nucleotide sequence of a human TMPRSS2 gene to form a humanized Tmprss2 gene. In other embodiments, a nucleotide sequence of an endogenous rodent Tmprss4 gene is operably linked to a nucleotide sequence of a human TMPRSS4 gene to form a humanized Tmprss4 gene. In still other embodiments, a nucleotide sequence of an endogenous rodent Tmprss11d gene is operably linked to a nucleotide sequence of a human TMPRSS11D gene to form a humanized Tmprss11d gene.

In some embodiments, a genetically modified rodent of this invention contains a humanized Tmprss gene in its genome, wherein the humanized Tmprss gene encodes a humanized Tmprss protein that contains an ectodomain that is substantially identical with the ectodomain of a human TMPRSS protein. The term "ectodomain" refers to the portion of a transmembrane protein that extends outside of the cell membrane, i.e., the extracellular portion of a transmembrane protein. The ectodomain of a TMPRSS molecule includes a protease domain and a stem region that links the transmembrane domain with the protease domain. By an ectodomain or polypeptide that is "substantially identical with the ectodomain of a human TMPRSS protein", it is meant in some embodiments, a polypeptide that is at least 85%, 90%, 95%, 95%, 99% or 100% identical in sequence with the ectodomain of a human TMPRSS protein; in some embodiments, a polypeptide that differs from the ectodomain of a human TMPRSS protein by not more than 10, 9, 8, 7, 6, 5, 4, 3, 2 or 1 amino acid(s); in some embodiments, a polypeptide that differs from the ectodomain of a human TMPRSS protein only at the N- or C-terminus of the ectodomain, e.g., by lacking amino acids or having additional amino acids at the at the N- or C-terminus of the ectodomain; and in some embodiments, a polypeptide that is substantially the ectodomain of a human TMPRSS protein. By "substantially the ectodomain" of a human TMPRSS protein, it is meant a polypeptide that is identical with the ectodomain, or differs from the ectodomain by lacking 1-5 (i.e., 1, 2, 3, 4 or 5) amino acids or having additional 1-5 amino acids at the N- or C-terminus.

In some embodiments, the humanized Tmprss gene encodes a humanized Tmprss protein that further contains a cytoplasmic and transmembrane portion that is substantially identical with the cytoplasmic and transmembrane portion of an endogenous rodent Tmprss protein. By a cytoplasmic and transmembrane portion or polypeptide that is "substantially identical with the cytoplasmic and transmembrane portion of an endogenous rodent Tmprss protein", it is meant in some embodiments, a polypeptide that is at least 85%, 90%, 95%, 95%, 99% or 100% identical in sequence with the cytoplasmic and transmembrane portion of an endogenous rodent Tmprss protein; in some embodiments, a polypeptide that differs from the cytoplasmic and transmembrane portion of an endogenous rodent Tmprss protein by not more than 10, 9, 8, 7, 6, 5, 4, 3, 2 or 1 amino acid(s); in some embodiments, a polypeptide that differs from the cytoplasmic and transmembrane portion of an endogenous rodent Tmprss protein only at the C-terminus, e.g., by lacking amino acids or having additional amino acids at the at the C-terminus of the transmembrane domain; and in some embodiments, a polypeptide composed of the cytoplasmic domain and substantially the transmembrane domain of an endogenous rodent Tmprss protein. By "substantially the transmembrane domain" of an endogenous rodent Tmprss protein, it is meant a polypeptide that is identical with the transmembrane domain, or differs from the transmembrane domain by lacking 1-5 amino acids or having additional 1-5 amino acids at the C-terminus.

In some embodiments, the humanized Tmprss gene in the genome of a genetically modified rodent includes a nucleotide sequence of an endogenous rodent Tmprss gene and a nucleotide sequence of a cognate human TMPRSS gene, wherein the nucleotide sequence of the cognate human TMPRSS gene encodes a polypeptide substantially identical to the ectodomain of the human TMPRSS protein encoded by the human TMPRSS gene. In certain embodiments, the nucleotide sequence of a cognate human TMPRSS gene in a humanized Tmprss gene encodes the ectodomain of the human TMPRSS protein encoded by the human TMPRSS gene.

In some embodiments, the humanized Tmprss gene in the genome of a genetically modified rodent includes a nucleotide sequence of an endogenous rodent Tmprss gene and a nucleotide sequence of a cognate human TMPRSS gene, wherein the nucleotide sequence of an endogenous rodent Tmprss gene encodes a polypeptide substantially identical to the cytoplasmic and transmembrane portion of the endogenous rodent Tmprss protein encoded by the rodent Tmprss gene. In specific embodiments, the nucleotide sequence of an endogenous rodent Tmprss gene present in a humanized Tmprss gene encodes the cytoplasmic and transmembrane domains of the endogenous rodent Tmprss protein encoded by the endogenous rodent Tmprss gene.

In some embodiments, a humanized Tmprss gene results from a replacement of a nucleotide sequence of an endogenous rodent Tmprss gene at an endogenous rodent Tmprss locus with a nucleotide sequence of a cognate human TMPRSS gene.

In some embodiments, a contiguous genomic sequence of a rodent Tmprss gene at an endogenous rodent Tmprss locus has been replaced with a contiguous genomic sequence of a cognate human TMPRSS gene to form a humanized Tmprss gene.

In specific embodiments, a contiguous genomic sequence of a human TMPRSS gene inserted into an endogenous rodent Tmprss gene includes exons, in full or in part, of a human TMPRSS gene, that encode an ectodomain that is substantially identical with the ectodomain of the human TMPRSS protein encoded by the human TMPRSS gene.

In certain embodiments, the genomic sequence of an endogenous rodent Tmprss gene that remains at an endogenous rodent Tmprss locus after the humanization replacement and is operably linked to the inserted contiguous human TMPRSS genomic sequence encodes a cytoplasmic and transmembrane portion that is substantially identical with the cytoplasmic and transmembrane portion of the endogenous rodent Tmprss protein encoded by the endogenous rodent Tmprss gene.

In circumstances where an endogenous Tmprss protein and a human TMPRSS protein share common amino acids near the junction between the transmembrane domain and the ectodomain, it may not be necessary to insert a human TMPRSS genomic sequence that encodes precisely the ectodomain of the human TMPRSS protein. It is possible to insert a slightly longer or shorter genomic sequence of a human TMPRSS gene, which encodes substantially the ectodomain of the human TMPRSS protein, in operable linkage to a genomic sequence of an endogenous rodent Tmprss gene that encodes the cytoplasmic domain and substantially the transmembrane domain of the endogenous rodent Tmprss protein, such that the humanized Tmprss protein encoded by the resulting humanized Tmprss gene includes an ectodomain that is identical with the ectodomain of the human TMPRSS protein and a transmembrane domain that is identical with the transmembrane domain of the endogenous rodent Tmprss protein.

In some embodiments, the nucleotide sequence of a human TMPRSS gene included in a humanized Tmprss gene also includes the 3' untranslated region ("UTR") of the human TMPRSS gene. In certain embodiments, in addition to the 3' UTR of a human TMPRSS gene, a humanized Tmprss gene also includes an additional human genomic sequence from the human TMPRSS gene locus, following the human TMPRSS 3' UTR. The additional human genomic sequence can consist of at least 10-200 bp, e.g., 50 bp, 75 bp, 100 bp, 125 bp, 150 bp, 175 bp, 200 bp, or more, found in the human TMPRSS gene locus immediately downstream of the 3' UTR of the human TMPRSS gene. In other embodiments, the nucleotide sequence of a human TMPRSS gene present in a humanized Tmprss gene does not include a human 3' UTR; instead, the 3' UTR of an endogenous rodent Tmprss gene is included and follows immediately the stop codon of the humanized Tmprss gene. For example, a humanized Tmprss gene can include a nucleotide sequence of an endogenous rodent Tmprss gene containing exon sequences encoding the cytoplasmic and transmembrane domains of the endogenous rodent Tmprss protein, followed by a nucleotide sequence of a human TMPRSS gene containing exon sequences encoding the ectodomain through the stop codon of the human TMPRSS protein, with the 3' UTR of the endogenous rodent Tmprss gene following immediately after the stop codon.

In some embodiments, a humanized Tmprss gene results in an expression of the encoded humanized Tmprss protein in a rodent. In some embodiments, a humanized Tmprss protein is expressed in a pattern comparable with, or substantially the same as, a counterpart rodent Tmprss protein in a control rodent (e.g., a rodent without the humanized Tmprss gene). In some embodiments, a humanized Tmprss protein is expressed at a level comparable with, or substantially the same as, a counterpart rodent Tmprss protein in a control rodent (e.g., a rodent without the humanized Tmprss gene). In certain embodiments, a humanized Tmprss protein is expressed and detected at the cell surface. In certain embodiments, a humanized Tmprss protein or a soluble form (e.g., a shed ectodomain form) is expressed and detected in serum of a rodent, e.g., at a level comparable with, or substantially the same as, a counterpart rodent Tmprss protein or a soluble form thereof in a control rodent. In the context of comparing a humanized gene or protein in a humanized rodent with an endogenous rodent gene or protein in a control rodent, the term "comparable" means that the molecules or levels being compared may not be identical to one another but are sufficiently similar to permit comparison there between so that conclusions may reasonably be drawn based on differences or similarities observed; and the term "substantially the same" in referring to expression levels means that the levels being compared are not different from one another by more than 20%, 19%, 18%, 17%, 16%, 15%, 14%, 13%, 12%, 11%, 10%, 9%, 8%, 7%, 6%, 5%, 4%, 3%, 2%, or 1%.

In some embodiments, the present invention further provides an isolated cell or tissue from a rodent animal as described herein. In some embodiments, a cell is selected from a dendritic cell, lymphocyte (e.g., a B or T cell), macrophage and a monocyte. In some embodiments, a tissue is selected from adipose, bladder, brain, breast, bone marrow, eye, heart, intestine, kidney, liver, lung, lymph node, muscle, pancreas, plasma, serum, skin, spleen, stomach, thymus, testis, ovum, and a combination thereof.

In some embodiments, the present invention provides a rodent embryonic stem cell whose genome contains a humanized Tmprss gene as described herein. In some embodiments, a rodent embryonic stem cell is a mouse embryonic stem cell. In other embodiments, a rodent embryonic stem cell is a rat embryonic stem cell. A rodent embryonic stem cell containing a humanized Tmprss gene in its genome can be used to make a humanized rodent animal, as further described herein below.

In some embodiments, a rodent provided herein is heterozygous for a humanized Tmprss gene in its genome. In other embodiments, a rodent provided herein is homozygous for a humanized Tmprss gene in its genome.

In certain embodiments, a rodent includes multiple, i.e., two or more, humanized Tmprss genes in its genome. In other words, two or more different endogenous Tmprss loci in a rodent have been humanized using nucleotide sequences of cognate human TMPRSS genes. For example, a rodent has been humanized at two or more of the gene loci selected from: Tmprss2, Tmprss4, and Tmprss11d.

Exemplary humanized Tmprss2 rodents (such as mice), humanized Tmprss4 rodents (such as mice), and humanized Tmprss11d rodents (such as mice) are further described below.

Humanized Tmprss2 Rodents

In some embodiments, this invention provides a rodent whose genome contains a humanized Tmprss2 gene that includes a nucleotide sequence of an endogenous rodent Tmprss2 gene and a nucleotide sequence of a human TMPRSS2 gene, and that is under control of a 5' regulatory element(s), such as the promoter and/or enhancer(s), of the endogenous rodent Tmprss2 gene. Examples of rodents include mice and rats.

In some embodiments, a humanized Tmprss2 gene encodes a humanized Tmprss2 protein that contains an ectodomain that is substantially identical with the ectodomain of a human TMPRSS2 protein.

In specific embodiments, the human TMPRSS2 protein has an amino acid sequence having at least 85%, 90%, 95%, 98%, 99% or 100% identity with the amino acid sequence as set forth in SEQ ID NO: 4.

In some embodiments, a humanized Tmprss2 protein contains the C-terminal 387 amino acids of a human TMPRSS2 protein, for example, amino acids 106 to 492 of a human TMPRSS2 protein. In some embodiments, a humanized Tmprss2 protein contains an ectodomain that is substantially identical with the amino acid sequence composed of W106 to G492 of SEQ ID NO: 4. In specific embodiments, a humanized Tmprss2 protein contains an ectodomain having at least 85%, 90%, 95%, 98%, 99% or 100% identity with the amino acid sequence composed of W106 to G492 of SEQ ID NO: 4; an ectodomain that differs from the amino acid sequence composed of W106 to G492 of SEQ ID NO: 4 by not more than 10, 9, 8, 7, 6, 5, 4, 3, 2 or 1 amino acid(s); or an ectodomain that differs from the amino acid sequence composed of W106 to G492 of SEQ ID NO: 4 only at the N- or C-terminus of the ectodomain, e.g., lacking 1-5 amino acids or having additional 1-5 amino acids at the at the N- or C-terminus.

In some embodiments, a humanized Tmprss2 protein further contains a cytoplasmic and transmembrane portion that is substantially identical with the cytoplasmic and transmembrane portion of an endogenous rodent Tmprss2 protein. In some embodiments, a humanized Tmprss2 protein further includes the transmembrane domain and the cytoplasmic domain of an endogenous rodent Tmprss2 protein.

In specific embodiments, a humanized Tmprss2 protein contains the transmembrane domain and the cytoplasmic domain of an endogenous rodent Tmprss2 protein, and the ectodomain of a human TMPRSS2 protein. In particular embodiments, a humanized Tmprss2 gene encodes a humanized Tmprss2 protein having the amino acid sequence as set forth in SEQ ID NO: 7.

In some embodiments, a humanized Tmprss2 gene results from a replacement of a nucleotide sequence of an endogenous rodent Tmprss2 gene at an endogenous rodent Tmprss2 locus with a nucleotide sequence of a human TMPRSS2 gene.

In some embodiments, a contiguous genomic sequence of an endogenous rodent Tmprss2 gene at an endogenous rodent Tmprss2 locus has been replaced with a contiguous genomic sequence of a human TMPRSS2 gene to form a humanized Tmprss2 gene.

In specific embodiments, the contiguous genomic sequence of a human TMPRSS2 gene inserted into an endogenous rodent Tmprss2 gene includes exon sequences, i.e., exons in full or in part, of a human TMPRSS2 gene, that encode an ectodomain that is substantially identical to the ectodomain of the human TMPRSS2 protein encoded by the human TMPRSS2 gene. In circumstances where an endogenous Tmprss2 protein and a human TMPRSS2 protein share common amino acids near the junction of the transmembrane domain and the ectodomain, it may not be necessary to insert a human TMPRSS2 genomic sequence that encodes precisely the ectodomain of the human TMPRSS2 protein, and it is possible to use a slightly longer or shorter human TMPRSS2 genomic sequence that encodes substantially the ectodomain of a human TMPRSS2 protein in order to make a humanized Tmprss2 protein having an ectodomain that is identical with the ectodomain of the human TMPRSS2 protein.

In specific embodiments, a contiguous genomic sequence of a human TMPRSS2 gene being inserted into an endogenous rodent Tmprss2 gene contains at least coding exon 4 through the stop codon in coding exon 13 of the human TMPRSS2 gene.

In certain embodiments, a contiguous genomic sequence of a human TMPRSS2 gene being inserted into an endogenous rodent Tmprss2 gene contains intron 3 and coding exon 4 through the stop codon in coding exon 13 of the human TMPRSS2 gene. In particular embodiments, a contiguous genomic sequence of a human TMPRSS2 gene being inserted into an endogenous rodent Tmprss 2 gene contains a 3' portion of coding exon 3, intron 3, and coding exon 4 through the stop codon in coding exon 13 of the human TMPRSS2 gene. In specific embodiments, the 3' portion of coding exon 3 of a human TMPRSS2 gene included in the humanization is about 5-10 base pair in length, i.e., about 5, 6, 7, 8, 9 or 10 base pair of the 3' end of coding exon 3.

In some embodiments, a contiguous genomic sequence of a human TMPRSS2 gene being inserted into an endogenous rodent Tmprss2 gene also contains the 3' UTR of the human TMPRSS2 gene. In specific embodiments, the entire coding exon 13 of a human TMPRSS2 gene is included in the contiguous human TMPRSS2 genomic sequence for humanization, which includes the 3' UTR of the human TMPRSS2 gene. In particular embodiments, a contiguous genomic sequence of a human TMPRSS2 gene includes an additional human genomic sequence downstream of the 3' UTR of the human TMPRSS2 gene. The additional human genomic sequence can be a sequence of at least 10-200 bp, or at least 10, 20, 30, 40, 50, 75, 100, 125, 150, 175, or 200 bp, that is found immediately downstream of the 3' UTR of the human TMPRSS2 gene at a human TMPRSS2 locus.

In some embodiments, the nucleotide sequence of an endogenous rodent Tmprss2 gene remaining at a humanized Tmprss2 locus encodes a polypeptide that is substantially identical with the cytoplasmic and transmembrane portion of the endogenous rodent Tmprss2 protein. In circumstances where an endogenous Tmprss2 protein and a human TMPRSS2 protein share common amino acids near the junction of the transmembrane domain and the ectodomain, it may not be necessary to maintain the endogenous rodent Tmprss2 genomic sequence that encodes precisely the transmembrane domain of the endogenous rodent Tmprss2 protein, and it is possible to maintain a slightly longer or shorter rodent Tmprss2 genomic sequence that encodes substantially the transmembrane domain of the endogenous rodent Tmprss2 protein in the humanization replacement in order to encode a humanized Tmprss2 protein having a transmembrane domain that is identical with the transmembrane of the endogenous rodent Tmprss2 protein. In some embodiments, the nucleotide sequence of an endogenous rodent Tmprss2 gene remaining at a humanized Tmprss2 locus includes exons 1-2 and a 5' portion of coding exon 3 of an endogenous rodent Tmprss2 gene, wherein the 5' portion of coding exon 3 is a substantial portion of codon exon 3, e.g., the entire coding exon 3 except 5-10 base pairs at the 3' end of coding exon 3.

In specific embodiments, a humanized Tmprss2 gene contains coding exons 1-2 and a 5' portion of coding exon 3 of an endogenous rodent Tmprss2 gene, and a 3' portion of coding exon 3 and coding exon 4 through coding exon 13 of a human TMPRSS2 gene, wherein the humanized Tmprss2 gene encodes a humanized Tmprss2 protein that contains a cytoplasmic and transmembrane portion that is substantially identical with the cytoplasmic and transmembrane portion of the rodent Tmprss2 protein, and an ectodomain that is substantially identical with the ectodomain of the human TMPRSS2 protein. In certain embodiments, the humanized Tmprss2 gene encodes a humanized Tmprss2 protein that contains the cytoplasmic domain and the transmembrane domain of the rodent Tmprss2 protein encoded by an endogenous rodent Tmprss2 gene, and the ectodomain of the human TMPRSS2 protein encoded by a human TMPRSS2 gene. In particular embodiments, a humanized Tmprss2 gene encodes a humanized Tmprss2 protein having the amino acid sequence as set forth in SEQ ID NO: 7.

In some embodiments, the exons and introns of a human TMPRSS2 gene and a rodent Tmprss2 gene used in the humanization are those found in SEQ ID NOS: 1, 3 and 5-6.

In some embodiments, a humanized Tmprss2 gene results in an expression of the encoded humanized Tmprss2 protein in a rodent. In some embodiments, a humanized Tmprss2 protein is expressed in a pattern comparable with, or substantially the same as, a counterpart rodent Tmprss2 protein in a control rodent (e.g., a rodent without the humanized Tmprss2 gene). In some embodiments, a humanized Tmprss2 protein is expressed at a level comparable with, or substantially the same as, a counterpart rodent Tmprss2 protein in a control rodent (e.g., a rodent without the humanized Tmprss2 gene). In certain embodiments, a humanized Tmprss2 protein is expressed and detected at the cell surface. In certain embodiments, a humanized Tmprss2 protein or a soluble form (e.g., a shed ectodomain form) is expressed and detected in serum of a rodent, e.g., at a level comparable with, or substantially the same as, a counterpart rodent Tmprss2 protein or a soluble form thereof in a control rodent.

Humanized Tmprss4 Rodents

In some embodiments, this invention provides a rodent whose genome contains a humanized Tmprss4 gene that includes a nucleotide sequence of an endogenous rodent Tmprss4 gene and a nucleotide sequence of a human TMPRSS4 gene, and that is under control of a 5' regulatory element(s), such as the promoter and/or an enhancer(s), of the endogenous rodent Tmprss4 gene. Examples of rodents include mice and rats.

In some embodiments, a humanized Tmprss4 gene encodes a humanized Tmprss4 protein that contains an ectodomain that is substantially identical with the ectodomain of a human TMPRSS4 protein. In specific embodiments, the human TMPRSS4 protein has an amino acid sequence having at least 85%, 90%, 95%, 98%, 99% or 100% identity with the amino acid sequence as set forth in SEQ ID NO: 11.

In some embodiments, a humanized Tmprss4 protein contains the C-terminal 384 amino acids of a human TMPRSS4 protein, for example, amino acids 54 to 437 of a human TMPRSS4 protein. In some embodiments, a humanized Tmprss4 protein contains an ectodomain that is substantially identical with the amino acid sequence composed of K54 to L437 of SEQ ID NO: 11. In specific embodiments, a humanized Tmprss4 protein contains an ectodomain having at least 85%, 90%, 95%, 98%, 99% or 100% identity with the amino acid sequence composed of K54 to L437 of SEQ ID NO: 11; an ectodomain that differs from the amino acid sequence composed of K54 to L437 of SEQ ID NO: 11 by not more than 10, 9, 8, 7, 6, 5, 4, 3, 2 or 1 amino acid(s); or an ectodomain that differs from the amino acid sequence composed of K54 to L437 of SEQ ID NO: 11 only at the N- or C-terminus of the ectodomain, e.g., lacking 1-5 amino acids or having additional 1-5 amino acids at the N- or C-terminus.

In some embodiments, a humanized Tmprss4 protein further contains a cytoplasmic and transmembrane portion that is substantially identical with the cytoplasmic and transmembrane portion of an endogenous rodent Tmprss4 protein. In some embodiments, a humanized Tmprss4 protein further includes the transmembrane domain and the cytoplasmic domain of an endogenous rodent Tmprss4 protein.

In specific embodiments, a humanized Tmprss4 protein contains the transmembrane domain and the cytoplasmic domain of an endogenous rodent Tmprss4 protein, and the ectodomain of a human TMPRSS4 protein. In particular embodiments, a humanized Tmprss4 gene encodes a humanized Tmprss4 protein having the amino acid sequence as set forth in SEQ ID NO: 14.

In some embodiments, a humanized Tmprss4 gene results from a replacement of a nucleotide sequence of an endogenous rodent Tmprss4 gene at an endogenous rodent Tmprss4 locus with a nucleotide sequence of a human TMPRSS4 gene.

In some embodiments, a contiguous genomic sequence of an endogenous rodent Tmprss4 gene at an endogenous rodent Tmprss4 locus has been replaced with a contiguous genomic sequence of a human TMPRSS4 gene to form a humanized Tmprss4 gene.

In specific embodiments, the contiguous genomic sequence of a human TMPRSS4 gene inserted into an endogenous rodent Tmprss4 gene includes exon sequences, i.e., exons in full or in part, of a human TMPRSS4 gene that encode an ectodomain that is substantially identical with the ectodomain of the human TMPRSS4 protein encoded by the human TMPRSS4 gene. In circumstances where an endogenous Tmprss4 protein and a human TMPRSS4 protein share common amino acids near the junction of the transmembrane domain and the ectodomain, it may not be necessary to insert a human TMPRSS4 genomic sequence that encodes precisely the ectodomain of the human TMPRSS4 protein, and it is possible to use a slightly longer or shorter human TMPRSS4 genomic sequence that encodes substantially the ectodomain of a human TMPRSS4 protein in order to make a humanized Tmprss4 protein having an ectodomain that is identical with the ectodomain of the human TMPRSS4 protein.

In specific embodiments, a contiguous genomic sequence of a human TMPRSS4 gene being inserted into an endogenous rodent Tmprss4 gene contains at least coding exon 4 through the stop codon in coding exon 13 of the human TMPRSS4 gene.

In certain embodiments, a contiguous genomic sequence of a human TMPRSS4 gene being inserted into an endogenous rodent Tmprss4 gene includes a 3' portion of intron 3, and coding exon 4 through the stop codon in coding exon 13 of a human TMPRSS4 gene. In specific embodiments, the 3' portion of intron 3 of a human TMPRSS4 gene included in the humanization is about 140-160 base pair in length, i.e., about 140, 145, 150, 155, 160 base pair of the 3' end of intron 3.

In some embodiments, a contiguous genomic sequence of a human TMPRSS4 gene being inserted into an endogenous rodent Tmprss4 gene contains the 3' UTR of the human TMPRSS4 gene. In specific embodiments, a contiguous genomic sequence of a human TMPRSS4 gene being inserted into an endogenous rodent Tmprss4 gene does not contain the 3' UTR of the human TMPRSS4 gene, and the 3' UTR of the endogenous rodent Tmprss4 gene follows immediately after the stop codon in the humanized Tmprss4 gene.

In some embodiments, the nucleotide sequence of an endogenous rodent Tmprss4 gene remaining at a humanized Tmprss4 locus encodes a polypeptide that is substantially identical with the cytoplasmic and transmembrane portion of the endogenous rodent Tmprss4 protein. In circumstances where an endogenous Tmprss4 protein and a human TMPRSS4 protein share common amino acids near the junction of the transmembrane domain and the ectodomain, it may not be necessary to maintain the endogenous rodent Tmprss4 genomic sequence that encodes precisely the transmembrane domain of the endogenous rodent Tmprss4 protein, and it is possible to maintain a slightly longer or shorter rodent Tmprss4 genomic sequence that encodes substantially the transmembrane domain of the endogenous rodent Tmprss4 protein in the humanization replacement in order to encode a humanized Tmprss4 protein having a transmembrane domain that is identical with the transmembrane of the endogenous rodent Tmprss4 protein.

In specific embodiments, a humanized Tmprss4 gene contains coding exons 1-3 of an endogenous rodent Tmprss4 gene, and coding exon 4 through the stop codon of coding exon 13 of a human TMPRSS4 gene. In particular embodiments, a humanized Tmprss4 gene contains coding exons 1-3 and a 5' portion of intron 3 of an endogenous rodent Tmprss4 gene, and a 3' portion of intron 3 and coding exon 4 through the stop codon of coding exon 13 of a human TMPRSS4 gene. In certain embodiments, the humanized Tmprss4 gene encodes a humanized Tmprss4 protein that contains the cytoplasmic domain and the transmembrane domain of the rodent Tmprss4 protein encoded by an endogenous rodent Tmprss4 gene, and the ectodomain of the human TMPRSS4 protein encoded by a human TMPRSS4 gene. In particular embodiments, a humanized Tmprss4 gene encodes a humanized Tmprss4 protein having the amino acid sequence as set forth in SEQ ID NO: 14.

In some embodiments, the exons and introns of a human TMPRSS4 gene and a rodent Tmprss4 gene used in the humanization are those found in SEQ ID NOS: 8, 10 and 12-13.

In some embodiments, a humanized Tmprss4 gene results in an expression of the encoded humanized Tmprss4 protein in a rodent. In some embodiments, a humanized Tmprss4 protein is expressed in a pattern comparable with, or substantially the same as, a counterpart rodent Tmprss4 protein in a control rodent (e.g., a rodent without the humanized Tmprss4 gene encoding the humanized Tmprss4 protein). In some embodiments, a humanized Tmprss4 protein is expressed at a level comparable with, or substantially the same as, a counterpart rodent Tmprss4 protein in a control rodent (e.g., a rodent without the humanized Tmprss4 gene encoding the humanized Tmprss4 protein). In certain embodiments, a humanized Tmprss4 protein is expressed and detected at the cell surface. In certain embodiments, a humanized Tmprss4 protein or a soluble form (e.g., a shed ectodomain form) is expressed and detected in serum of a rodent, e.g., at a level comparable with, or substantially the same as, a counterpart rodent Tmprss4 protein or a soluble form thereof in a control rodent.

Humanized Tmprss11d Rodents

In some embodiments, this invention provides a rodent whose genome contains a humanized Tmprss11d gene that includes a nucleotide sequence of an endogenous rodent Tmprss11d gene and a nucleotide sequence of a human TMPRSS11D gene, and that is under control of a 5' regulatory element(s), such as the promoter and/or enhancer(s) of the endogenous rodent Tmprss11d gene. Examples of rodents include mice and rats.

In some embodiments, a humanized Tmprss11d gene encodes a humanized Tmprss11d protein that contains an ectodomain that is substantially identical with the ectodomain of a human TMPRSS11D protein.

In specific embodiments, the human TMPRSS11D protein has an amino acid sequence having at least 85%, 90%, 95%, 98%, 99% or 100% identity with the amino acid sequence as set forth in SEQ ID NO: 18.

In some embodiments, a humanized Tmprss11d protein contains the C-terminal 377 amino acids of a human TMPRSS11D protein, for example, amino acids 42 to 418 of a human TMPRSS11D protein. In some embodiments, a humanized Tmprss11d protein contains an ectodomain that is substantially identical with the amino acid sequence composed of A42 to I418 of SEQ ID NO: 18. In specific embodiments, a humanized Tmprss11d protein contains an ectodomain having at least 85%, 90%, 95%, 98%, 99% or 100% identity with the amino acid sequence composed of A42 to I418 of SEQ ID NO: 18; an ectodomain that differs from the amino acid sequence composed of A42 to I418 of SEQ ID NO: 18 by not more than 10, 9, 8, 7, 6, 5, 4, 3, 2 or 1 amino acid(s); or an ectodomain that differs from the amino acid sequence composed of A42 to I418 of SEQ ID NO: 18 only at the N- or C-terminus, e.g., by lacking 1-5 amino acids or having additional 1-5 amino acids at the N- or C-terminus.

In some embodiments, a humanized Tmprss11d protein further contains a cytoplasmic and transmembrane portion that is substantially identical with the cytoplasmic and transmembrane portion of an endogenous rodent Tmprss11d protein. In some embodiments, a humanized Tmprss11d protein includes the transmembrane domain and the cytoplasmic domain of an endogenous rodent Tmprss11d protein.

In specific embodiments, a humanized Tmprss11d protein contains the transmembrane domain and the cytoplasmic domain of an endogenous rodent Tmprss11d protein, and the ectodomain of a human TMPRSS11D protein. In particular embodiments, a humanized Tmprss11d gene encodes a humanized Tmprss11d protein having the amino acid sequence as set forth in SEQ ID NO: 21.

In some embodiments, a humanized Tmprss11d gene results from a replacement of a nucleotide sequence of an endogenous rodent Tmprss11d gene at an endogenous rodent Tmprss11d locus with a nucleotide sequence of a human TMPRSS11D gene.

In some embodiments, a contiguous genomic sequence of an endogenous rodent Tmprss11d gene at an endogenous rodent Tmprss11d locus has been replaced with a contiguous genomic sequence of a human TMPRSS11D gene to form a humanized Tmprss11d gene. In specific embodiments, the contiguous genomic sequence of a human TMPRSS11D gene inserted into an endogenous rodent Tmprss11d gene includes exon sequences, i.e., exons in full or in part, of a human TMPRSS11D gene that encode an ectodomain that is substantially identical with the ectodomain of the human TMPRSS11D protein encoded by the human TMPRSS11D gene. In circumstances where an endogenous Tmprss11d protein and a human TMPRSS11D protein share common amino acids near the junction of the transmembrane domain and the ectodomain, it may not be necessary to insert a human TMPRSS11D genomic sequence that encodes precisely the ectodomain of the human TMPRSS11D protein, and it is possible to use a slightly longer or shorter human TMPRSS11D genomic sequence that encodes substantially the ectodomain of a human TMPRSS11D protein in order to make a humanized Tmprss11d protein having an ectodomain that is identical with the ectodomain of the human TMPRSS11D protein.

In specific embodiments, a contiguous genomic sequence of a human TMPRSS11D gene being inserted into an endogenous rodent Tmprss11d gene contains at least coding exon 3 through the stop codon in coding exon 10 of a human TMPRSS11D gene.

In certain embodiments, a contiguous genomic sequence of a human TMPRSS11D gene being inserted into an endogenous rodent Tmprss11d gene contains at least a 3' portion of intron 2 and coding exon 3 through the stop codon in coding exon 10 of the human TMPRSS11D gene. In specific embodiments, the 3' portion of intron 2 of a human TMPRSS2 gene included in the humanization is about 444 base pairs in length.

In some embodiments, a contiguous genomic sequence of a human TMPRSS11D gene being inserted into an endogenous rodent Tmprss11d gene contains the 3' UTR of the human TMPRSS11D gene. In specific embodiments, the entire coding exon 10 of a human TMPRSS11D gene is included in the contiguous human TMPRSS11D genomic sequence for humanization, which includes the 3' UTR of a human TMPRSS11D gene. In particular embodiments, a contiguous genomic sequence of a human TMPRSS11D gene includes an additional human genomic sequence downstream of the 3' UTR of the human TMPRSS11D gene. The additional human genomic sequence can be a sequence of 10-200 bp, 50-200 bp, or about 150, 160, 170, 180 bp, that is found immediately downstream of the 3' UTR of the human TMPRSS11D gene at a human TMPRSS11D locus.

In some embodiments, the nucleotide sequence of an endogenous rodent Tmprss11d gene remaining at a humanized Tmprss11d locus encodes a polypeptide that is substantially identical with the cytoplasmic and transmembrane portion of the endogenous rodent Tmprss11d protein encoded by the endogenous rodent Tmprss11d gene. In circumstances where an endogenous Tmprss11d protein and a human TMPRSS11D protein share common amino acids near the junction of the transmembrane domain and the ectodomain, it may not be necessary to maintain the endogenous rodent Tmprss11d genomic sequence that encodes precisely the transmembrane domain of the endogenous rodent Tmprss11d protein, and it is possible to maintain a slightly longer or shorter rodent Tmprss11d genomic sequence that encodes substantially the transmembrane domain of the endogenous rodent Tmprss11d protein in the humanization replacement in order to encode a humanized Tmprss11d protein having a transmembrane domain that is identical with the transmembrane of the endogenous rodent Tmprss11d protein.

In specific embodiments, a humanized Tmprss11d gene contains coding exons 1-2 of an endogenous rodent Tmprss11d gene, and coding exon 3 through coding exon 10 of a human TMPRSS11D gene. In certain embodiments, the humanized Tmprss11d gene encodes a humanized Tmprss11d protein that contains the cytoplasmic domain and the transmembrane domain of the rodent Tmprss11d protein encoded by an endogenous rodent Tmprss11d gene, and the ectodomain of the human TMPRSS11D protein encoded by a human TMPRSS11D gene. In particular embodiments, a humanized Tmprss11d gene encodes a humanized Tmprss11d protein having the amino acid sequence as set forth in SEQ ID NO: 21.

In some embodiments, the exons and introns of a human TMPRSS11D gene and a rodent Tmprss11d gene used in the humanization are those found in SEQ ID NOS: 15, 17 and 19-20.

In some embodiments, a humanized Tmprss11D gene results in an expression of the encoded humanized Tmprss11d protein in a rodent. In some embodiments, a humanized Tmprss11d protein is expressed in a pattern comparable with, or substantially the same as, a counterpart rodent Tmprss11d protein in a control rodent (e.g., a rodent without the humanized Tmprss11d gene encoding the humanized Tmprss11d protein). In some embodiments, a humanized Tmprss11d protein is expressed at a level comparable with, or substantially the same as, a counterpart rodent Tmprss11d protein in a control rodent (e.g., a rodent without the humanized Tmprss11d gene encoding the humanized Tmprss11d protein). In certain embodiments, a humanized Tmprss11d protein is expressed and detected at the cell surface. In certain embodiments, a humanized Tmprss11d protein or a soluble form (e.g., a shed ectodomain form) is expressed and detected in serum of a rodent, e.g., at a level comparable with, or substantially the same as, a counterpart rodent Tmprss11d protein or a soluble form thereof in a control rodent.

Methods of Making Humanized Tmprss Rodent Animals

Further aspects of this disclosure are directed to methods for making a humanized Tmprss rodent described above, as well as nucleic acid vectors and non-human embryonic stem cells suitable for use in making a humanized Tmprss rodent.

The rodents provided herein can be made using methods known in the art. In exemplary embodiments, a bacterial artificial chromosome (BAC) clone carrying a rodent Tmprss gene can be modified using bacterial homologous recombination and VELOCIGENE® technology (see, e.g., U.S. Pat. No. 6,586,251 and Valenzuela et al. (2003), High-throughput engineering of the mouse genome coupled with high-resolution expression analysis, *Nature Biotech.* 21(6): 652-659). As a result, a rodent Tmprss nucleotide sequence has been deleted from the original BAC clone, and a human Tmprss nucleotide sequence has been inserted, resulting in a modified BAC clone carrying a humanized Tmprss gene, flanked with 5' and 3' rodent homology arms. The modified BAC clone, once linearized, can be introduced into rodent embryonic stem (ES) by, e.g., electroporation. Both mouse ES cells and rat ES cells have been described in the art. See, e.g., U.S. Pat. No. 7,576,259, U.S. Pat. No. 7,659,442, U.S. Pat. No. 7,294,754, and US 2008-0078000 A1 (all of which are incorporated herein by reference) describe mouse ES cells and the VELOCIMOUSE® method for making a genetically modified mouse; US 2014/0235933 A1, US 2014/0310828 A1, Tong et al. (2010) *Nature* 467:211-215, and Tong et al. (2011) *Nat Protoc.* 6(6): doi: 10.1038/nprot.2011.338 (all of which are incorporated herein by reference) describe rat ES cells and methods for making a genetically modified rat.

ES cells having a humanized Tmprss gene integrated in the genome can be selected. In some embodiments, ES cells having a humanized Tmprss integrated into an endogenous rodent Tmprss locus can be selected based on loss of rodent allele and/or gain of human allele assays. Selected ES cells are then used as donor ES cells for injection into a pre-morula stage embryo (e.g., 8-cell stage embryo) by using the VELOCIMOUSE® method (see, e.g., U.S. Pat. No. 7,576,259, U.S. Pat. No. 7,659,442, U.S. Pat. No. 7,294,754, and US 2008-0078000 A1), or methods described in US 2014/0235933 A1 and US 2014/0310828 A1. The embryo comprising the donor ES cells is incubated until blastocyst stage and then implanted into a surrogate mother to produce an F0 rodent fully derived from the donor ES cells. Rodent pups bearing the humanized Tmprss gene can be identified by genotyping of DNA isolated from tail snips using loss of rodent allele and/or gain of human allele assays.

Rodents heterozygous for a humanized Tmprss gene can be crossed to generated homozygous rodents. Rodents containing one humanized Tmprss gene can be crossed with rodents containing another humanized Tmprss gene to make rodents containing multiple humanized Tmprss genes. For example, rodents containing a humanized Tmprss2 gene can be crossed with rodents containing a humanized Tmprss4 gene to make rodents containing a humanized Tmprss2 gene and a humanized Tmprss4 gene.

Methods Employing Rodents Having Humanized Tmprss Genes

Rodents disclosed herein provide a useful in vivo system and source of biological materials (e.g., cells) expressing humanized Tmprss proteins for identifying and testing compounds that specifically target human TMPRSS proteins.

In one aspect, a rodent disclosed herein is used to determine the ability of a candidate compound, such as an inhibitor of a human TMPRSS protein, to treat and/or prevent influenza virus infection.

In some embodiments, a rodent containing a humanized Tmprss gene and expressing a humanized Tmprss protein disclosed herein is administered with a candidate compound prior to experimental influenza virus infection. The prophylactic efficacy of the compound can be evaluated by determining whether the rodent exhibits fewer and/or less severe symptoms of influenza virus infection, and/or improved viability, as compared to control rodent(s).

In other embodiments, a rodent containing a humanized Tmprss gene and expressing a humanized Tmprss protein comprising the ectodomain of a human TMPRSS protein is administered with a candidate inhibitor of that human TMPRSS protein after experimental influenza virus infection. The treatment efficacy of the candidate inhibitor can be evaluated by determining whether the rodent exhibits fewer and/or less severe symptoms of influenza virus infection, and/or improved viability, as compared to control rodent(s).

Suitable control rodents include, e.g., rodents containing a humanized Tmprss gene without being subjected to the experimental infection; and rodents containing a humanized Tmprss gene subjected to the experimental infection without any compound; and rodents containing a humanized Tmprss gene subjected to the experimental infection and a compound known to be therapeutically effective.

Compounds that can be evaluated in the methods of this invention include candidate TMPRSS inhibitors, for example, a small molecule protease inhibitor, a nucleic acid-based inhibitor (e.g., siRNA, ribozyme, antisense construct, etc.), antigen-binding protein (e.g., antibody or antigen-binding fragment thereof), or a blocking peptide/peptide inhibitor. A TMPRSS inhibitor may function by inhibiting or reducing the ability of a TMPRSS protein to proteolytically cleave hemagglutinin precursor protein (HA0) into the HA1 and HA2 subunits.

In some embodiments, a candidate inhibitor is an antibody or antigen-binding fragment thereof. Both monoclonal and polyclonal antibodies are suitable for purposes of this invention. In specific embodiments, the antibody specifically binds to a TMPRSS protein and inhibits the protease activity of that TMPRSS protein and does not substantially inhibit the protease activity of another TMPRSS protein. For example, an anti-TMPRSS2 antibody inhibitor specifically binds to a TMPRSS2 protein and inhibits the protease activity of the TMPRSS2 protein, and has no effect on the proteolytic activity of TMPRSS4 or TMPRSS11D, or reduces the proteolytic activity of TMPRSS4 or TMPRSS11D by no more than 25% (e.g., by 20%, 15%, 10%, 5%, or less) relative to a non-inhibitory control molecule tested under identical or substantially identical experimental conditions.

In some embodiments, the inhibitor is an anti-TMPRSS2 antibody or antigen-binding fragment thereof. In some embodiments, the inhibitor is an anti-TMPRSS4 antibody or antigen-binding fragment thereof. In other embodiments, the inhibitor is an anti-TMPRSS11D antibody or antigen-binding fragment thereof.

Experimental influenza virus infection can be induced and monitored following known protocols. See, e.g., US 2013/0273070 A1. For example, rodent animals can be administered intranasally with influenza virus. The infected animals can be evaluated to determine the symptoms and severity of the infection. For example, the animals can be analyzed for (1) weight change and survival, (2) cellular changes via flow cytometry, (3) immunochemistry, PAS and H&E staining of whole lungs, and (4) cytokine levels in serum. Control animals known to be susceptible to the virus exhibit a significant increase in the frequency of dendritic cells, the levels influenza-positive alveolar macrophages, neutrophils or epithelial cells in the lungs, and the levels of IFNγ, as compared to uninfected animals.

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1. Humanization of an Endogenous Tmprss2 Gene

This example illustrates exemplary methods of humanizing an endogenous gene encoding Tmprss2 in a rodent (e.g., a mouse). The methods described in this example can be employed to humanize an endogenous Tmprss2 gene of a rodent using any human sequence, or combination of human sequences (or sequence fragments) as desired.

A targeting vector for humanization of an endogenous Tmprss2 gene was constructed using bacterial artificial chromosome (BAC) clones and VELOCIGENE® technology (see, e.g., U.S. Pat. No. 6,586,251 and Valenzuela et al. (2003) High-throughput engineering of the mouse genome coupled with high-resolution expression analysis, Nature Biotech. 21(6):652-659; incorporated herein by reference).

Figure 1B:
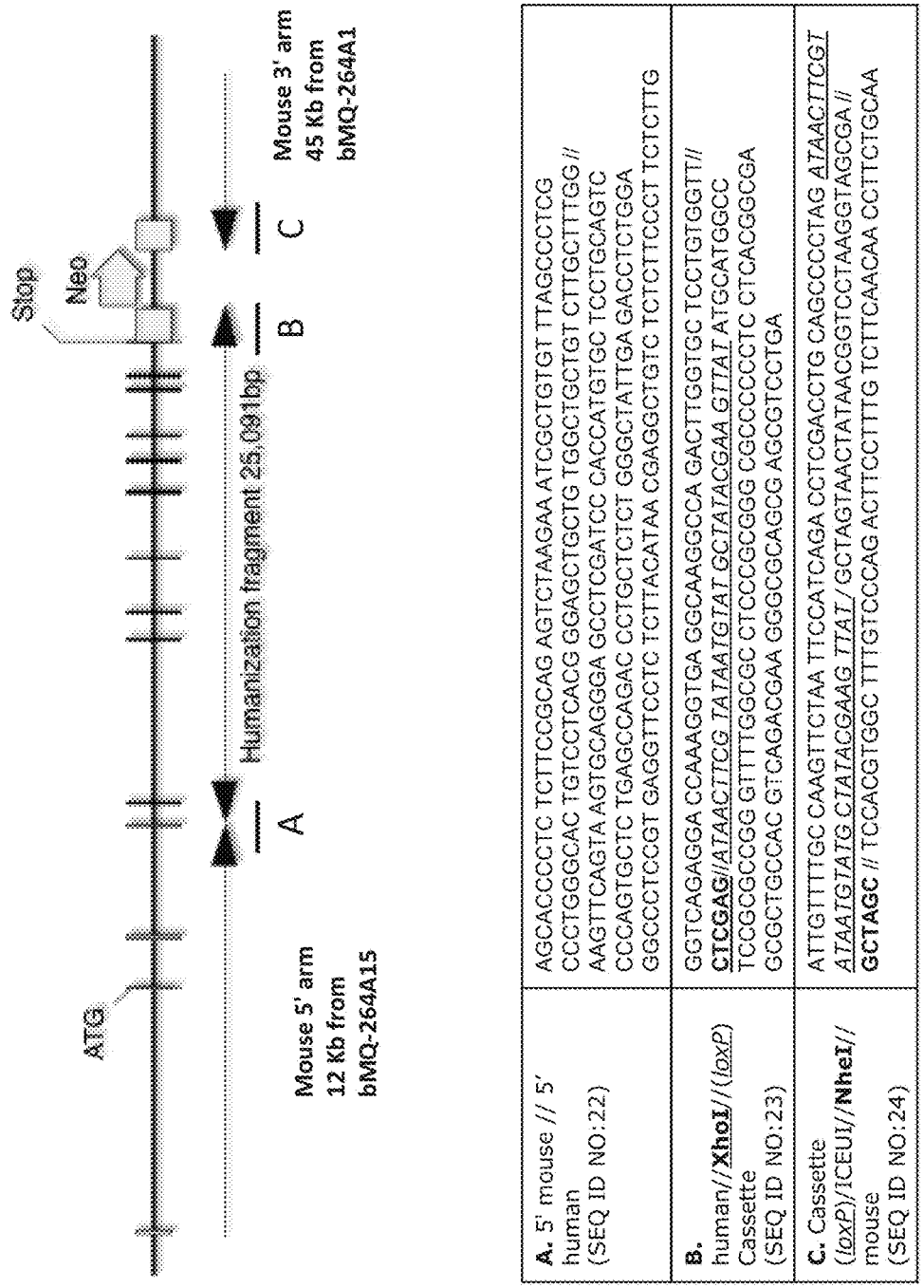

Briefly, mouse bacterial artificial chromosome (BAC) clone bMQ-264A15 containing a mouse Tmprss2 gene was used and modified as follows. A DNA fragment was generated to include a 5' mouse homology nucleotide sequence, a human TMPRSS2 genomic DNA of about 25,091 bp (containing the last 7 bp of coding exon 3, intron 3, and coding exon 4 through coding exon 13 (including the 3' UTR which is part of coding exon 13), of a human TMPRSS2 gene), a self-deleting neomycin cassette of about 2,691 bp, and a 3' mouse homology sequence. This DNA fragment was used to modify BAC clone bMQ-264A15 through homologous recombination in bacterial cells. As a result, an ectodomain-encoding mouse Tmprss2 genomic fragment (of about 25,291 bp) in the BAC clone was replaced with the human TMPRSS2 genomic fragment of about 25,091 bp, followed by a self-deleting neomycin cassette of about 2691 bp. Specifically, the mouse Tmprss2 genomic fragment that was replaced included the last 7 bp of coding exon 3, intron 3, and coding exon 4 through the stop codon in coding exon 13 of the mouse Tmprss2 gene (FIGS. 1A-1B). The human TMPRSS2 genomic fragment that was inserted included the last 7 bp of coding exon 3, intron 3, and coding exon 4 through coding exon 13 of a human TMPRSS2 gene (including the 3' UTR of human TMPRSS2), and a human 3' genomic sequence of 131 bp downstream of the 3' UTR of human TMPRSS2 (FIGS. 1A-1B). The resulting modified BAC clone included, from 5' to 3', (i) a 5' mouse homology arm containing about 12 kb of mouse genomic DNA including a mouse Tmprss2 5' UTR, mouse Tmprss2 exon 1 (non-coding), coding exons 1-3 (except the last 7 bp of coding exon 3); (ii) a human TMPRSS2 genomic fragment of about 25,091 bp including the last 7 bp of human coding exon 3, intron 3, human coding exons 4 through 13 (including the 3' UTR of human TMPRSS2), and a human 3' genomic sequence; (iii) a self-deleting neomycin cassette of about 2691 bp, followed by (iv) a 3' mouse homology arm of 45 kb containing the mouse Tmprss2 3'UTR and the remaining mouse genomic DNA in the original BAC clone. See FIGS. 1A-1B. The junction sequences are also set forth at the bottom of FIG. 1B. The part of the modified BAC clone containing the human TMPRSS2 genomic fragment and the neomycin cassette, as well as the upstream and downstream insertion junctions, is set forth in SEQ ID NO: 5. The amino acid sequence of the protein encoded by the humanized Tmprss2 gene is set forth in SEQ ID NO: 7. An alignment of this humanized Tmprss2 protein ("7010 mutant protein"), a mouse Tmprss2 protein (SEQ ID NO: 2), and a human TMPRSS2 protein (SEQ ID NO: 4), is provided in FIG. 1D.

Figure 1C:
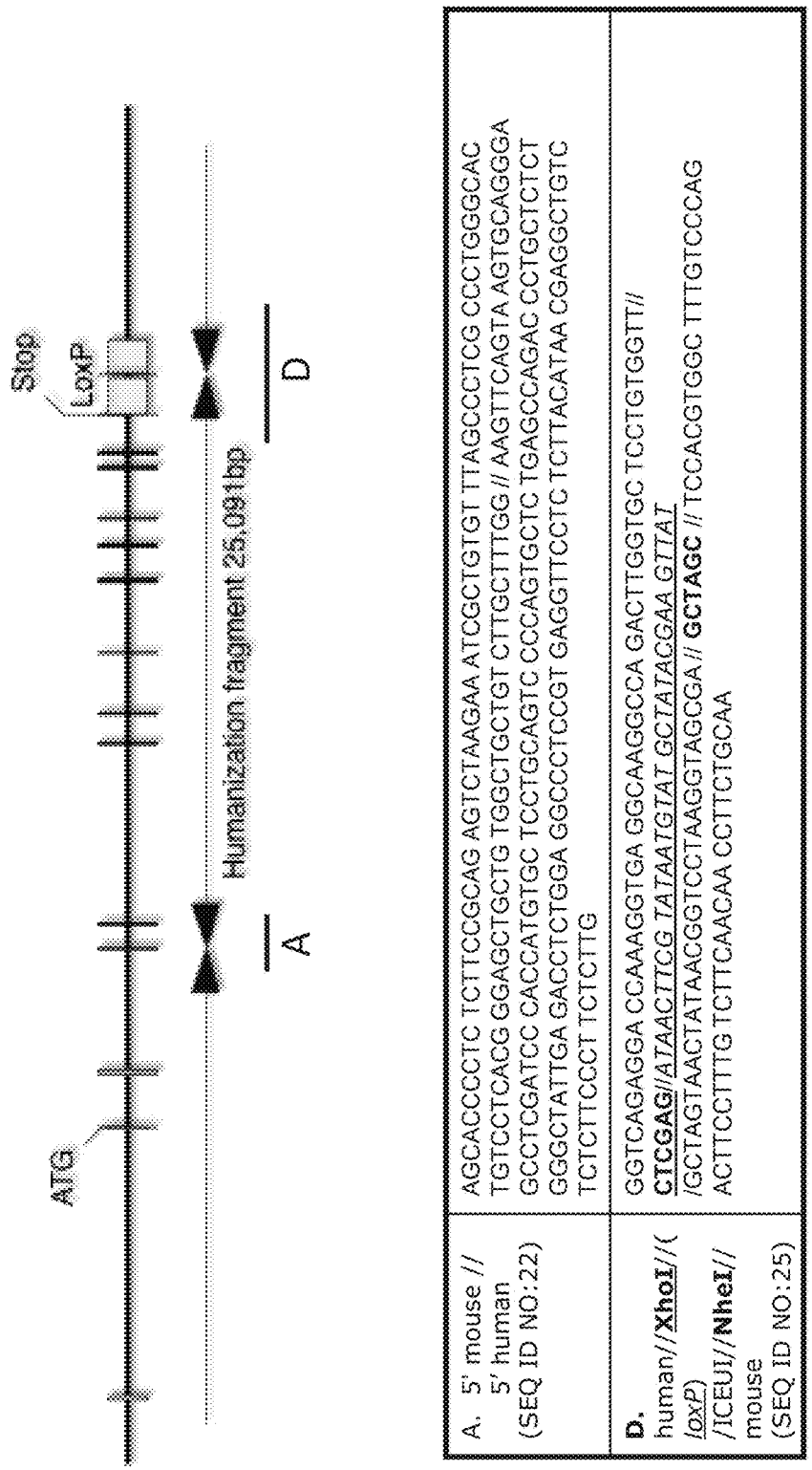

The modified BAC clone containing the humanized Tmprss2 gene, as described above, was used to electroporate mouse embryonic stem (ES) cells to create modified ES cells comprising a humanized Tmprss2 gene. Positively targeted ES cells containing a humanized Tmprss2 gene were identified by an assay (Valenzuela et al., supra) that detected the presence of the human TMPRSS2 sequences (e.g., coding exons 4-13 of human TMPRSS2) and confirmed the loss and/or retention of mouse Tmprss2 sequences (e.g., loss of coding exons 4-13 of mouse Tmprss2). Table 1 sets forth the primers and probes that were used to confirm humanization of an endogenous Tmprss2 gene as described above (FIGS. 1A-1B). Once a correctly targeted ES cell clone has been selected, the neomycin selection cassette can be excised by introducing a Cre recombinase, e.g., via electroporation. Alternatively, the neomycin selection cassette can be removed by crossing the progeny generated from the ES clone with a deletor rodent strain that expresses a Cre recombinase. The humanized Tmprss2 locus after the deletion of the cassette is depicted in FIG. 1C, with the junction sequences shown at the bottom of FIG. 1C.

Selected ES cell clones (with or without the cassette) were used to implant female mice using the VELOCIMOUSE® method (see, e.g., U.S. Pat. No. 7,294,754 and Poueymirou et al., F0 generation mice that are essentially fully derived from the donor gene-targeted ES cells allowing immediate phenotypic analyses, 2007, Nature Biotech. 25(1):91-99) to generate a litter of pups containing a humanized Tmprss2 allele in the genome. Mice bearing a humanized Tmprss2 allele can be again confirmed and identified by genotyping of DNA isolated from tail snips using a modification of allele assay (Valenzuela et al., supra) that detects the presence of the human TMPRSS2 gene sequences. Pups are genotyped and cohorts of animals heterozygous for the humanized Tmprss2 locus are selected for characterization. Animals homozygous for the humanized Tmprss2 locus are made by crossing heterozygous animals.

TABLE 1

| Name | Primer | Sequence (5'-3') | SEQ ID NO |
|---|---|---|---|
| 7010U | Forward | GCCGTGACTGTGACCTTCTC | (SEQ ID NO: 26) |
|  | Probe (BHQ) | TGGAGGAGCCACCTGATGCCTC | (SEQ ID NO: 27) |
|  | Reverse | GCCTTGCCCTCAATGGAAAC | (SEQ ID NO: 28) |

TABLE 1-continued

| Name | Primer | Sequence (5'-3') | SEQ ID NO |
|---|---|---|---|
| 7010D | Forward | GGTTGCACAGCAAGGAAGAAG | (SEQ ID NO: 29) |
| | Probe (BHQ) | CCAGGAGTTCCTGTGAGCCTACCC | (SEQ ID NO: 30) |
| | Reverse | TGGAATGGAAGGAGCTGGAG | (SEQ ID NO: 31) |
| 7010hU | Forward | GTCCCACCTCCTGCAACTG | (SEQ ID NO: 32) |
| | Probe (BHQ) | TGAGCCTTCCCATCAGCCTGGG | (SEQ ID NO: 33) |
| | Reverse | CCACAATGGCACATGGGTCTG | (SEQ ID NO: 34) |
| 7010hTD | Forward | GGTGCTTGCTCCCCAAGA | (SEQ ID NO: 35) |
| | Probe (BHQ) | CCTAAAAGGTGTTGTAATGG | (SEQ ID NO: 36) |
| | Reverse | GGCAATAAAGAAGGAAGACGTTTT | (SEQ ID NO: 37) |

Example 2. Humanization of an Endogenous Tmprss4 Gene

This example illustrates exemplary methods of humanizing an endogenous gene encoding Tmprss4 in a rodent (e.g., a mouse). The methods described in this example can be employed to humanize an endogenous Tmprss4 gene of a rodent using any human sequence, or combination of human sequences (or sequence fragments) as desired.

A targeting vector for humanization of an endogenous Tmprss4 gene was constructed using bacterial artificial chromosome (BAC) clones and VELOCIGENE® technology (see, e.g., U.S. Pat. No. 6,586,251 and Valenzuela et al. (2003), supra).

Figure 2A:
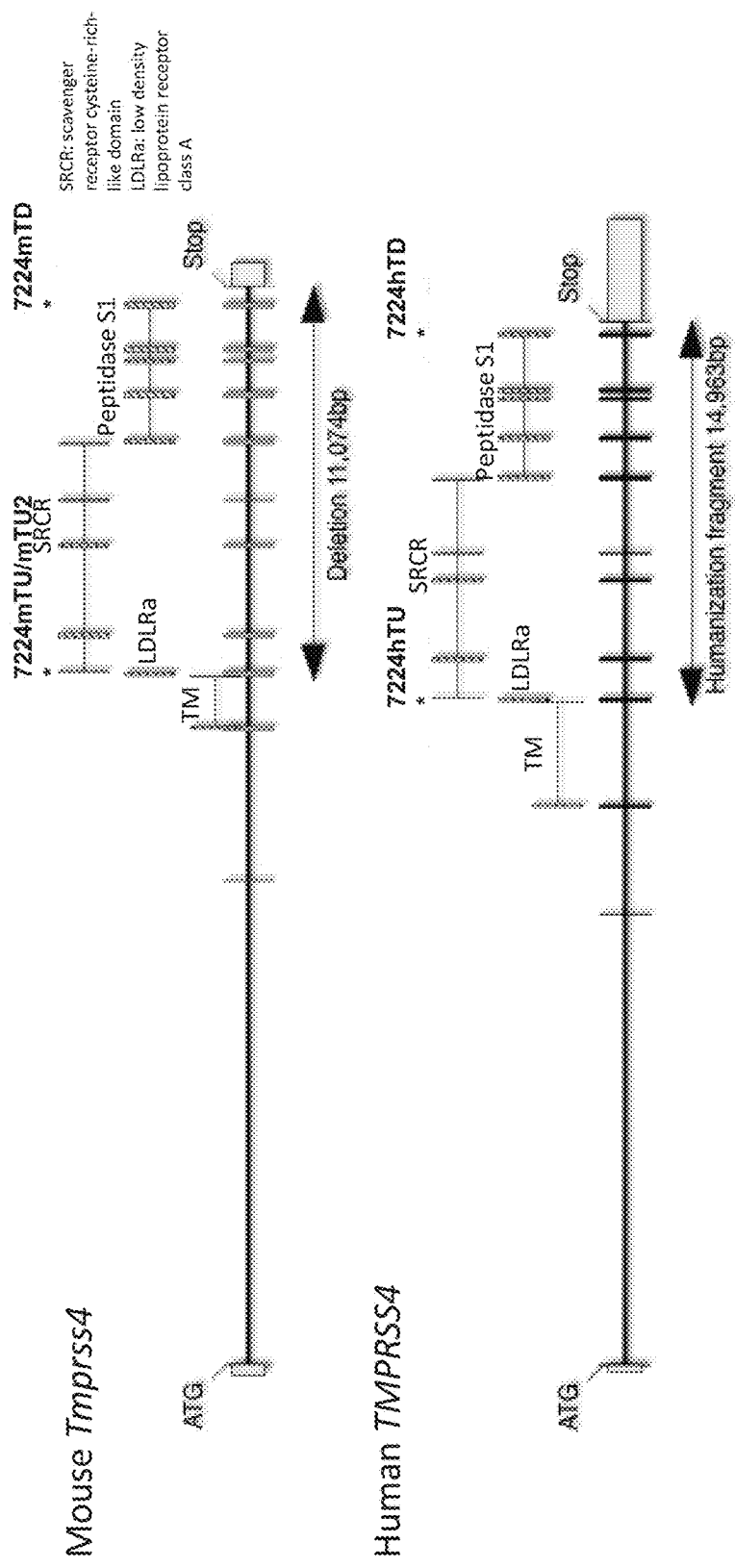
FIGS. 2A-2D. Exemplary strategy for humanization of mouse Tmprss4.
Figure 2B:
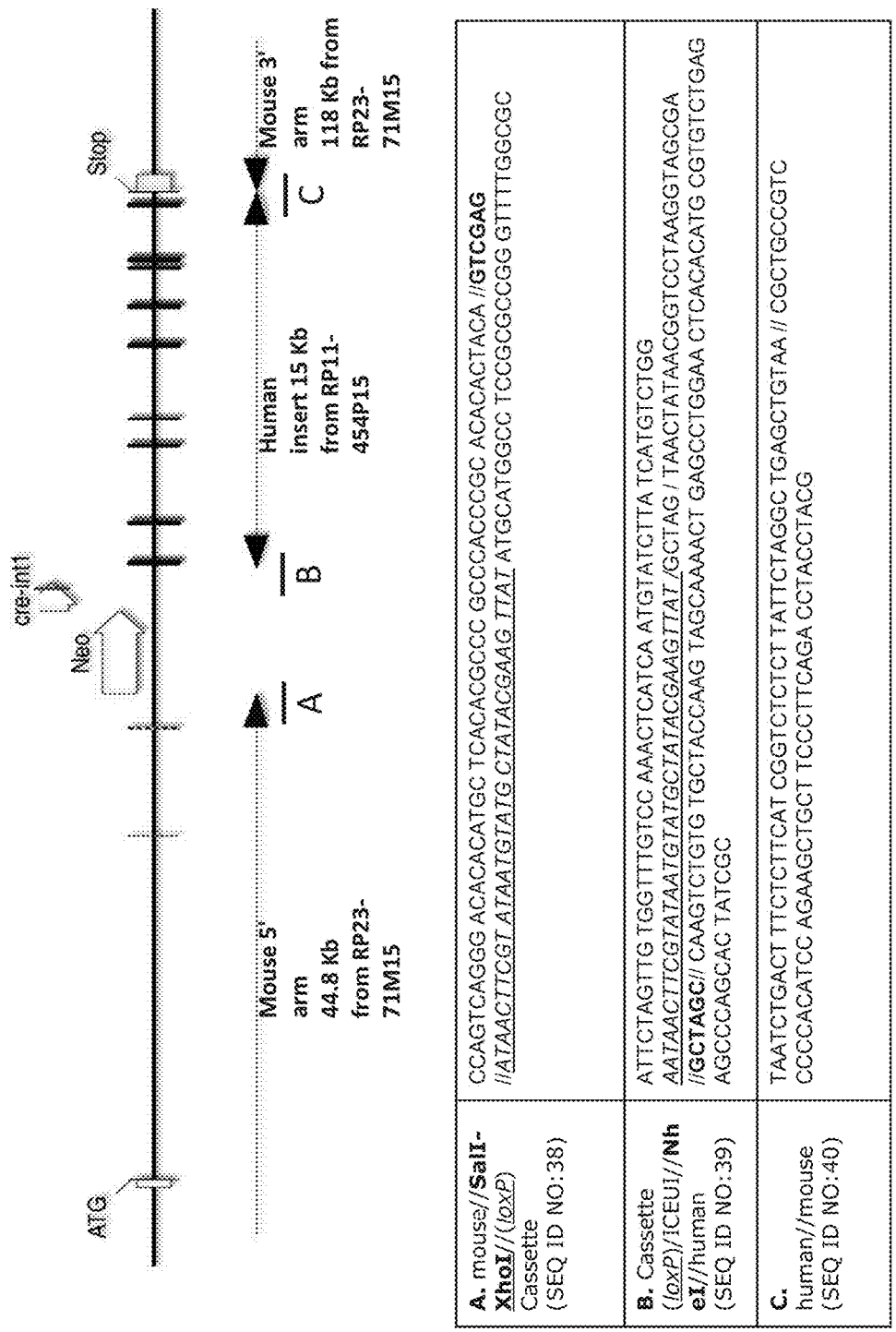

Briefly, mouse bacterial artificial chromosome (BAC) clone RP23-71M15 containing a mouse Tmprss4 gene was used and modified as follows. A DNA fragment was generated to include a 5' mouse homology nucleotide sequence, a self-deleting neomycin cassette of about 4,996 bp, a human genomic DNA of about 14,963 bp (containing coding exon 4 through the stop codon in coding exon 13 of a human TMPRSS4 gene), and a 3' mouse homology sequence. This DNA fragment was used to modify BAC clone RP23-71M15 through homologous recombination in bacterial cells. As a result, an ectodomain-encoding mouse genomic fragment (of about 11,074 bp) in the BAC clone was replaced with a self-deleting neomycin cassette of about 4,996 bp, followed by the human genomic DNA of about 14,963 bp. Specifically, the mouse genomic fragment that was deleted and replaced included the 3' 130 bp of mouse intron 3, coding exon 4 through the stop codon in coding exon 13 of the mouse Tmprss4 gene (FIGS. 2A-2B). The human genomic fragment that was inserted included a 3' portion of human TMPRSS4 intron 3 of about 150 bp, and human TMPRSS4 coding exon 4 through the stop codon in coding exon 13 (FIGS. 2A-2B). The resulting modified BAC clone included, from 5' to 3', a 5' mouse homology arm containing about 44.8 kb of mouse genomic DNA (including a mouse Tmprss4 5' UTR, mouse Tmprss4 coding exons 1 through 3, mouse Tmprss4 intron 3 in part (without the 3' 130 bp), a self-deleting neomycin cassette of about 4996 bp, a 3' portion of human TMPRSS4 intron 3 of about 150 bp, human TMPRSS4 coding exons 4 through the stop codon in coding exon 13, followed directly by the mouse Tmprss4 3' UTR and the remaining mouse genomic DNA in the original BAC clone (a 3' mouse homology arm of about 118 kb in total). See FIGS. 2A-2B. The junction sequences are also set forth at the bottom of FIG. 2B. The part of the modified BAC clone containing the neomycin cassette and the human TMPRSS4 genomic fragment, as well as the upstream and downstream insertion junctions, is set forth in SEQ ID NO: 12. The amino acid sequence of the protein encoded by the humanized Tmprss4 gene is set forth in SEQ ID NO: 14. An alignment of this humanized Tmprss4 protein ("7224 mutant pro"), a mouse Tmprss4 protein (SEQ ID NO: 9), and a human TMPRSS4 protein (SEQ ID NO: 11), is provided in FIG. 2D.

Figure 2C:
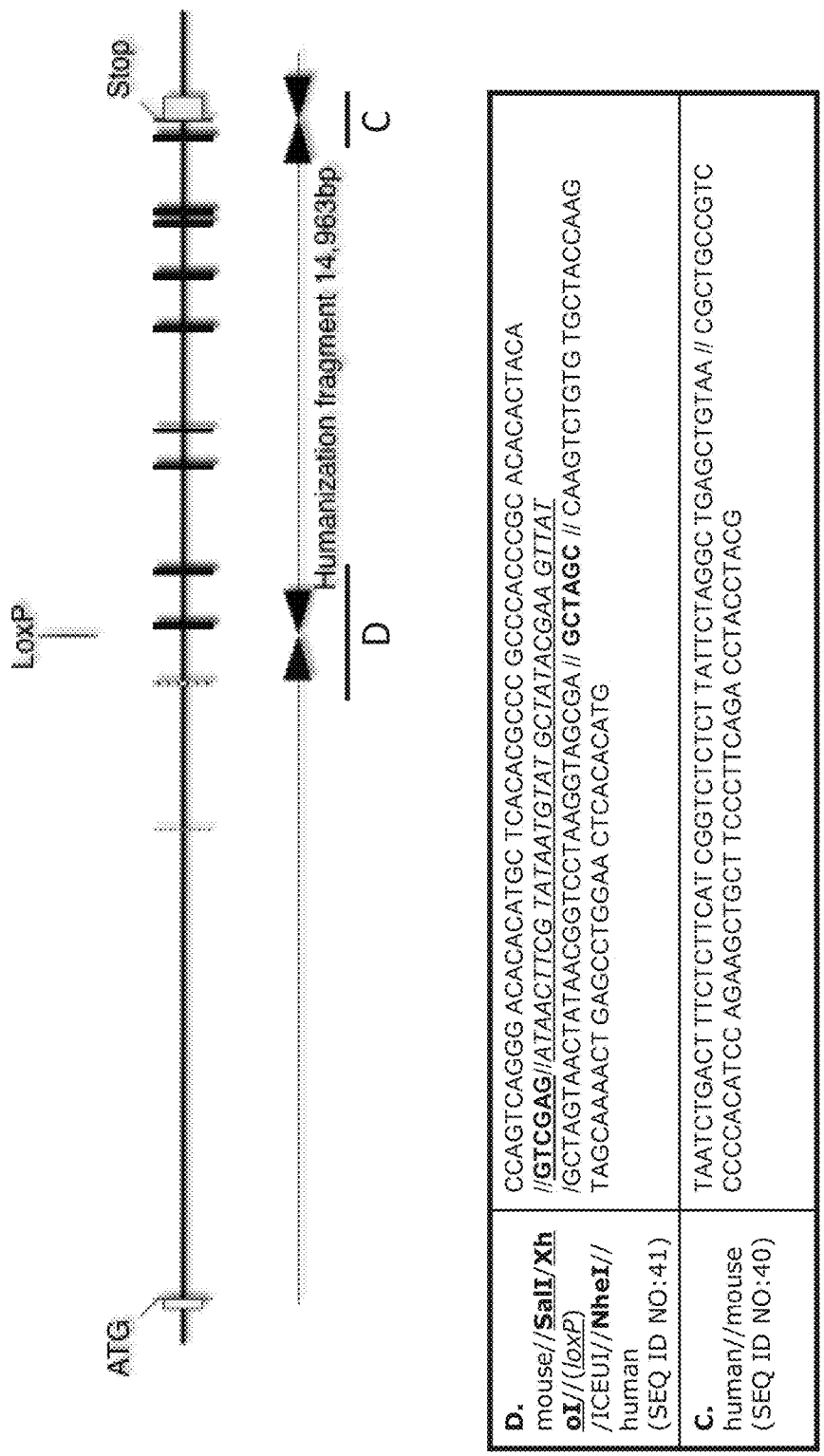
Figure 2D:
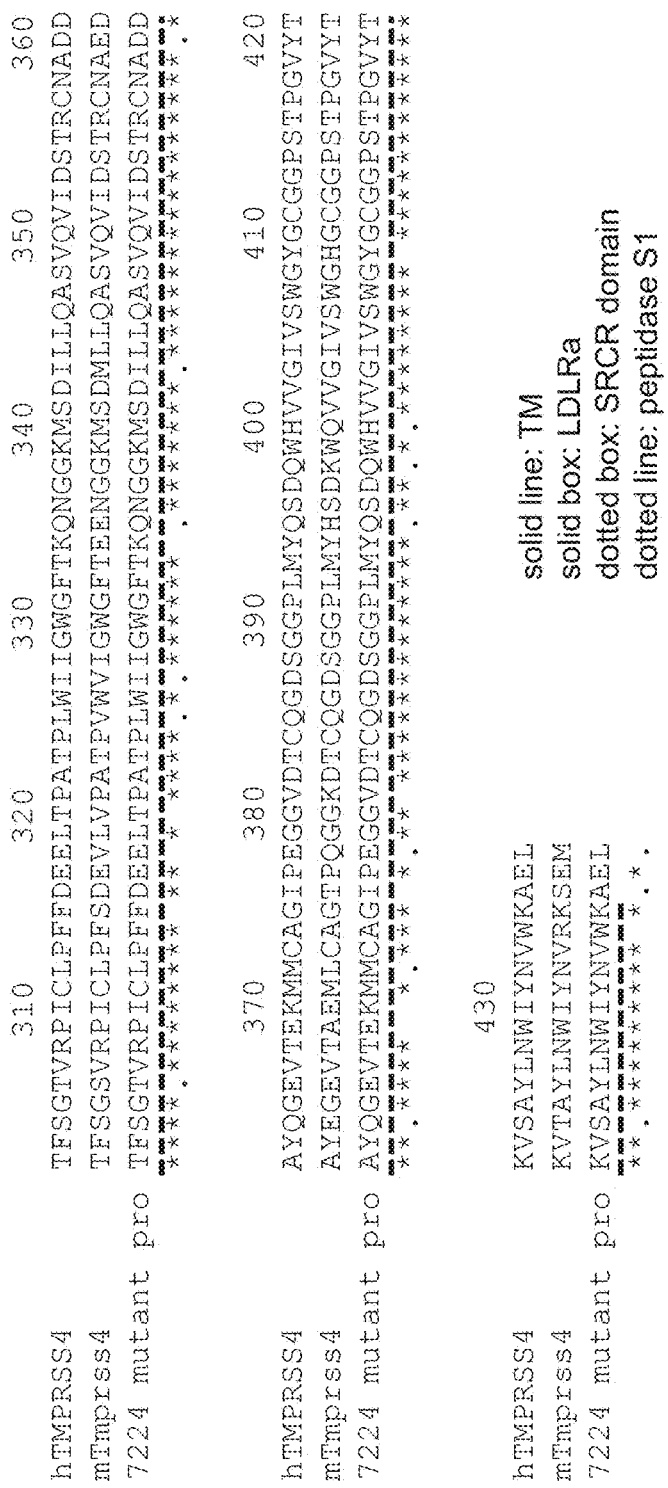

The modified BAC clone containing the humanized Tmprss4 gene, as described above, was used to electroporate mouse embryonic stem (ES) cells to create modified ES cells comprising a humanized Tmprss4 gene. Positively targeted ES cells containing a humanized Tmprss4 gene were identified by an assay (Valenzuela et al., supra) that detected the presence of the human TMPRSS4 sequences (e.g., coding exons 4-13 of human TMPRSS4) and confirmed the loss and/or retention of mouse Tmprss4 sequences (e.g., loss of coding exons 4-13 of mouse Tmprss4). Table 2 sets forth the primers and probes that were used to confirm humanization of an endogenous Tmprss4 gene as described above (FIGS. 2A-2B). Once a correctly targeted ES cell clone has been selected, the neomycin selection cassette can be excised by introducing a Cre recombinase, e.g., via electroporation. Alternatively, the neomycin selection cassette can be removed by crossing the progeny generated from the ES clone with a deletor rodent strain that expresses a Cre recombinase. The humanized Tmprss4 locus after the deletion of the cassette is depicted in FIG. 2C, with the junction sequences shown at the bottom of FIG. 2C.

Selected ES cell clones (with or without the cassette) were used to implant female mice using the VELOCIMOUSE® method (see, e.g., U.S. Pat. No. 7,294,754 and Poueymirou et al. (2007), supra) to generate a litter of pups containing a humanized Tmprss4 allele in the genome. Mice bearing a humanized Tmprss4 allele were again confirmed and identified by genotyping of DNA isolated from tail snips using a modification of allele assay (Valenzuela et al., supra) that detected the presence of the human TMPRSS4 gene sequences. Pups were genotyped and cohorts of animals heterozygous for the humanized Tmprss4 locus were selected for characterization. Animals homozygous for the humanized Tmprss4 locus were made by crossing heterozygous animals.

TABLE 2

| Name | Primer | Sequence (5'-3') | SEQ ID NO |
|---|---|---|---|
| 7224mTU | Forward | GAGCAGGGCCATGACACAT | (SEQ ID NO: 42) |
| | Probe (BHQ) | ACCATTAGATCCCAGCACTGGACA | (SEQ ID NO: 43) |
| | Reverse | AAACCCTTCCCGAGAGAGAA | (SEQ ID NO: 44) |
| 7224mTU2 | Forward | GAGGAACACTGTGTCAAGGACTT | (SEQ ID NO: 45) |
| | Probe (BHQ) | CCTGAAAAGCCCGGAGTGGCAG | (SEQ ID NO: 46) |
| | Reverse | GGGCAGAGACCACATCTGA | (SEQ ID NO: 47) |
| 7224mTD | Forward | GGAAGCCCTCTCTCGATACTTG | (SEQ ID NO: 48) |
| | Probe (BHQ) | TTCTACCCTGAGGGCATGCAGC | (SEQ ID NO: 49) |
| | Reverse | TGGGATGTAGAAGGTTGTCAGA | (SEQ ID NO: 50) |
| 7224hTU | Forward | CTGAGCCTGGAACTCACACATG | (SEQ ID NO: 51) |
| | Probe (BHQ) | TCTGAGAGCCCAGCACTATCGCC | (SEQ ID NO: 52) |
| | Reverse | GCTGAGGGTCAGGCTTGAG | (SEQ ID NO: 53) |
| 7224hTD | Forward | TCTGCAGGGTAGGGAGAGAAG | (SEQ ID NO: 54) |
| | Probe (BHQ) | TGTTTCAGAAAAGGAAGACTCACGTTACA | (SEQ ID NO: 55) |
| | Reverse | GAGACCGATGAAGAGAAAGTCAGA | (SEQ ID NO: 56) |

Example 3. Humanization of an Endogenous Tmprss11d Gene

This example illustrates exemplary methods of humanizing an endogenous gene encoding Tmprss11d in a rodent (e.g., a mouse). The methods described in this example can be employed to humanize an endogenous Tmprss11d gene of a rodent using any human sequence, or combination of human sequences (or sequence fragments) as desired.

A targeting vector for humanization of an endogenous Tmprss11d gene was constructed using bacterial artificial chromosome (BAC) clones and VELOCIGENE® technology (see, e.g., U.S. Pat. No. 6,586,251 and Valenzuela et al. (2003), supra).

Figure 3A:
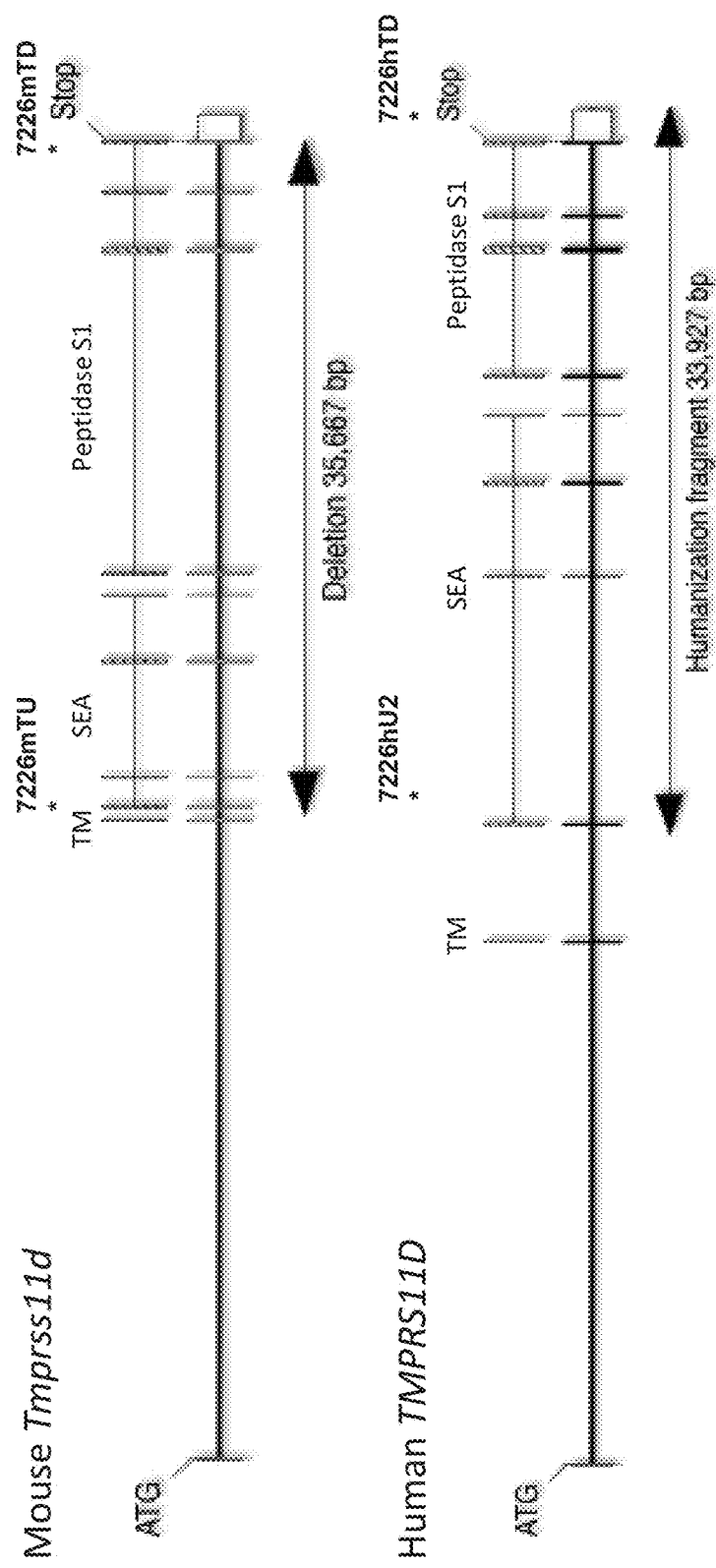
Figure 3B:
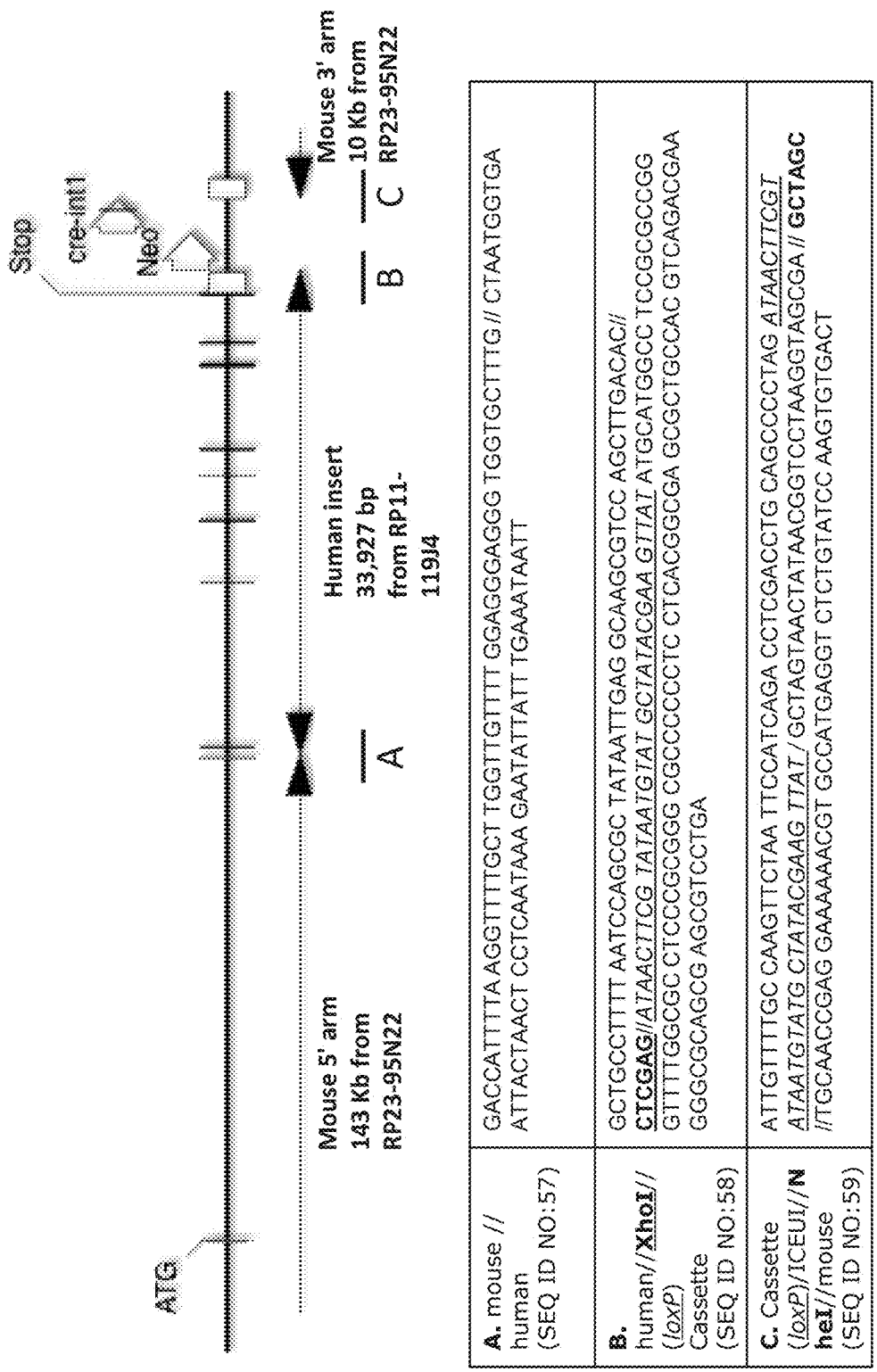

Briefly, mouse bacterial artificial chromosome (BAC) clone RP23-95N22 containing a mouse Tmprss11d gene was used and modified as follows. A DNA fragment was generated to include a 5' mouse homology nucleotide sequence, a human TMPRSS11D genomic DNA of about 33,927 bp (containing 444 bp at the 3' end of intron 2, and coding exon 3 through coding exon 10 (including the 3' UTR which is part of coding exon 10), of a human TMPRSS11D gene), a self-deleting neomycin cassette of about 4,996 bp, and a 3' mouse homology sequence. This DNA fragment was used to modify BAC clone RP23-95N22 through homologous recombination in bacterial cells. As a result, an ectodomain-encoding mouse Tmprss11d genomic fragment (of about 35,667 bp) in the BAC clone was replaced with the human TMPRSS11D genomic fragment of about 33,927 bp, followed by a self-deleting neomycin cassette of about 4,996 bp. Specifically, the mouse Tmprss11d genomic fragment that was replaced included a 3' portion of intron 2, and coding exon 3 through the stop codon in coding exon 10 of the mouse Tmprss11d gene (FIGS. 3A-3B). The human TMPRSS11D genomic fragment that was inserted included 444 bp at the 3' end of intron 2, and coding exon 3 through coding exon 10 of a human TMPRSS11D gene (including the 3' UTR of human TMPRSS11D), and a human 3' genomic sequence of about 172 bp downstream of the 3' UTR of human TMPRSS11D (FIGS. 3A-3B). The resulting modified BAC clone included, from 5' to 3', (i) a 5' mouse homology arm containing about 143 kb of mouse genomic DNA including a mouse Tmprss11d 5' UTR, mouse Tmprss11d coding exons 1-2 and a 5' portion of intron 2; (ii) a human TMPRSS11D genomic fragment including a 3' portion of intron 2 and coding exons 3 through 10 (including the 3' UTR) of human TMPRSS11D, and a human 3' genomic sequence; (iii) a self-deleting neomycin cassette of about 4,996 bp, followed by (iv) a 3' mouse homology arm of 10 kb containing the mouse Tmprss11d 3'UTR and the remaining mouse genomic DNA in the original BAC clone. See FIGS. 3A-3B. The junction sequences are also set forth at the bottom of FIG. 3B. The part of the modified BAC clone containing the human TMPRSS11D genomic fragment and the neomycin cassette, as well as the upstream and downstream insertion junctions, is set forth in SEQ ID NO: 19. The amino acid sequence of the protein encoded by the humanized Tmprss11d gene is set forth in SEQ ID NO: 21. An alignment of this humanized Tmprss11d protein ("7226 mutant pro"), a mouse Tmprss11d protein (SEQ ID NO: 16), and a human TMPRSS11D protein (SEQ ID NO: 18), is provided in FIG. 3D.

Figure 3C:
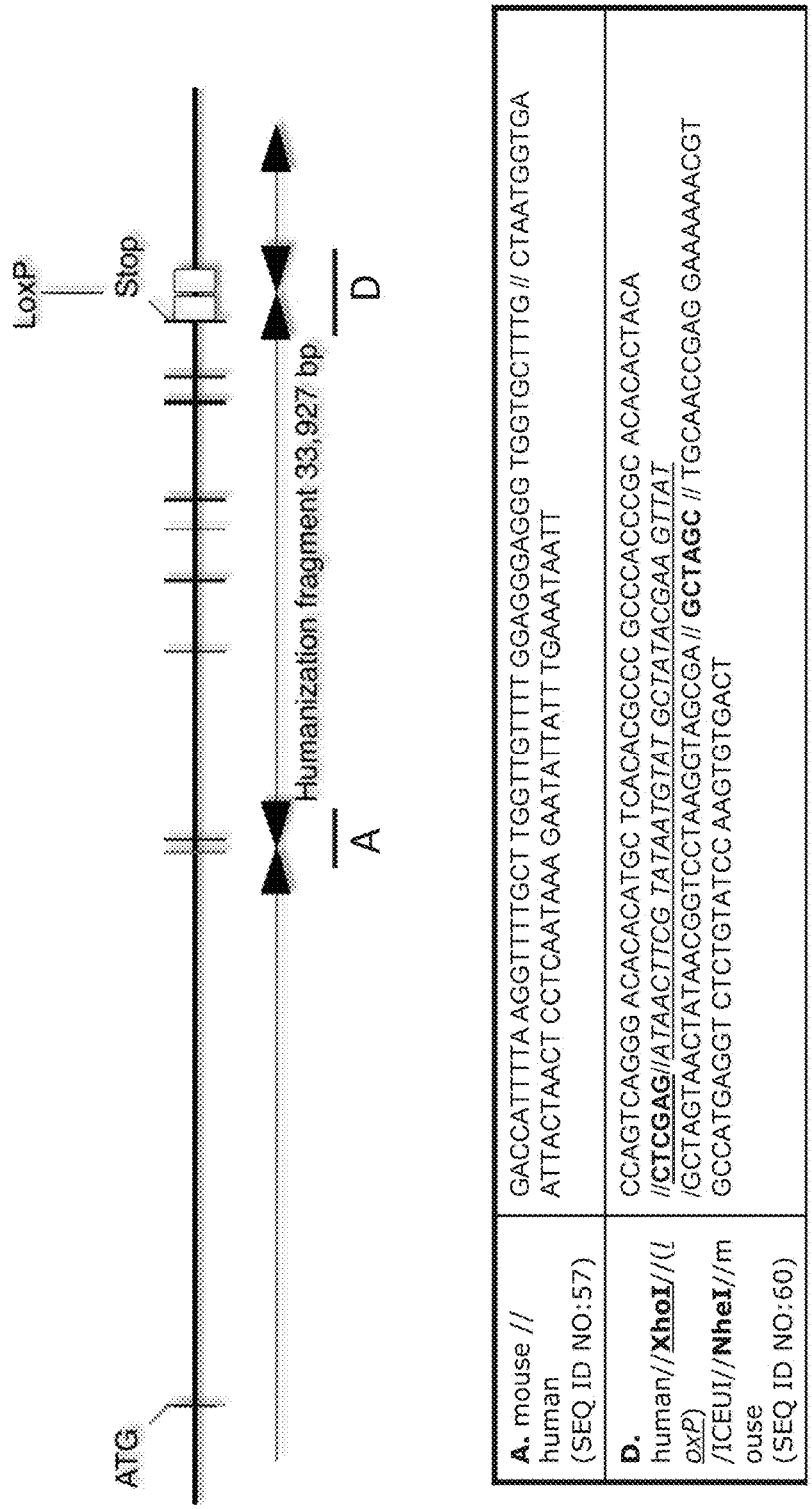
Figure 4:
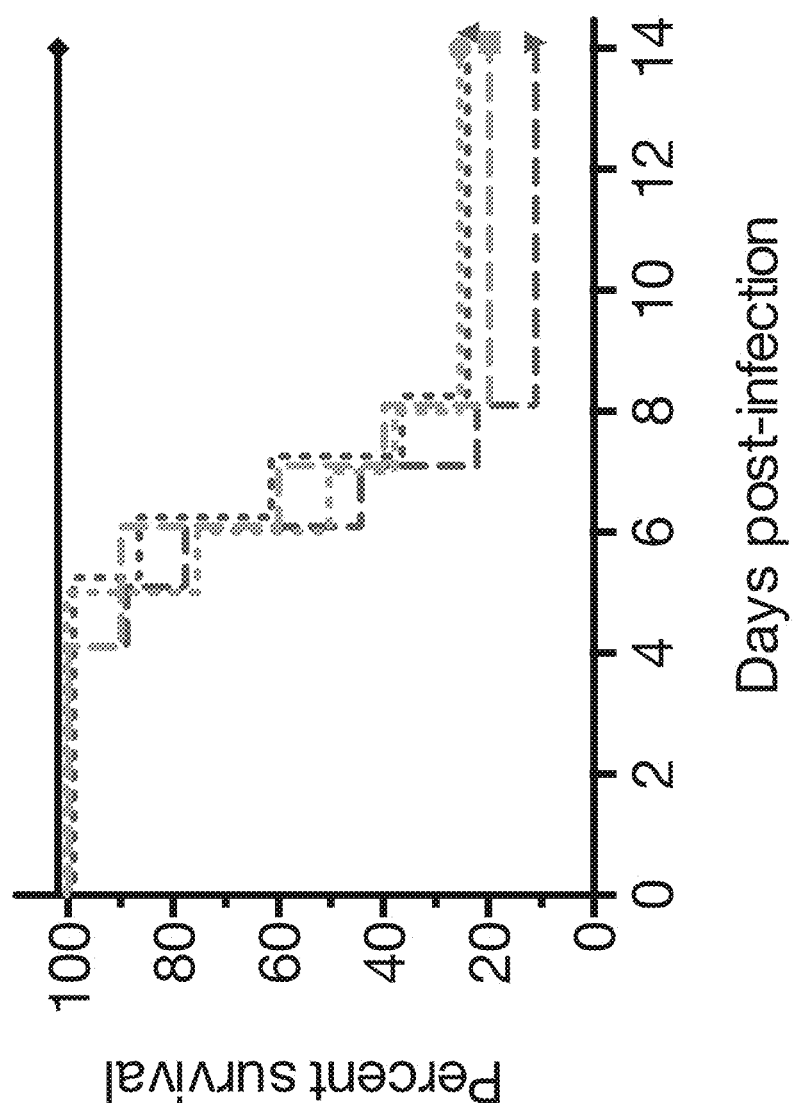
FIG. 4 depicts the results of an experiment showing that MAID7225 HumInTMPRSS4 mice do not differ in their susceptibility to challenge with high doses of severe influenza A H1N1 or severe, mouse-adapted H3N2. MAID7225 HumIn TMRPSS4 mice challenged with A/Puerto Rico/08/1934 (H1N1) (light gray circles, dotted line) showed similar survival rates compared to wild-type mice (light gray squares, dotted line). Likewise, MAID7225 HumIn TMRPSS4 mice challenged with A/Aichi/02/1968-X31 (H3N2) (dark gray triangles, dotted line) showed similar survival rates compared to wild-type mice (light gray inverse triangles, dashed line). Mice were infected IN on day 0 with either 1150 PFUs of A/Puerto Rico/08/1934 (H1N1) or 10,000 PFUs of A/Aichi/02/1968-X31 (H3N2). The control group included uninfected negative control MAID7225 HumIn TMPRSS4 and wild-type mice (black diamonds, solid line).

The modified BAC clone containing the humanized Tmprss11d gene, as described above, is used to electroporate mouse embryonic stem (ES) cells to create modified ES cells comprising a humanized Tmprss11d gene. Positively targeted ES cells containing a humanized Tmprss11d gene are identified by an assay (Valenzuela et al., supra) that detects the presence of the human TMPRSS11D sequences (e.g., coding exons 3-10 of human TMPRSS11D) and confirms the loss and/or retention of mouse Tmprss11d sequences (e.g., loss of coding exons 3-10 of mouse Tmprss11d). Table 3 sets forth the primers and probes that were used to confirm humanization of an endogenous Tmprss11d gene as described above (FIGS. 3A-3B). Once a correctly targeted ES cell clone has been selected, the neomycin selection cassette can be excised by introducing a Cre recombinase, e.g., via electroporation. Alternatively, the neomycin selection cassette can be removed by crossing the progeny generated from the ES clone with a deletor rodent strain that expresses a Cre recombinase. The humanized Tmprss11d locus after the deletion of the cassette is depicted in FIG. 3C, with the junction sequences shown at the bottom of FIG. 3C.

Selected ES cell clones (with or without the cassette) are used to implant female mice using the VELOCIMOUSE® method (see, e.g., U.S. Pat. No. 7,294,754 and Poueymirou et al. (2007), supra) to generate a litter of pups containing a humanized Tmprss11d allele in the genome. Mice bearing a humanized Tmprss11d allele are again confirmed and identified by genotyping of DNA isolated from tail snips using a modification of allele assay (Valenzuela et al., supra) that detects the presence of the human TMPRSS11D gene sequences. Pups are genotyped and cohorts of animals heterozygous for the humanized Tmprss11d locus are selected for characterization. Animals homozygous for the humanized Tmprss11d locus are made by crossing heterozygous animals.

TABLE 3

| Name | Primer | Sequence (5'-3') | SEQ ID NO |
|---|---|---|---|
| 7226mTU | Forward | TCCTCTCCAGACAAGAAAGCT | (SEQ ID NO: 61) |
| | Probe (BHQ) | TCATAGCAGCTTTCAAATCCTAAACGTTGA | (SEQ ID NO: 62) |
| | Reverse | TCGTGTGTAGCTGGTGAGTT | (SEQ ID NO: 63) |
| 7226mTD | Forward | CATGCGATCACAGGAGGAGATC | (SEQ ID NO: 64) |
| | Probe (BHQ) | AATTGGGCCCGAAGCCAGATGC | (SEQ ID NO: 65) |
| | Reverse | CGGAAGGCTTCTGTGACTTC | (SEQ ID NO: 66) |
| 7226hTU | Forward | GTCTCCCACTTCTGACATAATGAAC | (SEQ ID NO: 67) |
| | Probe (BHQ) | CCCAGTGTTAACCCTACATCTGGTTCC | (SEQ ID NO: 68) |
| | Reverse | TGGGAAGAGACTCTTGGACA | (SEQ ID NO: 69) |
| 7226hTD | Forward | ATGAGCTCCTAGTACAGCTAAAGTT | (SEQ ID NO: 70) |
| | Probe (MGB) | ATGCATGATCATCTATGCGTCAGAGC | (SEQ ID NO: 71) |
| | Reverse | TGCCCAGATGCAGGGAGTTAG | (SEQ ID NO: 72) |

Example 4. Evaluation of Group 1 and Group 2 Influenza A Viruses in MAID7225 HumIn Vs. Wild-Type Tmprss4 Mice To validate the use of humanized Tmprss rodents as an animal model of infection, experiments were conducted to evaluate the survival of MAID7225 HumIn TMPRSS4 mice versus wild-type (WT) littermates in an influenza A group 1 and group 2 model of severe influenza infection.

MAID7225 HumIn TMPRSS4 mice are homozygous for a humanized Tmprss4 gene in its genome and were generated as described in Example 2. The viral strains used in these studies included the historical A/Puerto Rico/08/1934 (H1N1) influenza A virus group 1 isolate and an in-house mouse-adapted A/Aichi/02/1968 (HA, NA) X-31 (H3N2) influenza A virus group 2 isolate. All experiments were performed in 6-8 week-old male and female MAID7225 HumIn TMPRSS4 mice or WT littermates. Mice were challenged with 1150 plaque-forming units (PFUs) of A/Puerto Rico/08/1934 (H1N1) or 10,000 PFUs of A/Aichi/02/1968-X31 (H3N2). In these survival models, mice were challenged intranasally (IN) on day 0 post-infection (p.i.). Mice were weighed and observed daily up to day 14 p.i. and were sacrificed when they lost 20% of their starting weight. Results are reported as percent survival (Table 4).

TABLE 4

| Group ID | Number of mice per group | Percent survival (no. of surviving mice/total no. of mice in the group) |
|---|---|---|
| Uninfected control (2 HumIn, 2 WT mice) | 4 | 100 (4/4) |
| WT TMPRSS4; H1_PR34 infected | 10 | 20 (2/10) |
| HumIn TMPRSS4; H1_PR34 infected | 8 | 25 (2/8) |
| WT TMPRSS4; H3_X31 infected | 9 | 11.1 (1/9) |
| HumIn TMPRSS4; H3_X31 infected | 8 | 25 (2/8) |

The survival of MAID7225 HumIn TMPRSS4 mice was compared to WT littermates after challenge with both severe Influenza A group 1 virus [A/Puerto Rico/08/1934 (H1N1)] and a severe, mouse-adapted Influenza A group 2 virus [A/Aichi/02/1968-X31 (H3N2)] (FIG. 4). Survival of MAID7225 HumIn TMPRSS4 mice was no different from wild-type mice with either the H1N1 challenge (25%; n=8 and 20%; n=10, respectively) or the H3N2 challenge (25%; n=8 and 11.1%; n=9, respectively).

The publications, websites and other reference materials referenced herein to describe the background of the invention and to provide additional detail regarding its practice are hereby incorporated by reference.

What is claimed is:

1. A rodent whose genome comprises a replacement of a nucleotide sequence of an endogenous rodent Tmprss2 gene at an endogenous Tmprss2 locus with a nucleotide sequence of a human TMPRSS2 gene to form a humanized Tmprss2 gene,
   wherein the humanized Tmprss2 gene is under control of the promoter of the endogenous rodent Tmprss2 gene at the endogenous Tmprss2 locus, and
   wherein the humanized Tmprss2 gene encodes a humanized Tmprss2 protein that comprises
   (i) an ectodomain of the human TMPRSS2 protein encoded by the human TMPRSS2 gene, and
   (ii) a cytoplasmic and transmembrane portion encoded by the endogenous rodent Tmprss2 gene.

2. The rodent of claim 1, wherein the ectodomain comprises amino acid residues W106 to G492 of SEQ ID NO: 4.

3. The rodent of claim 1, wherein the nucleotide sequence of the human TMPRSS2 gene comprises coding exon 4 through the stop codon in coding exon 13 of the human TMPRSS2 gene.

4. The rodent of claim 3, further comprising the 3' UTR of the human TMPRSS2 gene.

5. The rodent of claim 4, wherein the humanized Tmprss2 gene comprises coding exons 1-2 of the endogenous rodent Tmprss2 gene, and coding exon 4 through coding exon 13 of the human TMPRSS2 gene.

6. The rodent of claim 5, wherein the humanized Tmprss2 gene comprises an exon 3 that comprises a 5' portion of coding exon 3 of the endogenous rodent Tmprss2 gene and a 3' portion of coding exon 3 of the human TMPRSS2 gene.

7. The rodent of claim 1, wherein the rodent is a mouse or a rat.

8. A rodent whose genome comprises a replacement of a nucleotide sequence of an endogenous rodent Tmprss4 gene at an endogenous rodent Tmprss4 locus with a nucleotide sequence of a human TMPRSS4 gene to form a humanized Tmprss4 gene,
wherein the humanized Tmprss4 gene is under control of the promoter of the endogenous rodent Tmprss4 gene at the endogenous rodent Tmprss4 locus, and
wherein the humanized Tmprss4 gene encodes a humanized Tmprss4 protein that comprises
(i) an ectodomain of the human TMPRSS4 protein encoded by the human TMPRSS4 gene, and
(ii) a cytoplasmic and transmembrane portion encoded by the endogenous rodent Tmprss4 gene.

9. The rodent of claim 8, wherein the ectodomain comprises amino acid residues K54-L437 of SEQ ID NO: 11.

10. The rodent of claim 8, wherein the nucleotide sequence of the human TMPRSS4 gene comprises coding exon 4 through the stop codon in coding exon 13 of the human TMPRSS4 gene.

11. The rodent of claim 10, wherein the stop codon of the human TMPRSS4 gene is followed by the 3' UTR of the endogenous rodent Tmprss4 gene.

12. The rodent of claim 10, wherein the humanized Tmprss4 gene comprises coding exon 1 through coding exon 3 of the endogenous rodent Tmprss4 gene, and coding exon 4 through the stop codon in coding exon 13 of the human TMPRSS4 gene.

13. The rodent of claim 8, wherein the rodent is a mouse or a rat.

14. A rodent whose genome comprises a replacement of a nucleotide sequence of an endogenous rodent Tmprss11d gene at an endogenous rodent Tmprss11d locus with a nucleotide sequence of a human TMPRSS11D gene to form a humanized Tmprss11d gene,
wherein the humanized Tmprss11d gene is under control of the promoter of the endogenous rodent Tmprss11d gene at the endogenous rodent Tmprss11d locus, and
wherein the humanized Tmprss11d gene encodes a humanized Tmprss11d protein that comprises (i) an ectodomain of the human TMPRSS11D protein encoded by the human TMPRSS11D gene, and (ii) a cytoplasmic and transmembrane portion encoded by the endogenous rodent Tmprss11d gene.

15. The rodent of claim 14, wherein the ectodomain comprises amino acid residues A42 to 1418 of SEQ ID NO: 18.

16. The rodent of claim 14, wherein the nucleotide sequence of the human TMPRSS11D gene comprises coding exon 3 through the stop codon in coding exon 10 of the human TMPRSS11D gene.

17. The rodent of claim 16, further comprising the 3' UTR of the human TMPRSS11D gene.

18. The rodent of claim 14, wherein the humanized Tmprss11d gene comprises coding exons 1-2 of the endogenous rodent Tmprss11d gene, and coding exons 3 through coding exon 10 of the human TMPRSS11D gene.

19. The rodent of claim 14, wherein the rodent is a mouse or a rat.

20. The rodent of claim 1, wherein the rodent is a mouse.

21. The rodent of claim 8, wherein the rodent is a mouse.

22. The rodent of claim 14, wherein the rodent is a mouse.

* * * * *